United States Patent
Michaelides et al.

(10) Patent No.: US 7,560,552 B2
(45) Date of Patent: Jul. 14, 2009

(54) THIOPYRIMIDINE AND ISOTHIAZOLOPYRIMIDINE KINASE INHIBITORS

(75) Inventors: Michael R. Michaelides, Libertyville, IL (US); Lee D. Arnold, East Islip, NY (US); Michael L. Curtin, Pleasant Prairie, WI (US); Yujia Dai, Gurnee, IL (US); Steven K. Davidsen, Libertyville, IL (US); Robin R. Frey, Libertyville, IL (US); Yan Guo, Dallas, TX (US); Zhiqin Ji, Libertyville, IL (US); Neil Wishart, Jefferson, MA (US)

(73) Assignee: Abbott Laboratories, Abbott Park, IL (US)

( * ) Notice: Subject to any disclaimer, the term of this patent is extended or adjusted under 35 U.S.C. 154(b) by 982 days.

(21) Appl. No.: 10/392,951

(22) Filed: Mar. 20, 2003

(65) Prior Publication Data
US 2004/0014756 A1      Jan. 22, 2004

Related U.S. Application Data

(60) Provisional application No. 60/366,708, filed on Mar. 21, 2002.

(51) Int. Cl.
| | | |
|---|---|---|
| C07D 495/04 | (2006.01) | |
| A61K 31/519 | (2006.01) | |
| A61P 35/04 | (2006.01) | |
| A61P 19/02 | (2006.01) | |
| A61P 3/10 | (2006.01) | |
| A61P 37/06 | (2006.01) | |

(52) U.S. Cl. .................................. 544/255; 514/260.1
(58) Field of Classification Search ................ 544/182, 544/255, 278; 514/260.1
See application file for complete search history.

(56) References Cited

U.S. PATENT DOCUMENTS

| 3,470,183 | A | 9/1969 | Roth et al. |
| 2002/0004511 | A1 | 1/2002 | Luzzio et al. |
| 2003/0181468 | A1* | 9/2003 | Michaelides et al. ..... 514/260.1 |
| 2003/0225273 | A1* | 12/2003 | Michaelides et al. ........ 544/182 |
| 2005/0004142 | A1* | 1/2005 | Adams et al. ............ 514/260.1 |

FOREIGN PATENT DOCUMENTS

| EP | 0 438 261 | 7/1991 |
| WO | 97/13771 | 4/1997 |
| WO | 01/19828 | 3/2001 |
| WO | 03/022852 | 3/2003 |

OTHER PUBLICATIONS

Rosen LS., Hematol Oncol Clin North Am. Oct. 2002;16(5):1173-87.*
Wedge, S.R. et al, Cancer Research 60, 970-975, Feb. 15, 2000.*
Lutton, A. et al, Annals of the New York Academy of Sciences 979:80-93 (2002).*
Abdelraek et al., "Synthesis of novel thieno[2,3-d]pyrimidine, thieno[2,3-b]pyridine and thiazolo[3,2-a]pyrimidine derivates and their effect on the production of mycotoxins", Arch. Pharm. (Weinheim) 325:301-305 (1992).
Abdelrazek et al., "Heterocyclic synthesis with nitriles: a new approach to thiophene and tieno-[2,3-d]-pyrimidine derivatives", Journal f. prakt. Chemie. Band 330(4):585-589 (1988).
Abdelrazek et al., "Heterocyclic synthesis with nitriles: a novel synthesis of some thiophene and thieno[2,3-d]pyrimidine derivatives, II [1]", Z. Naturforsch, B.: Chemical Sci. 44(4):488-492 (1989).
Abdelrazek et al., "Heterocyclic synthesis with nitriles: synthesis of some new thiophene and thieno[2,3-d]pyrimidine derivatives IV", Phosphorus, Sulfur, and Silicon 1:271-277 (1996).
Abdelrazek et al., "Heterocyclic Synthesis with Nitriles: synthesis of some novel thiophene and thieno[2,3-d]pyrimidine derivatives", Phosphorus. Sulfur, and Silicon 71:93-97 (1992).
Dave et al., "Gold-Jacob type of reaction in the synthesis of thieno[3,2-e]pyrimido{1,2-c]pyrimidines: a comparison of classical heating vs solvent-free microwave irradiation", Heterocycles 51(8):1819-1826 (1999).
Kandeel et al., "Nitriles in heterocyclic synthesis: a novel synthesis of some thieno[2,3-d]pyrimidine and thieno[2,3-b]pyridine derivates", Heteroatom Chemistry 7(1):29-33 (1996).
Nelson et al., "Dicyclic and Tricyclic Diaminopyrimidine derivates as potent inhibitors of cryptosporidium parvum dihydrofolate reductase: structure-activity and structure-selectivity correlations", Antimicrobial Agents and Chemotherapy 45(12):3293-3303 (2001).
Rosowsky et al., "2,4-diaminothieno[2,3-d]pyrimidines as antifolates and antimalarials. 3. Synthesis of 5,6-disubstituted derivates and related tetracyclic analogs", Journal of Medicinal Chemistry 16(3):191-194 (1973).
Roth et al., "2,4-diaminopyrimidines. The cyclization of 6-phenacylthio and related derivates to thieno[2,3-d]pyrimidines and thiazolo[3,2-c]pyrimidines", J Med. Chemical 12(2):227-232 (1969).
Roth et al., "The protonation of 2,4-diaminopyrimidines. I. Dissociation constants and substituent effects", J. Organic Chemical 34(4):821-836 (1969).

(Continued)

*Primary Examiner*—Brenda L Coleman
*Assistant Examiner*—Susanna Moore
(74) *Attorney, Agent, or Firm*—Patricia Coleman James

(57) ABSTRACT

Compounds having the formula

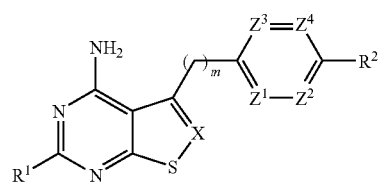

are useful for inhibiting protein tyrosine kinases. The present invention also discloses methods of making the compounds, compositions containing the compounds, and methods of treatment using the compounds.

2 Claims, No Drawings

OTHER PUBLICATIONS

Sherif et al., "Syntheses with heterocyclic beta-enaminonitriles: an expeditious synthetic approach to polyfunctionally substituted 5-phenyl-sulfonylthiophenes and their fused derivates", Monatshefte fur Chemie 128:687-696 (1997).

Taylor et al., "Synthesis of thieno[2,3-d]pyrimidine analogues of the potent antitumor agent N-{4-[2-[(2-amino-4(3H)-oxo-7H-pyrrolo[2,3-d]pyrimidin-5-yl)ethyl]-benzoyl}-1-glutamic acid (LY231514)," Heterocycles 43(2):349-365 (1996).

* cited by examiner

US 7,560,552 B2

THIOPYRIMIDINE AND ISOTHIAZOLOPYRIMIDINE KINASE INHIBITORS

CROSS-REFERENCE TO RELATED APPLICATIONS

This application claims priority to U.S. Provisional Patent Application Ser. No. 60/366,708, filed on Mar. 21, 2002, which is hereby incorporated by reference.

TECHNICAL FIELD

The present invention relates to compounds which are useful for inhibiting protein tyrosine kinases, methods of making the compounds, compositions containing the compounds, and methods of treatment using the compounds.

BACKGROUND OF THE INVENTION

Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation, or differentiation. Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

In its principle embodiment the present invention discloses a compound of formula (I)

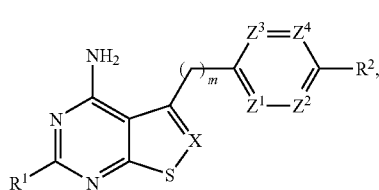

(I)

or a therapeutically acceptable salt thereof, wherein

X is selected from the group consisting of —N— and —CR$^3$—;
Z$^1$ is selected from the group consisting of —N— and —CR$^4$—;
Z$^2$ is selected from the group consisting of —N— and —CR$^5$—;
Z$^3$ is selected from the group consisting of —N— and —CR$^6$—;
Z$^4$ is selected from the group consisting of —N— and —CR$^7$—;
R$^1$ is selected from the group consisting of hydrogen and NH$_2$;
R$^2$ is selected from the group consisting of alkoxy, cyano, hydroxy, nitro, —NR$^a$R$^b$, and -LR$^8$;
R$^3$ is selected from the group consisting of hydrogen, alkenyl, alkoxyalkyl, alkyl, arylalkyl, carboxyalkyl, halo, haloalkyl, heteroarylalkyl, (heterocyclyl)alkyl, hydroxyalkyl, (NR$^a$R$^b$)alkyl, and (NR$^a$R$^b$)C(O)alkyl;
R$^4$, R$^5$, R$^6$, and R$^7$ are independently selected from the group consisting of hydrogen, alkoxy, alkyl, NR$^a$R$^b$, halo, and hydroxy;
R$^8$ is selected from the group consisting of alkoxyalkyl, alkyl, aryl, arylalkenyl, arylalkyl, cycloalkyl, heteroaryl, heteroarylalkyl, heterocyclyl, and (heterocyclyl)alkyl;
L is selected from the group consisting of —O—, —(CH$_2$)$_n$C(O)(CH$_2$)$_p$—, —C≡C—(CH$_2$)$_n$O—, —C(O)NR$^9$—, —NR$^9$C(O)—, —NR$^9$—, —(CH$_2$)$_n$NR$^9$C(O)NR$^{10}$(CH$_2$)$_p$—, —NR$^9$C(S)NR$^{10}$—, —NR$^9$C(=NCN)NR$^{10}$—, —NR$^9$C(=NCN)O—, —OC(=NCN)NR$^9$—, —NR$^9$SO$_2$—, and —SO$_2$NR$^9$—, wherein each group is drawn with its right side attached to R$^8$, and wherein R$^9$ and R$^{10}$ are independently selected from the group consisting of hydrogen, and alkyl;
m, n, and p are independently 0-2;
provided that at least one of Z$^1$, Z$^2$, Z$^3$, and Z$^4$ is other than —N—.

In another embodiment the present invention provides a compound of formula (I) wherein Z$^1$ is —CR$^4$—; Z$^3$ is —CR$^6$—; and Z$^4$ is —CR$^7$—.

In another embodiment the present invention provides a compound of formula (I) wherein X is —N—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; and m is 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; and m is 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; L is selected from the group consisting of —(CH$_2$)$_n$C(O)(CH$_2$)$_p$—, —C≡C—(CH$_2$)$_n$O—, —C(O)NR$^9$—, —NR$^9$C(O)—, —NR$^9$—, —NR$^9$C(S)NR$^{10}$—, —NR$^9$C(=NCN)NR$^{10}$—, —NR$^9$C(=NCN)O, and NR$^9$SO$_2$—; and m is 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; L is —(CH$_2$)$_n$NR$^9$C(O)NR$^{10}$(CH$_2$)$_p$—; and m is 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; L is —(CH$_2$)$_n$NR$^9$C(O)NR$^{10}$(CH$_2$)$_p$—; and m, n, and p are 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; R$^8$ is aryl; L is —(CH$_2$)$_n$NR$^9$C(O)NR$^{10}$(CH$_2$)$_p$—; and m, n, and p are 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; R$^3$ is selected from the group consisting of alkenyl, alkoxyalkyl, arylalkyl, halo, heteroarylalkyl, heterocyclylalkyl, hydroxyalkyl, and (NR$^a$R$^b$)alkyl; R$^8$ is aryl; L is —(CH$_2$)$_n$NR$^9$C(O)NR$^{10}$(CH$_2$)$_p$—; and m, n, and p are 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; R$^3$ is (NR$^a$R$^b$)C(O)alkyl; R$^8$ is aryl; L is —(CH$_2$)$_n$NR$^9$C(O)NR$^{10}$(CH$_2$)$_p$—; and m, n, and p are 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; R$^3$ is hydrogen; R$^8$ is aryl; L is —(CH$_2$)$_n$NR$^9$C(O)NR$^{10}$(CH$_2$)$_p$—; and m, n, and p are 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; R$^3$ is alkyl; R$^8$ is aryl; L is —(CH$_2$)$_n$NR$^9$C(O)NR$^{10}$(CH$_2$)$_p$—; and m, n, and p are 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; R$^3$ is alkyl, wherein the alkyl is selected from the group consisting of ethyl, isopropyl, and propyl; R$^8$ is aryl; L is —(CH$_2$)$_n$NR$^9$C(O)NR$^{10}$(CH$_2$)$_p$—; and m, n, and p are 0.

In another embodiment the present invention provides a compound of formula (I) wherein X is —CR$^3$—; Z$^1$ is —CR$^4$—; Z$^2$ is —CR$^5$—; Z$^3$ is —CR$^6$—; Z$^4$ is —CR$^7$—; R$^1$ is hydrogen; R$^2$ is -LR$^8$; R$^3$ is alkyl, wherein the alkyl is methyl; R$^8$ is aryl; L is —(CH$_2$)$_n$NR$^9$C(O)NR$^{10}$(CH$_2$)$_p$—; and m, n, and p are 0.

In another embodiment the present invention provides a compound which is N-[4-(4-aminothieno[2,3-d]pyrimidin-5-yl)phenyl]-N'-[2-fluoro-5-(trifluoromethyl)phenyl]urea.

In another embodiment the present invention provides a compound which is N-[4-(4-aminothieno[2,3-d]pyrimidin-5-yl)phenyl]-N'-(3-methylphenyl)urea.

In another embodiment the present invention provides a compound which is N-[4-(4-aminothieno[2,3-d]pyrimidin-5-yl)phenyl]-N'-(3-chlorophenyl)urea.

In another embodiment the present invention provides a compound which is N-[4-(4-aminothieno[2,3-d]pyrimidin-5-yl)-2-fluorophenyl]-N'-[3-(trifluoromethyl)phenyl]urea.

In another embodiment the present invention provides a compound which is N-[4-(4-aminothieno[2,3-d]pyrimidin-5-yl)-3-fluorophenyl]-N'-[3-(trifluoromethyl)phenyl]urea.

In another embodiment the present invention provides a pharmaceutical composition comprising a compound of formula (I) or a therapeutically acceptable salt thereof, in combination with a therapeutically acceptable carrier.

In another embodiment the present invention provides a method for inhibiting protein kinase in a patient in recognized need of such treatment comprising administering to the patient a therapeutically acceptable amount of a compound of formula (I), or a therapeutically acceptable salt thereof.

In another embodiment the present invention provides a method for inhibiting KDR in a patient in recognized need of such treatment comprising administering to the patient a therapeutically acceptable amount of a compound of formula (I), or a therapeutically acceptable salt thereof.

In another embodiment the present invention provides a method for inhibiting Tie-2 in a patient in recognized need of such treatment comprising administering to the patient a therapeutically acceptable amount of a compound of formula (I), or a therapeutically acceptable salt thereof.

In another embodiment the present invention provides a method for treating cancer in a patient in recognized need of such treatment comprising administering to the patient a therapeutically acceptable amount of a compound of formula (I), or a therapeutically acceptable salt thereof.

DETAILED DESCRIPTION OF THE INVENTION

As used herein, the singular forms "a", "an", and "the" include plural reference unless the context clearly dictates otherwise.

As used in the present specification the following terms have the meanings indicated:

The term "alkenyl," as used herein, refers to a straight or branched chain group of one to six carbon atoms containing at least one carbon—carbon double bond. Examples of alkenyl groups include, but are not limited to, ethenyl, 2-methyl-1-propenyl, and 1-butenyl.

The term "alkoxy," as used herein, refers to an alkyl group attached to the parent molecular moiety through an oxygen atom.

The term "alkoxyalkyl," as used herein, refers to an alkoxy group attached to the parent molecular moiety through an alkyl group.

The term "alkoxycarbonyl," as used herein, refers to an alkoxy group attached to the parent molecular moiety through a carbonyl group.

The term "alkoxycarbonylcarbonyl," as used herein, refers to an alkoxycarbonyl group attached to the parent molecular moiety through a carbonyl group.

The term "alkyl," as used herein, refers to a monovalent group derived from a straight or branched chain saturated hydrocarbon. Examples of alkyl groups include, but are not limited to, methyl, ethyl, propyl, and isopropyl.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a cycloalkenyl group, a cycloalkyl group, or another phenyl group. Tricyclic fused ring systems are exemplified by a bicyclic fused ring system fused to a cycloalkenyl group, a cycloalkyl group, or another phenyl group. Examples of aryl groups include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylsulfanyl, alkylsulfonyl, a second aryl group, arylalkoxy, arylalkyl, aryloxy, carboxy, cyano, halo, haloalkoxy, haloalkyl, heteroaryl, heteroarylalkoxy, heteroarylalkyl, heteroaryloxy, heterocyclyl, (heterocyclyl)alkyl, hydroxy, hydroxyalkyl, nitro, $NR^aR^b$, $(NR^aR^b)$alkyl, $(NR^aR^b)C(O)$, $(NR^aR^b)C(O)$alkyl, and oxo; wherein the second aryl group, the aryl part of the arylalkoxy, the arylalkyl, and the aryloxy, the heteroaryl, the heteroaryl part of the heteroarylalkoxy, the heteroarylalkyl, and the heteroaryloxy, the heterocyclyl, and the heterocyclyl part of the (heterocyclyl)alkyl can be further optionally substituted with one, two, three, four, or five groups independently selected from the group consisting of alkenyl, alkoxy, alkoxyalkyl, alkyl, alkylsulfanyl, cyano, halo, haloalkoxy, haloalkyl, hydroxy, hydroxyalkyl, nitro, $NR^aR^b$, and oxo.

The term "arylalkoxy," as used herein, refers to an aryl group attached to the parent molecular moiety through an alkoxy group.

The term "arylalkyl," as used herein, refers to an alkyl group substituted with at least one aryl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "carbonyl," as used herein, refers to —C(O)—.

The term "carboxy," as used herein, refers to —CO$_2$H.

The term "carboxyalkyl," as used herein, refers to an alkyl group substituted with at least one carboxy group.

The term "cyano," as used herein, refers to —CN.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Examples of cycloalkenyl groups include, but are not limited to, cyclobutenyl, cyclohexenyl, octahydronaphthalenyl, and norbornylenyl. The cycloalkenyl groups of the present invention can be optionally substituted with one, two, or three substituents independently selected from the group consisting of alkoxy, alkyl, aryl, arylalkyl, cyano, halo, haloalkyl, heteroaryl, heteroarylalkyl, heterocyclyl, heterocyclylalkyl, nitro, —NR$^c$R$^d$, and oxo.

The term "cycloalkenylalkyl," as used herein, refers to an alkyl group substituted with at least one cycloalkenyl group.

The term "cycloalkyl," as used herein, refers to a saturated monocyclic, bicyclic, or tricyclic hydrocarbon ring system having three to twelve carbon atoms. Examples of cycloalkyl groups include, but are not limited to, cyclopropyl, cyclopentyl, cyclohexyl, bicyclo[3.1.1]heptyl, and adamantyl. The cycloalkyl groups of the present invention can be optionally substituted with one, two, or three substituents independently selected from the group consisting of alkoxy, alkyl, aryl, arylalkyl, cyano, halo, haloalkyl, heteroaryl, heteroarylalkyl, heterocyclyl, heterocyclylalkyl, nitro, —NR$^c$R$^d$, and oxo.

The term "(cycloalkyl)alkyl," as used herein, refers to a cycloalkyl group attached to the parent molecular moiety through an alkyl group.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by at least one halogen atom.

The term "heteroaryl," as used herein, refers to an aromatic five- or six-membered ring where at least one atom is selected from the group consisting of N, O, and S, and the remaining atoms are carbon. The five-membered rings have two double bonds, and the six-membered rings have three double bonds. The heteroaryl groups are connected to the parent molecular group through a substitutable carbon or nitrogen atom in the ring. The term "heteroaryl" also includes systems where a heteroaryl ring is fused to an aryl group, a cycloalkenyl group, a cycloalkyl group, a heterocyclyl group, or another heteroaryl group. Examples of heteroaryl groups include, but are not limited to, benzodioxolyl, benzothienyl, benzoxadiazolyl, benzoxazolyl, cinnolinyl, furanyl, imidazolyl, indazolyl, indolyl, isoxazolyl, isoquinolinyl, isothiazolyl, naphthyridinyl, oxadiazolyl, oxadiazolyl, oxazolyl, thiazolyl, thienopyridinyl, thienyl, triazolyl, thiadiazolyl, pyridinyl, pyridazinyl, pyrimidinyl, pyrazinyl, pyrazolyl, pyrrolyl, quinolinyl, and triazinyl. The heteroaryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylsulfanyl, alkylsulfonyl, aryl, arylalkoxy, arylalkyl, aryloxy, cyano, halo, haloalkoxy, haloalkyl, a second heteroaryl group, heteroarylalkoxy, heteroarylalkyl, heteroaryloxy, heterocyclyl, (heterocyclyl) alkyl, hydroxy, hydroxyalkyl, nitro, $NR^aR^b$, $(NR^aR^b)$alkyl, $(NR^aR^b)C(O)$, $(NR^aR^b)C(O)$alkyl, and oxo; wherein the aryl, the aryl part of the arylalkoxy, the arylalkyl, and the aryloxy, the second heteroaryl group, the heteroaryl part of the hetoerarylalkoxy, the heteroarylalkyl, and the heteroaryloxy, the heterocyclyl, and the heterocyclyl part of the (heterocyclyl) alkyl can be further optionally substituted with one, two, three, four, or five groups independently selected from the group consisting of alkenyl, alkoxy, alkoxyalkyl, alkyl, alkylsulfanyl, cyano, halo, haloalkoxy, haloalkyl, hydroxy, hydroxyalkyl, nitro, $NR^aR^b$, and oxo.

The term "heteroarylalkoxy," as used herein, refers to a heteroaryl group attached to the parent molecular moiety through an alkoxy group.

The term "heteroarylalkyl," as used herein, refers to an alkyl group substituted by at least one heteroaryl group.

The term "heteroaryloxy," as used herein, refers to a heteroaryl group attached to the parent molecular moiety through an oxygen atom.

The term "heterocyclyl," as used herein, refers to cyclic, non-aromatic, five-, six-, or seven-membered rings containing at least one atom selected from the group consisting of oxygen, nitrogen, and sulfur. The five-membered rings have zero or one double bonds and the six- and seven-membered rings have zero, one, or two double bonds. The heterocyclyl groups of the invention are connected to the parent molecular group through a substitutable carbon or nitrogen atom in the ring. The term "heterocyclyl" also includes systems where a heterocyclyl ring is fused to an aryl group, a cycloalkenyl group, a cycloalkyl group, or another heterocyclyl group. Heterocyclyl groups include, but are not limited to, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, and thiomorpholinyl. The heterocyclyl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylsulfanyl, alkylsulfonyl, aminoalkyl, aminocarbonyl, aryl, arylalkoxy, arylalkyl, aryloxy, cyano, halo, haloalkoxy, haloalkyl, heteroaryl, heteroarylalkoxy, heteroarylalkyl, heteroaryloxy, a second heterocyclyl group, (heterocyclyl)alkyl, hydroxy, hydroxyalkyl, nitro, $NR^aR^b$, $(NR^aR^b)$alkyl, $(NR^aR^b)C(O)$, $(NR^aR^b)C(O)$alkyl, and oxo; wherein the aryl, the aryl part of the arylalkoxy, the arylalkyl, and the aryloxy, the heteroaryl, the heteroaryl part of the heteroarylalkoxy, the heteroarylalkyl, and the heteroaryloxy, the second heterocyclyl group, and the heterocyclyl part of the (heterocyclyl)alkyl can be further optionally substituted with one, two, three, four, or five groups independently selected from the group consisting of alkenyl, alkoxy, alkoxyalkyl, alkyl, alkylsulfanyl, cyano, halo, haloalkoxy, haloalkyl, hydroxy, hydroxyalkyl, nitro, $NR^aR^b$, and oxo.

The term "(heterocyclyl)alkyl," as used herein, refers to an alkyl group substituted with at least one heterocyclyl group.

The term "hydroxy," as used herein, refers to —OH.

The term "hydroxyalkyl," as used herein, refers to an alkyl group substituted with at least one hydroxy group.

The term "nitro," as used herein, refers to —$NO_2$.

The term "$NR^aR^b$," as used herein, refers to two groups, $R^a$ and $R^b$, which are attached to the parent molecular moiety through a nitrogen atom. $R^a$ and $R^b$ are independently selected from the group consisting of hydrogen, alkenyl, alkoxycarbonyl, alkyl, alkylcarbonyl, alkoxycarbonylcarbonyl, aryl, arylalkyl, arylcarbonyl, cycloalkenyl, (cycloalkenyl)alkyl, cycloalkyl, (cycloalkyl)alkyl, heteroaryl, heteroarylalkyl, heterocyclyl, heterocyclylalkyl, $(NR^cR^d)$alkyl, $(NR^cR^d)C(O)$, and $(NR^cR^d)C(O)$alkyl, wherein the aryl, the aryl part of the arylalkyl, and the arylcarbonyl, the heteroaryl, the heteroaryl part of the heteroarylalkyl and the heteroarylcarbonyl, the heterocyclyl, and the heterocyclyl part of the heterocyclylalkyl and the heterocyclylcarbonyl are further optionally substituted with one, two, three, four, or five substituents independently selected from the group consisting of alkoxy, alkyl, cyano, halo, haloalkoxy, nitro, and oxo.

The term "$(NR^aR^b)$alkyl," as used herein, refers to an alkyl group substituted with at least one $NR^aR^b$ group.

The term "$(NR^aR^b)C(O)$," as used herein, refers to an $NR^aR^b$ group attached to the parent molecular moiety through a carbonyl group.

The term "$(NR^aR^b)C(O)$alkyl," as used herein, refers to an alkyl group substituted with at least one $(NR^aR^b)C(O)$ group.

The term "$NR^cR^d$," as used herein, refers to two groups, $R^c$ and $R^d$, which are attached to the parent molecular moiety through a nitrogen atom. $R^c$ and $R^d$ are independently selected from the group consisting of hydrogen, alkenyl, alkoxycarbonyl, alkyl, alkylcarbonyl, aryl, and arylalkyl; wherein the aryl and the aryl part of the arylalkyl can be further optionally substituted with one, two, three, four, or five substituents independently selected from the group consisting of alkoxy, alkyl, cyano, halo, haloalkoxy, nitro, and oxo.

The term "$(NR^cR^d)$alkyl," as used herein, refers to an alkyl group substituted with at least one $NR^cR^d$ group.

The term "$(NR^cR^d)C(O)$," as used herein, refers to an $NR^cR^d$ group attached to the parent molecular moiety through a carbonyl group.

The term "$(NR^cR^d)C(O)$alkyl," as used herein, refers to an alkyl group substituted with at least one $(NR^cR^d)C(O)$ group.

The term "oxo," as used herein, refers to =O.

The term "sulfonyl," as used herein, refers to —$SO_2$.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, suitable nitrogen atoms in the compounds of the present invention can be quarternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

In accordance with methods of treatment and pharmaceutical compositions of the invention, the compounds can be administered alone or in combination with other anticancer agents. When using the compounds, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, monoglycerides, diglycerides, fatty acids such as oleic acid, and fixed oils such as monoglycerides or diglycerides.

The inhibitory effect of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches can also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents, and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable non-irritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Preferred compounds of the present invention are compounds of formula (I) where $R^2$ is -$LR^8$; L is —$(CH_2)_n NR^9 C(O)NR^{10}(CH_2)_p$—; $R^9$ and $R^{10}$ are hydrogen; and m is 0.

Determination of Biological Activity

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature*. 373:536-539) by a test compound relative to control.

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×10$^6$/mL, and were infected at 0.5 plaque forming units per cell (MOI). Cells were harvested at 48 hours post infection.

Purification of KDR

SF-9 cells expressing (His)$_6$KDR(aa789-1354) were lysed by adding 50 mL of Triton X-100 lysis buffer (20 mM Tris, pH 8.0, 137 mM NaCl, 10% glycerol, 1% Triton X-100, 1 mM PMSF, 10 µg/mL aprotinin, 1 µg/mL leupeptin) to the cell pellet from 1 L of cell culture. The lysate was centrifuged at 19,000 rpm in a Sorval SS-34 rotor for 30 minutes at 4° C. The cell lysate was applied to a 5 mL NiCl$_2$ chelating sepharose column, equilibrated with 50 mM HEPES, pH7.5, 0.3M NaCl. KDR was eluted using the same buffer containing 0.25M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Compounds of the present invention inhibited KDR at IC50's between about 0.003 µM and >50 µM. Preferred compounds inhibited KDR at IC50's between about 0.003 µM and about 0.5 µM.

Human Tie-2 Kinase Production and Purification

The coding sequence for the human Tie-2 intra-cellular domain (aa775-1124) was generated through PCR using cDNAs isolated from human placenta as a template. A poly-His$_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/mL, and were infected at MOI of 0.5. Purification of the His-tagged kinase used in screening was analogous to that described for KDR.

Compounds of the present invention inhibited Tie-2 at IC50's between about 0.01 µM and >50 µM. Preferred compounds inhibited Tie-2 at IC50's between about 0.01 µM and 0.5 µM.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786-1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat #E-3641; 500 units/50 µl) and the EGF ligand was acquired from Oncogene Research Products/Calbiochem (Cat #PFO11-100).

Expression of ZAP70

The baculoviral expression vector used was pVL1393. (Pharmingen, Los Angeles, Calif.) The nucleotide sequence encoding amino acids M(H)6 LVPR$_9$S was placed 5' to the region encoding the entirety of ZAP70 (amino acids 1-619). The nucleotide sequence encoding the ZAP70 coding region was generated through PCR using cDNA libraries isolated from Jurkat immortalized T-cells. The histidine residues enabled affinity purification of the protein (vide infra). The LVPR$_9$S bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 µg/mL leupeptin, 10 µg/mL aprotinin and 1 mM sodium orthovanadate. The soluble lysate was applied to a chelating sepharose HiTrap column (Pharmacia) equilibrated in 50 mM HEPES, pH 7.5, 0.3M NaCl. Fusion protein was eluted with 250 mM imidazole. The enzyme was stored in buffer containing 50 mM HEPES, pH 7.5, 50 mM NaCl and 5 mM DTT.

Protein Kinase Source

Lck, Fyn, Src, Blk, Csk, and Lyn, and truncated forms thereof may be commercially obtained (e.g., from Upstate Biotechnology Inc. (Saranac Lake, N.Y.) and Santa Cruz Biotechnology Inc. (Santa Cruz, Calif.)) or purified from known natural or recombinant sources using conventional methods.

Enzyme Linked Immunosorbent Assay (ELISA) for PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359-371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly(Glu$_4$ Tyr), 20,000-50,000 MW) was employed together with ATP (typically 5 µM) at concentrations approximately twice the apparent Km in the assay.

The following procedure was used to assay the inhibitory effect of compounds of this invention on KDR, Flt-1, Flt-4, Tie-1, Tie-2, EGFR, FGFR, PDGFR, IGF-1-R, c-Met, Lck, hck, Blk, Csk, Src, Lyn, fgr, Fyn and ZAP70 tyrosine kinase activity:

Buffers and Solutions:

PGTPoly (Glu,Tyr) 4:1

Store powder at −20° C. Dissolve powder in phosphate buffered saline (PBS) for 50 mg/mL solution. Store 1 mL aliquots at −20° C. When making plates dilute to 250 µg/mL in Gibco PBS.

Reaction Buffer: 100 mM Hepes, 20 mM MgCl$_2$, 4 mM MnCl$_2$, 5 mM DTT, 0.02% BSA, 200 µM NaVO$_4$, pH 7.10

ATP: Store aliquots of 100 mM at −20° C. Dilute to 20 µM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/mL, frozen) in PBS to a 250 µg/mL. Add 125 µL per well of Corning modified flat bottom high affinity ELISA plates (Corning #25805-96). Add 125 µL PBS to blank wells. Cover with sealing tape and incubate overnight 37° C. Wash 1× with 250 µL washing buffer and dry for about 2 hours in 37° C. dry incubator. Store coated plates in sealed bag at 4° C. until used.

2. Tyrosine Kinase Reaction:

Prepare inhibitor solutions at a 4× concentration in 20% DMSO in water.

Prepare reaction buffer

Prepare enzyme solution so that desired units are in 50 µL, e.g. for KDR make to 1 ng/µL for a total of 50 ng per well in the reactions. Store on ice Make 4×ATP solution to 20 µM from 100 mM stock in water. Store on ice Add 50 µL of the enzyme solution per well (typically 5-50 ng enzyme/well depending on the specific activity of the kinase)

Add 25 µL 4× inhibitor

Add 25 µL 4×ATP for inhibitor assay

Incubate for 10 minutes at room temperature

Stop reaction by adding 50 µL 0.05N HCl per well

Wash plate

**Final Concentrations for Reaction: 5 µM ATP, 5% DMSO

3. Antibody Binding

Dilute 1 mg/mL aliquot of PY20-HRP (Pierce) antibody(a phosphotyrosine antibody)to 50 ng/mL in 0.1% BSA in PBS by a 2 step dilution (100×, then 200×)

Add 100 μL Ab per well. Incubate 1 hour at room temperature. Incubate 1 hour at 4° C.

Wash 4× plate

4. Color Reaction

Prepare TMB substrate and add 100 μL per well

Monitor OD at 650 nm until 0.6 is reached

Stop with 1M phosphoric acid. Shake on plate reader.

Read OD immediately at 450 nm

Optimal incubation times and enzyme reaction conditions vary slightly with enzyme preparations and are determined empirically for each lot.

For Lck, the Reaction Buffer utilized was 100 mM MOPSO, pH 6.5, 4 mM $MnCl_2$, 20 mM $MgCl_2$, 5 mM DTT, 0.2% BSA, 200 mM $NaVO_4$ under the analogous assay conditions.

Cdc2 Source

The human recombinant enzyme and assay buffer may be obtained commercially (New England Biolabs, Beverly, Mass. USA) or purified from known natural or recombinant sources using conventional methods.

Cdc2 Assay

A protocol that can be used is that provided with the purchased reagents with minor modifications. In brief, the reaction is carried out in a buffer consisting of 50 mM Tris pH 7.5, 100 mM NaCl, 1 mM EGTA, 2 mM DTT, 0.01% Brij, 5% DMSO and 10 mM $MgCl_2$ (commercial buffer) supplemented with fresh 300 μM ATP (31 μCi/mL) and 30 μg/mL histone type IIIss final concentrations. A reaction volume of 80 μL, containing units of enzyme, is run for 20 minutes at 25 degrees C in the presence or absence of inhibitor. The reaction is terminated by the addition of 120 μL of 10% acetic acid. The substrate is separated from unincorporated label by spotting the mixture on phosphocellulose paper, followed by 3 washes of 5 minutes each with 75 mM phosphoric acid. Counts are measured by a betacounter in the presence of liquid scintillant.

PKC Kinase Source

The catalytic subunit of PKC may be obtained commercially (Calbiochem).

PKC Kinase Assay

A radioactive kinase assay is employed following a published procedure (Yasuda, I., Kirshimoto, A., Tanaka, S., Tominaga, M., Sakurai, A., Nishizuka, Y. *Biochemical and Biophysical Research Communication* 3:166, 1220-1227 (1990)). Briefly, all reactions are performed in a kinase buffer consisting of 50 mM Tris-HCl pH7.5, 10 mM $MgCl_2$, 2 mM DTT, 1 mM EGTA, 100 μM ATP, 8 μM peptide, 5% DMSO and $^{33}$P ATP (8 Ci/mM). Compound and enzyme are mixed in the reaction vessel and the reaction is initiated by addition of the ATP and substrate mixture. Following termination of the reaction by the addition of 10 μL stop buffer (5 mM ATP in 75 mM phosphoric acid), a portion of the mixture is spotted on phosphocellulose filters. The spotted samples are washed 3 times in 75 mM phosphoric acid at room temperature for 5 to 15 minutes. Incorporation of radiolabel is quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction is carried out in a buffer consisting of 50 μmM Tris pH 7.5, 1 mM EGTA, 2 mM DTT, 0.01% Brij, 5% DMSO and 10 mM $MgCl_2$ (commercial buffer) supplemented with fresh 100 μM ATP (31 μCi/mL) and 30 μM myelin basic protein under conditions recommended by the supplier. Reaction volumes and method of assaying incorporated radioactivity are as described for the PKC assay (vide supra).

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) can be purchased from Clonetics (San Diego, Calif.) and cultured according to the manufacturer directions. Only early passages (3-8) are used for this assay. Cells are cultured in 100 mm dishes (Falcon for tissue culture; Becton Dickinson; Plymouth, England) using complete EBM media (Clonetics).

2. For evaluating a compound's inhibitory activity, cells are trypsinized and seeded at $0.5\text{-}1.0 \times 10^5$ cells/well in each well of 6-well cluster plates (Costar; Cambridge, Mass.).

3. 3-4 days after seeding, plates are typically 90-100% confluent. Medium is removed from all the wells, cells are rinsed with 5-10 mL of PBS and incubated 18-24 h with 5 mL of EBM base media with no supplements added (i.e., serum starvation).

4. Serial dilutions of inhibitors are added in 1 mL of EBM media (25 μM, 5 μM, or 1 μM final concentration to cells and incubated for one hour at 37° C. Human recombinant $VEGF_{165}$ (R & D Systems) is then added to all the wells in 2 mL of EBM medium at a final concentration of 50 ng/mL and incubated at 37° C. for 10 minutes. Control cells untreated or treated with VEGF only are used to assess background phosphorylation and phosphorylation induction by VEGF.

All wells are then rinsed with 5-10 mL of cold PBS containing 1 mM Sodium Orthovanadate (Sigma) and cells are lysed and scraped in 200 μL of RIPA buffer (50 mM Tris-HCl) pH 7, 150 mM NaCl, 1% NP-40, 0.25% sodium deoxycholate, 1 mM EDTA) containing protease inhibitors (PMSF 1 mM, aprotinin 1 μg/mL, pepstatin 1 μg/mL, leupeptin 1 μg/mL, Na vanadate 1 mM, Na fluoride 1 mM) and 1 μg/mL of Dnase (all chemicals from Sigma Chemical Company, St. Louis, Mo.). The lysate is spun at 14,000 rpm for 30 minutes, to eliminate nuclei.

Equal amounts of proteins are then precipitated by addition of cold (−20° C.) ethanol (2 volumes) for a minimum of 1 hour or a maximum of overnight. Pellets are reconstituted in LaemLi sample buffer containing 5%-mercaptoethanol (Bio-Rad; Hercules, Calif.) and boiled for 5 minutes. The proteins are resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins are probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4° C. After washing and incubating for 1 hour with HRP-conjugated $F(ab)_2$ of goat anti-rabbit or goat-anti-mouse IgG the bands are visualized using the emission chemiluminescence (ECL) system (Amersham Life Sciences, Arlington Heights, Ill.).

In vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829-837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials:

All hormones can be purchased from Sigma (St. Louis, Mo.) or Cal Biochem (La Jolla, Calif.) as lyophilized powders and prepared according to supplier instructions. Vehicle components (DMSO, Cremaphor EL) can be purchased from Sigma (St. Louis, Mo.). Mice (Balb/c, 8-12 weeks old) can be purchased from Taconic (Germantown, N.Y.) and housed in a pathogen-free animal facility in accordance with institutional Animal Care and Use Committee Guidelines.

Method:

Day 1: Balb/c mice are given an intraperitoneal (i.p.) injection of 12.5 units of pregnant mare's serum gonadotropin (PMSG).

Day 3: Mice receive 15 units of human chorionic gonadotropin (hCG) i.p.

Day 4: Mice are randomized and divided into groups of 5-10. Test compounds are administered by i.p., i.v. or p.o. routes depending on solubility and vehicle at doses ranging from 1-100 mg/kg. Vehicle control group receive vehicle only and two groups are left untreated.

Thirty minutes later, experimental, vehicle and 1 of the untreated groups are given an i.p. injection of 17-estradiol (500 mg/kg). After 2-3 hours, the animals are sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri are blotted to remove fluid by pressing between two sheets of filter paper with a one liter glass bottle filled with water. Uteri are weighed following blotting (blotted weight). The difference between wet and blotted weights is taken as the fluid content of the uterus. Mean fluid content of treated groups is compared to untreated or vehicle treated groups. Significance is determined by Student's test. Non-stimulated control group is used to monitor estradiol response.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al., *Lab. Investig.* (1992), 67(4), 519-528; *Anat. Rec.* (1997), 249(1), 63-73; *Int. J. Cancer* (1995), 63(5), 694-701; *Vasc. Biol.* (1995), 15(11), 1857-6). The model preferably runs over 3-4 days and endpoints include macroscopic visual/image scoring of neovascularization, microscopic microvessel density determinations, and hemoglobin quantitation (Drabkin method) following removal of the implant versus controls from animals untreated with, inhibitors. The model may alternatively employ bFGF or HGF as the stimulus.

The compounds of the present invention may be used in the treatment of protein kinase-mediated conditions, such as benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (e.g., kidney rejection, graft versus host disease), benign and neoplastic proliferative diseases, human cancers such as lung, breast, stomach, bladder, colon, pancreatic, ovarian, prostate and rectal cancer and hematopoietic malignancies (leukemia and lymphoma), glioblastoma, infantile hemangioma, and diseases involving inappropriate vascularization (for example diabetic retinopathy, retinopathy of prematurity, choroidal neovascularization due to age-related macular degeneration, and infantile hemangiomas in human beings). Such inhibitors may be useful in the treatment of disorders involving VEGF mediated edema, ascites, effusions, and exudates, including for example macular edema, cerebral edema, acute lung injury and adult respiratory distress syndrome (ARDS). In addition, the compounds of the invention may be useful in the treatment of pulmonary hypertension, particularly in patients with thromboembolic disease (*J. Thorac. Cardiovasc. Surg.* 2001, 122 (1), 65-73).

Compounds of the invention may have therapeutic utility in the treatment of diseases involving both identified, including those not mentioned herein, and as yet unidentified protein tyrosine kinases. Preferred compounds of the invention are compounds which have shown the ability to inhibit multiple kinases and may not necessarily be the most potent inhibitors of any one particular kinase.

Synthetic Methods

Abbreviations which have been used in the descriptions of the scheme and the examples that follow are: TUF for tetrahydrofuran; NBS for N-bromosuccinimide; AIBN for 2,2'-azobisisobutyronitrile; DMF for N,N-dimethylformamide; NMP for 1-methyl-2-pyrrolidinone; EDC for 1-(3-dimethylaminopropyl)-3-ethylcarbodiimide hydrochloride; DCC for 1,3-dicyclohexylcarbodiimide; HOBT for 1-hydroxybenzotriazole; $PPh_3$ for triphenylphosphine; DMSO for dimethylsulfoxide; NMM for N-methylmorpholine; and TBAF for tetrabutylammonium fluoride.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups $R^3, R^8, R^9, R^{10}, X, Z^1, Z^2, Z^3, Z^4$, and m are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

Scheme 1

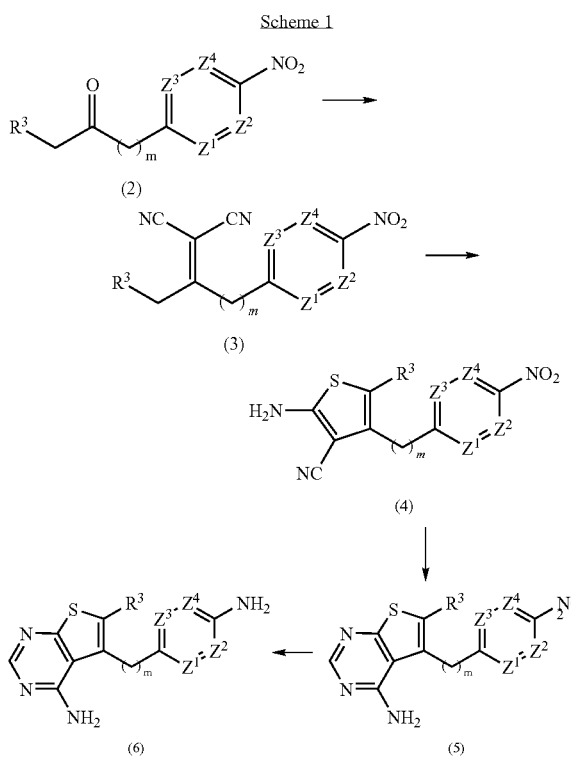

Scheme 1 shows the synthesis of compounds of formula (6). Compounds of formula (2) can be converted to compounds of formula (3) by treatment with malonitrile, ammonium acetate, and acetic acid. The reaction is typically conducted in benzene under azeotropic conditions at temperatures of about 80° C. to about 90° C. Reactions times are about 12 to about 96 hours.

Compounds of formula (4) can be formed from compounds of formula (3) by treatment with a base such as triethylamine, diethylamine, or diisopropylethylamine and sulfur. Examples of solvents used in these reactions include ethanol, methanol, and isopropanol. The reaction is typically conducted at about 25° C. to about 80° C. for about 1 to about 6 hours.

Conversion of compounds of formula (4) to compounds of formula (5) can be accomplished by treatment with formamide. The reaction is typically run neat at temperatures of about 150° C. to about 160° C. for about 8 to about 24 hours or in a microwave oven at temperatures of about 180° C. to about 250° C. for about 5 minutes to about 90 minutes.

Compounds of formula (4) can also be converted to compounds of formula (5) by treatment with ammonium sulfate in triethylorthoformate followed by treatment with ammonia. The reaction is typically conducted at temperatures between about 20° C. and about 180° C. for about 4 to about 12 hours.

Compounds of formula (5) can be converted to compounds of formula (6) by treatment with a reducing agent. Representative reducing agents include iron powder and ammonium chloride, iron powder and HCl, tin and HCl, and zinc and HCl. Examples of solvents used in these reactions include ethanol, THF, water, methanol, and mixtures thereof. The reaction is typically conducted at about 60° C. to about 85° C. and reaction times are about 1 to about 4 hours.

Scheme 2

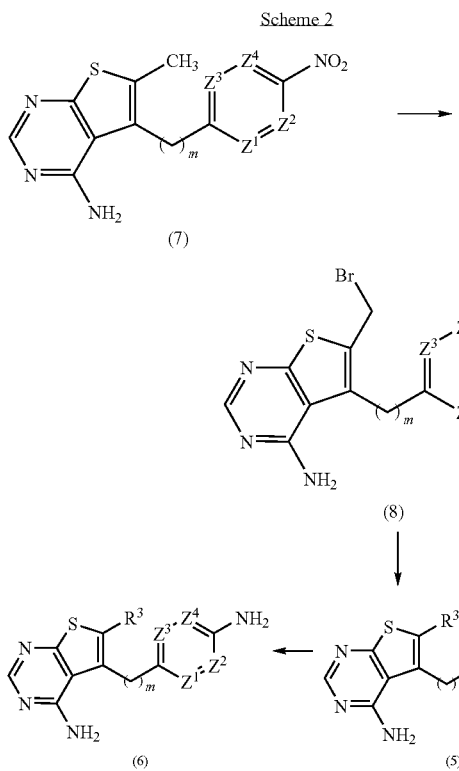

An alternative synthesis of compounds of formula (6) is shown in Scheme 2. Compounds of formula (7) (prepared according to the procedures described in Scheme 1), can be converted to compounds of formula (8) by radical bromination with NBS and AIBN. Representative solvents used in these reactions include benzene and THF. The reaction is typically conducted at about 70° C. to about 80° C. for about 2 to about 6 hours.

Compounds of formula (8) can be treated with a nucleophile such as a heterocyclyl group, an amine, or an alkoxy group to provide compounds of formula (5) where $R^3$ is alkoxyalkyl, $(NR^aR^b)$alkyl, or (heterocyclyl)alkyl. Representative solvents used in these reactions include DMF, NMP, and dioxane. The reaction is typically conducted at about 20° C. to about 35° C. for about 12 to about 24 hours.

Conversion of compounds of formula (5) to compounds of formula (6) can be accomplished by treatment with a reducing agent as described in Scheme 1.

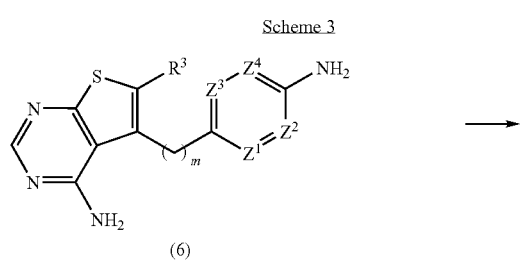

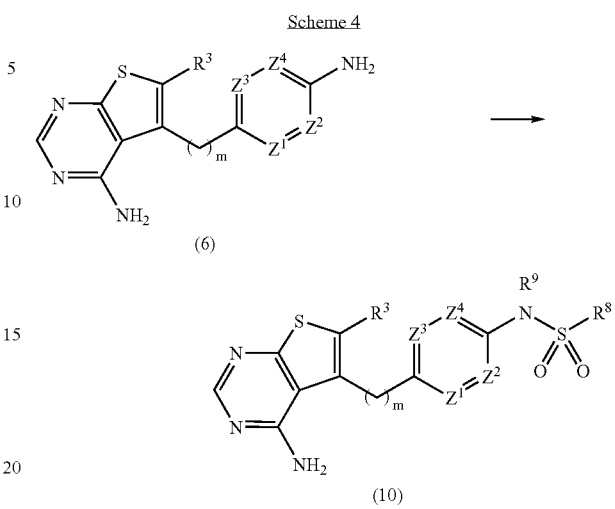

Scheme 4 shows the synthesis of compounds of formula (10) (compounds of formula (I) where $R^2$ is $—LR^8$ and L is $—NR^9SO_2—$). Compounds of formula (6) can be treated with an appropriately substituted sulfonyl chloride ($R^8SO_2Cl$) and a base such as pyridine or triethylamine. Representative solvents used in these reactions include dichloromethane, carbon tetrachloride, and chloroform. The reaction is typically conducted at about −10° C. to about 20° C. for about 12 to about 24 hours.

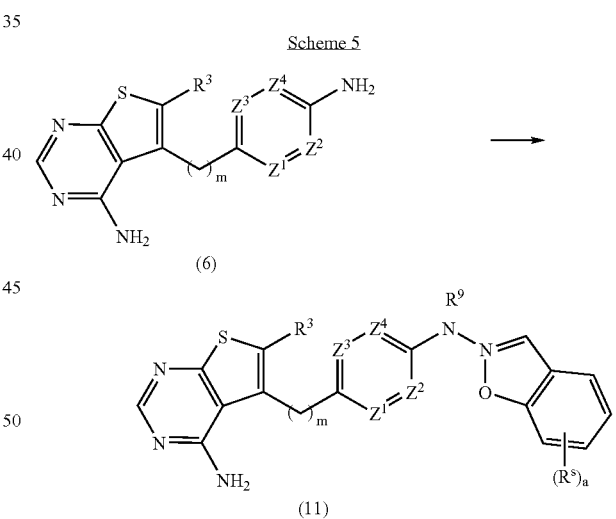

The synthesis of compounds of formula (9) (compounds of formula (I) where $R^2$ is $-LR^8$ and L is $—(CH_2)_nNR^9C(O)NR^{10}(CH_2)_p—$) is shown in Scheme 3. Compounds of formula (6) can be converted to compounds of formula (9) by treatment with an appropriately substituted isocyanate ($R^{10}N(R^8)C(O)$). Examples of solvents used in these reactions include dichloromethane, chloroform, and carbon tetrachloride, and DMF. The reaction is typically conducted at about −10° C. to about 25° C. for about 12 to about 24 hours.

Alternatively, compounds of formula (6) can be reacted with an acylating agent such as p-nitrophenyl chloroformate then treated with an appropriately substituted amine ($HNR^{10}R^8$) in the presence of a base such as triethylamine, diisopropylethylamine, or pyridine to provide compounds of formula (9). The reaction is typically conducted in a solvent such as THF, methyl tert-butyl ether, or diethyl ether. The reaction is commonly run at temperatures between −5° C. and 35° C. for between about 1 hour and 24 hours.

As shown in Scheme 5, compounds of formula (6) can be converted to compounds of formula (11) ($R^s$ is selected from the group of substituents listed in the definition of heteroaryl; a is 0, 1, 2, 3, or 4; these are compounds of formula (I) where $R^2$ is $-LR^8$; L is $—NR^9—$; and $R^8$ is heteroaryl) by treatment with 1,1-thiocarbonyldiimidazole in the presence of pyridine and an optionally substituted 2-aminophenol; followed by treatment with a coupling agent such as EDC or DCC. The reaction is typically conducted at about −5° C. to about 65° C. for about 32 to about 48 hours.

Scheme 6

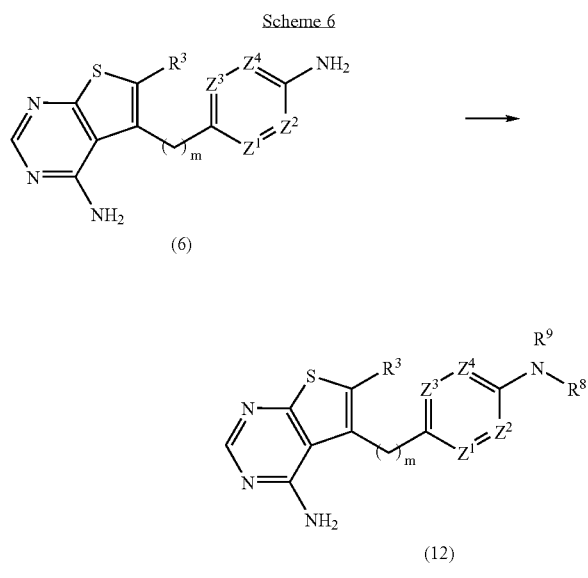

As shown in Scheme 6, compounds of formula (6) can be converted to compounds of formula (12) (compounds of formula (I) where $R^2$ is -$LR^8$; L is —$NR^c$—; and $R^8$ is heteroaryl) by treatment with a heteroaryl group substituted by a leaving group such as a chloride or a fluoride. Typically the reaction is run neat at temperatures of about 150° C. to about 210° C. Reaction times are about 10 minutes to about 24 hours.

Scheme 7

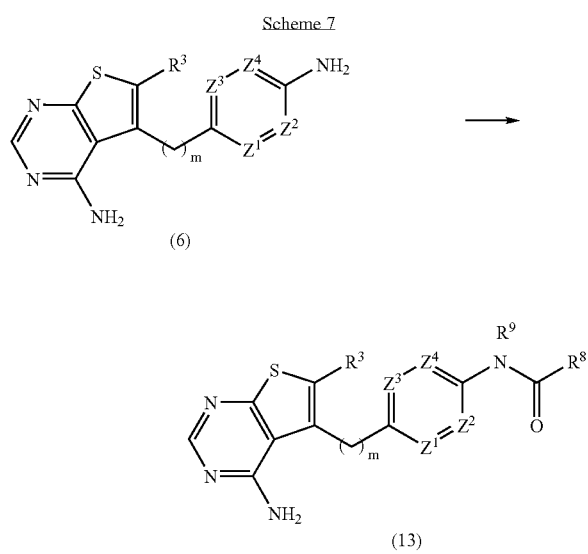

Scheme 7 shows the synthesis of compounds of formula (13) (compounds of formula (I) where $R^2$ is -$LR^8$ and L is —$NR^cC(O)$—). Compounds of formula (6) can be treated with an appropriately substituted acid chloride ($R^8C(O)Cl$) and a base such as pyridine, triethylamine, or diisopropylethylamine. Representative solvents used in these reactions include dichloromethane, chloroform, and diethyl ether. The reaction is typically conducted at about –5° C. to about 30° C. for about 2 to about 24 hours.

Scheme 8

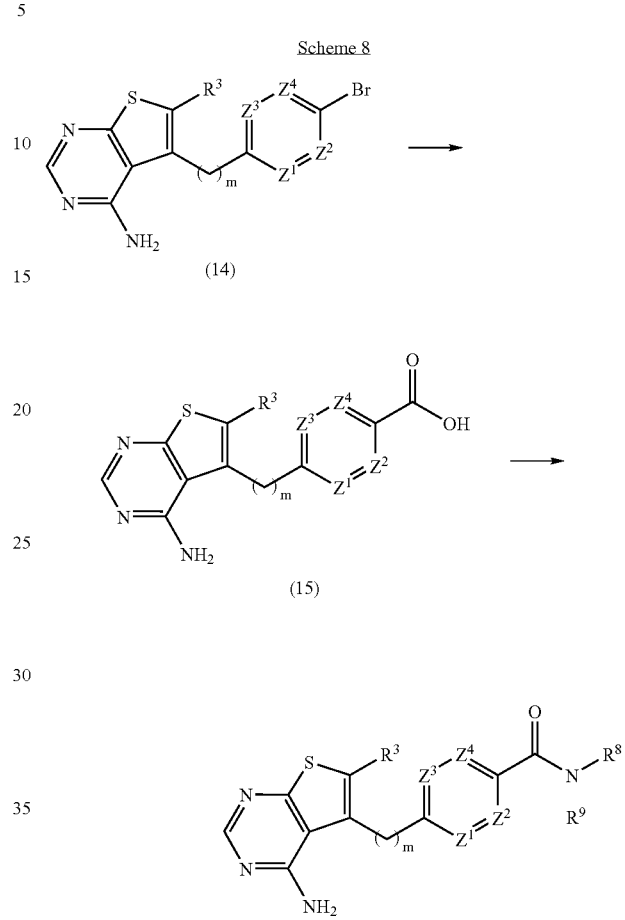

Compounds of formula (16) (compounds of formula (I) where $R^2$ is -$LR^8$ and L is —$C(O)NR^9$—) can be prepared as described in Scheme 8. Compounds of formula (14) (which can be prepared by substituting the corresponding 4-bromophenyl ketone for the compound of formula (2) in the synthesis of compounds of formula (5) described in Scheme 1) can be treated with an alkyllithium such as n-butyllithium or t-butyllithium and dry ice to provide compounds of formula (15). Representative solvents used in these reactions include hexanes, THF and heptane. The reaction is typically conducted at about –80° C. to about 0° C. for about 30 minutes to about 2 hours.

Conversion of compounds of formula (15) to compounds of formula (16) can be accomplished by treatment with an appropriately substituted amine ($HNR^9 R^8$) in the presence of agents such as HOBT and EDC or DCC or 1,1'-carbonyldiimidazole in the presence of a base such as N-methylmorpholine. Examples of solvents used in these reactions include DMF and NMP. The reaction is typically conducted at about 20° C. to about 35° C. for about 12 to about 24 hours.

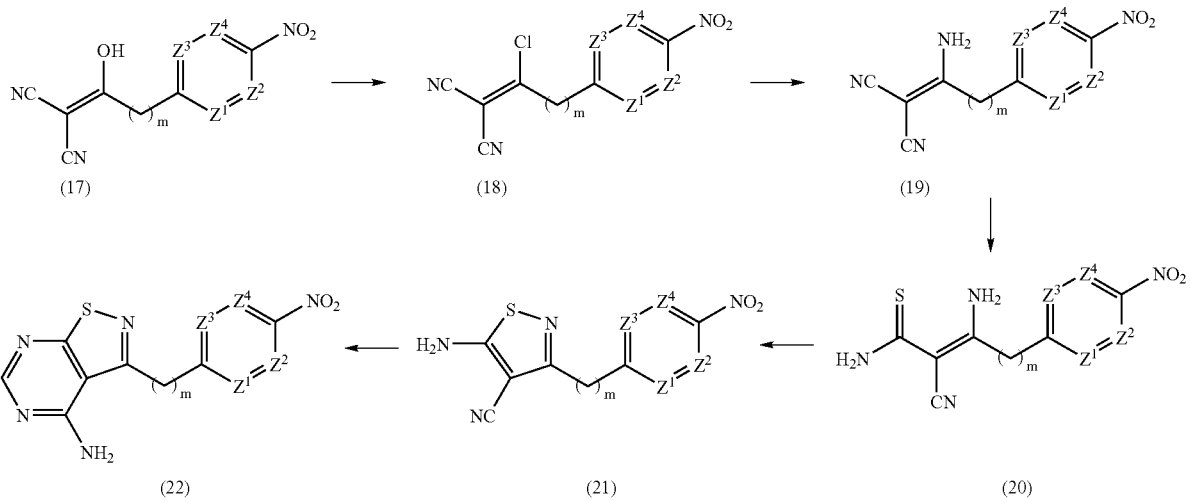

Scheme 9 shows the synthesis of compounds of formula (22) (compounds of formula (I) where X is N and $R^2$ is $NO_2$). Compounds of formula (17) can be treated with $PCl_5$ to provide compounds of formula (18). Representative solvents include dichloromethane, chloroform, and carbon tetrachloride. The reaction is typically run at about 25° C. to about 40° C. for about 10 to about 30 hours.

Conversion of compounds of formula (18) to compounds of formula (19) can be accomplished by treatment with ammonium hydroxide to provide compounds of formula (19). Examples of solvents include ethanol and methanol. The reaction is typically conducted at about 20° C. to about 30° C. for about 2 to about 6 hours.

Compounds of formula (19) can be converted to compounds of formula (20) by treatment with diethyl dithiophosphate. Representative solvents include ethanol and methanol. The reaction is typically conducted at about 70° C. to about 80° C. for about 12 to about 36 hours.

Conversion of compounds of formula (20) to compounds of formula (21) can be accomplished by treatment with hydrogen peroxide. Representative solvents used in these reactions include ethanol and methanol. The reaction is typically conducted at about 20° C. to about 30° C. for about 12 to about 24 hours.

Compounds of formula (21) can be converted to compounds of formula (22) following the procedures described in Scheme 1. Upon reducing the nitro group to an amine following the procedures in Scheme 1, these compounds can be further modified to provide compounds similar in structure to those shown in Schemes 3 through 8.

Scheme 10

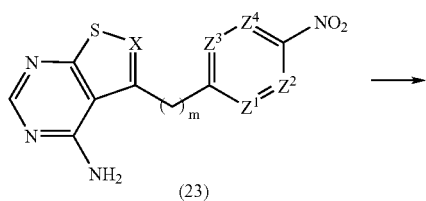

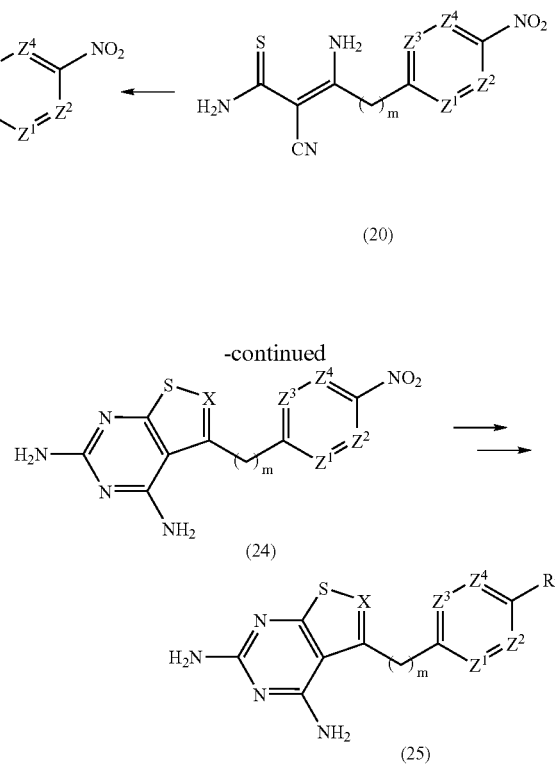

Scheme 10 shows the synthesis of compounds of formula (25) (compounds of formula (I) where $R^1$ is $NH_2$). Compounds of formula (23) (prepared according to the methods described in Schemes 1, 2, or 9) can be converted to compounds of formula (24) by treatment with chloroformamidine in diglyme. The reaction is typically conducted at temperatures of between about 120 and 140° C. for about 12 to about 18 hours.

Compounds of formula (24) can be converted to compounds of formula (25) using the procedures described in the previous schemes.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry

EXAMPLE 1

N-[4-(4-amino-6-methylthieno[2,3-d]pyrimidin-5-yl)phenyl]-N'-phenylurea

EXAMPLE 1A 1-(4-nitrophenyl)propan-1-one

A solution of 0.5M $ZnCl_2$ in THF (60 mL, 30 mmol) in THF (20 mL) was treated with 2M ethyl magnesium chloride in THF (15 mL, 30 mmol) dropwise by syringe, cooled with an ice bath for about 10 minutes, stirred at room temperature for about 20 minutes, cooled to 0° C., and treated sequentially with $Pd(PPh_3)_4$ (1.73 g, 1.5 mmol) and a solution of 4-nitrobenzoyl chloride (6.12 g, 33 mmol) in THF (20 mL). The mixture was stirred at 0° C. for 40 minutes, diluted with water, adjusted to pH 1 with 2N HCl and extracted three times with ethyl acetate. The combined extracts were washed sequentially with saturated $Na_2CO_3$, water, and brine, dried ($MgSO_4$), filtered, and concentrated. The concentrate was purified by flash column chromatography on silica gel with 6:1 hexanes/ethyl acetate to provide 2.17 g (40%) of the desired product as a yellow solid. $R_f$=0.6 (3:1 hexanes/ethyl acetate).

EXAMPLE 1B

2-[1-(4-nitrophenyl)propylidene]malononitrile

A solution of Example 1A (3.4 g, 19 mmol), malononitrile (1.25 g, 19 mmol) ammonium acetate (1.46 g) and acetic acid (2 mL) in benzene (50 mL) was heated to reflux in a flask fitted with a Dean-Stark trap for 14 hours. Additional ammonium acetate (1.46 g) and acetic acid (2 mL) were added and the reaction was stirred at reflux for 4 more hours. The mixture was cooled to room temperature and partitioned between water and ethyl acetate. The aqueous layer was extracted twice with ethyl acetate and the combined extracts were washed with brine, dried ($MgSO_4$), filtered, and concentrated. The concentrate was purified by flash column chromatography on silica gel with 3:1 hexanes/ethyl acetate to provide 4.01 g (93%) of the desired product as a yellow solid. $R_f$=0.45 (3:1 hexanes/ethyl acetate).

EXAMPLE 1C 2-amino-5-methyl-4-(4-nitrophenyl)thiophene-3-carbonitrile

Diethylamine (1.57 mL) was added dropwise to a suspension of Example 1B (4.0 g, 17.6 mmol) and sulfur (0.563 g, 17.6 mmol) in ethanol (60 mL). The mixture was heated to 70° C. for 2 hours, cooled to room temperature, and concentrated. The concentrate was purified by flash column chromatography on silica gel with 3:2 hexanes/ethyl acetate to provide 4.05 g (89%) of the desired product. MS (CI) m/e 277 $(M+NH_4)^+$.

EXAMPLE 1D 6-methyl-5-(4-nitrophenyl)thieno[2,3-d]pyrimidin-4-amine

A suspension of Example 1C (4.03 g, 15.5 mmol) in formamide (60 mL) was stirred at 155° C. for 17 hours, cooled to room temperature, diluted with water, and filtered. The filter cake was dried to provide 4.126 g (93%) of the desired product. MS (CI) m/e 287 $(M+H)^+$; $^1H$ NMR (300 MHz, DMSO-$d_6$) δ 8.36 (d, J=9.0 Hz, 2H); 8.30 (s, 1H); 7.68 (d, J=9.0 Hz, 2H); 2.32 (s, 3H); Anal. Calcd. for $C_{13}H_{10}N_4O_2S$: C, 54.53; H, 3.52; N, 19.57. Found: C, 54.75; H, 3.39; N, 19.17.

EXAMPLE 1E 5-(4-aminophenyl)-6-methylthieno[2,3-d]pyrimidin-4-amine

A suspension of Example 1D (1.01 g, 3.53 mmol) in ethanol (60 mL), THF (20 mL), and water (10 mL) was treated with $NH_4Cl$ (0.19 g, 3.53 mmol) and iron powder (1.18 g, 21.2 mmol), and stirred at 70-80° C. for 1 hour. The mixture was diluted with ethanol (40 mL) and filtered through a pad of diatomaceous earth (Celite®) while still hot. The pad was washed with ethanol and the filtrate was concentrated. The concentrate was diluted with water and extracted three times with ethyl acetate. The combined extracts were washed with brine, dried ($MgSO_4$), filtered, and concentrated to provide 1 g of the desired product. MS (CI) m/e 257 $(M+H)^+$; $^1H$ NMR (300 MHz, DMSO-$d_6$) δ 8.23 (s, 1H); 7.01 (d, J=8.4 Hz, 2H); 6.70 (d, J=8.4 Hz, 2H); 5.39 (s, 2H); 2.27 (s, 3H); Anal. Calcd. for $C_{13}H_{12}N_4S.0.2C_4H_8O_2.0.2H_2O$: C, 59.72; H, 5.08; N, 20.19. Found: 59.64; H, 4.99; N, 20.22.

EXAMPLE 1F

N-[4-(4-amino-6-methylthieno[2,3-d]pyrimidin-5-yl)phenyl]-N'-phenylurea

A 0° C. solution of Example 1E (80 mg, 0.3 mmol) in dichloromethane (4 mL) was treated with phenyl isocyanate (0.037 mL, 0.34 mmol), stirred overnight, and filtered. The filter cake was dried to provide 0.103 g (87%) of the desired product. MS (CI) m/e 376 $(M+H)^+$; $^1H$ NMR (300 MHz, DMSO-$d_6$) δ 8.89 (s, 1H); 8.75 (s, 1H); 8.26 (s, 1H); 7.63 (d, J=8.7 Hz, 2H); 7.47 (d, J=8.7 Hz, 2H); 7.33-7.26 (m, 4H); 6.99 (t, J=7.5 Hz, 1H); 2.30 (s, 3H); Anal. Calcd. for $C_{20}H_{17}N_5OS.0.1CH_2Cl_2$: C, 62.88; H, 4.52; N, 18.24. Found: C, 62.85; H, 4.64; N, 18.15.

EXAMPLE 2

N-[4-(4-amino-6-methylthieno[2,3-d]pyrimidin-5-yl)phenyl]benzenesulfonamide

A 0° C. solution of Example 1E (0.1 g, 0.39 mmol) in dichloromethane (4 mL) was treated with pyridine (0.038 mL, 0.47 mmol) and benzenesulfonyl chloride (0.05 mL, 0.4 mmol), stirred at 0° C. for 1 hour, then stirred at room temperature overnight. The reaction mixture was diluted with water and extracted twice with dichloromethane. The combined extracts were washed with brine, dried ($MgSO_4$), filtered, and concentrated. The concentrate was triturated from dichloromethane/hexanes to provide 91 mg (59%) of the desired product. MS(ESI(+)) m/e 397 $(M+H)^+$; $^1H$ NMR (300 MHz, DMSO-$d_6$) δ 10.49 (s, 1H); 8.25 (s, 1H); 7.77 (m, 2H);

7.65-7.55 (m, 3H); 7.24 (m, 4H); 1.99 (s, 3H); Anal. Calcd. for $C_{19}H_{16}N_4O_2S_2 \cdot 0.3C_2H4O_2$: C, 57.37; H, 4.39; N, 13.25. Found: C, 57.22; H, 4.48; N, 13.32.

EXAMPLE 3

5-[4-(1,3-benzoxazol-2-ylamino)phenyl]-6-methylthieno[2,3-d]pyrimidin-4-amine

A solution of Example 1E (100 mg, 0.39 mmol) in pyridine (3 mL) was added dropwise over 5 minutes to a 0° C. solution of 1,1-thiocarbonyldiimidazole (77 mg, 0.39 mmol) in pyridine (3 mL). The reaction was stirred at 0° C. for 1.5 hours, then treated with 2-aminophenol (43 mg, 0.39 mmol), stirred overnight at room temperature, treated with 1-ethyl-3-(3-dimethylaminopropyl)carbodiimide hydrochloride (90 mg, 0.47 mmol), and heated to 50° C. for 20 hours. The mixture was concentrated and the residue was partitioned between ethyl acetate and water. The aqueous phase was extracted twice with ethyl acetate and the combined extracts were washed with brine, dried (MgSO$_4$), filtered, and concentrated. The concentrate was purified by flash column chromatography on silica gel with ethyl acetate to provide 28 mg (20%) of the desired product. MS (CI) m/e 374 (M+H)$^+$; $^1$H NMR (300 MHz, DMSO-d$_6$) δ 10.89 (s, 1H); 8.27 (s, 1H); 7.94 (d, J=8.4 Hz, 2H); 7.51 (m, 2H); 7.42 (d, J=8.4 Hz, 2H); 7.25 (td, J=7.5 Hz, 1.5 Hz, 1H); 7.16 (td, J=7.5 Hz, 1.5 Hz, 1H); 3.10 (s, 3H); Anal. Calcd. for $C_{20}H_{15}N_5OS \cdot 0.2C_4H_8O_2 \cdot 0.2H_2O$: C, 63.30; H, 4.34; N, 17.75. Found: C, 63.52; H, 4.30; N, 17.33.

EXAMPLE 4

N-[4-(4-amino-6-methylthieno[2,3-d]pyrimidin-5-yl)phenyl]benzamide

A 0° C. solution of Example 1E (80 mg, 0.31 mmol) in dichloromethane (4 mL) was treated with pyridine (0.03 mL, 0.38 mmol) and benzoyl chloride (0.038 mL, 0.32 mmol), stirred at 0° C. for 1 hour, then at room temperature overnight. The reaction mixture was diluted with water and extracted twice with dichloromethane. The combined extracts were washed with brine, dried (MgSO$_4$), filtered, and concentrated. The concentrate was purified by flash column chromatography on silica gel with ethyl acetate to provide 39 mg (35%) of the desired product. $^1$H NMR (300 MHz, DMSO-d$_6$) δ 10.46 (s, 1H); 8.28 (s, 1H); 7.98 (d, J=8.1 Hz, 4H); 7.63-7.54 (m, 3H); 7.40 (d, J=8.1 Hz, 2H); 2.31 (s, 3H); HRMS(ESI) Calcd. for $C_{20}H_{17}N_4OS$: 361.1118. Found: 36.1122.

EXAMPLE 5

N-[4-(4-amino-6-isopropylthieno[2,3-d]pyrimidin-5-yl)phenyl]-N'-(4-methylphenyl)urea

EXAMPLE 5A 6-isopropyl-5-(4-nitrophenyl)thieno[2,3-d]pyrimidin-4-amine

The desired product was prepared by substituting isobutyl magnesium bromide for ethyl magnesium bromide in Examples 1A-1D. m.p. >260° C.; MS(ESI(+)) m/e 315 (M+H)$^+$; $^1$H NMR (300 MHz, DMSO-d$_6$) δ 1.20-1.22 (d, J=6.9 Hz, 6H); 2.94-3.03 (m, 1H); 7.68-7.70 (d, J=8.7 Hz, 2H); 8.29 (s, 1H); 8.35-8.38 (d, J=8.7 Hz, 2H); Anal. Calcd. for $C_{15}H_{14}N_4O_2S$: C, 57.31; H, 4.49; N, 17.82. Found: C, 57.42; H, 4.51; N, 17.89.

EXAMPLE 5B 5-(4-aminophenyl)-6-isopropylthieno[2,3-d]pyrimidin-4-amine

The desired product was prepared by substituting Example 5A for Example 1D in Example 1E. m.p. 187-189° C.; MS(ESI(+)) m/e 285 (M+H)$^+$; $^1$H NMR (300 MHz, DMSO-d$_6$) δ 1.18-1.21 (d, J=6.9 Hz, 6H); 3.02-3.11 (m, 1H); 6.68-6.71 (d, J=8.4 Hz, 2H); 6.99-7.02 (d, J=8.4 Hz, 2H); 8.22 (s, 1H); Anal. Calcd. for $C_{15}H_{16}N_4S \cdot 0.2C_4H_8O_2$: C, 62.84; H, 5.87; N, 18.55. Found: C, 62.90; H, 5.47; N, 18.35.

EXAMPLE 5C

N-[4-(4-amino-6-isopropylthieno[2,3-d]pyrimidin-5-yl)phenyl]-N'-(4-methylphenyl)urea The desired product was prepared by substituting Example 5B and 4-methylphenyl isocyanate for Example 1E and phenyl isocyanate, respectively, in Example 1F. MS(ESI(+)) m/e 418 (M+H)$^+$; $^1$H NMR (300 MHz, DMSO-d$_6$) δ 1.20-1.22 (d, J=6.9 Hz, 6H); 2.25 (s, 3H); 3.00-3.09 (m, 1H); 7.09-7.11 (d, J=8.1 Hz, 2H); 7.29-7.32 (d, J=8.7 Hz, 2H); 7.34-7.37 (d, J=8.7 Hz, 2H); 7.60-7.63 (d, J=8.7 Hz, 2H); 8.26 (s, 1H); 8.64 (s, 1H); 8.85 (s, 1H); Anal. Calcd. for $C_{23}H_{23}N_5OS \cdot 0.3H_2O$: C, 65.32; H, 5.62; N, 16.56. Found: C, 65.24; H, 5.68; N, 16.40.

EXAMPLE 6

N-[4-(4-amino-6-isopropylthieno[2,3-d]pyrimidin-5-yl)phenyl]-N'-(3-methylphenyl)urea The desired product was prepared by substituting Example 5B and 3-methylphenyl isocyanate for Example 1E and phenyl isocyanate, respectively, in Example 1F. m.p. 169-171° C.; MS(ESI(+)) m/e 418 (M+H)$^+$; $^1$H NMR (300 MHz, DMSO-d$_6$) δ 1.20-1.23 (d, J=6.9 Hz, 6H); 2.29 (s, 3H); 3.00-3.09 (m, 1H); 6.79-6.82 (d, 1H, J=7.8 Hz); 7.14-7.19 (t, J=7.5 Hz, 1H); 7.24-7.27 (d, 1H, 8.1 Hz); 7.30-7.33 (m, 3H); 7.61-7.64 (d, J=9 Hz, 2H); 8.26 (s, 1H); 8.67 (s, 1H); 8.88 (s, 1H); Anal. Calcd. for $C_{23}H_{23}N_5OS$: C, 66.16; H, 5.55; N, 16.77. Found: C, 65.95; H, 5.60; N, 16.53.

EXAMPLE 7

N-[4-(4-amino-6-isopropylthieno[2,3-d]pyrimidin-5-yl)phenyl]benzenesulfonamide

The desired product was prepared by substituting Example 5B for Example 1E in Example 2. MS(ESI(+)) m/e 425 (M+H)$^+$; $^1$H NMR (300 MHz, DMSO-d$_6$) δ 1.14-1.16 (d, J=6.6 Hz, 6H); 2.84-2.93 (m, 1H); 7.19-7.22 (d, J=8.4 Hz, 2H); 7.27-7.29 (d, J=8.4 Hz, 2H); 7.55-7.64 (m, 3H); 7.74-7.77 (d, 2H, J=6.6 Hz); 8.25 (s, 1H); 10.48 (s, 1H); Anal. Calcd. for $C_{21}H_{20}N_4O_2S_2$: C, 59.41; H, 4.75; N, 13.20. Found: C, 59.22; H, 4.48; N, 13.10.

EXAMPLE 8

N-[4-(4-amino-6-isopropylthieno[2,3-d]pyrimidin-5-yl)phenyl]benzamide

The desired product was prepared by substituting Example 5B for Example 1E in Example 4. m.p. >250° C.; MS(ESI) m/e 389 (M+H)$^+$, 387 (M−H)$^-$; $^1$H NMR (300 MHz, DMSO-d$_6$) δ 1.22-1.25 (d, J=6.6 Hz, 6H); 3.03-3.12 (m, 1H); 7.41-7.43 (d, J=8.7 Hz, 2H); 7.53-7.65 (m, 3H); 7.93-7.02 (m, 4H); 8.46 (s, 1H); 10.51 (s, 1H); HRMS (FAB) Calcd. for C$_{22}$H$_{20}$N$_4$OS: 389.1436. Found: 389.1451.

EXAMPLE 9

N-[4-(4-amino-6-benzylthieno[2,3-d]pyrimidin-5-yl)phenyl]-N'-(4-methylphenyl)urea

EXAMPLE 9A 6-benzyl-5-(4-nitrophenyl)thieno[2,3-d]pyrimidin-4-amine

The desired product was prepared by substituting phenethylmagnesium bromide for ethyl magnesium bromide in Examples 1A-1D. m.p. 231-233° C.; MS(ESI) m/e 363 (M+H)$^+$, 361 (M−H)$^-$; $^1$H NMR (300 MHz, DMSO-d$_6$) δ 4.00 (s, 2H); 7.11-7.14 (d, 2H, J=6.9 Hz); 7.19-7.31 (m, 3H); 7.70-7.73 (d, J=9 Hz, 2H); 8.29 (s, 1H); 8.35-8.38 (d, J=9 Hz, 2H); Anal. Calcd. for C$_{19}$H$_{14}$N$_4$O$_2$S: C, 62.97; H, 3.89; N, 15.46. Found: C, 62.78; H, 3.99; N, 15.47.

EXAMPLE 9B 5-(4-aminophenyl)-6-benzylthieno[2,3-d]pyrimidin-4-amine

The desired product was prepared by substituting Example 9A for Example 1D in Example 1E. m.p. 208-210° C.; MS(ESI) m/e 333 (M+H)$^+$, 331 (M−H)$^-$; $^1$H NMR (300 MHz, DMSO-d$_6$) δ 3.98 (s, 2H); 5.43 (s, 2H); 6.70-6.73 (d, J=8.4 Hz, 2H); 7.05-7.08 (d, J=8.4 Hz, 2H); 7.13-7.15 (d, 2H, 6.9 Hz); 7.18-7.32 (m, 3H); 8.23 (s, 1H); Anal. Calcd. for C$_{19}$H$_{16}$N$_4$S.0.1CH$_2$Cl$_2$: C, 67.29; H, 4.79; N, 16.43. Found: C, 67.47; H, 4.78; N, 16.52.

EXAMPLE 9C

N-[4-(4-amino-6-benzylthieno[2,3-d]pyrimidin-5-yl)phenyl]-N'-(4-methylphenyl)urea The desired product was prepared by substituting Example 9B and 4-methylphenyl isocyanate for Example 1E and phenyl isocyanate, respectively, in Example 1F. m.p. 169-173° C. MS(ESI) m/e 466 (M+H)$^+$, 464 (M−N)$^-$, 500 (M+Cl)$^-$; $^1$H NMR (300 MHz, DMSO-d$_6$) δ 2.25 (s, 3H); 3.99 (s, 2H); 7.08-7.37 (11H); 7.63-7.65 (d, 2H, J=8.7 Hz); 8.26 (s, 1H); 8.64 (s, 1H); 8.86 (s, 1H); Anal. Calcd. for C$_{27}$H$_{23}$N$_5$OS: C, 69.66; H, 4.98; N, 15.04. Found: C, 69.49; H, 4.94; N, 14.79.

EXAMPLE 10

N-[4-(4-amino-6-benzylthieno[2,3-d]pyrimidin-5-yl)phenyl]-N'-(3-methylphenyl)urea The desired product was prepared by substituting Example 9B and 3-methylphenyl isocyanate for Example 1E and phenyl isocyanate, respectively, in Example 1F. MS(ESI(+)) m/e 466 (M+H)$^+$; $^1$H NMR (300 MHz, DMSO-d$_6$) δ 2.29 (s, 3H); 3.99 (s, 2H); 6.79-6.82 (d, J=7.5 Hz, 1H); 7.14-7.32 (m, 8H); 7.35-7.38 (d, J=8.7 Hz, 2H); 7.63-7.66 (d, J=8.4 Hz, 2H); 8.26 (s, 1H); 8.67(s, 1H); 8.89 (s, 1H); Anal. Calcd. for C$_{27}$H$_{23}$N$_5$OS.0.75H$_2$O: C, 67.69; H, 5.15; N, 14.62. Found: C, 67.75; H, 5.01; N, 14.60.

EXAMPLE 11

N-[4-(4-amino-6-benzylthieno[2,3-d]pyrimidin-5-yl)phenyl]-N'-(2-methylphenyl)urea The desired product was prepared by substituting Example 9B and 2-methylphenyl isocyanate for Example 1E and phenyl isocyanate, respectively, in Example 1F. m.p. 245-248° C.; MS(ESI) m/e 466 (M+H)$^+$, 464 (M−H)$^-$; $^1$H NMR (300 MHz, DMSO-d$_6$) δ 2.26 (s, 3H); 3.99 (s, 2H); 6.94-6.99 (dt, J=1.2, 7.5 Hz, 1H); 7.14-7.32 (m, 7H); 7.35-7.38 (d, J=8.4 Hz, 2H); 7.65-7.68 (d, J=8.4 Hz, 2H); 7.80-7.83 (d, J=8.1 Hz, 1H); 8.02 (s, 1H); 8.26 (s, 1H); 9.25 (s, 1H); Anal. Calcd. for C$_{27}$H$_{23}$N$_5$OS.0.1CH$_2$Cl$_2$: C, 68.66; H, 4.93; N, 14.77. Found: C, 68.53; H, 4.74; N, 14.48.

EXAMPLE 12

N-[4-(4-amino-6-isopropylthieno[2,3-d]pyrimidin-5-yl)phenyl]-N'-(2-methylphenyl)urea The desired product was prepared by substituting Example 5B and 2-methylphenyl isocyanate for Example 1E and phenyl isocyanate, respectively, in Example 1F. m.p. 233-234° C.; MS(ESI(+)) m/e 418 (M+H)$^+$; $^1$H NMR (300 MHz, DMSO-d$_6$) δ 1.21-1.23 (d, J=6.6 Hz, 6H); 2.26 (s, 3H); 3.01-3.10 (m, 1H); 6.94-6.70 (dt, J=1.2, 7.5 Hz, 1H); 7.13-7.21 (m, 2H); 7.30-7.33 (d, J=8.7 Hz, 2H); 7.63-7.66 (d, J=8.4 Hz, 2H); 7.81-7.84 (d, J=8.1 Hz, 1H); 8.01 (s, 1H); 8.26 (s, 1H); 9.24 (s, 1H); Anal. Calcd. for C$_{23}$H$_{23}$N$_5$OS: C, 66.16; H, 5.55; N, 16.77. Found: C, 66.20; H, 5.49; N, 16.82.

EXAMPLE 13

N-[4-(4-amino-6-benzylthieno[2,3-d]pyrimidin-5-yl)phenyl]benzenesulfonamide

The desired product was prepared by substituting Example 9B for Example 1E in Example 2. m.p. 100-105° C.; MS(ESI) m/e 437 (M+H)$^+$, 435 (M−H)$^-$; $^1$H NMR (300 MHz, DMSO-d$_6$) δ 3.87 (s, 2H); 7.01-7.04 (d, 2H, J=8.1 Hz); 7.16-7.33 (m, 7H); 7.53-7.65 (m, 3H); 7.75-7.78 (d, 2H, J=8.1 Hz); 8.25 (s, 1H); 10.51 (s, 1H); Anal. Calcd. for C$_{25}$H$_{20}$N$_4$O$_2$S$_2$: C, 63.54; H, 4.27; N, 11.86. Found: C, 63.27; H, 4.14; N, 11.82.

EXAMPLE 14

N-{4-[4-amino-6-(pyridin-4-ylmethyl)thieno[2,3-d]pyrimidin-5-yl]phenyl}-N'-(3-methylphenyl)urea

EXAMPLE 14A (2E)-1-(4-nitrophenyl)-3-pyridin-4-ylprop-2-en-1-one

A suspension of 4'-nitroacetophenone (5 g, 30.3 mmol) and 4-pyridinecarboxaldehyde (2.89 mL, 30.3 mmol) in water (45 mL) at room temperature was treated with 6% NaOH in H$_2$O/ethanol (2:1)(0.606 mL), stirred overnight, and filtered.

The filter cake was washed with water and small amount of ethanol then triturated with dichloromethane to provide 1.95 g (25%) of the desired product. MS(ESI(+)) m/e 255 (M+H)⁺.

EXAMPLE 14B 1-(4-nitrophenyl)-3-pyridin-4-ylpropan-1-one

Trinbutyltin hydride (0.36 mL, 1.34 mmol) was added slowly by syringe pump to a room temperature mixture of Example 14A (0.2 g, 0.78 mmol) and Pd(PPh$_3$)$_4$ (27 mg, 0.023 mmol), stirred overnight, diluted with water, and extracted three times with ethyl acetate. The combined extracts were washed with brine, dried (Na$_2$SO$_4$), filtered, and concentrated. The concentrate was putrified by flash column chromatography on silica gel with 80% ethyl acetate/hexanes to provide 227 mg (100%) of the desired product. MS(ESI(−)) m/e 255 (M−H)⁻.

EXAMPLE 14C

N-{4-[4-amino-6-(pyridin-4-ylmethyl)thieno[2,3-d]pyrimidin-5-yl]phenyl}-N'-(3-methylphenyl)urea The desired product was prepared by substituting Example 14B and 3-methylphenyl isocyanate for Example 1A and phenyl isocyanate, respectively, in Examples 1B-1F. MS(ESI) m/e 467 (M+H)⁺, 465 (M−H)⁻; ¹H NMR (300 MHz, DMSO-d$_6$) δ 2.28 (s, 3H); 3.32 (s, 2H); 6.79-6.82 (d, J=7.5 Hz, 1H); 7.13-7.30 (m, 5H); 7.32-7.35 (d, J=8.4 Hz, 2H); 7.61-7.64 (d, J=8.4 Hz, 2H); 8.28 (s, 1H); 8.45-8.47 (dd, J=4.2, 1.5 Hz, 2H); 8.67 (s, 1H); 8.88 (s, 1H); HRMS (FAB) Calcd. for C$_{26}$H$_{23}$N$_6$OS: 467.1654. Found: 467.1649.

EXAMPLE 15

N-[4-(4-amino-6-methylthieno[2,3-d]pyrimidin-5-yl)phenyl]-N'-(4-methylphenyl)urea The desired product was prepared by substituting 4-methylphenyl isocyanate for phenyl isocyanate in Example 1F. MS(ESI(+)) m/e 390 (M+H)⁺; ¹H NMR (300 MHz, DMSO-d$_6$) δ 8.84 (s, 1H); 8.63 (s, 1H); 8.26 (s, 1H); 7.62 (d, J=8.4 Hz, 2H); 7.35 (d, J=8.4 Hz, 2H); 7.30 (d, J=8.4 Hz, 2H); 7.10 (d, J=8.4 Hz, 2H); 2.29 (s, 3H); 2.25 (s, 3H); Anal. Calcd. for C$_{21}$H$_{19}$N$_5$OS.0.5H$_2$O.0.1C$_8$H$_{18}$: C, 63.88; H, 5.36; N, 17.09. Found: C, 63.98; H, 5.41; N, 16.90.

EXAMPLE 16

N-[4-(4-amino-6-methylthieno[2,3-d]pyrimidin-5-yl)phenyl]-N'-(3-methylphenyl)urea The desired product was prepared by substituting 3-methylphenyl isocyanate for phenyl isocyanate in Example 1F. MS(ESI(−)) m/e 388 (M−H)⁻; ¹H NMR (300 MHz, DMSO-d$_6$) δ 8.87 (s, 1H); 8.67 (s, 1H); 8.26 (s, 1H); 7.63 (d, J=8.1 Hz, 2H); 7.32-7.23 (m, 4H); 7.17 (t, J=7.8 Hz, 1H); 6.81 (d, J=7.8 Hz, 1H); 2.30 (s, 3H); 2.29 (s, 3H); Anal. Calcd. for C$_{21}$H$_{19}$N$_5$OS.0.5H$_2$O: C, 63.30; H, 5.06; N, 17.58. Found: C, 63.62; H, 5.20; N, 17.38.

EXAMPLE 17

N-[4-(4-amino-6-methylthieno[2,3-d]pyrimidin-5-yl)phenyl]-N'-(2-methylphenyl)urea The desired product was prepared by substituting 2-methylphenyl isocyanate for phenyl isocyanate in Example 1F. MS(ESI(+)) m/e 390 (M+H)⁺; ¹H NMR (300 MHz, DMSO-d$_6$) δ 9.24 (s, 1H); 8.27 (s, 1H); 8.01 (s, 1H); 7.82 (d, J=7.5 Hz, 1H); 7.64 (d, J=8.1 Hz, 2H); 7.31 (d, J=8.1 Hz, 2H); 7.21-7.13 (m, 2H); 6.97 (t, J=7.5 Hz, 1H); 2.30 (s, 3H); 2.27 (s, 3H); Anal. Calcd. for C$_{21}$H$_{19}$N$_5$OS.0.7H$_2$O: C, 62.73; H, 5.11; N, 17.42. Found: C, 62.91; H, 5.15; N, 17.10.

EXAMPLE 18

N-[4-(4-amino-6-methylthieno[2,3-d]pyrimidin-5-yl)phenyl]-N'-(3,5-dimethylphenyl)urea The desired product was prepared by substituting 3,5-dimethylphenyl isocyanate for phenyl isocyanate in Example 1F. MS(ESI(+)) m/e 404 (M+H)⁺; ¹H NMR (300 MHz, 35 DMSO-d$_6$) δ 8.85 (s, 1H); 8.59 (s, 1H); 8.26 (s, 1H); 7.62 (d, J=8.4 Hz, 2H); 7.30 (d, J=8.4 Hz, 2H); 7.09 (s, 2H); 6.63 (s, 1H); 2.30 (s, 3H); 2.24 (s, 6H); Anal. Calc. for C$_{22}$H$_{21}$N$_5$OS: C, 65.49; H, 5.25; N, 17.36. Found: C, 65.19; H, 5.18; N, 17.24.

EXAMPLE 19

N-[4-(4-amino-6-methylthieno[2,3-d]pyrimidin-5-yl)phenyl]-N'-(3-methoxyphenyl)urea The desired product was prepared by substituting 3-methoxyphenyl isocyanate for phenyl isocyanate in Example 1F. MS(ESI(+)) m/e 406 (M+H)⁺; ¹H NMR (300 MHz, DMSO-d$_6$) δ 8.88 (s, 1H); 8.76 (s, 1H); 8.26 (s, 1H); 7.63 (d, J=8.7 Hz, 2H); 7.31 (d, J=8.7 Hz, 2H); 7.22-7.17 (m, 2H); 6.95 (m, 1H); 6.57 (m, 1H); 3.74 (s, 3H); 2.30 (s, 1H); Anal. Calcd. for C$_{21}$H$_{19}$N$_5$O$_2$S.0.3H$_2$O: C, 61.39; H, 4.81; N, 17.04. Found: C, 61.41; H, 4.65; N, 17.04.

EXAMPLE 20

N-[4-(4-amino-6-methylthieno[2,3-d]pyrimidin-5-yl)phenyl]-N'-[3-(trifluoromethyl)phenyl]urea The desired product was prepared by substituting 3-trifluoromethylphenyl isocyanate for phenyl isocyanate in Example 1F. MS(ESI(+)) m/e 444 (M+H)⁺; ¹H NMR (300 MHz, DMSO-d$_6$) δ 9.12 (s, 1H); 9.01 (s, 1H); 8.27 (s, 1H); 8.03 (s, 1H); 7.67-7.59 (m, 3H); 7.53 (t, J=7.8 Hz, 1H); 7.33 (m, 3H); 2.30 (s, 1H); Anal. Calcd. for C$_{21}$H$_{16}$F$_3$N$_5$OS: C, 5.88; H, 3.64; N, 15.79. Found: C, 56.65; H, 3.51; N, 15.52.

EXAMPLE 21

N-[4-(4-amino-6-methylthieno[2,3-d]pyrimidin-5-yl)phenyl]-N'-(3-bromophenyl)urea The desired product was prepared by substituting 3-bromophenyl isocyanate for phenyl isocyanate in Example 1F. MS(ESI(+)) m/e 454, 456 (M+H)⁺; ¹H NMR (300 MHz, DMSO-d$_6$) δ 8.97 (s, 1H); 8.96 (s, 1H); 8.27 (s, 1H); 7.88 (t, J=1.8 Hz, 1H); 7.64 (d, J=9.0 Hz, 2H); 7.36-7.29 (m, 3H); 7.25 (t, J=7.8 Hz, 1H); 7.19-7.14 (m, 1H); 2.30 (s, 3H); Anal. Calcd. for C$_{20}$H$_{16}$BrN$_5$OS: C, 52.87; H, 3.55; N, 15.41. Found: C, 52.56; H, 3.46; N, 15.21.

EXAMPLE 22

N-[4-(4-amino-6-methylthieno[2,3-d]pyrimidin-5-yl)phenyl]-N'-(4-bromophenyl)urea The desired product was prepared by substituting 4-bromophenyl isocyanate for phenyl isocyanate in Example 1F. MS(ESI(+)) m/e 454, 456 (M+H)$^+$; $^1$H NMR (300 MHz, DMSO-d$_6$) δ 8.93 (s, 1H); 8,90 (s, 1H); 8.26 (s, 1H); 7.63 (d, J=8.7 Hz, 2H); 7.46 (s, 4H); 7.32 (d, J=8.7 Hz, 2H); 2.29 (s, 3H); Anal. Calcd. for $C_{20}H_{16}BrN_5OS.0.4H_2O.0.2C_8H_{18}$: C, 53.56; H, 4.24; N, 14.46. Found: C, 53.32; H, 3.96; N, 14.24.

EXAMPLE 23

N-[4-(4-amino-6-methylthieno[2,3-d]pyrimidin-5-yl)phenyl]-N'-(2-fluorophenyl)urea The desired product was prepared by substituting 2-fluorophenyl isocyanate for phenyl isocyanate in Example 1F. MS(ESI(+)) m/e 394 (M+H)$^+$; $^1$H NMR (300 MHz, DMSO-d$_6$) δ 9.30 (s, 1H); 8.63 (d, J=2.4 Hz, 1H); 8.27 (s, 1H); 8.17 (td, J=8.1 Hz, 1.5 Hz, 1H); 7.64 (d, J=8.4 Hz, 2H); 7.33 (d, J=8.4 Hz, 2H); 7.26 (ddd, J=12.0 Hz, 8.1 Hz, 1.2 Hz, 1H); 7.16 (t, J=7.8 Hz, 1H); 7.05-6.99 (m, 1H); 2.30 (s, 3H); Anal. Calcd. for $C_{20}H_{16}FN_5OS.0.2C_8H_{18}$: C, 62.32; H, 4.10; N, 16.82. Found: C, 62.05; H, 4.68; N, 16.87.

EXAMPLE 24

N-[4-(4-amino-6-methylthieno[2,3-d]pyrimidin-5-yl)phenyl]-N'-(3-chlorophenyl)urea The desired product was prepared by substituting 3-chlorophenyl isocyanate for phenyl isocyanate in Example 1F. MS(ESI(+)) m/e 410 (M+H)$^+$; $^1$H NMR (300 MHz, DMSO-d$_6$) δ 8.97 (s, 2H); 8.27 (s, 1H); 7.73 (m, 1H); 7.64 (d, J=8.7 Hz, 2H); 7.34-7.29 (m, 4H); 7.06-7.02 (m, 1H); 2.30 (s, 1H); Anal. Calcd. for $C_{20}H_{16}ClN_5OS.0.2H_2O$: C, 58.09; H, 4.00; N, 16.94. Found: C, 58.45; H, 3.99; N, 16.58.

EXAMPLE 25

N-[4-(4-amino-6-methylthieno[2,3-d]pyrimidin-5-yl)phenyl]-N'-(3,5-dimethoxyphenyl)urea The desired product was prepared by substituting 3,5-dimethoxyphenyl isocyanate for phenyl isocyanate in Example 1F. MS(ESI(+)) m/e 436 (M+H)$^+$; $^1$H NMR (300 MHz, DMSO-d$_6$) δ 8.85 (s, 1H); 8.75 (s, 1H); 8.26 (s, 1H); 6.20 (d, J=8.4 Hz, 2H); 7.31 (d, J=8.4 Hz, 2H); 6.70 (d, J=2.1 Hz, 2H); 6.16 (t, J=2.1 Hz, 1H); 3.72 (s, 6H); 2.29 (s, 3H); Anal. Calcd. for $C_{22}H_{21}N_5O_3S$: C, 60.67; H, 4.86; N, 16.08. Found: C, 60.59; H, 4.89; N, 15.92

EXAMPLE 26

N-[4-(4-amino-6-methylthieno[2,3-d]pyrimidin-5-yl)phenyl]-N'-[3-fluoro-5-(trifluoromethyl)phenyl]urea The desired product was prepared by substituting 3-fluoro-5-trifluoromethylphenyl isocyanate for phenyl isocyanate in Example 1F. MS(ESI(+)) m/e 462 (M+H)$^+$; $^1$H NMR (300 MHz, DMSO-d$_6$) δ 9.33 (s, 1H); 9.13 (s, 1H); 8.27 (s, 1H); 7.73 (s, 1H); 7.67-7.62 (m, 3H); 7.33 (d, J=8.7 Hz, 2H); 7.25 (d, J=8.4 Hz, 1H); 2.30 (s, 3H); Anal. Calcd. for $C_{21}H_{15}F_4N_5OS$: C, 54.66; H, 3.28; N, 15.18. Found: 54.47; H, 3.06; N, 15.02.

EXAMPLE 27

N-[4-(4-amino-6-methylthieno[2,3-d]pyrimidin-5-yl)phenyl]-N'-[4-fluoro-3-(trifluoromethyl)phenyl]urea The desired product was prepared by substituting 4-fluoro-3-trifluoromethylphenyl isocyanate for phenyl isocyanate in Example 1F. MS(ESI(+)) m/e 462 (M+H)$^+$; $^1$H NMR (300 MHz, DMSO-d$_6$) δ 9.12 (s, 1H); 9.02 (s, 1H); 8.27 (s, 1H); 8.02 (dd, J=6.6 Hz, 2.7 Hz, 1H); 7.70-7.62 (m, 3H); 7.45 (t, J=9.6 Hz); 7.32 (d, J=8.4 Hz, 2H); 2.30 (s, 3H); Anal. Calcd. for $C_{21}H_{15}F_4N_5OS.0.2H_2O$: C, 54.24; H, 3.34; N, 15.06. Found: C, 54.13; H, 2.98; N, 14.85.

EXAMPLE 28

N-[4-(4-amino-6-methylthieno[2,3-d]pyrimidin-5-yl)phenyl]-N-1,3-benzodioxol-5-ylurea The desired product was prepared by substituting 5-isocyanato-1,3-benzodioxole for phenyl isocyanate in Example 1F. MS(ESI(+)) m/e 420 (M+H)$^+$; $^1$H NMR (300 MHz, DMSO-d$_6$) δ 8.82 (s, 1H); 8.63 (s, 1H); 8.26 (s, 1H); 7.61 (d, J=8.4 Hz, 2H); 7.30 (d, J=8.4 Hz, 2H); 7.22 (d, J=1.8 Hz, 1H); 6.86-6.76 (m, 2H); 5.98 (s, 2H); 2.29 (s, 3H); Anal. Calcd. for $C_{21}H_{17}N_5O_3S$: C, 60.13; H, 4.09; N, 16.70. Found: C, 57.91; H, 4.07; N, 15.65.

EXAMPLE 29

N-[4-(4-amino-6-methylthieno[2,3-d]pyrimidin-5-yl)phenyl]-N'-(4-methoxyphenyl)urea The desired product was prepared by substituting 4-methoxyphenyl isocyanate for phenyl isocyanate in Example 1F. MS(ESI(+)) m/e 406 (M+H)$^+$; $^1$H NMR (300 MHz, DMSO-d$_6$) δ 8.81 (s, 1H); 8.56 (s, 1H); 8.27 (s, 1H); 7.62 (d, J=8.1 Hz, 2H); 7.38 (d, J=9.0 Hz, 2H); 7.30 (d, J=8.1 Hz, 2H); 6.89 (d, J=9.0 Hz, 2H); 3.73 (s, 3H); 2.30 (s, 3H).

EXAMPLE 30

N-[4-(4-amino-6-methylthieno[2,3-d]pyrimidin-5-yl)phenyl]-N'-(4-chlorophenyl)urea The desired product was prepared by substituting 4-chlorophenyl isocyanate for phenyl isocyanate in Example 1F. MS(ESI(+)) m/e 410 (M+H)$^+$; $^1$H NMR (300 MHz, DMSO-d$_6$) δ 8.92 (s, 1H); 8.89 (s, 1H); 8.26 (s, 1H); 7.63 (d, J=8.7 Hz, 2H); 7.51 (s, J=9.0 Hz, 2H); 3.37-7.29 (m, 4H); 2.29 (s, 3H).

EXAMPLE 31

N-[4-(4-amino-6-methylthieno[2,3-d]pyrimidin-5-yl)phenyl]-N'-[2-fluoro-5-(trifluoromethyl)phenyl]urea The desired product was prepared by substituting 2-fluoro-5-trifluoromethylphenyl isocyanate for phenyl isocyanate in Example 1F. MS(ESI(+)) m/e 462 (M+H)$^+$; $^1$H NMR (300 MHz, DMSO-d$_6$) δ 9.39 (s, 1H); 8.98 (d, J=2.7 Hz, 1H); 8.64 (dd, J=7.2 Hz, 1.8 Hz, 1H); 8.27 (s, 1H); 7.65 (d, J=8.4 Hz, 2H); 7.52 (t, J=9.0 Hz, 1H); 7.44-7.37 (m, 1H); 7.34 (d, J=8.4 Hz, 2H); 2.30 (s, 3H).

EXAMPLE 32 methyl 3-[({[4-(4-amino-6-methylthieno[2,3-d]pyrimidin-5-yl)phenyl]amino}carbonyl)amino]benzoate The desired product was prepared by substituting methyl 3-isocyanatobenzoate for phenyl isocyanate in Example 1F. MS(ESI(+)) m/e 434 (M+H)+; $^1$H NMR (300 MHz, DMSO-$d_6$) δ 9.04 (s, 1H); 8.94 (s, 1H); 8.27 (s, 1H); 8.22 (t, 1H); 7.65 (d, 3H); 7.59 (dt, 1H); 7.44 (t, 1H); 7.32 (d, 2H); 3.86 (s, 3H); 2.30 (s, 3H).

EXAMPLE 33

N-[4-(4-amino-6-methylthieno[2,3-d]pyrimidin-5-yl)phenyl]-N'-(4-phenoxyphenyl)urea The desired product was prepared by substituting 4-phenoxyphenyl isocyanate for phenyl isocyanate. MS(ESI) m/e 468 (M+H)+; $^1$H NMR (300 MHz, DMSO-$d_6$) δ 8.88 (s, 1H); 8.77 (s, 1H); 8.26 (s, 1H); 7.64 (d, J=8.4 Hz, 2H); 7.50 (d, J=8.4 Hz, 2H); 7.40-7.28 (m, 4H); 7.11 (t, J=7.1 Hz, 1H); 7.02-6.94 (m, 4H); 2.30 (s, 3H).

EXAMPLE 34

N-[4-(4-amino-6-methylthieno[2,3-d]pyrimidin-5-yl)phenyl]-N'-[3-(methylsulfanyl)phenyl]urea The desired product was prepared by substituting 1-isocyanato-3-(methylsulfanyl)benzene for phenyl isocyanate in Example 1F. MS(ESI(+)) m/e 422 (M+H)+; $^1$H NMR (300 MHz, DMSO-$d_6$) δ 8.91 (s, 1H); 8.80 (s, 1H); 8.27 (s, 1H); 7.63 (d, J=8.4 Hz, 2H); 7.49 (t, J=1.5 Hz, 1H); 7.31 (d, J=8.4 Hz, 2H); 7.23 (t, J=7.5 Hz, 1H); 7.17 (dt, J=9.0 Hz, 1.5 Hz, 1H); 6.88 (dt, J=8.4 Hz, 1.5 Hz, 1H); 2.30 (s, 3H).

EXAMPLE 35

N-[4-(4-amino-6-methylthieno[2,3-d]pyrimidin-5-yl)phenyl]-N'-(2,5-dimethylphenyl)urea The desired product was prepared by substituting 2,5-dimethylphenyl isocyanate for phenyl isocyanate in Example 1F. MS(ESI(+)) m/e 404 (M+H)+; $^1$H NMR (300 MHz, DMSO-$d_6$) δ 9.22 (s, 1H); 8.27 (s, 1H); 7.94 (s, 1H); 7.66 (s, 1H); 7.64 (d, J=9.0 Hz, 2H); 7.30 (d, J=9.0 Hz, 2H); 7.06 (d, J=7.2 Hz, 1H); 7.87 (d, J=7.4 Hz, 1H); 2.30 (s, 3H); 2.26 (s, 3H); 2.21 (s, 3H).

EXAMPLE 36

N-[4-(4-amino-6-methylthieno[2,3-d]pyrimidin-5-yl)phenyl]-N'-(2-chlorophenyl)urea The desired product was prepared by substituting 2-chlorophenyl isocyanate for phenyl isocyanate in Example 1F. MS(ESI(+)) m/e 410, 412 (M+H)+; $^1$H NMR (300 MHz, DMSO-$d_6$) δ 9.64 (s, 1H); 8.40 (s, 1H); 8.27 (s, 1H); 8.17 (dd, J=8.4 Hz, 1.8 Hz, 1H); 7.65 (d, J=8.4 Hz, 2H); 7.48 (dd, J=7.8 Hz, 1.8 Hz, 1H); 7.36-7.28 (m, 3H); 7.05 (td, J=8.4 Hz, 1.8 Hz, 1H); 2.30 (s, 1H).

EXAMPLE 37

N-[4-(4-amino-6-methylthieno[2,3-d]pyrimidin-5-yl)phenyl]-N'-(3,5-dichlorophenyl)urea The desired product was prepared by substituting 3,5-dichlorophenyl isocyanate for phenyl isocyanate in Example 1F. MS(ESI(+)) m/e 444, 446 (M+H)+; $^1$H NMR (300 MHz, DMSO-$d_6$) δ 9.14 (s, 1H); 9.11 (s, 1H); 8.27 (s, 1H); 7.64 (d, J=8.4 Hz, 2H); 7.56 (d, J=1.8 Hz, 2H); 7.33 (d, J=8.4 Hz, 2H); 7.19 (t, J=1.8 Hz, 1H); 2.29 (s, 3H).

EXAMPLE 38

N-[4-(4-amino-6-methylthieno[2,3-d]pyrimidin-5-yl)phenyl]-N'-(3-chloro-4-methylphenyl)urea The desired product was prepared by substituting 3-chloro-4-methylphenyl isocyanate for phenyl isocyanate in Example 1F. MS(ESI(+)) m/e 424 (M+H)+; $^1$H NMR (300 MHz, DMSO-$d_6$) δ 8.93 (s, 1H); 8.85 (s, 1H); 8.27 (s, 1H); 7.71 (d, J=1.8 Hz, 1H); 7.63 (d, J=8.4 Hz, 2H); 7.31 (d, J=8.4 Hz, 2H); 7.26 (d, J=8.4 Hz, 1H); 7.21 (dd, J=8.4 Hz, 1.8 Hz, 1H); 2.29 (s, 3H); 2.27 (s, 3H).

EXAMPLE 39

N-[4-(4-amino-6-methylthieno[2,3-d]pyrimidin-5-yl)phenyl]-N'-(2,6-difluorophenyl)urea The desired product was prepared by substituting 2,6-difluorophenyl isocyanate for phenyl isocyanate in Example 1F. MS(ESI(+)) m/e 412 (M+H)+; $^1$H NMR (300 MHz, DMSO-$d_6$) δ 9.18 (s, 1H); 8.26 (s, 1H); 8.20 (s, 1H); 7.63 (d, 1H); 7.36-7.27 (m, 3H); 7.22-7.10 (m, 2H); 2.29 (s, 1H).

EXAMPLE 40

N-[4-(4-amino-6-methylthieno[2,3-d]pyrimidin-5-yl)phenyl]-N'-[2-chloro-5-(trifluoromethyl)phenyl]urea The desired product was prepared by substituting 2-chloro-5-trifluoromethylphenyl isocyanate for phenyl isocyanate in Example 1F. MS(ESI) m/e 478 (M+H)+; $^1$H NMR (300 MHz, DMSO-$d_6$) δ 9.78 (s, 1H); 8.70 (s, 1H); 8.65 (d, J=2.1 Hz, 1H); 8.27 (s, 1H); 7.74 (d, J=8.4 Hz, 1H); 7.66 (d, J=8.7 Hz, 2H); 4.41 (dd, J=8.4 Hz, 2.1 Hz, 1H); 7.35 (d, J=8.7 Hz, 2H); 2.30 (s, 3H).

EXAMPLE 41

N-[4-(4-amino-6-methylthieno[2,3-d]pyrimidin-5-yl)phenyl]-N'-(3-ethylphenyl)urea The desired product was prepared by substituting 3-ethylphenyl isocyanate for phenyl isocyanate in Example 1F. MS(ESI(+)) m/e 404 (M+H)+; $^1$H NMR (300 MHz, DMSO-$d_6$) δ 8.86 (s, 1H); 8.68 (s, 1H); 8.27 (s, 1H); 7.63 (d, J=8.7 Hz, 2H); 7.31 (d, J=8.7 Hz, 2H); 7.35-7.25 (m, 2H); 7.20 (t, J=7.8 Hz, 1H); 6.84 (d, J=7.2 Hz, 1H); 2.58 (q, J=7.5 Hz, 2H); 2.30 (s, 3H); 1.19 (t, J=7.5 Hz, 3H).

EXAMPLE 42

N-[4-(4-amino-6-methylthieno[2,3-d]pyrimidin-5-yl)phenyl]-N'-(4-ethylphenyl)urea The desired product was prepared by substituting 4-ethylphenyl isocyanate for phenyl isocyanate in Example 1F.

MS(ESI(+)) m/e 404 (M+H)$^+$; $^1$H NMR (300 MHz, DMSO-d$_6$) δ 8.85 (s, 1H); 8.65 (s, 1H); 8.27 (s, 1H); 7.63 (d, J=8.4 Hz, 2H); 9.38 (d, J=8.4 Hz, 2H); 7.30 (d, J=8.4 Hz, 2H); 7.13 (d, J=8.4 Hz, 2H); 2.51 (q, J=7.8 Hz, 2H); 2.29 (s, 3H); 1.16 (t, J=7.8 Hz, 3H).

EXAMPLE 43

N-[4-(4-amino-6-methylthieno[2,3-d]pyrimidin-5-yl)phenyl]-N'-(4-bromo-2-fluorophenyl)urea The desired product was prepared by substituting 2-fluoro-4-bromophenyl isocyanate for phenyl isocyanate in Example 1F. MS(ESI(+)) m/e 474 (M+H)$^+$; $^1$H NMR (300 MHz, DMSO-d$_6$) δ 9.31 (s, 1H); 8.73 (d, J=2.4 Hz, 1H); 8.27 (s, 1H); 8.15 (t, J=8.7 Hz, 1H); 7.63 (d, J=8.7 Hz, 2H); 7.59 (dd, J=10.8 Hz, 2.1 Hz, 1H); 7.38 (m, 1H); 7.33 (d, J=8.7 Hz, 2H); 2.29 (s, 1H).

EXAMPLE 44

N-[4-(4-amino-6-methylthieno[2,3-d]pyrimidin-5-yl)phenyl]-N'-(2-fluoro-5-methylphenyl)urea The desired product was prepared by substituting 2-fluoro-5-methylphenyl isocyanate for phenyl isocyanate in Example 1F. MS(ESI) m/e 408 (M+H)$^+$; $^1$H NMR (300 MHz, DMSO-d$_6$) δ 9.28 (s, 1H); 8.56 (d, J=2.7 Hz, 1H); 8.27 (s, 1H); 8.00 (dd, J=8.1 Hz, 2.1 Hz, 1H); 7.63 (d, J=9.0 Hz, 2H); 7.32 (d, J=9.0 Hz, 2H); 7.12 (dd, J=11.4 Hz, 8.1 Hz, 1H); 6.82 (m, 1H); 2.30 (s, 3H); 2.28 (s, 3H).

EXAMPLE 45

N-[4-(4-amino-6-methylthieno[2,3-d]pyrimidin-5-yl)phenyl]-N'-[4-chloro-3-(trifluoromethyl)phenyl]urea The desired product was prepared by substituting 4-chloro-3-trifluoromethylphenyl isocyanate for phenyl isocyanate in Example 1F. MS(ESI(+)) m/e 478 (M+H)$^+$; $^1$H NMR (300 MHz, DMSO-d$_6$) δ 9.25 (s, 1H); 9.07 (s, 1H); 8.27 (s, 1H); 8.13 (d, J=2.4 Hz, 1H); 7.70-7.60 (m, 4H); 7.33 (d, J=8.4 Hz, 2H); 2.30 (s, 3H).

EXAMPLE 46

N-[4-(4-amino-6-methylthieno[2,3-d]pyrimidin-5-yl)phenyl]-N'-(3,4-dimethylphenyl)urea The desired product was prepared by substituting 3,4-dimethylphenyl isocyanate for phenyl isocyanate in Example 1F. MS(ESI(+)) m/e 404 (M+H)$^+$; $^1$H NMR (300 MHz, DMSO-d$_6$) δ 8.83 (s, 1H); 8.56 (s, 1H); 8.26 (s, 1H); 7.62 (d, J=8.4 Hz, 2H); 7.30 (d, J=8.4 Hz, 2H); 7.25 (s, 1H); 7.19 (d, J=8.1 Hz, 1H); 7.04 (d, J=8.1 Hz, 1H); 2.30 (s, 3H); 2.20 (s, 3H); 2.16 (s, 3H).

EXAMPLE 47

N-[4-(4-amino-6-methylthieno[2,3-d]pyrimidin-5-yl)phenyl]-N'-(2-chloro-5-methylphenyl)urea The desired product was prepared by substituting 2-chloro-5-methylphenyl isocyanate for phenyl isocyanate in Example 1F. MS(ESI(+)) m/e 424 (M+H)$^+$; $^1$H NMR (300 MHz, DMSO-d$_6$) δ 9.61 (s, 1H); 8.32 (s, 1H); 8.27 (s, 1H); 8.02 (d, J=2.1 Hz, 1H); 7.65 (d, J=8.7 Hz, 2H); 7.36-7.31 (m, 3H); 6.87 (dd, J=8.7 Hz, 2.1 Hz, 1H); 2.30 (s, 6H).

EXAMPLE 48

N-[4-(4-amino-6-methylthieno[2,3-d]pyrimidin-5-yl)phenyl]-N'-(2-methoxyphenyl)urea The desired product was prepared by substituting 2-methoxyphenyl isocyanate for phenyl isocyanate in Example 1F. MS(ESI(+)) m/e 406 (M+H)$^+$; $^1$H NMR (300 MHz, DMSO-d$_6$) δ 9.55 (s, 1H); 8.31 (s, 1H); 8.27 (s, 1H); 8.15 (dd, J=7.8 Hz, 2.1 Hz, 1H); 7.63 (d, J=8.7 Hz, 2H); 7.31 (d, J=8.7 Hz, 2H); 7.04 (dd, J=8.1 Hz, 1.8 Hz, 1H); 6.70-6.87 (m, 2H); 3.90 (s, 3H); 2.30 (s, 3H).

EXAMPLE 49

N-[4-(4-amino-6-methylthieno[2,3-d]pyrimidin-5-yl)phenyl]-N'-(2,5-dichlorophenyl)urea The desired product was prepared by substituting 2,5-dichlorophenyl isocyanate for phenyl isocyanate in Example 1F. MS(ESI(+)) m/e 444 (M+H)$^+$; $^1$H NMR (300 MHz, DMSO-d$_6$) δ 9.74 (s, 1H); 8.55 (s, 1H); 8.33 (d, J=2.4 Hz, 1H); 8.27 (s, 1H); 7.65 (d, J=8.7 Hz, 2H); 7.52 (d, J=8.4 Hz, 1H); 7.34 (d, J=8.7 Hz, 2H); 7.12 (dd, J=8.4 Hz, 2.4 Hz, 1H); 2.20 (s, 3H).

EXAMPLE 50

N-[4-(4-amino-6-methylthieno[2,3-d]pyrimidin-5-yl)phenyl]-N'-(2,4-difluorophenyl)urea The desired product was prepared by substituting 2,4-difluorophenyl isocyanate for phenyl isocyanate in Example 1F. MS(ESI(+)) m/e 412 (M+H)$^+$; $^1$H NMR (300 MHz, DMSO-d$_6$) δ 9.24 (s, 1H); 8.59 (s, 1H); 8.27 (s, 1H); 8.09 (td, J=9.6 Hz, 6.0 Hz, 1H); 7.63 (d, J=8.4 Hz, 2H); 7.37-7.28 (m, 3H); 7.07 (m, 1H); 2.29 (s, 3H).

EXAMPLE 51

N-[4-(4-amino-6-methylthieno[2,3-d]pyrimidin-5-yl)phenyl]-N'-(3,4,5-trimethoxyphenyl)urea The desired product was prepared by substituting 3,4,5-trimethoxyphenyl isocyanate for phenyl isocyanate in Example 1F. MS(ESI(+)) m/e 466 (M+H)$^+$; $^1$H NMR (300 MHz, DMSO-d$_6$) δ 8.31 (s, 1H); 8.70 (s, 1H); 8.27 (s, 1H); 7.63 (d, J=8.4 Hz, 2H); 7.31 (d, J=8.4 Hz, 2H); 6.83 (s, 2H); 3.76 (s, 6H); 3.62 (s, 3H); 2.30 (s, 3H).

EXAMPLE 52

N-[4-(4-amino-6-methylthieno[2,3-d]pyrimidin-5-yl)phenyl]-N'-(2,5-dimethoxyphenyl)urea The desired product was prepared by substituting 2,5-dimethoxyphenyl isocyanate for phenyl isocyanate in Example 1F. MS(ESI(+)) m/e 436 (M+H)$^+$; $^1$H NMR (300 MHz, DMSO-d$_6$) δ 9.58 (s, 1H); 8.33 (s, 1H); 8.27 (s, 1H); 7.88 (d, J=3.0 Hz, 1H); 7.63 (d, J=8.7 Hz, 2H); 7.31 (d, J=8.7

Hz, 2H); 6.94 (d, J=9.0 Hz, 1H); 6.51 (dd, J=9.0 Hz, 3.0 Hz, 1H); 3.84 (s, 3H); 3.70 (s, 3H); 2.30 (s, 3H).

EXAMPLE 53

N-[4-(4-amino-6-methylthieno[2,3-d]pyrimidin-5-yl) phenyl]-N'-2-naphthylurea

The desired product was prepared by substituting 2-naphthyl isocyanate for phenyl isocyanate in Example 1F. MS(ESI) m/e 426 (M+H)$^+$; $^1$H NMR (300 MHz, DMSO-d$_6$) δ 8.99 (s, 1H); 8.98 (s, 1H); 8.27 (s, 1H); 8.13 (d, J=2.1 Hz, 1H); 7.83 (m, 3H); 7.68 (d, J=8.4 Hz, 2H); 7.52 (dd, J=8.7 Hz, 2.1 Hz, 1H); 7.46 (t, J=7.5 Hz, 1H); 7.40-7.31 (m, 3H).

EXAMPLE 54

N-[4-(4-amino-6-methylthieno[2,3-d]pyrimidin-5-yl) phenyl]-N'-benzylurea

The desired product was prepared by substituting benzyl isocyanate for phenyl isocyanate in Example 1F. MS(ESI(+)) m/e 390 (M+H)$^+$; $^1$H NMR (300 MHz, DMSO-d$_6$) δ 8.81 (s, 1H); 8.26 (s, 1H); 7.59 (d, J=8.7 Hz, 2H); 8.38-7.28 (m, 4H); 7.27-7.22 (m, 3H); 6.71 (t, J=6.0 Hz, 1H); 4.33 (d, J=6.0 Hz, 2H); 2.28 (s, 3H).

EXAMPLE 55

N-[4-(4-amino-6-methylthieno[2,3-d]pyrimidin-5-yl) phenyl]-N'-(4-cyanophenyl)urea The desired product was prepared by substituting 4-cyanophenyl isocyanate for phenyl isocyanate in Example 1F. MS(ESI(+)) m/e 401 (M+H)$^+$; $^1$H NMR (300 MHz, DMSO-d$_6$) δ 9.29 (s, 1H); 9.08 (s, 1H); 8.27 (s, 1H); 7.75 (d, J=9.0 Hz, 2H); 7.69-7.62 (m, 4H); 7.34 (d, J=8.4 Hz, 2H); 2.29 (s, 3H).

EXAMPLE 56

N-[4-(4-amino-6-methylthieno[2,3-d]pyrimidin-5-yl) phenyl]-N'-[4-(dimethylamino)phenyl]urea The desired product was prepared by substituting 4-dimethylaminophenyl isocyanate for phenyl isocyanate in Example 1F. MS(ESI(+)) m/e 419 (M+H)$^+$; $^1$H NMR (300 MHz, DMSO-d$_6$) δ 8.75 (s, 1H); 8.37 (s, 1H); 8.26 (s, 1H); 7.61 (d, J=8.4 Hz, 2H); 7.28 (m, 4H); 6.71 (d, J=9.0 Hz, 2H); 2.84 (s, 6H); 2.29 (s, 3H).

EXAMPLE 57

N-(4-{4-amino-6-[(4-methylpiperazin-1-yl)methyl] thieno[2,3-d]pyrimidin-5-yl}phenyl)-N'-(3-methylphenyl)urea

EXAMPLE 57A 6-(bromomethyl)-5-(4-nitrophenyl)thieno[2,3-d] pyrimidin-4-amine A suspension of Example 1D (500 mg, 1.75 mmol) in benzene (50 mL) was treated with NBS (340 mg, 1.91 mmol) and AIBN (50 mg), stirred at reflux for 3.5 hours, and concentrated. The concentrate was absorbed onto silica gel and purified by flash column chromatography with ethyl acetate to provide 330 mg of a 1.7:1 mixture of the desired product and recovered starting material.

EXAMPLE 57B

6-[(4-methylpiperazin-1-yl)methyl]-5-(4-nitrophenyl)thieno[2,3-d]pyrimidin-4-amine A mixture of Example 57A (330 mg) and N-methylpiperazine (0.3 mL, 2.71 mmol) in DMF (6 mL) was stirred at room temperature overnight and concentrated. The concentrate was absorbed on silica gel and purified by flash column chromatography with ethyl acetate followed by 12% methanol/dichloromethane to provide 115 mg the desired product. R$_f$=0.38 (12% methanol/dichloromethane).

EXAMPLE 57C 5-(4-aminophenyl)-6-[(4-methylpiperazin-1-yl)methyl]thieno[2,3-d]pyrimidin-4-amine The desired product was prepared by substituting Example 57B for Example 1D in Example 1E. MS(ESI(+)) m/e 355 (M+H)$^+$; $^1$H NMR (300 MHz, DMSO-d$_6$) δ 8.24 (s, 1H); 6.98 (d, J=8.4 Hz, 2H); 6.68 (d, J=8.4 Hz, 2H); 5.41 (br s, 2H); 3.50 (s, 2H); 2.48 (s, 3H); 2.45 (br s, 4H); 2.26 (br s, 4H).

EXAMPLE 57D

N-(4-{4-amino-6-[(4-methylpiperazin-1-yl)methyl] thieno[2,3-d]pyrimidin-5-yl}phenyl)-N'-(3-methylphenyl)urea The desired product was prepared by substituting Example 57C and 3-methylphenyl isocyanate for Example 1E and phenyl isocyanate, respectively, in Example 1F. $^1$H NMR (300 MHz, DMSO-d$_6$) δ 8.88 (s, 1H); 8.68 (s, 1H); 8.27 (s, 1H); 7.62 (d, J=9.0 Hz, 2H); 7.32-7.23 (m, 4H); 7.17 (t, J=7.5 Hz, 1H); 6.81 (d, J=7.5 Hz, 1H); 3.50 (s, 2H); 2.45-2.20 (br s, 8H); 2.29 (s, 3H); 2.14 (s, 3H).

EXAMPLE 58

N-[4-(4-aminothieno[2,3-d]pyrimidin-5-yl)phenyl]-N'-(3-methylphenyl)urea

EXAMPLE 58A

2-[1-(4-nitrophenyl)ethylidene]malononitrile

A mixture of 1-(4-nitrophenyl)ethanone (15 g, 90.8 mmol), malononitrile (6 g, 90.8 mmol), ammonium acetate (7 g, 90.8 mmol) and acetic acid (10 mL) in benzene (200 mL) was stirred at reflux overnight in a flask equipped with a Dean-Stark trap. The reaction mixture was cooled to room temperature, poured into water, and extracted three times with ethyl acetate. The combined organic extracts were washed with water and brine, dried (MgSO$_4$), filtered, and concentrated. The residue was purified by silica gel chromatography eluting with 25% ethyl acetate/hexanes to provide 9.42 g of the desired product. R$_f$=0.33 (25% ethyl acetate/hexanes).

EXAMPLE 58B 2-amino-4-(4-nitrophenyl)thiophene-3-carbonitrile

A solution of Example 58A (4.14 g, 19.6 mmol) in ethanol (200 mL) and THF (80 mL) at room temperature was treated sequentially with sulfur (621 mg, 19.4 mmol) and triethylamine (1.82 mL, 19.4 mmol), stirred overnight, and filtered. The filter cake was absorbed on silica and purified by flash column chromatography with 3:2 hexanes/ethyl acetate to provide 2.51 g of the desired product.

EXAMPLE 58C 5-(4-nitrophenyl)thieno[2,3-d]pyrimidin-4-amine

A suspension of Example 58B (1.23 g, 5.01 mmol) in formamide (20 mL) was heated to between 150 and 160° C. for 19 hours, cooled to room temperature, and filtered. The filter cake was dried to give 1.09 g of the desired product. MS (ESI(+)) m/e 273 (M+H)$^+$.

EXAMPLE 58D 5-(4-aminophenyl)thieno[2,3-d]pyrimidin-4-amine

A suspension of Example 58C (0.5 g, 1.83 mmol) in THF (30 mL), water (15 mL), and ethanol (40 mL) was heated to 50° C., treated with iron powder (0.616 g, 11.02 mmol), heated to between 70 and 80° C. for two hours, and filtered while hot through diatomaceous earth (Celite®). The pad was washed with TBF (10 mL) and ethanol and the combined filtrates were concentrated. The residue was partitioned between water and ethyl acetate and the aqueous phase was extracted three times with ethyl acetate. The combined extracts were washed with brine, dried (MgSO$_4$), filtered, and concentrated to give 0.432 g of the desired product. MS (CI) m/e 243 (M+H)$^+$; $^1$H NMR (300 MHz, DMSO-d$_6$) δ 8.30 (s, 1H); 7.28 (s, 1H); 7.11 (d, J=8.4 Hz, 2H); 6.68 (d, J=8.4 Hz, 2H); 5.39 (br s, 2H).

EXAMPLE 58E

N-[4-(4-aminothieno[2,3-d]pyrimidin-5-yl)phenyl]-N'-(3-methylphenyl)urea

The desired product was prepared by substituting Example 58D and 3-methylphenyl isocyanate for Example 1E and phenyl isocyanate, respectively, in Example 1F. MS(ESI(+)) m/e 376 (M+H)$^+$; $^1$H NMR (300 MHz, DMSO-d$_6$) δ 8.88 (s, 1H); 8.67 (s, 1H); 8.34 (s, 1H); 7.61 (d, J=8.7 Hz, 2H); 7.43 (s, 1H); 7.39 (d, J=8.7 Hz, 2H); 7.31 (s, 1H); 7.25 (d, J=7.5 Hz, 1H); 7.17 (t, J=7.5 Hz, 1H); 6.81 (d, J=7.5 Hz, 1H); Anal. Calcd. for C$_{20}$H$_{17}$N$_5$OS: C, 63.98; H, 4.56; N, 18.65. Found: C, 63.65; H, 4.56; N, 18.36.

EXAMPLE 59

N-[4-(4-aminothieno[2,3-d]pyrimidin-5-yl)phenyl]-N'-phenylurea

The desired product was prepared by substituting Example 58D for Example 1E in Example 1F. MS(ESI(+)) m/e 362 (M+H)$^+$; $^1$H NMR (300 MHz, DMSO-d$_6$) δ 8.89 (s, 1H); 8.75 (s, 1H); 8.34 (s, 1H); 7.61 (d, J=8.4 Hz, 2H); 7.47 (d, J=7.5 Hz, 2H); 7.43 (s, 1H); 7.40 (d, J=8.4 Hz, 2H); 7.30 (t, J=7.5 Hz, 1H); 6.98 (t, J=7.5 Hz, 1H); Anal. Calcd. for C$_{19}$H$_{15}$N$_5$OS.0.2H$_2$O: C, 62.52; H, 4.25; N, 19.19. Found: C, 52.65; H, 4.13; N, 18.86.

EXAMPLE 60

N-[4-(4-aminothieno[2,3-d]pyrimidin-5-yl)phenyl]-N'-(3-ethylphenyl)urea

The desired product prepared by substituting Example 58D and 3-ethylphenyl isocyanate for Example 1E and phenyl isocyanate, respectively, in Example 1F. MS(ESI(+)) m/e 390 (M+H)$^+$; $^1$H NMR (300 MHz, DMSO-d$_6$) δ 8.86 (s, 1H); 8.68 (s, 1H); 8.33 (s, 1H); 7.61 (d, 2H); 7.43 (s, 1H); 7.39 (d, 2H); 7.34 (s, 1H); 7.27 (d, 1H); 7.19 (s, 1H); 6.83 (s, 1H); 2.58 (q, 2H); 1.18 (t, 3H); Anal. Calcd. for C$_{21}$H$_{19}$N$_5$OS: C, 64.76; H, 4.92; N, 17.98. Found: C, 64.38; H, 4.93; N, 17.68.

EXAMPLE 61

N-[4-(4-amino-6-bromothieno[2,3-d]pyrimidin-5-yl)phenyl]-N'-(3-methylphenyl)urea

EXAMPLE 61A 6-bromo-5-(4-nitrophenyl)thieno[2,3-d]pyrimidin-4-amine

A suspension of Example 58C (50 mg, 0.18 mmol) in acetic acid (1 mL) and DMF (3 mL) was heated with a heat gun to obtain a clear solution, cooled to 0° C., and treated with bromine (0.02 mL). The reaction mixture was stirred at 0° C. for 1 hour, diluted with saturated NaHCO$_3$, and filtered. The filter cake was dried to provide 56 mg of the desired product.

EXAMPLE 61B 5-(4-aminophenyl)-6-bromothieno[2,3-d]pyrimidin-4-amine

The desired product was prepared by substituting Example 61A for Example 1D in Example 1E. MS(ESI(+)) m/e 321, 323 (M+H)$^+$; $^1$H NMR (300 MHz, DMSO-d$_6$) δ 8.29 (s, 1H); 7.05 (d, J=8.4 Hz, 2H); 6.70 (d, J=8.4 Hz, 2H); 5.50 (s, 2H).

EXAMPLE 61C

N-[4-(4-amino-6-bromothieno[2,3-d]pyrimidin-5-yl)phenyl]-N'-(3-methylphenyl)urea The desired product was prepared by Example 61B for and 3-methylphenyl isocyanate for Example 1E and phenyl isocyanate, respectively, in Example 1F. MS(ESI(+)) m/e 454, 456 (M+H)$^+$; $^1$H NMR (300 MHz, DMSO-d$_6$) δ 8.92 (s, 1H); 8.69 (s, 1H); 8.33 (s, 1H); 7.65 (d, J=8.4 Hz, 2H); 7.36 (d, J=8.4 Hz, 2H); 7.32 (s, 1H); 7.26 (d, J=7.8 Hz, 1H); 7.17 (t, J=7.8 Hz, 1H); 6.81 (d, J=7.8 Hz, 1H); Anal. Calcd. for C$_{20}$H$_{16}$BrN$_5$OS.0.4H$_2$O: C, 52.05; H, 3.67; N, 15.17. Found: C, 52.07; H, 3.36; N, 15.13.

EXAMPLE 62

4-(4-amino-6-methylthieno[2,3-d]pyrimidin-5-yl)-N-(3-chlorophenyl)benzamide

The desired product was prepared by substituting 3-chloroaniline for aniline in Example 66. MS(ESI(−)) m/e 393 (M−H)$^-$; $^1$H NMR (300 MHz, DMSO-d$_6$) δ 10.57 (s, 1H); 8.30 (s, 1H); 8.12 (d, J=8.4 Hz, 2H); 8.01 (t, J=1.8 Hz, 1H); 7.73 (m, 1H); 7.60 (d, J=8.4 Hz, 2H); 7.41 (t, J=7.2 Hz, 1H); 7.19 (m, 1H); 2.32 (s, 3H).

EXAMPLE 63

5-{4-[(5,7-dimethyl-1,3-benzoxazol-2-yl)amino]phenyl}-6-methylthieno[2,3-d]pyrimidin-4-amine The desired product was prepared by substituting 2-amino-4,6-dimethylphenol for 2-aminophenol in Example 3. MS(ESI(+)) m/e 402 (M+H)$^+$; $^1$H NMR (300 MHz, DMSO-d$_6$) δ 10.89 (s, 1H); 8.27 (s, 1H); 7.93 (d, J=8.4 Hz, 2H); 7.41 (d, J=8.4 Hz, 2H); 7.11 (s, 1H); 6.80 (s, 1H); 2.41 (s, 3H); 2.34 (s, 3H); 2.31 (s, 3H); Anal. Calcd. for C$_{22}$H$_{19}$N$_5$OS.0.2H$_2$O: C, 65.78; H, 5.08; N, 16.82. Found: C, 65.41; H, 4.90; N, 17.15.

EXAMPLE 64

N-[4-(4-amino-6-methylthieno[2,3-d]pyrimidin-5-yl)phenyl]-2-(3-methylphenyl)acetamide The desired product was prepared by substituting 3-methylphenylacetyl chloride for benzoyl chloride in Example 4. MS(ESI(+)) 389 (M+H)$^+$; $^1$H NMR (300 MHz, DMSO-d$_6$) δ 10.37 (s, 1H); 8.26 (s, 1H); 7.78 (d, J=8.4 Hz, 2H); 7.32 (d, J=8.4 Hz, 2H); 7.26-7.13 (m, 3H); 7.07 (d, J=7.5 Hz, 1H); 3.64 (s, 2H); 2.31 (s, 3H); 2.27 (s, 3H); Anal. Calcd. for C$_{22}$H$_{20}$N$_4$OS: C, 68.02; H, 5.19; N, 14.42. Found: C, 67.76; H, 5.29; N, 14.31.

EXAMPLE 65

N-[4-(4-amino-6-methylthieno[2,3-d]pyrimidin-5-yl)phenyl]-3-methylbenzamide

The desired product was prepared by substituting 3-methylbenzoyl chloride for benzoyl chloride in Example 4. MS (CI) m/e 375 (M+H)$^+$; $^1$H NMR (300 MHz, DMSO-d$_6$) δ 10.42 (s, 1H); 8.28 (s, 1H); 7.98 (d, J=8.4 Hz, 2H); 7.80-7.75 (m, 2H); 7.45-7.36 (m, 4H); 2.42 (s, 3H); 2.31 (s, 3H); Anal. Calcd. for C$_{12}$H$_{18}$N$_4$OS.0.2C$_4$H$_8$O$_2$: C, 66.78; H, 5.04; N, 14.29. Found: H, 66.55; H, 6.29; N, 13.95.

EXAMPLE 66

4-(4-amino-6-methylthieno[2,3-d]pyrimidin-5-yl)-N-phenylbenzamide

EXAMPLE 66A

5-(4-bromophenyl)-6-methylthieno[2,3-d]pyrimidin-4-amine

The desired product was prepared by substituting 4-bromophenylethyl ketone for Example 1A in Examples 1B and 1C. MS(ESI(+)) 320, 322 (M+H)$^+$; $^1$H NMR (300 MHz, DMSO-d$_6$) δ 8.278 (s, 1H); 7.74 (d, J=8.1 Hz, 2H); 7.36 (d, J=8.1 Hz, 2H); 2.28 (s, 3H).

EXAMPLE 66B

4-(4-amino-6-methylthieno[2,3-d]pyrimidin-5-yl)benzoic acid

A −78° C. solution of Example 66A (1.5 g, 4.68 mmol) in THF (50 mL) was treated dropwise with 2.5M n-butyllithium in hexanes (4.7 mL, 11.71 mmol), stirred for 30 minutes at −78° C., then treated with excess dry ice. The reaction was stirred at −78° C. for 30 minutes, warmed to room temperature, diluted with water, adjusted to pH 3 with 2N HCl, and filtered. The filter cake was dried to provide 686 mg (51%) of the desired product. MS (CI) m/e 285 (M$^+$); $^1$H NMR (300 MHz, DMSO-d$_6$) δ 13.13 (br s, 1H); 8.29 (s, 1H); 8.09 (d, J=8.4 Hz, 2H); 7.53 (d, J=8.4 Hz, 2H); 2.28 (s, 3H).

EXAMPLE 66C

4-(4-amino-6-methylthieno[2,3-d]pyrimidin-5-yl)-N-phenylbenzamide

A suspension of Example 66B (89 mg, 0.31 mmol) and HOBT (46 mg, 0.35 mmol) in DMF (4 mL) at room temperature was treated with aniline (0.029 mL, 0.31 mmol), NMM (0.086 mL, 0.78 mmol) and EDC.HCl (66 mg, 0.34 mmol), stirred overnight, and partitioned between water and ethyl acetate. The aqueous phase was extracted three times with ethyl acetate and the combined organic extracts ware washed with water, and brine, dried (Na$_2$SO$_4$), filtered, and concentrated to a volume of about 3 mL. The product was treated with hexanes and the resulting precipitate was collected by filtration to provide 84 mg (75%) of the desired product. MS(ESI(+)) m/e 361 (M+H)$^+$; $^1$H NMR (300 MHz, DMSO-d$_6$) δ 10.40 (s, 1H); 8.30 (s, 1H); 8.12 (d, J=8.4 Hz, 2H); 7.80 (d, J=7.5 Hz, 2H); 7.58 (d, J=8.4 Hz, 2H); 7.37 (t, J=7.5 Hz, 2H); 7.12 (t, J=7.5 Hz, 1H); 2.32 (s, 3H); Anal. Calcd. for C$_{20}$H$_{16}$N$_4$OS.0.1C$_4$H$_8$O$_2$: C, 66.36; H, 4.59; N, 15.17. Found: 66.07; H, 4.76; N, 15.32.

EXAMPLE 67

4-(4-amino-6-methylthieno[2,3-d]pyrimidin-5-yl)-N-(3-methylphenyl)benzamide

The desired product was prepared by substituting 3-methylaniline for aniline in Example 66C. MS(ESI(+)) 375 (M+H)$^+$; $^1$H NMR (300 MHz, DMSO-d$_6$) δ 10.33 (s, 1H); 8.30 (s, 1H); 8.11 (d, J=8.1 Hz, 2H); 7.66 (s, 1H); 7.61-7.55 (m, 3H); 7.25 (t, J=7.5 Hz, 1H); 6.94 (d, J=7.5 Hz, 1H); 2.32 (s, 6H).

EXAMPLE 68

N-(4-{4-amino-6-[(dimethylamino)methyl]thieno[2,3-d]pyrimidin-5-yl}phenyl)-N'-(3-methylphenyl)urea The desired product was prepared by substituting dimethylamine for N-methylpiperazine in Examples 57B-D. MS(ESI(+)) m/e 433 (M+H)$^+$; $^1$H NMR (300 MHz, DMSO-d$_6$) δ 8.92 (s, 1H); 8.71 (s, 1H); 8.28 (s, 1H); 7.32-7.22 (m, 4H); 7.17 (t, J=7.8 Hz, 1H); 6.81 (d, J=7.8 Hz, 1H); 3.45 (br s, 2H); 2.29 (s, 3H); 2.17 (s, 6H).

EXAMPLE 69

N-{4-[4-amino-6-(morpholin-4-ylmethyl)thieno[2,3-d]pyrimidin-5-yl]phenyl}-N'-(3-methylphenyl)urea The desired product was prepared by substituting morpholine for N-methylpiperazine in Examples 57B-D. MS(ESI(+)) m/e 475 (M+H)$^+$; $^1$H NMR (300 MHz, DMSO-d$_6$) δ 8.90 (s, 1H); 8.69 (s, 1H); 8.28 (s, 1H); 7.63 (d, J=8.7 Hz, 2H); 7.33-7.23 (m, 4H); 7.17 (t, J=7.5 Hz, 1H); 6.81 (d, J=7.5 Hz, 1H); 3.56 (br s, 4H); 3.51 (s, 2H); 2.36 (br s, 4H); 2.29 (s, 3H); Anal. Calcd. for C$_{25}$H$_{26}$N$_6$O$_2$S.0.5H$_2$O: C, 62.09; H, 5.63; N, 17.38. Found: C, 62.20; H, 5.46; N, 17.41.

EXAMPLE 70

N-[4-(4-amino-6-methylthieno[2,3-d]pyrimidin-5-yl)-2-methoxyphenyl]benzenesulfonamide

EXAMPLE 70A 5-(4-amino-3-methoxyphenyl)-6-methylthieno[2,3-d]pyrimidin-4-amine The desired product was prepared by substituting 3-methoxy-4-nitrobenzoyl chloride for 4-nitrobenzoyl chloride in Examples 1A-1E.

EXAMPLE 70B

N-[4-(4-amino-6-methylthieno[2,3-d]pyrimidin-5-yl)-2-methoxyphenyl]benzenesulfonamide The desired product was prepared by substituting Example 70A for Example 1E in Example 2. MS(ESI(+)) m/e 427 (M+H)$^+$; $^1$H NMR (DMSO-d$_6$) δ 9.64 (s, 1H); 8.26 (s, 1H); 7.70-7.67 (m, 2H); 7.65-7.53 (m, 3H); 7.37 (d, 1H, J=7.8 Hz); 6.93-6.90 (m, 2H); 3.44 (s, 3H); 2.26 (s, 3H).

EXAMPLE 71

5-[4-(1,3-benzoxazol-2-ylamino)-3-methoxyphenyl]-6-methylthieno[2,3-d]pyrimidin-4-amine The desired product was prepared by substituting Example 70A for Example 1E in Example 3. MS(ESI (+)) m/e 404 (M+H)$^+$; $^1$H NMR (DMSO-d$_6$) δ 9.86 (s, 1H); 8.44 (d, 1H, J=8.1 Hz); 8.28 (s, 1H); 7.51-7.46 (m, 2H); 7.26-7.21 (m, 1H); 7.17-7.10 (m, 2H); 7.05 (dd, 1H, J=1.7, 8.1 Hz); 3.90 (s, 3H); 2.35 (s, 3H).

EXAMPLE 72

N-[4-(4-amino-6-methylthieno[2,3-d]pyrimidin-5-yl)-2-methoxyphenyl]-N'-(3-chlorophenyl)urea The desired product was prepared by substituting Example 70A and 3-chlorophenyl isocyanate for Example 1E and phenyl isocyanate, respectively, in Example 1F. MS(ESI(+)) m/e 440 (M+H)$^+$; $^1$H NMR (DMSO-d$_6$) δ 9.60 (s, 1H); 8.45 (s, 1H); 8.29 (d, J=8.1 Hz, 1H); 8.27 (s, 1H); 7.76 (t, J=2.0 Hz, 1H); 7.32 (t, J=8.1 Hz, 1H); 7.26-7.22 (m, 1H); 7.06-7.01 (m, 2H); 6.93 (dd, J=1.7, 8.1 Hz, 1H); 3.92 (s, 3H); 2.33 (s, 3H).

EXAMPLE 73

N-[4-(4-amino-6-methylthieno[2,3-d]pyrimidin-5-yl)-2-methoxyphenyl]-N'-(4-methylphenyl)urea The desired product was prepared by substituting Example 70A and 4-methylphenyl isocyanate for Example 1E and phenyl isocyanate, respectively, in Example 1F. MS(ESI(+)) m/e 420 (M+H)$^+$; $^1$H NMR (DMSO-d$_6$) δ 9.29 (s, 1H); 8.37 (s, 1H); 8.31 (d, 1H, J=8.1 Hz); 8.26 (s, 1H); 7.35 (d, 2H, J=8.5 Hz); 7.10 (d, 2H, J=8.1 Hz); 7.03 (d, 1H, J=2.0 Hz); 6.93-6.89 (m, 1H); 3.91 (s, 3H); 2.32 (s, 3H); 2.25 (s, 3H).

EXAMPLE 74

N-[4-(4-amino-6-methylthieno[2,3-d]pyrimidin-5-yl)-2-methoxyphenyl]-N'-(3-methylphenyl)urea The desired product was prepared by substituting Example 70A and 3-methylphenyl isocyanate for Example 1E and phenyl isocyanate, respectively, in Example 1F. MS(ESI(+)) m/e 420 (M+H)$^+$; $^1$H NMR (DMSO-d$_6$) δ 9.32 (s, 1H); 8.40 (s, 1H); 8.32 (d, 1H, J=8.1 Hz); 8.27 (s, 1H); 7.33-7.31 (br s, 1H); 7.27-7.24 (m, 1H); 7.17 (t, 1H, J=7.5 Hz); 7.04 (d, 1H, J=1.7 Hz); 6.92 (dd, 1H, J=1.7, 8.2 Hz); 6.80 (d, 1H, J=7.5 Hz); 3.91 (s, 3H); 2.33 (s, 3H); 2.29 (s, 3H).

EXAMPLE 75

N-[4-(4-amino-6-methylthieno[2,3-d]pyrimidin-5-yl)-2-methoxyphenyl]-N'-(3,5-dimethylphenyl)urea The desired product was prepared by substituting Example 70A and 3,5-dimethylphenyl isocyanate for Example 1E and phenyl isocyanate, respectively, in Example 1F. MS(ESI(+)) m/e 434 (M+H)$^+$; $^1$H NMR (DMSO-d$_6$) δ 9.25 (s, 1H); 8.38 (s, 1H);8.31 (d, 2H, J=8.1 Hz); 8.27 (s, 1H); 7.10 (s, 2H); 7.03 (d, 1H, J=1.7 Hz); 6.91 (dd, 2H, J=1.7, 8.1 Hz); 6.63 (s, 1H); 3.91 (s, 3H); 2.33 (s, 3H); 2.24 (s, 6H).

EXAMPLE 76

N-[4-(4-amino-6-methylthieno[2,3-d]pyrimidin-5-yl)-2-methoxyphenyl]-2,3-dichlorobenzenesulfonamide The desired product was prepared by substituting Example 70A for and 2,3-dichlorobenzenesulfonyl chloride for Example 1E and benzenesulfonyl chloride, respectively, in Example 2. MS(ESI(+)) m/e 495 (M+H)$^+$; $^1$H NMR (DMSO-d$_6$) δ 10.03 (s, 1H); 8.26 (s, 1H); 7.91 (d, 1H, J=7.8 Hz); 7.80-7.77 (m, 1H); 7.48 (t, 1H, J=7.8 Hz); 7.33 (d, 1H, J=8.8 Hz); 6.93-6.90 (m, 2H); 3.46 (s, 3H); 2.26 (s, 3H).

EXAMPLE 77

N-[4-(4-amino-6-methylthieno[2,3-d]pyrimidin-5-yl)-2-methoxyphenyl]quinolin-2-amine A mixture of Example 70A (100 mg, 0.35 mmol) and 2-chloroquinoline (62 mg, 0.38 mmol) was heated to 200° C. under nitrogen for 20 minutes, cooled to room temperature, and partitioned between saturated NaHCO$_3$ and dichloromethane. The aqueous phase was extracted three times with dichloromethane and the combined organic extracts were dried (Na$_2$SO$_4$), filtered, and concentrated. The concentrate was triturated with diethyl ether to provide 6 mg (5%) of the desired product. MS(ESI(+)) m/e 414 (M+H)$^+$; $^1$H NMR (DMSO-d$_6$) δ 9.08 (d, 1H, J=8.2 Hz); 8.70 (s, 1H); 8.28 (s, 1H); 8.08 (d, 1H, J=8.8 Hz); 7.73 (t, 2H, J=8.8 Hz); 7.61-7.56 (m, 1H); 7.44 (d, 1H, J=9.1 Hz); 7.34-7.29 (m, 1H); 7.06 (d, 1H, J=2.0 Hz); 7.02-6.99 (m, 1H); 3.93 (s, 3H); 2.37 (s, 3H).

EXAMPLE 78

N-[4-(4-amino-6-ethylthieno[2,3-d]pyrimidin-5-yl)phenyl]-N'-(3-methylphenyl)urea

EXAMPLE 78A 5-(4-aminophenyl)-6-ethylthieno[2,3-d]pyrimidin-4-amine

The desired product was prepared by substituting n-propylmagnesium chloride for ethylmagnesium chloride in Examples 1A-1E. $^1$H NMR (DMSO-$d_6$) δ 8.22 (s, 1H); 7.00 (d, J=8.4 Hz, 2H); 6.68 (d, J=8.4 Hz, 2H); 5.39 (s, 2H); 2.63 (q, J=7.5 Hz, 2H); 1.17 (t, J=7.5 Hz, 3H).

EXAMPLE 78B

N-[4-(4-amino-6-ethylthieno[2,3-d]pyrimidin-5-yl)phenyl]-N'-(3-methylphenyl)urea The desired product was prepared substituting Example 78A and 3-methylphenyl isocyanate for Example 1E and phenyl isocyanate, respectively, in Example 1F. MS(ESI(+)) m/e 404.10 (M+H)$^+$; $^1$H NMR (DMSO-$d_6$) δ 8.84 (s, 1H); 8.64 (s, 1H); 8.24 (s, 1H); 7.62 (d, J=8.5 Hz, 2H); 7.10-7.35 (m, 5H); 6.80 (d, J=7.2 Hz, 1H); 2.62 (q, J=7.5 Hz, 2H); 2.24 (s, 3H); 1.18 (t, J=7.5 Hz, 3H).

EXAMPLE 79

N-[4-(4-amino-6-ethylthieno[2,3-d]pyrimidin-5-yl)phenyl]-N'-(2-fluoro-5-methylphenyl)urea The desired product was prepared by substituting Example 78A and 2-fluoro-5-methylphenyl isocyanate for Example 1E and phenyl isocyanate, respectively, in Example 1F. $^1$H NMR (DMSO-$d_6$) δ 9.24 (s, 1H); 8.59 (d, J=2 Hz, 1H); 8.24 (s, 1H); 8.00 (dd, J=8.1, 2.4 Hz, 1H); 7.63 (d, J=8.4 Hz, 2H); 7.32 (d, J=8.4 Hz, 2H); 7.12 (dd, J=12.0, 8.5 Hz, 1H); 6.92 (m, 1H); 3.24 (s, 3H); 2.64 (q, J=7.5 Hz, 2H); 1.19 (t, J=7.5 Hz, 3H).

EXAMPLE 80

N-[4-(4-amino-6-ethylthieno[2,3-d]pyrimidin-5-yl)phenyl]-N'-(4-methoxyphenyl)urea The desired product was prepared by substituting Example 78A and 4-methoxyphenyl isocyanate for Example 1E and phenyl isocyanate, respectively, in Example 1F. $^1$H NMR (DMSO-$d_6$) δ 8.81 (s, 1H); 8.58 (s, 1H); 8.23 (s, 1H); 7.61 (d, J=8.7 Hz, 2H); 7.38 (d, J=9.2 Hz, 2H); 7.29 (d, J=8.7 Hz, 2H); 6.88 (d, J=9.2 Hz, 2H); 3.66 (s, 3H); 2.63 (q, J=7.5 Hz, 2H); 1.18 (t, J=7.5 Hz, 3H).

EXAMPLE 81

N-[4-(4-amino-6-ethylthieno[2,3-d]pyrimidin-5-yl)phenyl]-N'-(4-chlorophenyl)urea The desired product was prepared by substituting Example 78A and 4-chlorophenyl isocyanate for Example 1E and phenyl isocyanate, respectively, in Example 1F. $^1$H NMR (DMSO-$d_6$) δ 8.93 (s, 1H); 8.90 (s, 1H); 7.62 (d, J=8.7 Hz, 2H); 7.51 (d, J=9.0 Hz, 2H); 7.20-7.40 (m, 4H); 2.63 (q, J=7.5 Hz, 2H); 1.16 (t, J=7.5 Hz, 3H).

EXAMPLE 82

N-[4-(4-amino-6-ethylthieno[2,3-d]pyrimidin-5-yl)phenyl]-N'-[4-fluoro-3-(trifluoromethyl)phenyl]urea The desired product was prepared by substituting Example 78A and 3-trifluoromethyl-4-fluorophenyl isocyanate for Example 1E and phenyl isocyanate, respectively, in Example 1F. $^1$H NMR (DMSO-$d_6$) δ 9.16 (s, 1H); 9.07 (s, 1H); 8.31 (s, 1H); 8.28 (dd, J=6.3, 2.5 Hz, 1H); 7.64 (d, J=8.4 Hz, 3H); 7.45 (t, J=9.9 Hz, 1H); 7.33 (d, J=8.4 Hz, 2H); 2.64 (q, J=7.5 Hz, 2H); 1.18 (t, J=7.5 Hz, 3H).

EXAMPLE 83

N-[4-(4-amino-6-ethylthieno[2,3-d]pyrimidin-5-yl)phenyl]-N'-(2,5-difluorophenyl)urea The desired product was prepared by substituting Example 78A and 2,5-difluorophenyl isocyanate for Example 1E and phenyl isocyanate, respectively, in Example 1F. $^1$H NMR (DMSO-$d_6$) δ 9.38 (s, 1H); 8.83 (s, 1H); 8.32 (s, 1H); 8.0-8.10 (m, 1H); 7.62 (d, J=8.4 Hz, 2H); 7.35 (d, J=8.4 Hz, 2H); 7.26 (m, 1H); 6.8-6.90 (m, 1H); 2.63 (q, J=7.5 Hz, 2H); 1.18 (t, J=7.5 Hz, 3H).

EXAMPLE 84

N-[4-(4-amino-6-ethylthieno[2,3-d]pyrimidin-5-yl)phenyl]-N'-(2-fluorophenyl)urea The desired product was prepared by substituting Example 78A and 2-fluorophenyl isocyanate for Example 1E and phenyl isocyanate, respectively, in Example 1F. $^1$H NMR (DMSO-$d_6$) δ 9.30 (s, 1H); 8.62 (d, J=2.7 Hz, 1H); 8.32 (s, 1H); 8.17 (dt, J=8.7, 1.5 Hz, 1H); 7.63 (d, J=8.4 Hz, 2H); 7.35 (d, J=8.4 Hz, 2H); 7.0-7.32 (m, 3H); 2.66 (q, J=7.5 Hz, 2H); 1.98 (t, J=7.5 Hz, 3H).

EXAMPLE 85

N-[4-(4-amino-6-ethylthieno[2,3-d]pyrimidin-5-yl)phenyl]-N'-(2,4-difluorophenyl)urea The desired product was prepared by substituting Example 78A and 2,4-difluorophenyl isocyanate for Example 1E and phenyl isocyanate, respectively, in Example 1F. $^1$H NMR (DMSO-$d_6$) δ 9.25 (s, 1H); 8.60 (d, J=2.0 Hz, 1H); 8.32 (s, 1H); 8.00-8.15 (m, 1H); 7.62 (d, J=8.4 Hz, 2H); 7.25-8.00 (m, 3H); 7.00-7.16 (m, 1H); 2.63 (q, J=7.5 Hz, 2H); 1.98 (t, J=7,5 Hz, 3H).

EXAMPLE 86

N-[4-(4-amino-6-ethylthieno[2,3-d]pyrimidin-5-yl)phenyl]-N'-(2,6-difluorophenyl)urea The desired product was prepared by substituting Example 78A and 2,6-difluorophenyl isocyanate for Example 1E and phenyl isocyanate, respectively, in Example 1F. $^1$H NMR (DMSO-$d_6$) δ 9.22 (s, 1H); 8.32 (s, 1H); 8.22 (s, 1H); 7.63 (d, J=8.4 Hz, 2H); 7.22-7.40 (m, 3H); 7.10-7.20 (m, 2H); 2.62 (q, J=7.5 Hz, 2H); 1.98 (t, J=7.5 Hz, 3H).

EXAMPLE 87

N-[4-(4-amino-6-ethylthieno[2,3-d]pyrimidin-5-yl)phenyl]-N'-(3-methoxyphenyl)urea The desired product was prepared by substituting Example 78A and 3-methoxyphenyl isocyanate for Example 1E and phenyl isocyanate, respectively, in Example 1F. $^1$H NMR (DMSO-d$_6$) δ 8.95 (s, 1H); 8.80 (s, 1H); 8.32 (s, 1H); 7.62 (d, J=8.4 Hz, 2H); 7.32 (d, J=8.4 Hz, 2H); 7.12-7.22 (m, 2H); 6.90-7.00 (m, 1H); 6.50-6.60 (m, 1H); 3.75 (s, 3H); 2.62 (q, J=7.5 Hz, 2H); 1.98 (t, J=7.5 Hz, 3H).

EXAMPLE 88

N-[4-(4-amino-6-ethylthieno[2,3-d]pyrimidin-5-yl)phenyl]-N'-[3-(trifluoromethyl)phenyl]urea The desired product was prepared by substituting Example 78A and 3-trifluoromethylphenyl isocyanate for Example 1E and phenyl isocyanate, respectively, in Example 1F. $^1$H NMR (DMSO-d$_6$) δ 9.18 (s, 1H); 9.06 (s, 1H); 8.32 (s, 1H); 8.02 (s, 1H); 7.50-7.70 (m, 4H); 7.32 (d, J=8.4 Hz, 3H); 2.62 (q, J=7.5 Hz, 2H); 1.98 (t, J=7.5 Hz, 3H).

EXAMPLE 89

N-[4-(4-amino-6-ethylthieno[2,3-d]pyrimidin-5-yl)phenyl]-N'-(2-methoxyphenyl)urea The desired product was prepared by substituting Example 78A and 2-methoxyphenyl isocyanate for Example 1E and phenyl isocyanate, respectively, in Example 1F. $^1$H NMR (DMSO-d$_6$) δ 9.58 (s, 1H); 8.30 (s, 2H); 8.17 (dd, J=9.0, 1.5 Hz, 1H); 7.62 (d, J=8.4 Hz, 2H); 7.32 (d, J=8.4 Hz, 2H); 6.80-7.10 (m, 3H); 3.92 (s, 3H); 2.62 (q, J=7.5 Hz, 2H); 1.98 (t, J=7.5 Hz, 3H).

EXAMPLE 90

N-[4-(4-amino-6-ethylthieno[2,3-d]pyrimidin-5-yl)phenyl]-N'-(3-bromophenyl)urea

The desired product was prepared by substituting Example 78A and 3-bromophenyl isocyanate for Example 1E and phenyl isocyanate, respectively, in Example 1F. $^1$H NMR (DMSO-d$_6$) δ 9.04 (s, 1H); 9.01 (s, 1H); 8.35 (s, 1H); 7.88 (t, J=1.8 Hz, 1H); 7.62 (d, J=8.4 Hz, 2H); 7.10-7.40 (m, 5H); 2.62 (q, J=7.5 Hz, 2H); 1.98 (t, J=7.5 Hz, 3H).

EXAMPLE 91

N-[4-(4-amino-6-ethylthieno[2,3-d]pyrimidin-5-yl)phenyl]-N'-[4-(trifluoromethyl)phenyl]urea The desired product was prepared by substituting Example 78A and 4-trifluoromethylphenyl isocyanate for Example 1E and phenyl isocyanate, respectively, in Example 1F. $^1$H NMR (DMSO-d$_6$) δ 9.22 (s, 1H); 9.03 (s, 1H); 8.35 (s, 1H); 7.60-7.80 (m, 6H); 7.37 (d, J=8.4 Hz, 2H); 2.62 (q, J=7.5 Hz, 2H); 1.98 (t, J=7.5 Hz, 3H).

EXAMPLE 92

5-[4-(1,3-benzoxazol-2-ylamino)phenyl]-6-ethylthieno[2,3-d]pyrimidin-4-amine

The desired product was prepared by substituting Example 78A for Example 1E in Example 3. $^1$H NMR (DMSO-d$_6$) δ 10.90 (s, 1H); 8.28 (s, 1H); 7.96 (d, J=8.4 Hz, 2H); 7.50 (dd, J=12, 7.4 Hz, 2H); 7.42 (d, J=8.4 Hz, 2H); 7.10-7.30 (m, 2H); 2.62 (q, J=7.5 Hz, 2H); 1.98 (t, J=7.5 Hz, 3H).

EXAMPLE 93

N-[4-(4-amino-6-ethylthieno[2,3-d]pyrimidin-5-yl)phenyl]benzamide

The desired product was prepared by substituting Example 78A for Example 1E in Example 4. m.p. 213-214° C.; $^1$H NMR (DMSO-d$_6$) δ 10.46 (s, 1H); 8.26 (s, 1H); 7.98 (d, J=8.4 Hz, 4H); 7.50-7.70 (m, 3H); 7.40 (d, J=8.4 Hz, 2H); 2.66 (q, J=7.5 Hz, 2H); 1.17 (t, J=7.5 Hz, 3H).

EXAMPLE 94

N-[4-(4-amino-6-ethylthieno[2,3-d]pyrimidin-5-yl)phenyl]benzenesulfonamide

The desired product was prepared by substituting Example 78A for Example 1E in Example 2. m.p. 209-210° C.; $^1$H NMR (DMSO-d$_6$) δ 10.44 (s, 1H); 8.22 (s, 1H); 7.70-7.80 (m, 2H); 7.50-7.70 (m, 3H); 7.10-7.30 (m, 4H); 2.56 (q, J=7.5 Hz, 2H); 1.04 (t, J=7.5 Hz, 3H).

EXAMPLE 95

N-[4-(4-amino-6-ethylthieno[2,3-d]pyrimidin-5-yl)phenyl]-2-(3-methylphenyl)acetamide The desired product was prepared by substituting Example 78A and 3-methylphenylacetyl chloride for Example 1E and benzoyl chloride, respectively, in Example 4. $^1$H NMR (DMSO-d$_6$) 10.36 (s, 1H); 8.26 (s, 1H); 7.78 (d, J=9.0 Hz, 2H); 7.33 (d, J=9.0 Hz, 2H); 7.00-7.30 (m, 4H); 3.63 (s, 2H); 2.62 (q, J=7.5 Hz, 2H); 2.31 (s, 3H); 1.14 (t, J=7.5 Hz, 3H).

EXAMPLE 96

3-(4-nitrophenyl)isothiazolo[5,4-d]pyrimidin-4-amine

EXAMPLE 96A

2-[hydroxy(4-nitrophenyl)methylene]malononitrile

A 0° C. solution of 4-nitrobenzoyl chloride (24.12 g, 130 mmol) and malononitrile (8.60 g, 130 mmol) in dichloromethane (200 mL) was treated with PhCH$_2$N(CH$_2$CH$_3$)$_3$Cl (3.0 g), treated dropwise with 10N NaOH (30 mL), stirred at 0° C. for 1 hour, and filtered. The filter cake was washed with dichloromethane and diethyl ether, dissolved in 5% HCl, and extracted with ethyl acetate. The extract was dried (MgSO$_4$), filtered, and concentrated. The concentrate was recrystallized from ethyl acetate/hexanes to provide 23 g of the desired product. MS(ESI(−)) m/e 214 (M−H)⁻.

EXAMPLE 96B

2-[chloro(4-nitrophenyl)methylene]malononitrile

A mixture of $PCl_5$ (16.6 g, 80 mmol) in dichloromethane (500 mL) was added dropwise to a suspension of Example 96A (8.6 g, 40 mmol) in dichloromethane (80 mL). The resulting mixture was heated to reflux for 20 hours, cooled to room temperature, and concentrated. The residue was dissolved in a minimal amount of dichloromethane and filtered through a plug of silica gel. The plug was washed with dichloromethane and the filtrate was concentrated. The concentrate was recrystallized from dichloromethane/hexanes to provide 5.4 g (57% yield) of the desired product. $R_f$=0.7 (5% methanol/dichloromethane).

EXAMPLE 96C

2-[amino(4-nitrophenyl)methylene]malononitrile

A suspension of Example 96B (5.4 g) in ethanol (100 mL) at room temperature was treated dropwise with concentrated $NH_4OH$ (100 mL), stirred for 4 hours, poured into ice water, and filtered. The filter cake was dried to provide 4.7 g (93% yield) the desired product. MS(ESI(−)) m/e 213 (M−H)⁻.

EXAMPLE 96D (2Z)-3-amino-2-cyano-3-(4-nitrophenyl)prop-2-enethioamide

A suspension of Example 96C (2.1 g, 9.8 mmol) and 90% diethyl dithiophosphate (1.8 mL, 10.8 mmol) in ethanol (15 mL) and water (15 mL) was heated to reflux for 24 hours, cooled to room temperature, poured into ice water (300 mL), and filtered. The filter cake was dried to provide 2.3 g (95% yield) of the desired product. MS(ESI(−)) m/e 247 (M−H)⁻.

EXAMPLE 96E 5-amino-3-(4-nitrophenyl)isothiazole-4-carbonitrile

A suspension of Example 96D (23 g, 9.26 mmol) in ethanol (100 mL) was treated with 31% $H_2O_2$ (2 mL, 1.85 mmol), stirred at room temperature overnight, poured into ice water, and filtered. The filter cake was washed with water and dried to provide 2.2 g (96% yield) of the desired product. MS(ESI(−)) m/e 245 (M−H)⁻.

EXAMPLE 96F 3-(4-nitrophenyl)isothiazolo[5,4-d]pyrimidin-4-amine

A mixture of Example 96E (200 mg) in formamide (5 mL) in a capped vial was heated to 210° C. in a Smith microwave oven at 300W for 25 minutes, poured into water, and filtered. The filter cake was dried to provide 2.02 g (84% yield) of the desired product. MS(ESI(+)) m/e 274 (M+H)⁺.

EXAMPLE 97

3-(4-aminophenyl)isothiazolo[5,4-d]pyrimidin-4-amine

A mixture of Example 96F (0.95 g, 3.5 mmol), iron (0.78 g, 13.9 mmol), and $NH_4Cl$ (0.19 g, 3.5 mmol) in 9:1 ethanol/water (80 mL) was heated to 60° C. for 4 hours, cooled to room temperature, and filtered through a pad of diatomaceous earth (Celite®). The pad was washed with THF and the filtrate was concentrated. The concentrate was suspended in water and filtered. The filter cake was washed with water and dried to provide 0.82 g (97% yield) of the desired product.

EXAMPLE 98

N-[4-(4-aminoisothiazolo[5,4-d]pyrimidin-3-yl)phenyl]-N'-[3-(trifluoromethyl)phenyl]urea The desired product was prepared by substituting Example 97 and 3-trifluoromethylphenyl isocyanate for Example 1E and phenyl isocyanate, respectively, in Example 1F. MS(ESI (−)) m/e 429 (M−H)⁻; ¹H NMR (DMSO-$d_6$) δ 9.18 (s, 1H); 9.12 (s, 1H); 8.46 (s, 1H); 8.04 (s, 1H); 7.50-7.80 (m, 6H); 7.35 (d, 1H, J=8.4 Hz).

EXAMPLE 99

N-[4-(4-aminoisothiazolo[5,4-d]pyrimidin-3-yl)phenyl]-N'-(3-methylphenyl)urea

The desired product was prepared by substituting Example 97 and 3-methylphenyl isocyanate for Example 1E and phenyl isocyanate, respectively, in Example 1F. MS(ESI(−)) m/e 375 (M−H)⁻; ¹H NMR (DMSO-$d_6$) δ 8.80 (s, 1H); 8.65 (s, 1H); 8.44 (s, 1H); 7.50-7.80 (m, 4H); 7.10-7.40 (m, 3H); 6.80 (d, J=8.4 Hz, 1H); 2.28 (s, 3H).

EXAMPLE 100

N-[4-(4-aminoisothiazolo[5,4-d]pyrimidin-3-yl)phenyl]-N'-(3-chlorophenyl)urea

The desired product was prepared by substituting Example 97 and 3-chlorophenyl isocyanate for Example 1E and phenyl isocyanate, respectively, in Example 1F. MS(ESI(−)) m/e 395 (M−H)⁻; ¹H NMR (DMSO-$d_6$) δ 9.08 (s, 1H); 9.00 (s, 1H); 8.42 (s, 1H); 7.50-8.00 (m, 5H); 7.20-7.40 (m, 2H); 7.00-7.10 (m, 1H).

EXAMPLE 101

N-[4-(4-aminoisothiazolo[5,4-d]pyrimidin-3-yl)phenyl]-N'-(3-ethylphenyl)urea

The desired product was prepared by substituting Example 97 and 3-ethylphenyl isocyanate for Example 1E and phenyl isocyanate, respectively, in Example 1F. MS(ESI(+)) m/e 391 (M+H)⁺; ¹H NMR (DMSO-$d_6$) δ 8.98 (s, 1H); 8.72 (s, 1H); 8.45 (s, 1H); 7.50-7.80 (m, 4H); 7.10-7.40 (m, 3H); 6.84 (d, 1H); 2.58 (q, J=7.2 Hz, 2H); 1.18 (t, J=7.2 Hz, 3H); Anal. Calcd. for $C_{20}H_{18}N_6OS \cdot 0.7H_2O$: C, 59.60; H, 4.85; N, 20.85. Found: C, 60.07; H, 4.65; N, 20.34.

EXAMPLE 102

3-(4-phenoxyphenyl)isothiazolo[5,4-d]pyrimidin-4-amine

EXAMPLE 102A

2-[amino(4-phenoxyphenyl)methylene]malononitrile

The desired product was prepared by substituting 4-phenoxybenzoyl chloride for 4-nitrobenzoyl chloride in Examples 96A-C.

EXAMPLE 102B (2E)-3-amino-2-cyano-3-(4-phenoxyphenyl)prop-2-enethioamide

A solution of Example 102A (1.6 g, 6.12 mmol) in pyridine (10 mL) was treated with triethylamine (0.76 mL, 5.5 mmol) and heated to 80° C. $H_2S$ gas was bubbled through the solution for 4 hours, the mixture was cooled to room temperature, and partitioned between water and ethyl acetate. The organic phase was dried ($MgSO_4$), filtered, and concentrated. The concentrate was purified by flash column chromatography on silica gel with 5% ethyl acetate/hexanes to provide 1.4 g (77% yield) of the desired product. MS(DCI/$NH_3$) m/e 296 $(M+H)^+$.

EXAMPLE 102C 3-(4-phenoxyphenyl)isothiazolo[5,4-d]pyrimidin-4-amine

The desired product was prepared by substituting Example 102B for Example 96D in Example 96E and Example 96F. MS(ESI(+)) m/e 321 $(M+H)^+$; $^1H$ NMR (DMSO-$d_6$) δ 8.45 (s, 1H); 7.60-7.70 (m, 2H); 7.40-7.50 (m, 2H); 7.10-7.30 (m, 5H).

EXAMPLE 103

N-[4-(4-aminoisothiazolo[5,4-d]pyrimidin-3-yl)phenyl]-N'-[2-fluoro-5-(trifluoromethyl)phenyl]urea The desired product was prepared by substituting Example 97 and 2-fluoro-5-trifluoromethylphenyl isocyanate for Example 1E and phenyl isocyanate, respectively, in Example 1F. MS(ESI(+)) m/e 449 $(M+H)^+$; $^1H$ NMR (DMSO-$d_6$) δ 9.44 (s, 1H); 9.00 (d, J=3 Hz, 1H); 9.63 (dd, J=7.2, 2.0 Hz, 1H); 8.47 (s, 1H); 7.30-7.80 (m, 6H).

EXAMPLE 104

N-{4-[4-amino-6-(2-hydroxyethyl)thieno[2,3-d]pyrimidin-5-yl]phenyl}-N'-(3-methylphenyl)urea

EXAMPLE 104A

4-{[tert-butyl(dimethyl)silyl]oxy}-1-(4-nitrophenyl)butan-1-one

A mixture of Zn—Cu couple (2.68 g, 41.3 mmol) and tert-butyl(3-iodopropoxy)dimethylsilane (8.26 g, 27.5 mmol) in benzene (55 mL) and DMF (3.6 mL) was stirred vigorously at room temperature for 1 hour, heated to 60° C. for 4 hours, cooled to room temperature, and treated with a solution of 4-nitrobenzoyl chloride (3.4 g, 18.3 mmol) and $(Ph_3P)_4Pd$ (0.847 g, 0.73 mmol) in benzene (36 mL) by cannula. The mixture was stirred for 1 hour, filtered through diatomaceous earth (Celite™), and partitioned between saturated $NH_4Cl$ and ethyl acetate. The aqueous phase was extracted three times with ethyl acetate and the combined extracts were washed with water and brine, dried ($Na_2SO_4$), filtered, and concentrated. The concentrate was purified by flash column chromatography on silica gel with 5% ethyl acetate/hexanes to provide 2.81 g of the desired product. MS(ESI(−)) m/e 322 $(M–H)^-$.

EXAMPLE 104B 5-(4-aminophenyl)-6-(2-{[tert-butyl(dimethyl)silyl]oxy}ethyl)thieno[2,3-d]pyrimidin-4-amine The desired product was prepared by substituting Example 104A for Example 1A in Examples 1B-1E.

EXAMPLE 104C

N-{4-[4-amino-6-(2-{[tert-butyl(dimethyl)silyl]oxy}ethyl)thieno[2,3-d]pyrimidin-5-yl]phenyl}-N'-(3-methylphenyl)urea The desired product was prepared by substituting Example 104B and 3-methylphenyl isocyanate for phenyl isocyanate and Example 1E, respectively, in Example 1F.

EXAMPLE 104D

N-{4-[4-amino-6-(2-hydroxyethyl)thieno[2,3-d]pyrimidin-5-yl]phenyl}-N'-(3-methylphenyl)urea A solution of Example 104C (92 mg, 0.17 mmol) in THF (5 mL) at room temperature was treated dropwise with a solution of 1M TBAF in THF (0.3 mL, 0.3 mmol), stirred overnight, and partitioned between water and ethyl acetate. The aqueous phase was extracted three times with ethyl acetate and the combined extracts were dried ($Na_2SO_4$), filtered, and concentrated. The concentrate was recrystallized from dichloromethane to provide 54 mg (75%) of the desired product. MS(ESI) m/e 420 $(M+H)^+$, 418 $(M–H)^-$; $^1H$ NMR (300 MHz, DMSO-$d_6$) δ 2.29 (s, 3H); 2.75-2.80 (t, J=6.6 Hz, 2H); 3.54-3.60 (m, 2H); 4.85-4.89 (t, J=5.7 Hz, 1H); 6.79-6.82 (d, J=7.5 Hz, 2H); 7.14-7.19 (t, J=7.5 Hz, 1H); 7.24-7.32 (m, 4H); 7.61-7.63 (d, J=8.4 Hz, 2H); 8.26 (s, 1H); 8.67 (s, 1H); 8.87 (s, 1H); Anal. Calcd. for $C_{22}H_{21}N_5O_2S \cdot 0.4H_2O$: C, 61.93; H, 5.15; N, 16.41. Found: C, 61.80; H, 4.95; N, 16.31.

EXAMPLE 105

N-{4-[4-amino-6-(2-hydroxyethyl)thieno[2,3-d]pyrimidin-5-yl]phenyl}-N'-(4-methylphenyl)urea The desired product was prepared by substituting Example 104B and 4-methylphenyl isocyanate for Example 1E and phenyl isocyanate, respectively, in Example 1F, then substituting the product for Example 104C in Example 104D. MS(ESI(+)) m/e 420 $(M+H)^+$; $^1H$ NMR (300 MHz, DMSO-$d_6$) δ 2.25 (s, 3H); 2.75-2.80 (m, 2H); 3.52-3.63 (m, 2H); 4.53-4.54 (m, 1H); 7.08-7.11 (d, J=7.8 Hz, 2H); 7.29-7.32 (d, J=8.7 Hz, 2H); 7.3-7.37 (d, J=8.1 Hz, 2H); 7.60-7.63 (d, J=8.4 Hz, 2H); 8.26 (s, 1H); 8.64 (s, 1H); 8.84 (s, 1H).

EXAMPLE 106

N-{4-[4-amino-6-(2-hydroxyethyl)thieno[2,3-d]pyrimidin-5-yl]phenyl}-N'-(3-chlorophenyl)urea The desired product was prepared by substituting Example 104B and 3-chlorophenyl isocyanate for Example 1E and phenyl isocyanate, respectively, in Example 1F, then substituting the resulting product for Example 104C in Example 104D. MS(ESI(+)) m/e 440, 442 (M+H)$^+$; $^1$H NMR (300 MHz, DMSO-d$_6$) δ 2.74-2.79 (t, J=6.3 Hz, 2H); 3.54-3.60 (m, 2H); 4.86-4.89 (t, J=5.1 Hz, 1H); 7.02-7.05 (td, J=2.4, 6.3 Hz, 1H); 7.30-7.35 (m, 4H); 7.61-7.64 (d, J=8.4 Hz, 2H); 7.73-7.74 (m, 1H); 8.27 (s, 1H); 8.98 (s, 2H).

EXAMPLE 107

N-{4-[4-amino-6-(2-hydroxyethyl)thieno[2,3-d]pyrimidin-5-yl]phenyl}-N'-(2-methylphenyl)urea The desired product was prepared by substituting Example 104B and 2-methylphenyl isocyanate for Example 1E and phenyl isocyanate, respectively, in Example 1F, then substituting the resulting product for Example 104C in Example 104D. m.p. 159-162° C.; MS(ESI(+)) m/e 420 (M+H)$^+$; $^1$H NMR (300 MHz, DMSO-d$_6$) δ 2.26 (s, 3H); 2.75-2.79 (t, J=6.9 Hz, 2H); 3.54-3.60 (m, 2H); 4.86-4.89 (t, J=5.4 Hz, 1H); 6.94-6.99 (t, J=7.2 Hz, 1H); 7.13-7.21 (m, 2H); 7.29-7.33 (d, J=9 Hz, 2H); 7.62-7.65 (d, J=8.4 Hz, 2H); 7.81-7.83 (d, J=9.2 Hz, 1H); 8.01 (s, 1H); 8.26 (s, 1H); 9.23 (s, 1H).

EXAMPLE 108

5-(4-aminophenyl)-6-(2-methoxyethyl)thieno[2,3-d]pyrimidin-4-amine

The desired product was prepared by substituting 1-iodo-3-methoxypropane for tert-butyl (3-iodopropoxy)dimethylsilane in Examples 104A and 104B. m.p. 144-146° C.

EXAMPLE 109

N-{4-[4-amino-6-(2-methoxyethyl)thieno[2,3-d]pyrimidin-5-yl]phenyl}-N'-(3-methylphenyl)urea The desired product was prepared by substituting Example 108 and 3-methylphenyl isocyanate for Example 1E and phenyl isocyanate, respectively, in Example 1F. MS(ESI(+)) m/e 434 (M+H)$^+$; $^1$H NMR (300 MHz, DMSO-d$_6$) δ 2.29 (s, 3H); 2.83-2.87 (t, J=6.6 Hz, 2H); 3.22 (s, 3H); 3.47-3.52 (t, J=6.6 Hz, 2H); 6.79-6.82 (d, J=7.5 Hz, 2H); 7.14-7.19 (t, J=7.5 Hz, 1H); 7.24-7.32 (m, 4H); 7.61-7.64 (d, J=9 Hz, 2H); 8.27 (s, 1H); 8.67 (s, 1H); 8.87 (s, 1H).

EXAMPLE 110

N-{4-[4-amino-6-(2-methoxyethyl)thieno[2,3-d]pyrimidin-5-yl]phenyl}-N'-(4-methylphenyl)urea The desired product was prepared by substituting Example 108 and 4-methylphenyl isocyanate for Example 1E and phenyl isocyanate, respectively, in Example 1F. m.p. 128-132° C.; MS(ESI(+)) m/e 434 (M+H)$^+$; $^1$H NMR (300 MHz, DMSO-d$_6$) δ 2.25 (s, 3H); 2.83-2.87 (t, J=6.6 Hz, 2H); 3.22 (s, 3H); 3.47-3.52 (t, J=6.6 Hz, 2H); 7.09-7.11 (d, J=8.1 Hz, 2H); 7.28-7.32 (d, J=8.4 Hz, 2H); 7.34-7.37 (d, J=8.4 Hz, 2H); 7.60-7.63 (d, J=9 Hz, 2H); 8.27 (s, 1H); 8.64 (s, 1H); 8.84 (s, 1H).

EXAMPLE 111

N-{4-[4-amino-6-(2-methoxyethyl)thieno[2,3-d]pyrimidin-5-yl]phenyl}benzenesulfonamide The desired product was prepared by substituting Example 108 for Example 1E in Example 2. m.p. 206-208° C.; MS(ESI(+)) m/e 441 (M+H)$^+$; $^1$H NMR (300 MHz, DMSO-d$_6$) δ 2.72-2.76 (t, J=6.3 Hz, 2H); 3.14 (s, 3H); 3.39-3.44 (t, J=6.6 Hz, 2H); 7.19-7.28 (m, 4H); 7.57-7.59 (m, 3H); 7.74-7.77 (d, J=6.9 Hz, 2H); 8.26 (s, 1H); 10.49 (s, 1H).

EXAMPLE 112

N-{4-[4-amino-6-(2-methoxyethyl)thieno[2,3-d]pyrimidin-5-yl]phenyl}-2-(3-methylphenyl)acetamide The desired product was prepared by substituting Example 108 and 3-methylphenylacetyl chloride for Example 1E and benzoyl chloride, respectively, in Example 4. m.p. 200-202° C.; MS(ESI(+)) m/e 433 (M+H)$^+$; $^1$H NMR (300 MHz, DMSO-d$_6$) δ 2.31 (s, 3H); 2.80-2.84 (t, J=6.6 Hz, 2H); 3.21 (s, 3H); 3.45-3.49 (t, J=6.6 Hz, 2H); 3.64 (s, 2H); 7.06-7.08 (d, J=7.5 Hz, 1H); 7.13-7.25 (m, 3H); 7.31-7.34 (d, J=8.4 Hz, 2H); 7.75-7.78 (d, J=9 Hz, 2H); 8.26 (s, 1H); 10.36 (s, 1H).

EXAMPLE 113

N-{4-[4-amino-6-(2-methoxyethyl)thieno[2,3-d]pyrimidin-5-yl]phenyl}benzamide

The desired product was prepared by substituting Example 108 for Example 1E in Example 4. m.p. 200-202° C.; MS(ESI(+)) m/e 405 (M+H)$^+$; $^1$H NMR (300 MHz, DMSO-d$_6$) δ 2.84-2.88 (t, J=6.3 Hz, 2H); 3.23 (s, 3H); 3.48-3.53 (d, J=6.3 Hz, 2H); 7.38-7.41 (d, J=8.4 Hz, 2H); 7.54-7.62 (m, 3H); 7.96-7.99 (m, 4H); 8.28 (s, 1H); 10.47 (s, 1H); Anal. Calcd. for C$_{22}$H$_{20}$N$_4$O$_2$S.0.4H$_2$O: C, 64.18; H, 5.09; N, 13.61. Found: C, 64.28; H, 4.96; N, 13.34.

EXAMPLE 114

N-{4-[4-amino-6-(2-methoxyethyl)thieno[2,3-d]pyrimidin-5-yl]phenyl}-N'-[3-(trifluoromethyl)phenyl]urea The desired product was prepared by substituting Example 108 and 3-(trifluoromethyl)phenyl isocyanate for Example 1E and phenyl isocyanate, respectively, in Example 1F. MS(ESI(+)) m/e 488 (M+H)$^+$; $^1$H NMR (300 MHz, DMSO-d$_6$) δ 2.83-2.87 (t, J=6.3 Hz, 2H); 3.22 (s, 3H); 3.48-3.52 (d, J=6.3 Hz, 2H); 7.31-7.34 (d, J=9 Hz, 3H); 7.51-7.56 (t, J=8.1 Hz, 1H); 7.62-7.67 (m, 3H); 8.04 (s, 1H); 8.27 (s, 1H); 9.02 (s, 1H); 9.14 (s, 1H); Anal. Calcd. for C$_{23}$H$_{20}$N$_5$O$_2$SF$_3$: C, 56.67; H, 4.13; N, 14.37. Found: C, 56.40; H, 4.18; N, 14.15.

EXAMPLE 115

N-{4-[4-amino-6-(pyridin-3-ylmethyl)thieno[2,3-d]pyrimidin-5-yl]phenyl}-N'-(3-methylphenyl)urea

EXAMPLE 115A 1-(4-nitrophenyl)-3-pyridin-3-ylpropan-1-one

The desired product was prepared by substituting 3-pyridinecarboxaldehyde for 4-pyridinecarboxaldehyde in Example 14A, then substituting the resulting product for Example 14A in Example 14B. MS(ESI(+)) m/e 257 (M+H)$^+$.

EXAMPLE 115B

N-{4-[4-amino-6-(pyridin-3-ylmethyl)thieno[2,3-d]pyrimidin-5-yl]phenyl}-N'-(3-methylphenyl)urea The desired product was prepared by substituting Example 115A and 3-methylphenyl isocyanate for Example 1A and phenyl isocyanate, respectively, in Examples 1B-1F. MS(ESI(+)) m/e 467 (M+H)$^+$; $^1$H NMR (300 MHz, DMSO-d$_6$) δ 2.29 (s, 3H); 4.04 (s, 2H); 6.79-6.82 (d, J=7.5 Hz, 1H); 7.14-7.19 (t, J=7.8 Hz, 1H); 7.24-7.33 (m, 3H); 7.35-7.37 (d, J=8.4 Hz, 2H); 7.53-7.56 (td, J=2.1 Hz, 7.8 Hz, 1H); 7.63-7.66 (d, J=8.4 Hz, 2H); 8.27 (s, 1H); 8.34-8.35 (d, J=1.8 Hz, 1H); 8.42-8.44 (dd, J=1.5, 4.8 Hz, 1H); 8.67 (s, 1H); 8.89 (s, 1H); Anal. Calcd. for C$_{26}$H$_{22}$N$_6$OS.0.2H$_2$O: C, 66.42; H, 4.80; N, 17.87. Found: C, 66.38; H, 4.80; N, 17.92.

EXAMPLE 116

N-{4-[4-amino-6-(pyridin-3-ylmethyl)thieno[2,3-d]pyrimidin-5-yl]phenyl}-N'-(4-methylphenyl)urea The desired product was prepared by substituting Example 115A and 4-methylphenyl isocyanate for Example 1A and phenyl isocyanate, respectively, in Examples 1B-1F. mp: 220-223° C.; MS(ESI(+)) m/e 467 (M+H)$^+$; $^1$H NMR (300 MHz, DMSO-d$_6$) δ 2.25 (s, 3H); 4.04 (s, 2H); 7.08-7.11 (d, J=8.1 Hz, 2H); 7.29-7.37 (m, 5H); 7.52-7.56 (td, J=2.1, 7.8 Hz, 1H); 7.62-7.65 (d, J=8.7 Hz, 2H); 8.27 (s, 1H); 8.34-8.35 (d, J=2.1 Hz, 1H); 8.41-8.43 (dd, J=1.2, 4.5 Hz, 1H); 8.64 (s, 1H); 8.86 (s, 1H); Anal. Calcd. for C$_{26}$H$_{22}$N$_6$OS: C, 66.93; H, 4.75; N, 18.01. Found: C, 66.69; H, 4.65; N, 18.05.

EXAMPLE 117

N-{4-[4-amino-6-(pyridin-3-ylmethyl)thieno[2,3-d]pyrimidin-5-yl]phenyl}-N'-(3-chlorophenyl)urea The desired product was prepared by substituting Example 115A and 3-chlorophenyl isocyanate for Example 1A and phenyl isocyanate, respectively, in Examples 1B-1F. m.p. 169-172° C.; MS(ESI(+)) m/e 487 (M+H)$^+$; $^1$H NMR (300 MHz, DMSO-d$_6$) δ 4.04 (s, 2H); 7.02-7.06 (td, 1H, J=2.4, 6.6 Hz); 7.29-7.35(m, 3H); 7.36-7.39 (d, 2H, J=8.7 Hz); 7.52-7.56 (td, 1H, J=1.8, 7.8 Hz); 7.64-7.67 (d, 2H, J=8.7 Hz); 7.72-7.73 (m, 1H); 8.27 (s, 1H); 8.34-8.35 (d, 1H, J=2.4 Hz); 8.41-8.44 (dd, 1H, J=1.5, 4.8 Hz); 8.97 (s, 1H); 8.99 (s, 1H); Anal. Calcd. for C$_{25}$H$_{19}$N$_6$OSCl0.4H$_2$O: C, 60.76; H, 4.04; N, 17.01. Found: C, 60.81; H, 4.04; N, 16.77.

EXAMPLE 118

N-[4-(4-amino-6-methylthieno[2,3-d]pyrimidin-5-yl)phenyl]-N'-(3-fluorophenyl)urea The desired product was prepared by substituting 3-fluorophenyl isocyanate for phenyl isocyanate in Example 1F. MS(ESI(+)) m/e 394 (M+H)$^+$; $^1$H NMR (300 MHz, DMSO-d$_6$) δ 9.00 (s, 1H); 8.97 (s, 1H); 8.27 (s, 1H); 7.64 (d, J=8.4 Hz, 2H); 7.51 (dt, J=12.0 Hz, 2.1 Hz, 1H); 7.36-7.28 (m, 3H); 7.15 (d, J=8.1 Hz, 1H); 6.80 (td, J=8.1 Hz, 2.4 Hz); 2.30 (s, 3H).

EXAMPLE 119

N-[4-(4-amino-6-methylthieno[2,3-d]pyrimidin-5-yl)phenyl]-N'-(4-fluorophenyl)urea The desired product was prepared by substituting 4-fluorophenyl isocyanate for phenyl isocyanate in Example 1F. MS(ESI(+)) m/e 394 (M+H)$^+$; $^1$H NMR(300 MHz, DMSO-d$_6$) δ 8.89 (s, 1H); 8.79 (s, 1H); 8.26 (s, 1H); 7.63 (d, J=8.4 Hz, 2H); 7.51-7.46 (m, 2H); 7.31 (d, J=8.4 Hz, 2H); 7.14 (t, J=9.0 Hz, 2H); 2.29 (s, 3H).

EXAMPLE 120

N-[4-(4-amino-6-methylthieno[2,3-d]pyrimidin-5-yl)phenyl]-N'-(3,5-difluorophenyl)urea The desired product was prepared by substituting 3,5-difluorophenyl isocyanate for phenyl isocyanate in Example 1F. MS(ESI(+)) m/e 412 (M+H)$^+$; $^1$H NMR (300 MHz, DMSO-d$_6$) δ 9.17 (s, 1H); 9.07 (s, 1H); 8.27 (s, 1H); 7.64 (d, J=8.7 Hz, 2H); 7.33 (d, J=8.7 Hz, 2H); 7.22 (dd, J=9.9 Hz, 2.4 Hz, 2H); 6.81 (tt, J=9.3 Hz, 2.4 Hz); 2.29 (s, 3H).

EXAMPLE 121

N-[4-(4-amino-6-methylthieno[2,3-d]pyrimidin-5-yl)phenyl]-N'-(3-phenoxyphenyl)urea The desired product was prepared by substituting 3-phenoxyphenyl isocyanate for phenyl isocyanate in Example 1F. MS(ESI(+)) m/e 466 (M+H)$^+$; $^1$H NMR (300 MHz, DMSO-d$_6$) δ 8.88 (s, 1H); 8.86 (s, 1H); 8.26 (s, 1H); 7.60 (d, J=9.0 Hz, 2H); 7.41 (t, J=8.1 Hz, 2H); 7.32-7.26 (m, 4H); 7.16 (t, J=7.5 Hz, 2H); 7.05 (d, J=7.5 Hz, 2H); 6.63 (dd, J=8.1 Hz, 2.4 Hz, 1H); 2.29 (s, 3H).

EXAMPLE 122

N-[4-(4-aminothieno[2,3-d]pyrimidin-5-yl)phenyl]-N'-(3-phenoxyphenyl)urea

The desired product was prepared by substituting Example 58D and 3-phenoxyphenyl isocyanate for Example 1E and phenyl isocyanate, respectively, in Example 1F. MS(ESI(+)) m/e 454 (M+H)$^+$; $^1$H NMR (300 MHz, DMSO-d$_6$) δ 8.88 (s, 1H); 8.87 (s, 1H); 8.33 (s, 1H); 7.58 (d, J=8.4 Hz, 2H); 7.44-7.36 (m, 5H); 7.32-7.26 (m, 2H); 7.20-7.12 (m, 2H); 7.07-7.03 (m, 2H); 6.65-6.61 (m, 1H).

EXAMPLE 123

N-[4-(4-amino-6-methylthieno[2,3-d]pyrimidin-5-yl)phenyl]-N'-(3-cyanophenyl)urea The desired product was prepared by substituting 3-cyanophenyl isocyanate for phenyl isocyanate in Example 1F. MS(ESI(+)) m/e 401 (M+H)$^+$; $^1$H NMR (300 MHz, DMSO-d$_6$) δ 9.11 (s, 1H); 9.06 (s, 1H); 8.27 (s, 1H); 8.00 (s, 1H); 7.70 (d, J=8.1 Hz, 1H); 7.65 (d, J=8.4 Hz, 2H); 7.52 (t, J=8.1 Hz, 1H); 7.44 (d, J=8.1 Hz, 2H); 7.33 (d, J=8.4 Hz, 2H); 2.30 (s, 3H).

EXAMPLE 124

N-[4-(4-amino-6-methylthieno[2,3-d]pyrimidin-5-yl)phenyl]-N'-[4-(trifluoromethyl)phenyl]urea The desired product was prepared by substituting 4-(trifluoromethyl)phenyl isocyanate for phenyl isocyanate in Example 1F. MS(ESI(+)) m/e 444 (M+H)$^+$; $^1$H NMR (300 MHz, DMSO-d$_6$) δ 9.29 (s, 1H); 9.02 (s, 1H); 8.27 (s, 1H); 7.71-7.63 (m, 6H); 7.33 (d, J=8.7 Hz, 2H); 2.30 (s, 3H).

EXAMPLE 125

N-[4-(4-aminothieno[2,3-d]pyrimidin-5-yl)phenyl]-N'-(3-chlorophenyl)urea

The desired product was prepared by substituting Example 58D and 3-chlorophenyl isocyanate for Example 1E and phenyl isocyanate, respectively, in Example 1F. MS(ESI(+)) m/e 396 (M+H)$^+$; $^1$H NMR (300 MHz, DMSO-d$_6$) δ 8.96 (s, 1H); 8.34 (s, 1H); 7.73 (s, 1H); 7.61 (d, J=8.4 Hz, 2H); 7.44 (s, 1H); 7.40 (d, J=8.4 Hz, 2H); 7.32-7.28 (m, 2H); 7.03 dt, J=2.1 Hz, 1H).

EXAMPLE 126

N-[4-(4-aminothieno[2,3-d]pyrimidin-5-yl)phenyl]-N'-[3-(trifluoromethyl)phenyl]urea The desired product was prepared by substituting Example 58D and 3-(trifluoromethyl)phenyl isocyanate for Example 1E and phenyl isocyanate, respectively, in Example 1F. MS(ESI(+)) m/e 428 (M−H)$^−$; $^1$H NMR (300 MHz, DMSO-d$_6$) δ 9.18 (s, 1H); 9.06 (s, 1H); 8.36 (s, 1H); 8.03 (s, 1H); 7.65-7.58 (m, 3H); 7.53 (t, J=7.8 Hz, 1H); 7.46 (s, 1H); 7.41 (d, J=8.4 Hz, 2H); 7.33 (d, J=7.8 Hz, 1H).

EXAMPLE 127

N-[4-(4-aminothieno[2,3-d]pyrimidin-5-yl)phenyl]-N'-[2-fluoro-5-(trifluoromethyl)phenyl]urea A suspension of Example 58D (0.04 g, 0.165 mmol) in dichloromethane (3 mL) under nitrogen was cooled to 0° C., treated with 1-fluoro-2-isocyanato-4-(trifluoromethyl)benzene (0.024 mL, 0.165 mmol), and stirred overnight while gradually warming to room temperature. The suspension was filtered and the filter cake was dried in a vacuum oven to provide 0.056 g of the desired product. MS(ESI(+)) m/e 448 (M+H)$^+$; $^1$H NMR (300 MHz, DMSO-d$_6$) δ 9.40 (s, 1H); 8.98 (d, J=2.7 Hz, 1H); 8.63 (dd, J=7.2 Hz, 2.1 Hz, 1H); 8.35 (s, 1H); 7.63 (d, J=8.7 Hz, 2H); 7.55-7.39 (m, 5H).

EXAMPLE 128

N-[4-(4-amino-6-bromothieno[2,3-d]pyrimidin-5-yl)phenyl]-N-[2-fluoro-5-(trifluoromethyl)phenyl]urea The desired product was prepared by substituting Example 61B and 2-fluoro-5-(trifluoromethyl)phenyl isocyanate for Example 1E and phenyl isocyanate, respectively, in Example 1F. MS(ESI(+)) m/e 526, 528 (M+H)$^+$; $^1$H NMR (300 MHz, DMSO-d$_6$) δ 9.43 (s, 1H); 9.00 (d, J=2.7 Hz, 1H); 8.63 (dd, J=7.5 Hz, 2.1 Hz, 1H); 8.33 (s, 1H); 7,68 (d, J=8.7 Hz, 2H); 7.52 (t, J=8.7 Hz, 1H); 7.45-7.37 (m, 3H).

EXAMPLE 129

N-[4-(4-amino-6-bromothieno[2,3-d]pyrimidin-5-yl)phenyl]-N'-[3-(trifluoromethyl)phenyl]urea The desired product was prepared by substituting Example 61B and 3-(trifluoromethyl)phenyl isocyanate for Example 1E and phenyl isocyanate, respectively, in Example 1F. MS(ESI(+)) m/e 508, 510 (M+H)$^+$; $^1$H NMR (300 MHz, DMSO-d$_6$) δ 9.15 (s, 1H); 9.06 (s, 1H); 8.33 (s, 1H); 8.04 (s, 1H); 7.68 (d, J=8.7 Hz, 2H); 7.61 (d, J=8.1 Hz, 1H); 7.53 (t, J=8.1 Hz, 1H); 7.38 (d, J=8.7 Hz, 2H); 7.33 (d, J=8.1 Hz, 1H).

EXAMPLE 130

N-[4-(4-amino-6-bromothieno[2,3-d]pyrimidin-5-yl)phenyl]-N'-(3-chlorophenyl)urea The desired product was prepared by substituting Example 61B and 3-chlorophenyl isocyanate for Example 1E and phenyl isocyanate, respectively, in Example 1F. MS(ESI(+)) m/e 474, 476 (M+H)$^+$; $^1$H NMR (300 MHz, DMSO-d$_6$) δ 9.02 (s, 1H); 8.99 (s, 1H); 8.33 (s, 1H); 7.73 (s, 1H); 7.66 (d, J=8.7 Hz, 2H); 7.37 (d, J=8.7 Hz, 2H); 7.33-7.30 (m, 2H); 7.04 (dt, J=6.6 Hz, 2.4 Hz, 1H).

EXAMPLE 131

N-[4-(4-amino-6-methylthieno[2,3-d]pyrimidin-5-yl)phenyl]-1H-indole-2-carboxamide The desired compound was prepared by substituting 1H-indole-2-carbonyl chloride for benzoyl chloride in Example 4. MS(ESI(+)) m/e 400 (M+H)$^+$; $^1$H NMR(300 MHz, DMSO-d$_6$) δ 11.80 (s, 1H); 10.40 (s, 1H); 8.28 (s, 1H); 8.01 (d, J=8.7 Hz, 2H); 7.70 (d, J=7.5 Hz, 1H); 7.48 (d, J=7.5 Hz, 2H); 7.42 (d, J=8.7 Hz, 2H); 7.24 (t, J=7.5 Hz, 1H); 7.08 (t, J=7.5 Hz, 1H); 2.32 (s, 3H).

EXAMPLE 132 phenyl N-[4-(4-amino-6-methylthieno[2,3-d]pyrimidin-5-yl)phenyl]-N'-cyanoimidocarbamate A solution of Example 1E (0.4 g, 1.56 mmol) and diphenyl cyanocarbonimidate (0.372 g, 1.56 mmol) in DMF (10 mL) was heated to 90° C. for 2 days, cooled to room temperature, quenched with water, and filtered. The filter cake was suspended in ethanol and filtered. The filtrate was concentrated and purified by flash column chromatography on silica gel with 5 to 8% methanol/dichloromethane to provide the desired product (150 mg). MS(ESI(+)) m/e 401(M+H)$^+$; $^1$H NMR (300 MHz, DMSO-d$_6$) δ 11.06 (s, 1H); 8.27 (s, 1H); 7.67 (d, J=8.4 Hz, 2H); 7.50-7.43 (m, 4H); 7.36-7.29 (m, 3H); 2.29 (s, 3H).

EXAMPLE 133

N-[4-(4-amino-6-methylthieno[2,3-d]pyrimidin-5-yl) phenyl]-N''-cyano-N'-(3-methylphenyl)guanidine A solution of Example 132 (40 mg, 0.01 mmol) and 3-methylaniline (0.012 mL, 0.01 mmol) in DMF (1 mL) was heated in a Smith synthesizer microwave to 180° C. for 22 minutes and partitioned between water and ethyl acetate. The aqueous phase was extracted three times with ethyl acetate and the combined extracts were washed with water and brine, dried (Na$_2$SO$_4$), filtered and concentrated. The concentrate was purified by flash column chromatography on silica gel with 8% methanol/dichloromethane to provide the desired product (15 mg). MS(ESI(+)) m/e 414 (M+H)$^+$; $^1$H NMR (300 MHz, DMSO-d$_6$) δ 9.65 (s, 1H); 9.48 (s, 1H); 8.26 (s, 1H); 7.45 (d, J=8.4 Hz, 2H); 7.35 (d, J=8.4 Hz, 2H); 7.23 (t, J=7.8 Hz, 1H); 7.15-7.10 (m, 2H); 6.96 (d, J=7.8 Hz, 1H); 2.29 (s, 6H).

EXAMPLE 134

N-[4-(4-amino-6-methylthieno[2,3-d]pyrimidin-5-yl) phenyl]-N-methyl-N'-(3-methylphenyl)urea

EXAMPLE 134A 6-methyl-5-[4-(methylamino)phenyl]thieno[2,3-d] pyrimidin-4-amine A −20° C. suspension of Example 1E (400 mg, 1.56 mmol) in dichloromethane (10 mL) and THF (10 mL) was treated with formic acetic anhydride (0.135 mL, 1.7 mmol), stirred for 1 hour, and concentrated. The concentrate was suspended in benzene (50 mL), treated with 65% Red-Al in toluene (2.4 mL, 7.8 mmol), stirred at room temperature for 20 minutes than heated to reflux for 6 hours. The reaction was cooled to room temperature and partitioned between Rochelle's salt and ethyl acetate. The aqueous phase was extracted three times with ethyl acetate and the combined extracts were washed with water and brine, dried (Na$_2$SO$_4$), filtered, and concentrated. The concentrate was purified by flash column chromatography on silica gel with 7% methanol/dichloromethane to provide the desired product (86 mg). MS(ESI(+)) m/e 271 (M+H)$^+$.

EXAMPLE 134B

N-[4-(4-amino-6-methylthieno[2,3-d]pyrimidin-5-yl) phenyl]-N-methyl-N'-(3-methylphenyl)urea The desired product was prepared by substituting Example 134A and 3-methylphenyl isocyanate for Example 1E and phenyl isocyanate, respectively, in Example 1F. MS(ESI(+)) m/e 404 (M+H)$^+$; $^1$H NMR (300 MHz, DMSO-d$_6$) δ 8.32 (s, 1H); 8.28 (s, 1H); 7.47 (d, J=8.4 Hz, 2H); 7.40 (d, J=8.4 Hz, 2H); 7.29-7.23 (m, 2H); 7.12 (t, J=7.8 Hz, 1H); 6.78 (d, J=7.8 Hz, 1H); 3.33 (s, 3H); 2.33 (s, 3H); 2.25 (s, 3H).

EXAMPLE 135

N-[4-(4-amino-6-methylthieno[2,3-d]pyrimidin-5-yl) phenyl]-N-methyl-N'-[3-(trifluoromethyl)phenyl] urea The desired product was prepared by substituting Example 134A and 3-(trifluoromethyl)phenyl isocyanate for Example 1E and phenyl isocyanate, respectively, in Example 1F. MS(ESI(+)) m/e 458 (M+H)$^+$; $^1$H NMR (300 MHz, DMSO-d$_6$) δ 8.73 (s, 1H); 8.28 (s, 1H); 7.97 (s, 1H); 7.69 (d, J=7.5 Hz, 1H); 7.53-7.40 (m, 5H); 7.30 (d, J=7.5 Hz, 1H); 2.33 (s, 3H).

EXAMPLE 136

N-[4-(4-amino-6-methylthieno[2,3-d]pyrimidin-5-yl) phenyl]-N'-(3-methylphenyl)thiourea A solution of Example 1E (60 mg, 0.23 mmol) and 3-methylphenyl isothiocyanate in DMF (2 mL) was stirred at room temperature, for 48 hours, quenched with water, and filtered. The filter cake was dried to provide the desired product (75 mg, 80%). MS(ESI(+)) m/e 406 (M+H)$^+$; $^1$H NMR (300 MHz, DMSO-d$_6$) δ 9.96 (s, 1H); 9.84 (s, 1H); 8.27 (s, 1H); 7.65 (d, J=8.4 Hz, 2H); 7.35 (d, J=8.4 Hz, 2H); 7.30-7.18 (m, 3H); 6.97 (d, J=6.9 Hz, 1H); 2.30 (s, 6H).

EXAMPLE 137

N-{4-[4-amino-6-(2-methoxyethyl)thieno[2,3-d] pyrimidin-5-yl]phenyl}-N'-(2-methylphenyl)urea The desired product was prepared by substituting Example 108 and 2-methylphenyl isocyanate for Example 1E and phenyl isocyanate, respectively, in Example 1F. m.p. 217-219° C.; MS(ESI(+)) m/e 434 (M+H)$^+$; $^1$H NMR (300 MHz, DMSO-d$_6$) δ 2.26 (s, 3H); 2.83-2.87 (t, J=6.6 Hz, 2H); 3.22 (s, 3H); 3.48-3.52 (t, J=6.6 Hz, 2H); 6.95-6.99 (t, J=7.5 Hz, 1H); 7.14-7.21 (m, 2H); 7.29-7.32 (d, J=8.7 Hz, 2H); 7.63-7.65 (d, J=8.7 Hz, 2H); 7.81-7.83 (d, J=8.1 Hz, 1H); 8.01 (s, 1H); 8.27 (s, 1H); 9.23 (s, 1H).

EXAMPLE 138

N-{4-[4-amino-6-(pyridin-3-ylmethyl)thieno[2,3-d] pyrimidin-5-yl]phenyl}-N'-[3-(trifluoromethyl)phenyl]urea The desired product was prepared by substituting Example 115A and 3-trifluoromethylphenyl isocyanate for Example 1A and phenyl isocyanate, respectively, in Examples 1B-1F. MS(ESI(+)) m/e 521 (M+H)$^+$; $^1$H NMR (300 MHz, DMSO-d$_6$) δ 4.04 (s, 2H); 7.29-7.34 (m, 2H); 7.37-7.39 (d, 2H, J=8.4 Hz); 7.50-7.62 (m, 3H); 7.65-7.68 (d, 2H, J=8.7 Hz); 8.03 (s, 1H); 8.28 (s, 1H); 8.34-8.35 (d, 1H, J=2.1 Hz); 8.42-8.44 (dd, 1H, J=1.5, 4.8 Hz); 9.05 (s, 1H); 9.15 (s, 1H).

EXAMPLE 139

N-{4-[4-amino-6-(2-hydroxyethyl)thieno[2,3-d]pyrimidin-5-yl]phenyl}-N'-[3-(trifluoromethyl)phenyl] urea The desired product was prepared by substituting Example 104B and 3-trifluoromethylphenyl isocyanate for Example 1E and phenyl isocyanate, respectively, in Example 1F, then substituting the resulting product for Example 104C in Example 104D. m.p. 155-158° C.; MS(ESI(+)) m/e 474 (M+H)$^+$; $^1$H NMR (300 MHz, DMSO-d$_6$) δ 2.75-2.79 (t, J=6.9 Hz, 2H); 3.56-3.57 (m, 2H); 4.85-4.90 (m, 1H); 7.32-7.34 (d, J=8.7 Hz, 3H); 7.50-7.59 (m, 2H); 7.62-7.65 (d, J=9 Hz, 2H); 8.03 (s, 1H); 8.27 (s, 1H); 9.03 (s, 1H); 9.15 (s, 1H).

EXAMPLE 140

N-{4-[4-amino-6-(2-methoxyethyl)thieno[2,3-d]pyrimidin-5-yl]phenyl}-N'-[2-fluoro-5-(trifluoromethyl)phenyl]urea The desired product was prepared by substituting Example 108 and 2-fluoro-5-trifluoromethylphenyl isocyanate for Example 1E and phenyl isocyanate, respectively, in Example 1F. m.p. 209-211° C.; MS(ESI(+)) m/e 506 (M+H)$^+$; $^1$H NMR (300 MHz, DMSO-d$_6$) δ 2.83-2.87 (t, J=6 Hz, 2H); 3.22 (s, 3H); 3.48-3.52 (t, J=6.3 Hz, 2H); 7.33-7.36 (d, J=8.7 Hz, 2H); 7.40-7.55 (m, 2H); 7.63-7.66 (d, J=8.4 Hz, 2H); 8.27 (s, 1H); 8.62-8.65 (dd, J=2.1, 6.9 Hz, 1H); 8.98-8.99 (d, J=2.7 Hz, 1H); 9.39 (s, 1H).

EXAMPLE 141

N-{4-[4-amino-6-(pyridin-3-ylmethyl)thieno[2,3-d]pyrimidin-5-yl]phenyl}-N'-[2-fluoro-5-(trifluoromethyl)phenyl]urea The desired product was prepared by substituting Example 115A and 3-trifluoromethylphenyl isocyanate for Example 1A and phenyl isocyanate, respectively, in Examples 1B-1F. MS(ESI(+)) m/e 539 (M+H)$^+$; $^1$H NMR (300 MHz, DMSO-d$_6$) δ 4.04 (s, 2H); 7.29-7.33 (m, 1H); 7.38-7.44 (m, 3H); 7.48-7.57 (m, 2H); 7.65-7.68 (d, J=8.7 Hz, 2H); 8.28 (s, 1H); 8.34-8.35 (d, J=1.8 Hz, 1H); 8.42-8.44 (dd, J=1.8, 4.8 Hz, 1H); 8.62-8,65 (dd, J=2.4, 7.5 Hz, 1H); 8.98-8.99 (d, J=2.7 Hz, 1H); 9.41 (s, 1H).

EXAMPLE 142

N-{4-[4-amino-6-(pyridin-4-ylmethyl)thieno[2,3-d]pyrimidin-5-yl]phenyl}-N'-[3-(trifluoromethyl)phenyl]urea The desired product was prepared by substituting Example 14B and 3-trifluoromethylphenyl isocyanate for Example 1A and phenyl isocyanate, respectively, in Examples 1B-1F. m.p. 162-166° C.; MS(ESI(+)) m/e 521 (M+H)$^{30}$; $^1$H NMR (300 MHz, DMSO-d$_6$) δ 4.04 (s, 2H); 7.15-7.16 (m, 2H); 7.32-7.37 (m, 3H); 7.50-7.66 (m, 4H); 8.03 (s, 1H); 8.29 (s, 1H); 8.38-8.54 (m, 2H); 9.03 (s, 1H); 9.14 (s, 1H).

EXAMPLE 143

N-[4-(4-amino-6-methylthieno[2,3-d]pyrimidin-5-yl)-2-chlorophenyl]-N'-(3-methylphenyl)urea

EXAMPLE 143A 5-(3-chlorophenyl)-6-methylthieno[2,3-d]pyrimidin-4-amine

The desired product was prepared by substituting 1-(3-chlorophenyl)propan-1-one for Example 1A in Examples 1B-1D. MS(ESI(+)) m/e 276, 278 (M+H)$^+$.

EXAMPLE 143B 5-(3-chloro-4-nitrophenyl)-6-methylthieno[2,3-d]pyrimidin-4-amine A 0° C. suspension of Example 143A (2.13 g, 7.74 mmol) in concentrated H$_2$SO$_4$ (15 mL) was treated dropwise over 3 minutes with a solution of fuming nitric acid (0.38 mL) in concentrated H$_2$SO$_4$ (5 mL). The mixture was stirred for 30 minutes while warming to room temperature, poured onto ice, adjusted to pH 7 with solid Na$_2$CO$_3$, and extracted with ethyl acetate. The extract was dried (MgSO$_4$), filtered, and concentrated to provide 2.31 g (93% yield) of the desired product. MS(ESI(+)) m/e 321 (M+H)$^+$.

EXAMPLE 143C 5-(4-amino-3-chlorophenyl)-6-methylthieno[2,3-d]pyrimidin-4-amine The desired product was prepared by substituting Example 143B for Example 1D in Example 1E. MS(ESI(+)) m/e 276, 278 (M+H)$^+$.

EXAMPLE 143D

N-[4-(4-amino-6-methylthieno[2,3-d]pyrimidin-5-yl)-2-chlorophenyl]-N'-(3-methylphenyl)urea The desired product was prepared by substituting Example 143C and 3-methylphenyl isocyanate for Example 1E and phenyl isocyanate, respectively, in Example 1F. MS (ESI(+)) m/e 424.0 (M+H)$^+$; $^1$H NMR (300 MHz, DMSO-d$_6$) δ 2.30 (s, 3H); 2.31 (s, 3H); 6.83 (d, J=7.5 Hz, 1H); 7.19 (t, J=7.5 Hz, 1H); 7.24-7.29 (m, 1H); 7.32-7.34 (m, 2H); 7.53 (d, J=2.0 Hz, 1H); 8.27 (s, 1H); 8.37 (d, J=8.5 Hz, 1H); 8.46 (s, 1H); 9.45 (s, 1H).

EXAMPLE 144

N-[4-(4-amino-6-methylthieno[2,3-d]pyrimidin-5-yl)-2-chlorophenyl]-N'-(3,5-dimethylphenyl)urea The desired product was prepared by substituting Example 143C and 3,5-dimethylphenyl isocyanate for Example 1E and phenyl isocyanate, respectively, in Example 1F. MS (ESI(+)) m/e 438.1 (M+H)$^+$; $^1$H NMR (400 MHz, DMSO-d$_6$) δ 2.25 (s, 6H); 2.31 (s, 3H); 6.66 (s, 1H); 7.11 (s, 2H); 7.31 (dd, J=8.4, 2.0 Hz, 1H); 7.52 (d, J=2.1Hz, 1H); 8.28 (s, 1H); 8.37 (d, J=8.6 Hz, 1H); 8.44 (s, 1H); 9.37 (s, 1H).

EXAMPLE 145

N-[4-(4-amino-6-methylthieno[2,3-d]pyrimidin-5-yl)-2-chlorophenyl]-N'-[2-fluoro-5-(trifluoromethyl)phenyl]urea The desired product was prepared by substituting Example 143C and 2-fluoro-5-trifluoromethylphenyl isocyanate for Example 1E and phenyl isocyanate, respectively, in Example 1F. MS (ESI(+)) m/e 496.0 (M+H)$^+$; $^1$H NMR (400 MHz, DMSO-d$_6$) δ 2.32 (s, 3H); 7.34 (dd, J=8.6, 2.1 Hz, 1H); 7.41-7.45 (m, 1H); 7.52 (d, J=10.7 Hz, 1H); 7.55 (d, J=2.1 Hz, 1H); 8.28 (s, 1H); 8.35 (d, J=8.3 Hz, 1H); 8.66 (dd, J=7.4, 2.1 Hz, 1H); 9.09 (s, 1H); 9.79 (s, 1H).

EXAMPLE 146

N-[4-(4-amino-6-methylthieno[2,3-d]pyrimidin-5-yl)-2-chlorophenyl]-N'-(3-ethylphenyl)urea The desired product was prepared by substituting Example 143C and 3-ethylphenyl isocyanate for Example 1E and phenyl isocyanate, respectively, in Example 1F. MS (ESI(+)) m/e 438.0 (M+H)$^+$; $^1$H NMR (300 MHz, DMSO-d$_6$) δ 1.19 (t, J=7.6 Hz, 3H); 2.31 (s, 3H); 2.60 (q, J=7.6 Hz, 2H); 6.87 (d, J=7.1 Hz, 1H); 7.22 (t, J=7.8 Hz, 1H); 7.28-7.37 (m, 3H); 7.53 (d, J=2.0 Hz, 1H); 8.27 (s, 1H); 8.37 (d, J=8.5 Hz, 1H); 8.46 (s, 1H); 9.47 (s, 1H.

EXAMPLE 147

N-[4-(4-amino-6-methylthieno[2,3-d]pyrimidin-5-yl)-2-chlorophenyl]-N'-[3-(trifluoromethyl)phenyl]urea The desired product was prepared by substituting Example 143C and 3-trifluoromethylphenyl isocyanate for Example 1E and phenyl isocyanate, respectively, in Example 1F. MS (ESI(+)) m/e 478.0 (M+H)$^+$; $^1$H NMR (300 MHz, DMSO-d$_6$) δ 2.31 (s, 3H); 7.34 (dd, J=8.5, 2.0 Hz, 1H); 7.35-7.37 (m, 1H); 7.53-7.60 (m, 3H); 8.06 (s, 1H); 8.28 (s, 1H); 8.35 (d, J=8.5 Hz, 1H); 8.55 (s, 1H); 9.86 (s, 1H).

EXAMPLE 148

N-[4-(4-amino-6-methylthieno[2,3-d]pyrimidin-5-yl)-2-chlorophenyl]-N'-[4-fluoro-3-(trifluoromethyl)phenyl]urea The desired product was prepared by substituting Example 143C and 4-fluoro-3-trifluromethylphenyl isocyanate for Example 1E and phenyl isocyanate, respectively, in Example 1F. $^1$H NMR (300 MHz, DMSO-d$_6$) δ 2.31 (s, 3H); 7.34 (dd, J=8.5, 2.0 Hz, 1H); 7.48 (app t, J=9.2 Hz, 1H); 7.55 (d, J=2.0 Hz, 1H); 7.64 (ddd, J=8.7, 3.8, 3.0 Hz, 1H); 8.04 (dd, J=6.3, 2.5 Hz, 1H); 8.28 (s, 1H); 8.33 (d, J=8.5 Hz, 1H); 8.53 (s, 1H); 9.84 (s, 1H).

EXAMPLE 149

N-[4-(4-amino-6-methylthieno[2,3-d]pyrimidin-5-yl)-2-chlorophenyl]-N'-(3-fluorophenyl)urea The desired product was prepared by substituting Example 143C and 3-fluorophenyl isocyanate for Example 1E and phenyl isocyanate, respectively, in Example 1F. MS (ESI(+)) m/e 428.0 (M+H)$^+$; $^1$H NMR (300 MHz, DMSO-d$_6$) δ 2.31 (s, 3H); 6.83 (td, J=8.2, 2.2 Hz, 1H); 7.13 (ddd, J=8.2, 1.9, 0.7 Hz, 1H); 7.31-7.36 (m, 2H); 7.53 (dt, J=12.2, 2.4 Hz, 1H); 7.54 (d, J=2.0 Hz, 1H); 8.28 (s, 1H); 8.34 (d, J=8.5 Hz, 1H); 8.53 (s, 1H); 9.73 (s, 1H).

EXAMPLE 150

N-[4-(4-amino-6-methylthieno[2,3-d]pyrimidin-5-yl)-2-chlorophenyl]-N'-(3,4-dimethylphenyl)urea The desired product was prepared by substituting Example 143C and 3,4-dimethylphenyl isocyanate for Example 1E and phenyl isocyanate, respectively, in Example 1F. MS (ESI(+)) m/e 438.1 (M+H)$^+$; $^1$H NMR (300 MHz, DMSO-d$_6$) δ 2.17 (s, 3H); 2.21 (s, 3H); 2.31 (s, 3H); 7.06 (d, J=8.1 Hz, 1H); 7.20 (dd, J=8.5, 2.4 Hz, 1H); 7.26 (d, J=2.0 Hz, 1H); 7.31 (dd, J=8.5, 2.0 Hz, 1H); 7.52 (d, J=2.0 Hz, 1H); 8.27 (s, 1H); 8.37 (d, J=8.5 Hz, 1H); 8.42 (s, 1H); 9.35 (s, 1H).

EXAMPLE 151

N-[4-(4-amino-6-methylthieno[2,3-d]pyrimidin-5-yl)-2-chlorophenyl]-N'-(3-chlorophenyl)urea The desired product was prepared by substituting Example 143C and 3-chlorophenyl isocyanate for Example 1E and phenyl isocyanate, respectively, in Example 1F. MS (ESI(+)) m/e 443.9 (M+H)$^+$; $^1$H NMR (300 MHz, DMSO-d$_6$) δ 2.31 (s, 3H); 7.07 (ddd, J=7.7, 2.1, 1.0 Hz, 1H); 7.26 (ddd, J=8.3, 2.0, 1.2 Hz, 1H); 7.33 (d, J=8.1 Hz, 1H); 7.35 (dd, J=8.5, 5.1 Hz, 1H); 7.54 (d, J=2.0 Hz, 1H); 7.76 (t, J=2.0 Hz, 1H); 8.27 (s, 1H); 8.34 (d, J=8.5 Hz, 1H); 8.53 (s, 1H); 9.70 (s, 1H).

EXAMPLE 152

N-[4-(4-amino-6-methylthieno[2,3-d]pyrimidin-5-yl)-2-fluorophenyl]-N'-(3-methylphenyl)urea

EXAMPLE 152A 5-(4-amino-3-fluorophenyl)-6-methylthieno[2,3-d]pyrimidin-4-amine The desired product was prepared by substituting 1-(3-fluorophenyl)propan-1-one for 1-(3-chlorophenyl)propan-1-one) in Examples 143A-C. MS (ESI(+)) m/e 275 (M+H)$^+$.

EXAMPLE 152B

N-[4-(4-amino-6-methylthieno[2,3-d]pyrimidin-5-yl)-2-fluorophenyl]-N'-(3-methylphenyl)urea The desired product was prepared by substituting Example 152A and 3-methylphenyl isocyanate for Example 1E and phenyl isocyanate, respectively, in Example 1F. MS (ESI(+)) m/e 408.1 (M+H)$^+$; $^1$H NMR (300 MHz, DMSO-d$_6$) δ 2.30 (s, 3H); 2.31 (s, 3H); 6.83 (d, J=7.1 Hz, 1H); 7.15-7.37 (m, 5H); 8.27 (s, 1H); 8.35 (t, J=8.5 Hz, 1H); 8.73 (s, 1H); 9.08 (s, 1H).

EXAMPLE 153

N-[4-(4-amino-6-methylthieno[2,3-d]pyrimidin-5-yl)-2-fluorophenyl]-N'-(3,5-dimethylphenyl)urea The desired product was prepared by substituting Example 152A and 3,5-dimethylphenyl isocyanate for Example 1E and phenyl isocyanate, respectively, in Example 1F. MS (ESI(+)) m/e 422.1 (M+H)$^+$; $^1$H NMR (300 MHz, DMSO-d$_6$) δ 2.25 (s, 6H); 2.31 (s, 3H); 6.65 (s, 1H); 7.09 (s, 2H); 7.15 (dd, J=8.3, 1.5 Hz, 1H); 7.34 (dd, J=12.0, 1.9 Hz, 1H); 8.27 (s, 1H); 8.35 (t, J=8.5 Hz, 1H); 8.71 (d, J=2.4 Hz, 1H); 9.01 (s, 1H).

EXAMPLE 154

N-[4-(4-amino-6-methylthieno[2,3-d]pyrimidin-5-yl)-2-fluorophenyl]-N'-(3-chlorophenyl)urea The desired product was prepared by substituting Example 152A and 3-chlorophenyl isocyanate for Example 1E and phenyl isocyanate, respectively, in Example 1F. MS (ESI(+)) m/e 428.0 (M+H)+; $^1$H NMR (300 MHz, DMSO-$d_6$) δ 2.31 (s, 3H); 7.06 (ddd, J=7.8, 2.0, 1.0 Hz, 1H); 7.18 (dd, J=8.5, 1.4 Hz, 1H); 7.26 (ddd, J=8.1, 2.0, 1.4 Hz, 1H); 7.31-7.38 (m, 2H); 7.75 (t, J=2.0 Hz, 1H); 8.27 (s, 1H); 8.31 (t, J=8.5 Hz, 1H); 8.80 (d, J=2.4 Hz, 1H); 9.34 (s, 1H).

EXAMPLE 155

N-[4-(4-amino-6-methylthieno[2,3-d]pyrimidin-5-yl)-2-fluorophenyl]-N'-[3-(trifluoromethyl)phenyl]urea The desired product was prepared by substituting Example 152A and 3-trifluoromethylphenyl isocyanate for Example 1E and phenyl isocyanate, respectively, in Example 1F. MS (ESI(+)) m/e 462.1 (M+H)+; $^1$H NMR (300 MHz, DMSO-$d_6$) δ 2.31 (s, 3H); 7.18 (d, J=8.5 Hz, 1H); 7.35-7.39 (m, 2H); 7.52-7.56 (m, 2H); 8.06 (s, 1H); 8.27 (s, 1H); 8.31 (t, J=8.5 Hz, 1H); 8.83 (s, 1H); 9.49 (s, 1H).

EXAMPLE 156

N-[4-(4-amino-6-methylthieno[2,3-d]pyrimidin-5-yl)-2-fluorophenyl]-N'-(3,4-dimethylphenyl)urea The desired product was prepared by substituting Example 152A and 3,4-dimethylphenyl isocyanate for Example 1E and phenyl isocyanate, respectively, in Example 1F. MS (ESI(+)) m/e 422.1 (M+H)+; $^1$H NMR (300 MHz, DMSO-$d_6$) δ 2.17 (s, 3H); 2.21 (s, 3H); 2.31 (s, 3H); 7.05 (d, J=8.1 Hz, 1H); 7.15 (dd, J=8.7, 1.5 Hz, 1H); 7.19 (dd, J=8.1, 2.0 Hz, 1H); 7.25 (d, J=2.0 Hz, 1H); 7.33 (dd, J=11.9, 1.7 Hz, 1H); 8.27 (s, 1H); 8.35 (t, J=8.5 Hz, 1H); 8.68 (d, J=2.7 Hz, 1H); 8.98 (s, 1H).

EXAMPLE 157

N-[4-(4-amino-6-methylthieno[2,3-d]pyrimidin-5-yl)-2-fluorophenyl]-N'-(3-ethylphenyl)urea The desired product was prepared by substituting Example 152A and 3-ethylphenyl isocyanate for Example 1E and phenyl isocyanate, respectively, in Example 1F. MS (ESI(+)) m/e 422.1 (M+H)+; $^1$H NMR (300 MHz, DMSO-$d_6$) δ 1.19 (t, J=7.5 Hz, 3H); 2.31 (s, 3H); 2.59 (q, J=7.5 Hz, 2H); 6.86 (d, J=7.1 Hz, 1H); 7.16 (dd, J=8.1, 1.7 Hz, 1H); 7.21 (t, J=7.6 Hz, 1H); 7.33-7.35 (m, 1H); 7.34 (dd, J=11.7, 2.2 Hz, 1H); 8.27 (s, 1H); 8.35 (t, J=8.7 Hz, 1H); 8.72 (d, J=2.4 Hz, 1H); 9.10 (s, 1H).

EXAMPLE 158

N-[4-(4-amino-6-methylthieno[2,3-d]pyrimidin-5-yl)-2-fluorophenyl]-N'-phenylurea The desired product was prepared by substituting Example 152A for Example 1E in Example 1F. MS (ESI(+)) m/e 394.0 (M+H)+; $^1$H NMR (300 MHz, DMSO-$d_6$) δ 2.31 (s, 3H); 7.01 (m, 1H); 7.17 (dd, J=8.3, 1.5 Hz, 1H); 7.31 (t, J=8.5 Hz, 2H); 7.35 (dd, J=12.0, 1.9 Hz, 1H); 7.48 (dd, J=7.8, 1.0 Hz, 2H); 8.27 (s, 1H); 8.35 (t, J=8.5 Hz, 1H); 8.74 (d, J=2.7 Hz, 1H); 9.15 (s, 1H).

EXAMPLE 159

N-[4-(4-amino-6-methylthieno[2,3-]pyrimidin-5-yl)-2-fluorophenyl]-N'-[2-fluoro-5-(trifluoromethyl)phenyl]urea The desired product was prepared by substituting Example 152A and 2-fluoro-5-trifluoromethylphenyl isocyanate for Example 1E and phenyl isocyanate, respectively, in Example 1F. MS (ESI(+)) m/e 480.0 (M+H)+; $^1$H NMR (300 MHz, DMSO-$d_6$) δ 2.31 (s, 3H); 7.18 (dd, J=8.3, 1.5 Hz, 1H); 7.38 (dd, J=11.9, 2.0 Hz, 1H); 7.44 (dd, J=4.2, 2.2 Hz, 1H); 7.53 (dd, J=10.9, 8.8 Hz, 1H); 8.27 (s, 1H); 8.36 (t, J=8.7 Hz, 1H); 8.66 (dd, J=7.5, 2.0 Hz, 1H); 9.35 (d, J=2.0 Hz, 1H); 9.46 (d, J=2.7 Hz, 1H).

EXAMPLE 160

N-[4-(4-amino-6-methylthieno[2,3-d]pyrimidin-5-yl)-2-fluorophenyl]-N'-(3-fluorophenyl)urea The desired product was prepared by substituting Example 152A and 3-fluorophenyl isocyanate for Example 1E and phenyl isocyanate, respectively, in Example 1F. MS (ESI(+)) m/e 412.0 (M+H)+; $^1$H NMR (300 MHz, DMSO-$d_6$) δ 2.31 (s, 3H); 6.82 (tdd, J=8.5, 2.7, 0.7 Hz, 1H); 7.12 (ddd, J=8.2, 2.0, 0.7 Hz, 1H); 7.17 (ddd, J=8.5, 2.0, 0.7 Hz, 1H); 7.30-7.38 (m, 2H); 7.53 (dt, J=11.9, 2.4 Hz, 1H); 8.27 (s, 1H); 8.32 (t, J=8.5 Hz, 1H); 8.79 (d, J=2.7 Hz, 1H); 9.36 (s, 1H).

EXAMPLE 161

5-[4-(1,3-benzoxazol-2-ylamino)-3-fluorophenyl]-6-methylthieno[2,3-d]pyrimidin-4-amine The desired product was prepared by substituting Example 152A for Example 1E in Example 3. MS (ESI(+)) m/e 392.0 (M+H)+; $^1$H NMR (300 MHz, DMSO-$d_6$) δ 2.33 (s, 3H); 7.17 (td, J=7.7, 1.2 Hz, 1H); 7.22-7.31 (m, 2H); 7.40 (dd, J=11.7, 1.9 Hz, 1H); 7.50 (d, J=7.1 Hz, 1H); 7.54 (d, J=7.8 Hz, 1H); 8.28 (s, 1H); 8.51 (t, J=8.5 Hz, 1H); 10.66 (s, 1H).

EXAMPLE 162

N-[4-(4-amino-6-methylthieno[2,3-d]pyrimidin-5-yl)-2-methylphenyl]-N'-(3-chlorophenyl)urea

EXAMPLE 162A 5-(4-amino-3-methylphenyl)-6-methylthieno[2,3-d]pyrimidin-4-amine The desired product was prepared by substituting 3-methyl-4-nitrobenzoyl chloride for 4-nitrobenzoyl chloride in Examples 1A-1E. MS(ESI(+)) m/e 271 (M+H)+.

EXAMPLE 162B

N-[4-(4-amino-6-methylthieno[2,3-d]pyrimidin-5-yl)-2-methylphenyl]-N'-(3-chlorophenyl)urea The desired product was prepared by substituting Example 162A and 3-chlorophenyl isocyanate for Example 1E and phenyl isocyanate, respectively, in Example 1F. MS (ESI(+)) m/e 424.0 (M+H)$^+$; $^1$H NMR (300 MHz, DMSO-d$_6$) δ 2.30 (s, 3H); 2.32 (s, 3H); 7.04 (ddd, J=7.5, 2.0, 1.4 Hz, 1H); 7.19 (dd, J=8.3, 2.2 Hz, 1H); 7.24-7.28 (m, 2H); 7.33 (t, J=7.8 Hz, 1H); 7.77 (t, J=2.0 Hz, 1H); 8.06 (d, J=8.1 Hz, 1H); 8.15 (s, 1H); 8.26 (s, 1H); 9.33 (s, 1H).

EXAMPLE 163

N-[4-(4-amino-6-methylthieno[2,3-d]pyrimidin-5-yl)-2-methylphenyl]-N'-[3-(trifluoromethyl)phenyl]urea The desired product was prepared by substituting Example 162A and 3-trifluoromethylphenyl isocyanate for Example 1E and phenyl isocyanate, respectively, in Example 1F. MS (ESI(+)) m/e 458.1 (M+H)$^+$; $^1$H NMR (300 MHz, DMSO-d$_6$) δ 2.30 (s, 3H); 2.33 (s, 3H); 7.19 (dd, J=8.3, 1.9 Hz, 1H); 7.25 (d, J=1.7 Hz, 1H); 7.31-7.34 (m, 1H); 7.53 (t, J=8.1 Hz, 1H); 7.58 (dt, J=8.5, 1.7 Hz, 1H); 8.04-8.08 (m, 2H); 8.18 (s, 1H); 8.27 (s, 1H); 9.49 (s, 1H).

EXAMPLE 164

N-[4-(4-amino-6-methylthieno[2,3-d]pyrimidin-5-yl)-2-methylphenyl]-N'-[2-fluoro-5-(trifluoromethyl)phenyl]urea The desired product was prepared by substituting Example 162A and 2-fluoro-5-trifluoromethylphenyl isocyanate for Example 1E and phenyl isocyanate, respectively, in Example 1F. MS (ESI(+)) m/e 476.0 (M+H)$^+$; $^1$H NMR (300 MHz, DMSO-d$_6$) δ 2.30 (s, 3H); 2.34 (s, 3H); 7.20 (dd, J=8.5, 2.0 Hz, 1H); 7.26 (d, J=2.0 Hz, 1H); 7.40 (ddd, J=8.8, 4.0, 2.4 Hz, 1H); 7.52 (dd, J=10.5, 8.8 Hz, 1H); 8.10 (d, J=8.5 Hz, 1H); 8.27 (s, 1H); 8.64 (s, 1H); 8.68 (dd, J=7.6, 2.2 Hz, 1H); 9.45 (d, J=2.7 Hz, 1H).

EXAMPLE 165

N-[4-(4-aminothieno[2,3-d]pyrimidin-5-yl)-2-methoxyphenyl]-N'-(3-chlorophenyl)urea

EXAMPLE 165A 1-(3-methoxy-4-nitrophenyl)ethanone

A suspension of MgCl$_2$ (932 mg, 9.8 mmol) in toluene (13 mL) was treated with triethylamine (4.65 mL, 33.4 mmol), dimethyl malonate (1.9 mL, 16.6 mmol), stirred for 1.5 hours, and treated portionwise over 30 minutes with 3-methoxy-4-nitrobenzoyl chloride (3 g, 13.9 mmol). The reaction mixture was stirred for 45 minutes, then carefully treated with concentrated HCl (4 mL). The layers were separated and the organic phase was dried (Na$_2$SO$_4$), filtered, and concentrated. The residue was dissolved in DMSO (11.5 mL) and water (0.5 mL), heated to reflux overnight, cooled to room temperature, and partitioned between water and ethyl acetate. The organic phase was washed sequentially with saturated NaHCO$_3$, water, and brine, dried (MgSO$_4$), filtered, and concentrated to provide 1.63 g (60% yield) of the desired product. MS (ESI(-)) m/e 194 (M-H)$^-$.

EXAMPLE 165B

2-[1-(3-methoxy-4-nitrophenyl)ethylidene]malononitrile

A flask equipped with a condenser and a drying tube was charged with acetic acid (35 mL) and hexamethyldisilazane (11.2 mL, 53.1 mmol). The mixture was stirred while cooling to room temperature, treated with Example 165A (6.89 g, 35.3 mmol) and malononitrile (4.66 g, 70.5 mmol), stirred at 65° C. for 3 hour, cooled to room temperature, stirred overnight, and partitioned between water and toluene. The organic phase was washed with saturated NaHCO$_3$, water, brine, dried (MgSO$_4$), filtered, and concentrated. The concentrate was recrystallized from ethanol to provide 6.11 g (71% yield) of the desired product. MS (ESI(-)) m/e 242 (M-H)$^-$.

EXAMPLE 165C 2-amino-4-(3-methoxy-4-nitrophenyl)-3-thiophenecarbonitrile

A solution of Example 165B (6.11 g, 25.1 mmol) in THF (38 mL) was treated with sulfur powder (305 mg, 25.1 mmol) and a solution of NaHCO$_3$ (422 mg, 5 mmol) in water (12 mL). The suspension was stirred at room temperature for 4 hours and filtered to provide 4.71 g (68% yield) of the desired product. $^1$H NMR (300 MHz, DMSO-d$_6$) δ 3.98 (s, 3H); 6.85 (s, 1H); 7.28 (dd, J=8.53, 1.7 Hz, 1H); 7.40 (s, 2H); 7.48 (d, J=1.7 Hz, 1H); 7.97 (d, J=8.5 Hz, 1H).

EXAMPLE 165D 5-(4-amino-3-methoxyphenyl)thieno[2,3-d]pyrimidin-4-amine

The desired product was prepared by substituting Example 165C for Example 1C in Examples 1D-1E. MS(ESI(+)) m/e 273 (M+H)$^+$.

EXAMPLE 165E

N-[4-(4-aminothieno[2,3-d]pyrimidin-5-yl)-2-methoxyphenyl]-N'-(3-chlorophenyl)urea The desired product was prepared by substituting Example 165D and 3-chlorophenyl isocyanate for Example 1E and phenyl isocyanate, respectively, in Example 1F. MS (ESI(+)) m/e 426.0 (M+H)$^+$; $^1$H NMR (300 MHz, DMSO-d$_6$) δ 3.94 (s, 3H); 7.02 (dd, J=8.3, 2.0 Hz, 1H); 7.03 (ddd, J=7.8, 2.0, 1.3 Hz, 1H); 7.14 (d, J=2.0 Hz, 1H); 7.24 (ddd, J=8.3, 2.0, 1.3 Hz, 1H); 7.32 (t, J=7.8 Hz, 1H); 7.47 (s, 1H); 7.75 (t, J=2.0 Hz, 1H); 8.27 (d, J=8.1 Hz, 1H); 8.34 (s, 1H); 8.44 (s, 1H); 9.59 (s, 1H).

EXAMPLE 166

N-[4-(4-aminothieno[2,3-d]pyrimidin-5-yl)-2-methoxyphenyl]-N'-[3-(trifluoromethyl)phenyl]urea The desired product was prepared by substituting Example 165D and 3-trifluoromethylphenyl isocyanate for Example 1E and phenyl isocyanate, respectively, in Example 1F. MS (ESI(+)) m/e 460.0 (M+H)$^+$; $^1$H NMR (300 MHz, DMSO-d$_6$) δ 3.94 (s, 3H); 7.02 (dd, J=8.3, 1.9 Hz, 1H); 7.15 (d, J=1.7 Hz, 1H); 7.31-7.35 (m, 1H); 7.47 (s, 1H); 7.53-7.56 (m, 2H); 8.05 (s, 1H); 8.28 (d, J=8.1 Hz, 1H); 8.34 (s, 1H); 8.46 (s, 1H); 9.75 (s, 1H).

EXAMPLE 167

N-[4-(4-aminothieno[2,3-d]pyrimidin-5-yl)-2-methoxyphenyl]-N'-[2-fluoro-5-(trifluoromethyl)phenyl]urea The desired product was prepared by substituting Example 165D and 2-fluoro-5-trifluoromethylphenyl isocyanate for Example 1E and phenyl isocyanate, respectively, in Example 1F. MS (ESI(+)) m/e 478.0 (M+H)$^+$; $^1$H NMR (300 MHz, DMSO-d$_6$) δ 3.94 (s, 3H); 7.02 (dd, J=8.3, 1.9 Hz, 1H); 7.15 (d, J=1.7 Hz, 1H); 7.39 (m, 1H); 7.51 (m, 2H); 8.28 (d, J=8.5 Hz, 1H); 8.34 (s, 1H); 8.68 (dd, J=7.1, 2.0 Hz, 1H); 9.08 (s, 1H); 9.65 (d, J=2.7 Hz, 1H).

EXAMPLE 168

N-[4-(4-aminothieno[2,3-d]pyrimidin-5-yl)-2-methoxyphenyl]-N'-(2-fluoro-5-methylphenyl)urea The desired product was prepared by substituting Example 165D and 2-fluoro-5-methylphenyl isocyanate for Example 1E and phenyl isocyanate, respectively, in Example 1F. MS (ESI(+)) m/e 424.1 (M+H)$^+$; $^1$H NMR (300 MHz, DMSO-d$_6$) d 2.28 (s, 3H); 3.93 (s, 3H); 6.78-6.83 (m, 1H); 7.01 (dd, J=8.3, 1.9 Hz, 1H); 7.07-7.15 (m, 2H); 7.47 (s, 1H); 8.02 (dd, J=8.1, 2.0 Hz, 1H); 8.28 (d, J=8.5 Hz, 1H); 8.34 (s, 1H); 8.92 (s, 1H); 9.24 (d, J=2.0 Hz, 1H).

EXAMPLE 169

N-[4-(4-aminothieno[2,3-d]pyrimidin-5-yl)-2-methoxyphenyl]-N'-(4-chloro-3-methylphenyl)urea The desired product was prepared by substituting Example 165D and 4-chloro-3-methylphenyl isocyanate for Example 1E and phenyl isocyanate, respectively, in Example 1F. MS (ESI(+)) m/e 440.0 (M+H)$^+$; $^1$H NMR (300 MHz, DMSO-d$_6$) δ 2.27 (s, 3H); 3.93 (s, 3H); 7.01 (dd, J=8.3, 1.9 Hz, 1H); 7.13 (d, J=2.0 Hz, 1H); 7.16 (dd, J=8.1, 2.0 Hz, 1H); 7.26 (d, J=8.5 Hz, 1H); 7.46 (s, 1H); 7.73 (d, J=2.0 Hz, 1H); 8.26 (d, J=8.1 Hz, 1H); 8.34 (s, 1H); 8.39 (s, 1H); 9.47 (s, 1H).

EXAMPLE 170

N-[4-(4-aminothieno[2,3-d]pyrimidin-5-yl)-2-methoxyphenyl]-N'-(4-bromo-3-methylphenyl)urea The desired product was prepared by substituting Example 165D and 4-bromo-3-methylphenyl isocyanate for Example 1E and phenyl isocyanate, respectively, in Example 1F. MS (ESI(+)) m/e 483.9, 485.9, (M+H)$^+$; $^1$H NMR (300 MHz, DMSO-d$_6$) δ 2.33 (s, 3H); 3.93 (s, 3H); 7.01 (dd, J=8.3, 1.9 Hz, 1H); 7.13 (d, J=1.7 Hz, 1H); 7.26 (dd, J=8.8, 2.7 Hz, 1H); 7.45-7.48 (m, 3H); 8.27 (d, J=8.1 Hz, 1H); 8.34 (s, 1H); 8.41 (s, 1H); 9.45 (s, 1H).

EXAMPLE 171

N-[4-(4-aminothieno[2,3-d]pyrimidin-5-yl)-2-methoxyphenyl]-N'-(4-chloro-3-methoxyphenyl)urea The desired product was prepared by substituting Example 165D and 4-chloro-3-methoxyphenyl isocyanate for Example 1E and phenyl isocyanate, respectively, in Example 1F. MS (ESI(+)) m/e 456.0 (M+H)$^+$; $^1$H NMR (300 MHz, DMSO-d$_6$) δ 3.82 (s, 3H); 3.93 (s, 3H); 7.01 (dd, J=8.3, 1.9 Hz, 1H); 7.10 (d, J=9.1 Hz, 1H); 7.13 (d, J=1.7 Hz, 1H); 7.24 (dd, J=8.8, 2.7 Hz, 1H); 7.46 (s, 1H); 7.69 (d, J=2.4 Hz, 1H); 8.26 (d, J=8.5 Hz, 1H); 8.34 (app s, 2H); 9.36 (s, 1H).

EXAMPLE 172

N-[4-(4-aminothieno[2,3-d]pyrimidin-5-yl)-2-methoxyphenyl]-N'-(3-methylphenyl)urea The desired product was prepared by substituting Example 165D and 3-methylphenyl isocyanate for Example 1E and phenyl isocyanate, respectively, in Example 1F. MS (ESI(+)) m/e 406.1 (M+H)$^+$; $^1$H NMR (300 MHz, DMSO-d$_6$) δ 2.29 (s, 3H); 3.94 (s, 3H); 6.80 (d, J=7.5 Hz, 1H); 7.01 (dd, J=8.3, 1.7 Hz, 1H); 7.12 (d, J=1.7 Hz, 1H); 7.17 (t, J=7.8 Hz, 1H); 7.24 (d, J=8.5 Hz, 1H); 7.32 (s, 1H); 7.46 (s, 1H); 8.29 (d, J=8.5 Hz, 1H); 8.34 (s, 1H); 8.38 (s, 1H); 9.31 (s, 1H).

EXAMPLE 173

N-[4-(4-aminothieno[2,3-d]pyrimidin-5-yl)-2-fluorophenyl]-N'-[2-fluoro-5-(trifluoromethyl)phenyl]urea

EXAMPLE 173A 5-(4-amino-3-fluorophenyl)thieno[2,3-d]pyrimidin-4-amine

The desired product was prepared by substituting 1-(3-fluorophenyl)propan-1-one for 1-(3-chlorophenyl)propan-1-one Examples 143A-C. MS(ESI(+)) m/e 261 (M+H)$^+$.

EXAMPLE 173B

N-[4-(4-aminothieno[2,3-d]pyrimidin-5-yl)-2-fluorophenyl]-N'-[2-fluoro-5-(trifluoromethyl)phenyl]urea The desired product was prepared by substituting Example 173A and 2-fluoro-5-trifluoromethylphenyl isocyanate for Example 1E and phenyl isocyanate, respectively, in Example 1F. MS (ESI(+)) m/e 466.0 (M+H)$^+$; $^1$H NMR (300 MHz, DMSO-d$_6$) δ 7.27 (dd, J=8.7, 1.5 Hz, 1H); 7.40-7.45 (m, 2H); 7.51 (s, 1H); 7.53 (dd, J=10.5, 9.2 Hz, 1H); 8.33 (t, J=8.5 Hz, 1H); 8.34 (s, 1H); 8.66 (dd, J=7.1, 2.4 Hz, 1H); 9.33 (d, J=1.7 Hz, 1H); 9.45 (d, J=2.4 Hz, 1H).

EXAMPLE 174

N-[4-(4-aminothieno[2,3-d]pyrimidin-5-yl)-2-fluorophenyl]-N'-[3-(trifluoromethyl)phenyl]urea The desired product was prepared by substituting Example 173A and 3-trifluoromethylphenyl isocyanate for Example 1E and phenyl isocyanate, respectively, in Example 1F. MS (ESI(+)) m/e 447.9 (M+H)$^+$; $^1$H NMR (300 MHz, DMSO-d$_6$) δ 7.26 (dd, J=8.5, 1.4 Hz, 1H); 7.34-7.37 (m, 1H); 7.41 (dd, J=12.2, 2.0 Hz, 1H); 7.51 (s, 1H); 7.54-7.58 (m, 2H); 8.06 (s, 1H); 8.29 (t, J=8.3 Hz, 1H); 8.34 (s, 1H); 8.81 (d, J=2.7 Hz, 1H); 9.47 (s, 1H).

EXAMPLE 175

N-[4-aminothienol[2,3-d]pyrimidin-5-yl)-2-fluorophenyl]-N'-(3-methylphenyl)urea

The desired product was prepared by substituting Example 173A and 3-methylphenyl isocyanate for Example 1E and phenyl isocyanate, respectively, in Example 1F. MS (ESI(+)) m/e 394.0 (M+H)$^+$; $^1$H NMR (300 MHz, DMSO-$d_6$) δ 2.30 (s, 3H); 6.83 (d, J=7.1 Hz, 1H); 7.18 (t, J=7.6 Hz, 1H); 7.23-7.27 (m, 2H); 7.32 (br. s, 1H); 7.39 (dd, J=12.0, 1.9 Hz, 1H); 7.49 (s, 1H); 8.30 (d, J=8.5 Hz, 1H); 8.34 (s, 1H); 8.70 (d, J=2.7 Hz, 1H); 9.06 (s, 1H).

EXAMPLE 176

N-[4-(4-aminothieno[2,3-d]pyrimidin-5-yl)-2-chlorophenyl]-N'-(3-methylphenyl)urea

EXAMPLE 176A 2-amino-4-(3-chlorophenyl)-3-thiophenecarbonitrile

The desired product was prepared by substituting 1-(3-chlorophenyl)ethanone for Example 165A in Examples 165B-C. MS (ESI(+)) m/e 233 (M−H)$^-$.

EXAMPLE 176B 5-(3-chlorophenyl)thieno[2,3-d]pyrimidin-4-amine

The desired product was prepared by substituting Example 176A for Example 1C in Example 1D.

EXAMPLE 176C 5-(4-amino-3-chlorophenyl)thieno[2,3-d]pyrimidin-4-amine

The desired product was prepared by substituting Example 176B for Example 143A in Examples 143B and 143C.

EXAMPLE 176D

N-[4-(4-aminothieno[2,3-d]pyrimidin-5-yl)-2-chlorophenyl]-N'-(3-methylphenyl)urea The desired product was prepared by substituting Example 176C and 3-methylphenyl isocyanate for Example 1E and phenyl isocyanate, respectively, in Example 1F. MS (ESI(+)) m/e 409.9 (M+H)$^+$; $^1$H NMR (300 MHz, DMSO-$d_6$) δ 2.30 (s, 3H); 6.83 (d, J=7.1 Hz, 1H); 7.19 (app t, J=7.6 Hz, 1H); 7.26 (d, J=8.1 Hz, 1H); 7.33 (s, 1H); 7.39 (dd, J=8.7, 2.2 Hz, 1H); 7.52 (s, 1H); 7.58 (d, J=2.0 Hz, 1H); 8.34 (d, J=8.8 Hz, 1H); 8.34 (s, 1H); 8.44 (s, 1H); 9.43 (s, 1H).

EXAMPLE 177

N-[4-(4-aminothieno[2,3-d]pyrimidin-5-yl)-2-chlorophenyl]-N'-[2-fluoro-5-(trifluoromethyl)phenyl]urea The desired product was prepared by substituting Example 176C and 2-fluoro-5-trifluoromethylphenyl isocyanate for Example 1E and phenyl isocyanate, respectively, in Example 1F. MS (ESI(+)) m/e 481.9 (M+H)$^+$; $^1$H NMR (300 MHz, DMSO-$d_6$) δ 7.42 (dd, J=8.5, 2.0 Hz, 1H); 7.41-7.45 (m, 1H); 7.50-7.57 (m, 2H); 7.61 (d, J=2.0 Hz, 1H); 8.32 (d, J=8.8 Hz, 1H); 8.35 (s, 1H); 8.66 (dd, J=7.6, 2.2 Hz, 1H); 9.08 (s, 1H); 9.78 (d, J=2.0 Hz, 1H).

EXAMPLE 178

N-[4-(4-aminothieno[2,3-d]pyrimidin-5-yl)-2-chlorophenyl]-N'-[3-(trifluoromethyl)phenyl]urea The desired product was prepared by substituting Example 176C and 3-trifluoromethylphenyl isocyanate for Example 1E and phenyl isocyanate, respectively, in Example 1F. MS (ESI(+)) m/e 463.9 (M+H)$^+$; $^1$H NMR (300 MHz, DMSO-$d_6$) δ 7.34-7.38 (m, 1H); 7.41 (dd, J=8.5, 2.0 Hz, 1H); 7.53 (s, 1H); 7.55-7.59 (m, 2H); 7.61 (d, J=2.0 Hz, 1H); 8.06 (s, 1H); 8.32 (d, J=8.5 Hz, 1H); 8.35 (s, 1H); 8.54 (s, 1H); 9.83 (s, 1H).

EXAMPLE 179

N-[4-(4-aminothieno[2,3-d]pyrimidin-5-yl)phenyl]-N'-(3-methylbutyl)urea

A 0° C. solution of Example 58D (150 mg, 0.62 mmol) in THF (5 mL) was treated with triethylamine (0.09 mL) and 4-nitrophenyl chloroformate (137 mg, 0.68 mmol), stirred at 0° C. for 1 hour, treated with 3-methylbutylamine (0.145 mL, 1.2 mmol) and triethylamine (0.09 mL), warmed to room temperature, and stirred overnight. The reaction mixture was concentrated and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minute run time) at a flow rate of 40 mL/minute to provide 24 mg (11% yield) of the desired product. MS (ESI(+)) m/e 356.0 (M+H)$^+$; $^1$H NMR (300 MHz, DMSO-$d_6$) δ 0.90 (d, J=6.4 Hz, 6H); 1.34 (q, J=6.9 Hz, 2H); 1.57-1.66 (m, 1H); 3.12 (q, J=6.4 Hz, 2H); 6.16 (t, J=5.8 Hz, 1H); 7.32 (d, J=8.8 Hz, 2H); 7.39 (s, 1H); 7.53 (d, J=8.8 Hz, 2H); 8.33 (s, 1H); 8.60 (s, 1H).

EXAMPLE 180

N-[4-(4-aminothieno[2,3-d]pyrimidin-5-yl)phenyl]-N'-(2-ethylbutyl)urea

The desired product was prepared by substituting 2-ethylbutylamine for 3-methylbutylamine in Example 179. MS (ESI(+)) m/e 370.0 (M+H)$^+$; $^1$H NMR (300 MHz, DMSO-$d_6$) δ 0.81-0.90 (m, 6H); 1.25-1.33 (m, 5H); 3.07 (t, J=5.7 Hz, 2H); 6.19 (t, J=5.7 Hz, 1H); 7.32 (d, J=8.8 Hz, 2H); 7.39 (s, 1H); 7.53 (d, J=8.8 Hz, 2H); 8.33 (s, 1H); 8.60 (s, 1H).

EXAMPLE 181

N-[4-(4-aminothieno[2,3-d]pyrimidin-5-yl)-3-fluorophenyl]-N'-(3-methylphenyl)urea

EXAMPLE 181A 5-(4-amino-2-fluorophenyl)thieno[2,3-d]pyrimidin-4-amine

The desired product was prepared by substituting 2-fluoro-4-nitrobenzoyl chloride for 3-methoxy-4-nitrobenzoyl chloride in Examples 165A-D. MS (ESI(+)) m/e 260.9 (M+H)$^+$.

EXAMPLE 181B

N-[4-(4-aminothieno[2,3-d]pyrimidin-5-yl)-3-fluorophenyl]-N'-(3-methylphenyl)urea The desired product was prepared by substituting Example 181A and 3-methylphenyl isocyanate for Example 1E and phenyl isocyanate, respectively, in Example 1F. MS (ESI(+)) m/e 394.0 (M+H)$^+$; $^1$H NMR (500 MHz, DMSO-d$_6$) δ 2.29 (s, 3H); 6.82 (d, J=7.5 Hz, 1H); 7.18 (t, J=7.8 Hz, 1H); 7.25 (d, J=10.0 Hz, 1H); 7.27 (dd, J=8.6, 2.0 Hz, 1H); 7.32 (s, 1H); 7.37 (t, J=8.4 Hz, 1H); 7.52 (s, 1H); 7.66 (dd, J=12.6, 2.0 Hz, 1H); 8.34 (s, 1H); 8.75 (s, 1H); 9.09 (s, 1H).

EXAMPLE 182

N-[4-(4-aminothieno[2,3-d]pyrimidin-5-yl)-3-fluorophenyl]-N'-[2-fluoro-5-(trifluoromethyl)phenyl]urea The desired product was prepared by substituting Example 181A and 2-fluoro-5-trifluoromethylphenyl isocyanate for Example 1E and phenyl isocyanate, respectively, in Example 1F. MS (ESI(+)) m/e 466.0 (M+H)$^+$; $^1$H NMR (500 MHz, DMSO-d$_6$) δ 7.28 (dd, J=8.4, 2.2 Hz, 1H); 7.40 (t, J=8.4 Hz, 1H); 7.40-7.43 (m, 1H); 7.50 (d, J=10.6 Hz, 1H); 7.52 (s, 1H); 7.66 (dd, J=12.2, 1.9 Hz, 1H); 8.33 (s, 1H); 8.58 (dd, J=7.5, 2.2 Hz, 1H); 9.04 (s, 1H); 9.57 (s, 1H).

EXAMPLE 183

N-[4-(4-aminothieno[2,3-d]pyrimidin-5-yl)-3-fluorophenyl]-N'-[3-(trifluoromethyl)phenyl]urea The desired product was prepared by substituting Example 181A and 3-trifluoromethylphenyl isocyanate for Example 1E and phenyl isocyanate, respectively, in Example 1F. MS (ESI(+)) m/e 448.0 (M+H)$^+$; $^1$H NMR (500 MHz, DMSO-d$_6$) δ 7.31 (dd, J=8.4, 2.2 Hz, 1H); 7.33 (d, J=7.8 Hz, 1H); 7.38 (t, J=8.4 Hz, 1H); 7.52 (s, 1H); 7.53 (t, J=8.1 Hz, 1H); 7.61 (d, J=8.4 Hz, 1H); 7.65 (dd, J=12.3, 2.0 Hz, 1H); 8.01 (s, 1H); 8.33 (s, 1H); 9.20 (s, 1H); 9.22 (s, 1H).

EXAMPLE 184

N-[4-(4-aminothieno[2,3-d]pyrimidin-5-yl)-3-fluorophenyl]-N'-(2-fluoro-5-methylphenyl)urea The desired product was prepared by substituting Example 181A and 2-fluoro-5-methylphenyl isocyanate for Example 1E and phenyl isocyanate, respectively, in Example 1F. MS (ESI(+)) m/e 412.0 (M+H)$^+$; $^1$H NMR (500 MHz, DMSO-d$_6$) δ 2.27 (s, 3H); 6.83 (ddd, J=8.4, 4.7, 1.6 Hz, 1H); 7.11 (dd, J=11.4, 8.3 Hz, 1H); 7.24 (dd, J=8.5, 1.9 Hz, 1H); 7.37 (t, J=8.5 Hz, 1H); 7.51 (s, 1H); 7.66 (dd, J=12.3, 2.0 Hz, 1H); 7.94 (dd, J=8.0, 1.7 Hz, 1H); 8.33 (s, 1H); 8.62 (s, 1H); 9.47 (s, 1H).

EXAMPLE 185

N-[4-(4-aminothieno[2,3-d]pyrimidin-5-yl)-3-fluorophenyl]-N'-(3-chlorophenyl)urea The desired product was prepared by substituting Example 181A and 3-chlorophenyl isocyanate for Example 1E and phenyl isocyanate, respectively, in Example 1F. MS (ESI(−)) m/e 412.0 (M−H)$^-$; $^1$H NMR (500 MHz, DMSO-d$_6$) δ 7.04 (td, J=4.4, 2.2 Hz, 1H); 7.28-7.33 (m, 3H); 7.37 (t, J=8.4 Hz, 1H); 7.51 (s, 1H); 7.64 (dd, J=12.3, 2.0 Hz, 1H); 7.71 (s, 1H); 8.33 (s, 1H); 9.06 (s, 1H); 9.20 (s, 1H).

EXAMPLE 186

N-[4-(4-aminothieno[2,3-d]pyrimidin-5-yl)-3-fluorophenyl]-N'-(3,5-dimethylphenyl)urea The desired product was prepared by substituting Example 181A and 3,5-dimethylphenyl isocyanate for Example 1E and phenyl isocyanate, respectively, in Example 1F. MS (ESI(+)) m/e 408.0 (M+H)$^+$; $^1$H NMR (500 MHz, DMSO-d$_6$) δ 2.23 (s, 6H); 6.64 (s, 1H); 7.08 (s, 2H); 7.25 (dd, J=8.4, 2.2 Hz, 1H); 7.36 (t, J=8.4 Hz, 1H); 7.50 (s, 1H); 7.65 (dd, J=12.5, 2.2 Hz, 1H); 8.32 (s, 1H); 8.67 (s, 1H); 9.08 (s, 1H).

EXAMPLE 187

N-[4-(4-aminothieno[2,3-d]pyrimidin-5-yl)-3-fluorophenyl]-N'-(4-chloro-3-methylphenyl)urea The desired product was prepared by substituting Example 181A and 4-chloro-3-methylphenyl isocyanate for Example 1E and phenyl isocyanate, respectively, in Example 1F. MS (ESI(−)) m/e 426.0 (M−H)$^-$; $^1$H NMR (500 MHz, DMSO-d$_6$) δ 2.27 (s, 3H); 7.23 (dd, J=8.3, 2.0 Hz, 1H); 7.26 (d, J=8.4 Hz, 1H); 7.29 (dd, J=8.3, 2.0 Hz, 1H); 7.38 (t, J=8.4 Hz, 1H); 7.52 (s, 1H); 7.64 (dd, J=12.2, 1.9 Hz, 1H); 7.70 (d, J=1.9 Hz, 1H); 8.34 (s, 1H); 8.97 (s, 1H); 9.19 (s, 1H).

EXAMPLE 188

N-[4-(4-aminothieno[2,3-d]pyrimidin-5-yl)-3-fluorophenyl]-N'-(3-cyanophenyl)urea The desired product was prepared by substituting Example 181A and 3-cyanophenyl isocyanate for Example 1E and phenyl isocyanate, respectively, in Example 1F. MS (ESI(−)) m/e 403.0 (M−H)$^-$; $^1$H NMR (500 MHz, DMSO-d$_6$) δ 7.32 (dd, J=8.4, 2.2 Hz, 1H); 7.40 (t, J=8.4 Hz, 1H); 7.45 (ddd, J=7.6, 1.3, 1.1 Hz, 1H); 7.52 (t, J=8.0 Hz, 1H); 7.53 (s, 1H); 7.65 (dd, J=12.3, 2.0 Hz, 1H); 7.71 (ddd, J=8.1, 2.2, 0.9 Hz, 1H); 7.99 (s, 1H); 8.34 (s, 1H); 9.19 (s, 1H); 9.28 (s, 1H).

EXAMPLE 189

N-[4-(4-aminothieno[2,3-d]pyrimidin-5-yl)phenyl]-N'-(2-methylbenzyl)urea

The desired product was prepared substituting 2-methylbenzylamine for 3-methylbutylamine in Example 179. MS (ESI(+)) m/e 390.0 (M+H)$^+$; $^1$H NMR (300 MHz, DMSO-d$_6$)

δ 2.31 (s, 3H); 4.30 (d, J=5.4 Hz, 2H); 6.58 (t, J=5.6 Hz, 1H); 7.17-7.19 (m, 3H); 7.25-7.29 (m, 1H); 7.33 (d, J=8.5 Hz, 2H); 7.39 (s, 1H); 7.55 (d, J=8.5 Hz, 2H); 8.33 (s, 1H); 8.73 (s, 1H).

EXAMPLE 190

N-[4-(4-aminothieno[2,3-d]pyrimidin-5-yl)phenyl]-N'-butylurea

The desired product was prepared substituting butylamine for 3-methylbutylamine in Example 179. MS (ESI(+)) m/e 342.0 (M+H)$^+$; $^1$H NMR (300 MHz, DMSO-d$_6$) δ 0.90 (t, J=7.1 Hz, 3H); 1.26-1.47 (m, 4H); 3.10 (q, J=6.4 Hz, 2H); 6.20 (t, J=5.3 Hz, 1H); 7.32 (d, J=8.8 Hz, 2H); 7.43 (s, 1H); 7.54 (d, J=8.8 Hz, 2H); 8.36 (s, 1H); 8.61 (s, 1H).

EXAMPLE 191

N-[4-(4-aminothieno[2,3-d]pyrimidin-5-yl)phenyl]-N'-(2-methylbutyl)urea

The desired product was prepared substituting 2-methylbutylamine for 3-methylbutylamine in Example 179. MS (ESI(+)) m/e 356.0 (M+H)$^+$; $^1$H NMR (300 MHz, DMSO-d$_6$) δ 0.87 (d, J=6.8 Hz, 3H); 0.88 (t, J=7.8 Hz, 3H); 1.05-1.19 (m, 1H); 1.32-1.57 (m, 2H); 2.89-2.98 (m, 1H); 3.01-3.10 (m, 1H); 6.23 (t, J=5.9 Hz, 1H); 7.32 (d, J=8.5 Hz, 2H); 7.39 (s, 1H); 7.53 (d, J=8.5 Hz, 2H); 8.32 (s, 1H); 8.60 (s, 1H).

EXAMPLE 192

N-[4-(4-aminothieno[2,3-d]pyrimidin-5-yl)phenyl]-N'-(2-methoxy-1-methylethyl)urea The desired product was prepared substituting 1-methyl-2-methoxyethylamine for 3-methylbutylamine in Example 179. MS (ESI(+)) m/e 358.0 (M+H)$^+$; $^1$H NMR (300 MHz, DMSO-d$_6$) δ 1.10 (d, J=6.8 Hz, 3H); 3.25-3.37 (m, 2H); 3.30 (s, 3H); 3.82-3.90 (m, 1H); 6.16 (d, J=8.1 Hz, 1H); 7.32 (d, J=8.5 Hz, 2H); 7.40 (s, 1H); 7.52 (d, J=8.5 Hz, 2H); 8.34 (s, 1H); 8.65 (s, 1H).

EXAMPLE 193

N-[4-(4-aminothieno[2,3-d]pyrimidin-5-yl)phenyl]-N'-(3-methylbenzyl)urea

The desired product was prepared substituting 3-methylbenzylamine for 3-methylbutylamine in Example 179. MS (ESI(+)) m/e 390.0 (M+H)$^+$; $^1$H NMR (300 MHz, DMSO-d$_6$) δ 2.30 (s, 3H); 4.28 (d, J=5.8 Hz, 2H); 6.67 (t, J=6.1 Hz, 1H); 7.05-7.13 (m, 3H); 7.23 (t, J=7.3 Hz, 1H); 7.34 (d, J=8.8 Hz, 2H); 7.42 (s, 1H); 7.56 (d, J=8.8 Hz, 2H); 8.35 (s, 1H); 8.77 (s, 1H).

EXAMPLE 194

N-[4-(4-aminothieno[2,3-d]pyrimidin-5-yl)phenyl]-N'-[4-(dimethylamino)phenyl]urea The desired product was prepared as the TFA salt by substituting 4-N,N-dimethyl aniline for 3-methylbutylamine in Example 179. MS (ESI(+)) m/e 405.0 (M+H)$^+$; $^1$H NMR (300 MHz, DMSO-d$_6$) δ 2.84 (s, 6H); 6.71 (d, J=9.2 Hz, 2H); 7.27 (d, J=9.2 Hz, 2H); 7.37 (d, J=8.8 Hz, 2H); 7.42 (s, 1H); 7.59 (d, J=8.8 Hz, 2H); 8.33 (s, 1H); 8.37 (s, 1H); 8.74 (s, 1H).

EXAMPLE 195

N-[4-(4-aminothieno[2,3-d]pyrimidin-5-yl)phenyl]-N'-(3-hydroxyphenyl)urea

The desired product was prepared as the TFA salt by substituting 3-hydroxyaniline for 3-methylbutylamine in Example 179. MS (ESI(+)) m/e 378.0 (M+H)$^+$; $^1$H NMR (300 MHz, DMSO-d$_6$) δ 6.39 (dd, J=8.1, 2.4 Hz, 1H); 6.81 (dd, J=7.6, 1.5 Hz, 1H); 7.00-7.08 (m, 2H); 7.39 (d, J=8.5 Hz, 2H); 7.47 (s, 1H); 7.60 (d, J=8.5 Hz, 2H); 8.38 (s, 1H); 8.65 (s, 1H); 8.83 (s, 1H); 9.34 (s, 1H).

EXAMPLE 196

N-[4-(4-aminothieno[2,3-d]pyrimidin-5-yl)phenyl]-N'-isobutylurea

The desired product was prepared substituting 2-methylpropylamine for 3-methylbutylamine in Example 179. MS (ESI(+)) m/e 342.0 (M+H)$^+$; $^1$H NMR (300 MHz, DMSO-d$_6$) δ 0.88 (d, J=6.4 Hz, 6H); 1.66-1.75 (m, 1H); 2.94 (app t, J=6.3 Hz, 2H); 6.26 (t, J=5.9 Hz, 1H); 7.33 (d, J=8.5 Hz, 2H); 7.44 (s, 1H); 7.54 (d, J=8.5 Hz, 2H (s, 1H).

EXAMPLE 197

N-[4-(4-aminothieno[2,3-d]pyrimidin-5-yl)-3-chlorophenyl]-N'-[3-(trifluoromethyl)phenyl]urea

EXAMPLE 197A

2-amino-4-(2-chloro-4-nitrophenyl)-3-thiophenecarbonitrile

The desired product was prepared substituting 2-chloro-4-nitrobenzoyl chloride for 3-methoxy-4-nitrobenzoyl chloride in Examples 165A-C. MS (ESI(+)) m/e 277.9 (M+H)$^+$.

EXAMPLE 197B

5-(2-chloro-4-nitrophenyl)thieno[2,3-d]pyrimidin-4-amine

A suspension of Example 197A (3.95 g, 141.1 mmol) in triethylorthoformate(50 mL) was treated with ammonium sulfate (186 mg, 1.4 mmol), heated to reflux for 4 hours, cooled to room temperature, treated with 2M ammonia in ethanol (100 mL), stirred for 2 hours, and filtered. The filter cake (2.6 g) was suspended in o-dichlorobenzene (30 mL) and heated to reflux until all the material dissolved (about 2 hours). The solution of was cooled to room temperature and filtered. The filter cake was dried to provide 2.14 g of the desired product. MS (ESI(+)) m/e 306.9, 308.9 (M+H)$^+$.

EXAMPLE 197C

5-(4-amino-2-chlorophenyl)thieno[2,3-d]pyrimidin-4-amine

The desired product was prepared by substituting Example 197B for Example 1D in Example 1E. MS (ESI(+)) m/e 277, 279 (M+H)$^+$.

EXAMPLE 197D

N-[4-(4-aminothieno[2,3-d]pyrimidin-5-yl)-3-chlorophenyl]-N'-[3-(trifluoromethyl)phenyl]urea The desired product was prepared by substituting Example 197C and 3-trifluoromethylphenyl isocyanate for Example 1E and phenyl isocyanate, respectively, in Example 1F. MS (ESI(+)) m/e 463.9, 465.9 (M+H)$^+$; $^1$H NMR (300 MHz, DMSO-d$_6$) δ 7.35 (d, J=7.5 Hz, 1H); 7.43 (d, J=8.1 Hz, 1H); 7.47 (dd, J=8.5, 2.0 Hz, 1H); 7.49 (s, 1H); 7.54 (t, J=8.1 Hz, 1H); 7.62 (d, J=8.5 Hz, 1H); 7.91 (d, J=1.7 Hz, 1H); 8.03 (br. s, 1H); 8.34 (s, 1H); 9.20 (s, 1H); 9.22 (s, 1H).

EXAMPLE 198

N-[4-(4-aminothieno[2,3-d]pyrimidin-5-yl)-3-chlorophenyl]-N'-(3-chlorophenyl)urea The desired product was prepared by substituting Example 197C and 3-chlorophenyl isocyanate for Example 1E and phenyl isocyanate, respectively, in Example 1F. MS (ESI(+)) m/e 429.9, 431.9 (M+H)$^+$, $^1$H NMR (300 MHz, DMSO-d$_6$) δ 7.04-7.07 (m, 1H); 7.31-7.33 (m, 2H); 7.42-7.44 (m, 2H); 7.49 (s, 1H); 7.72 (dd, J=2.7, 1.7 Hz, 1H); 7.90 (d, J=1.0 Hz, 1H); 8.33 (s, 1H); 9.05 (s, 1H); 9.16 (s, 1H).

EXAMPLE 199

N-[4-(4-aminothieno[2,3-d]pyrimidin-5-yl)-3-chlorophenyl]-N'-[2-fluoro-5-(trifluoromethyl)phenyl] urea The desired product was prepared by substituting Example 197C and 2-fluoro-5-trifluoromethylphenyl isocyanate for Example 1E and phenyl isocyanate, respectively, in Example 1F. MS (ESI(+)) m/e 481.9, 483.9 (M+H)$^+$; $^1$H NMR (300 MHz, DMSO-d$_6$) δ 7.40-7.47 (m, 3H); 7.50 (s, 1H); 7.51-7.58 (m, 1H); 7.92 (d, J=1.4 Hz, 1H); 8.34 (s, 1H); 8.59 (dd, J=7.5, 2.0 Hz, 1H); 9.03 (d, J=2.7 Hz, 1H); 9.52 (s, 1H).

EXAMPLE 200

N-[4-(4-aminothieno[2,3-d]pyrimidin-5-yl)-3-chlorophenyl]-N'-(3-methylphenyl)urea The desired product was prepared by substituting Example 197C and 3-methylphenyl isocyanate for Example 1E and phenyl isocyanate, respectively, in Example 1F. MS (ESI(+)) m/e 409.9,411.9 (M+H)$^+$; $^1$H NMR (300 MHz, DMSO-d$_6$) δ 2.29 (s, 3H); 6.82 (d, J=7.5 Hz, 1H); 7.18 (t, J=7.5 Hz, 1H); 7.23-7.26 (m, 1H); 7.31-7.34(br. s, 1H); 7.41-7.42 (m, 2H); 7.49 (s, 1H); 7.91 (br. s, 1H); 8.33 (s, 1H); 8.75 (s, 1H); 9.05 (s, 1H).

EXAMPLE 201

N-[4-(4-aminothieno[2,3-d]pyrimidin-5-yl)-3-methoxyphenyl]-N'-(3-methylphenyl)urea

EXAMPLE 201A 5-(4-amino-2-methoxyphenyl)thieno[2,3-d]pyrimidin-4-amine

The desired product was prepared by substituting 2-methoxy-4-nitrobenzoyl chloride for 3-methoxy-4-nitrobenzoyl chloride in Examples 165A-D. MS (ESI(+)) m/e 273 (M+H)$^+$.

EXAMPLE 201B

N-[4-(4-aminothieno[2,3-d]pyrimidin-5-yl)-3-methoxyphenyl]-N'-(3-methylphenyl)urea The desired product was prepared by substituting Example 201A and 3-methylphenyl isocyanate for Example 1E and phenyl isocyanate, respectively, in Example 1F. The product was purified by HPLC using the conditions described in Example 179 to provide the trifluoroacetate salt. MS (ESI(+)) m/e 406.0 (M+H)$^+$; $^1$H NMR (300 MHz, DMSO-d$_6$) δ 2.29 (s, 3H); 3.72 (s, 3H); 6.81 (d, J=7.1 Hz, 1H); 7.05 (dd, J=8.1, 2.0 Hz, 1H); 7.14-7.25 (m, 3H); 7.34 (s, 1H); 7.38 (s, 1H); 7.50 (d, J=2.0 Hz, 1H); 8.36 (s, 1H); 8.67 (s, 1H); 8.93 (s, 1H).

EXAMPLE 202

N-[4-(4-aminothieno[2,3-d]pyrimidin-5-yl)-3-methoxyphenyl]-N'-[3-(trifluoromethyl)phenyl]urea The desired product was prepared by substituting Example 201A and 3-trifluoromethylphenyl isocyanate for Example 1E and phenyl isocyanate, respectively, in Example 1F. MS (ESI(+)) m/e 460.0 (M+H)$^+$; $^1$H NMR (300 MHz, DMSO-d$_6$) δ 3.72 (s,3H); 7.08 (dd, J=8.3, 1.9 Hz, 1H); 7.23 (d, J=8.1 Hz, 1H); 7.32-7.35 (m, 2H); 7.49 (d, J=2.0 Hz, 1H); 7.53 (t, J=8.0 Hz, 1H); 7.60 (d, J=8.5 Hz, 1H); 8.04 (s, 1H); 8.32 (s, 1H); 9.05 (s, 1H); 9.12 (s, 11H).

EXAMPLE 203

N-[4-(4-aminothieno[2,3-d]pyrimidin-5-yl)-3-methoxyphenyl]-N'-(3-chlorophenyl)urea The desired product was prepared by substituting Example 201A and 3-chlorophenyl isocyanate for Example 1E and phenyl isocyanate, respectively, in Example 1F. MS (ESI(+)) m/e 425.9 (M+H)$^+$; $^1$H NMR (300 MHz, DMSO-d$_6$) δ 3.72 (s, 3H); 7.04 (dt, J=6.7, 2.0 Hz, 1H); 7.07 (dd, J=8.1, 2.0 Hz, 1H); 7.23 (d, J=8.1 Hz, 1H); 7.27-7.35 (m, 2H); 7.39 (s, 1H); 7.49 (d, J=1.7 Hz, 1H); 7.75 (t, J=2.0 Hz, 1H); 8.36 (s, 1H); 9.00 (s, 1H); 9.06 (s, 1H).

EXAMPLE 204

N-[4-(4-aminothieno[2,3-d]pyrimidin-5-yl)-3-methoxyphenyl]-N'-[2-fluoro-5-(trifluoromethyl)phenyl] urea The desired product was prepared by substituting Example 201A and 2-fluoro-5-trifluoromethylphenyl isocyanate for Example 1E and phenyl isocyanate, respectively, in Example 1F. MS (ESI(+)) m/e 478.0 (M+H)$^+$; $^1$H NMR (300 MHz, DMSO-d$_6$) δ 3.74 (s, 3H); 7.06 (dd, J=8.1, 2.0 Hz, 1H); 7.24 (d, J=8.1 Hz, 1H); 7.35 (s, 1H); 7.42 (ddd, J=8.5, 4.4, 2.4 Hz, 1H); 7.47 (d, J=2.0 Hz, 1H); 7.52 (dd, J=10.5, 8.8 Hz, 1H); 8.31 (s, 1H); 8.62 (dd, J=7.3, 2.2 Hz, 1H); 8.96 (d, J=3.0 Hz, 1H); 9.43 (s, 1H).

EXAMPLE 205

N-[5-(4-aminothieno[2,3-d]pyrimidin-5-yl)-2-pyridinyl]-N'-(3-methylphenyl)urea

EXAMPLE 205A 5-(6-chloro-3-pyridinyl)thieno[2,3-d]pyrimidin-4-amine

The desired product was prepared by substituting 6-chloronicotinoyl chloride for 3-methoxy-4-nitrobenzoyl chloride in Examples 197A-B. MS (ESI(+)) m/e 263 (M+H)$^+$.

EXAMPLE 205B 5-(6-amino-3-pyridinyl)thieno[2,3-d]pyrimidin-4-amine

A solution of Example 205A (1.64 g, 6.25 mmol) in dioxane (75 mL) and NH$_4$OH (75 mL) was heated to 175° C. in a sealed tube for 2.5 days. The crude solution was filtered and the filtrate was concentrated under a stream of nitrogen. The residue was purified by silica gel chromatography with 3 to 5% methanol/dichloromethane to provide 0.69 g (45% yield) of Example 205B as a yellow solid. MS (ESI(+)) m/e 244 (M+H)$^+$.

EXAMPLE 205C

N-[5-(4-aminothieno[2,3-d]pyrimidin-5-yl)-2-pyridinyl]-N'-(3-methylphenyl)urea

The desired product was prepared by substituting Example 205B and 3-methylphenyl isocyanate for Example 1E and phenyl isocyanate, respectively, in Example 1F. MS (ESI(+)) m/e 377.0 (M+H)$^+$; $^1$H NMR (300 MHz, DMSO-d$_6$) δ 2.30 (s, 3H); 6.85 (d, J=7.5 Hz, 1H); 7.20 (t, J=7.5 Hz, 1H); 7.35 (d, J=8.1 Hz, 1H); 7.37 (s, 1H); 7.54 (s, 1H); 7.62 (d, J=8.5 Hz, 1H); 7.83 (dd, J=8.5, 2.4 Hz, 1H); 8.35 (s, 1H); 8.39 (d, J=2.4 Hz, 1H); 9.60 (s, 1H); 10.42 (s, 1H).

EXAMPLE 206

N-{4-[4-amino-6-(3-hydroxypropyl)thieno[2,3-d]pyrimidin-5-yl]phenyl}-N'-(3-methylphenyl)urea The desired product was prepared by substituting tert-butyl (4-iodobutoxy)dimethylsilane) for tert-butyl(3-iodopropoxy)dimethylsilane) in Examples 104A-D. MS (ESI(+)) m/e 434 (M+H)$^+$; $^1$H NMR (300 MHz, DMSO-d$_6$) δ 1.70 (m, 2H); 2.29 (s, 3H); 2.68 (m, J=6.27 Hz, 2H); 3.37 (t, J=6.27 Hz, 2H); 6.81 (d, J=7.80 Hz, 1H); 7.17 (t, J=7.63 Hz, 1H); 7.23-7.33 (m, 4H); 7.62 (d, J=8.81 Hz, 2H); 8.27 (s, 1H); 8.69 (s, 1H); 8.90 (s, 1H).

EXAMPLE 207

N-{4-[4-amino-6-(3-hydroxypropyl)thieno[2,3-d]pyrimidin-5-yl]phenyl}-N'-[3-(trifluoromethyl)phenyl]urea The desired product was prepared by substituting tert-butyl (4-iodobutoxy)dimethylsilane) and 3-trifluoromethylphenyl isocyanate for tert-butyl(3-iodopropoxy)dimethylsilane) and 3-methylphenyl isocyanate, respectively, in Examples 104A-D. MS (ESI(+)) m/e 488 (M+H)$^+$; $^1$H NMR (300 MHz, DMSO-d$_6$) δ 1.70 (m, 2H); 2.68 (t, J=7.5 Hz, 2H); 3.37 (q, J=6.0 Hz, 2H); 4.48 (t, J=5.09 Hz, 1H); 7.32 (m, 3H); 7.29-7.35 (t, J=7.97 Hz, 1H); 7.58-7.67 (m, 3H); 8.03 (s, 1H); 8.27 (s, 1H); 9.03 (s, 1H); 9.15 (s, 1H).

EXAMPLE 208

N-{4-[4-amino-6-(3-hydroxypropyl)thieno[2,3-d]pyrimidin-5-yl]phenyl}-N'-(3-chlorophenyl)urea The desired product was prepared by substituting tert-butyl (4-iodobutoxy)dimethylsilane) and 3-chloromethylphenyl isocyanate for tert-butyl(3-iodopropoxy)dimethylsilane) and 3-methylphenyl isocyanate respectively, in Examples 104A-D. MS (ESI(+)) m/e 454 (M+H)$^+$; $^1$H NMR (300 MHz, DMSO-d$_6$) δ 1.71 (m, 2H); 2.68 (t, J=6.0 Hz, 2H); 3.37 (m, 1H); 4.48 (t, J=6.0 Hz, 1H); 7.04 (m, 1H); 7.31 (m, 4H); 7.63 (d, J=8.48 Hz, 2H); 7.73 (t, J=1.86 Hz, 1H); 8.26 (s, 1H); 8.98 (s, 2H).

EXAMPLE 209

N-[4-(4-aminothieno[2,3-d]pyrimidin-5-yl)phenyl]-N'-(3-fluorophenyl)urea

The desired product was prepared by substituting Example 58D and 3-fluorophenyl isocyanate for Example 1E and phenyl isocyanate, respectively, in Example 1F. MS (ESI(+)) m/e 380 (M+H)$^+$; $^1$H NMR (300 MHz, DMSO-d$_6$) δ 6.80 (m, 1H); 7.14 (m, J=7.29, 1H); 7.32 (m, 1H); 7.40 (m, 3H); 7.51 (m, 1H); 7.60 (m, 2H); 8.34 (s, 1H); 8.96 (s, 1H); 8.99 (s, 1H).

EXAMPLE 210

N-[4-(4-aminothieno[2,3-d]pyrimidin-5-yl)phenyl]-N'-(3-cyanophenyl)urea

The desired product was prepared by substituting Example 58D and 3-cyanophenyl isocyanate for Example 1E and phenyl isocyanate, respectively, in Example 1F. MS (ESI(+)) m/e 3878 (M+H)$^+$; $^1$H NMR (300 MHz, DMSO-d$_6$) δ 7.38-7.47 (m, 3H); 7.51 (t, J=7.80 Hz, 2H); 7.62 (d, J=8.82 Hz, 2H); 7.71 (m, 1H); 7.99 (s, 1H); 8.34 (s, 1H); 9.06 (s, 1H); 9.10 (s, 1H).

EXAMPLE 211

N-[4-(4-aminothieno[2,3-d]pyrimidin-5-yl)phenyl]-N'-(3,5-dimethylphenyl)urea

The desired product was prepared by substituting Example 58D and 3,5-dimethylphenyl isocyanate for Example 1E and phenyl isocyanate, respectively, in Example 1F. MS (ESI(+)) m/e 390 (M+H)$^+$; $^1$H NMR (300 MHz, DMSO-d$_6$) δ 6.63 (s, 1H); 7.09 (s, 2H); 7.39 (d, J=8.48 Hz, 2H); 7.43 (s, 1H); 7.60 (d, J=8.82 Hz, 2H); 8.34 (s, 1H); 8.58 (s, 1H); 8.84 (s, 1H).

EXAMPLE 212

N-[4-(4-aminothieno[2,3-d]pyrimidin-5-yl)phenyl]-N'-(3-bromophenyl)urea

The desired product was prepared by substituting Example 58D and 3-bromophenyl isocyanate for Example 1E and phenyl isocyanate, respectively, in Example 1F. MS (ESI(+)) m/e 440,442 (M+H)$^+$; $^1$H NMR (300 MHz, DMSO-d$_6$) δ 7.17 (d, J=7.80 Hz, 1H); 7.25 (t, J=7.80 Hz, 1H); 7.34 (m, 1H); 7.40

(d, J=8.48 Hz, 2H); 7.44 (s, 1H); 7.61 (d, J=8.82 Hz, 2H); 7.87 (t, J=1.87 Hz, 1H); 8.34 (s, 1H); 8.95 (s, 1H); 8.97 (s, 1H).

EXAMPLE 213

N-[4-(4-aminothieno[2,3-d]pyrimidin-5-yl)phenyl]-N'-(3,4-dimethylphenyl)urea

The desired product was prepared by substituting Example 58D and 3,4-dimethylphenyl isocyanate for Example 1E and phenyl isocyanate, respectively, in Example 1F. MS (ESI(+)) m/e 390 (M+H)$^+$; $^1$H NMR (300 MHz, DMSO-d$_6$) δ 2.16 (s, 3H); 2.20 (s, 3H); 7.03 (d, J=8.14 Hz, 1H); 7.18 (m, 1H); 7.24 (s, 1H); 7.38 (d, J=8.81 Hz, 2H); 7.43 (s, 1H); 7.60 (d, J=8.48 Hz, 2H); 8.34 (s, 1H); 8.55 (s, 1H); 8.82 (s, 1H).

EXAMPLE 214

N-[4-(4-aminothieno[2,3-d]pyrimidin-5-yl)phenyl]-N'-2,3-dihydro-1H-inden-5-ylurea The desired product was prepared by substituting Example 58D and 5-isocyanatoindane for Example 1E and phenyl isocyanate, respectively, in Example 1F. MS (ESI(+)) m/e 402 (M+H)$^+$; $^1$H NMR (300 MHz, DMSO-d$_6$) δ 2.00 (m, 2H); 2.82 (m, 4H); 7.14 (m, 2H); 7.38 (d, J=8.82 Hz, 2H); 7.40 (s, 1H); 7.43 (s, 1H); 7.60 (d, J=8.48 Hz, 2H); 8.34 (s, 1H); 8.60 (s, 1H); 8.83 (s, 1H).

EXAMPLE 215

N-[4-(4-aminothieno[2,3-d]pyrimidin-5-yl)phenyl]-N'-(4-bromo-3-methylphenyl)urea The desired product was prepared by substituting Example 58D and 4-bromo-3-methylphenyl isocyanate for Example 1E and phenyl isocyanate, respectively, in Example 1F. MS (ESI(+)) m/e 454, 456 (M+H)$^+$; $^1$H NMR (300 MHz, DMSO-d$_6$) δ 2.32 (s, 3H); 7.28 (m, 1H); 7.39 (d, J=8.82 Hz, 2H); 7.43 (s, 1H); 7.47 (m, 2H); 7.61 (d, J=8.48 Hz, 2H); 8.34 (s, 1H); 8.81 (s, 1H); 8.92 (s, 1H).

EXAMPLE 216

N-[4-(4-aminothieno[2,3-d]pyrimidin-5-yl)phenyl]-N'-(4-fluorophenyl)urea

The desired product was prepared by substituting Example 58D and 4-fluorophenyl isocyanate for Example 1E and phenyl isocyanate, respectively, in Example 1F. MS (ESI(+)) m/e 380 (M+H)$^+$; $^1$H NMR (300 MHz, DMSO-d$_6$) δ 7.13 (t, J=8.81 Hz, 2H); 7.39 (d, J=8.81 Hz, 2H); 7.43 (s, 1H); 7.48 (m, J=9.15, 5.09 Hz, 2H); 7.60 (d, J=8.81 Hz, 2H); 8.34 (s, 1H); 8.78 (s, 1H); 8.88 (s, 1H).

EXAMPLE 217

N-[4-(4-amino-6-bromothieno[2,3-d]pyrimidin-5-yl)phenyl]-N'-(4-fluorophenyl)urea The desired product was prepared by substituting Example 61B and 4-fluorophenyl isocyanate for Example 1E and phenyl isocyanate, respectively, in Example 1F. MS (ESI(+)) m/e 458, 460 (M+H)$^+$; $^1$H NMR (300 MHz, DMSO-d$_6$) δ 7.14 (t, J=8.82 Hz, 2H); 7.36 (d, J=8.48 Hz, 2H); 7.49 (dd, J=8.99, 4.92 Hz, 2H); 7.65 (d, J=8.48 Hz, 2H); 8.33 (s, 1H); 8.81 (s, 1H); 8.94 (s, 1H).

EXAMPLE 218

N-[4-(4-amino-6-bromothieno[2,3-d]pyrimidin-5-yl)phenyl]-N'-(3-fluorophenyl)urea The desired product was prepared by substituting Example 61B and 3-fluorophenyl isocyanate for Example 1E and phenyl isocyanate, respectively, in Example 1F. MS (ESI(+)) m/e 458, 460 (M+H)$^+$; $^1$H NMR (300 MHz, DMSO-d$_6$) δ 6.81 (m, 1H); 7.15 (d, J=7.80 Hz, 1H); 7.34 (m, 3H); 7.51 (d, J=11.87 Hz, 1H); 7.66 (d, J=8.48 Hz, 2H); 8.33 (s, 1H); 9.02 (s, 2H).

EXAMPLE 219

N-[4-(4-amino-6-bromothieno[2,3-d]pyrimidin-5-yl)phenyl]-N'-(3-cyanophenyl)urea

The desired product was prepared by substituting Example 61B and 3-cyanophenyl isocyanate for Example 1E and phenyl isocyanate, respectively, in Example 1F. MS (ESI(+)) m/e 465, 467 (M+H)$^+$; $^1$H NMR (300 MHz, DMSO-d$_6$) δ 7.38 (d, J=8.48 Hz, 2H); 7.45 (d, J=7.80 Hz, 1H); 7.52 (t, J=7.80 Hz, 1H); 7.67 (d, J=8.48 Hz, 2H); 7.71 (d, J=8.82 Hz, 1H); 8.00 (s, 1H); 8.33 (s, 1H); 9.12 (s, 1H); 9.14 (s, 1H).

EXAMPLE 220

N-[4-(4-amino-6-bromothieno[2,3-d]pyrimidin-5-yl)phenyl]-N'-(3,5-dimethylphenyl)urea The desired product was prepared by substituting Example 61B and 3,5-dimethylphenyl isocyanate for Example 1E and phenyl isocyanate, respectively, in Example 1F. MS (ESI(+)) m/e 468, 470 (M+H)$^+$; $^1$H NMR (300 MHz, DMSO-d$_6$) δ 2.24 (s, 6H); 6.64 (s, 1H); 7.09 (s, 2H); 7.35 (d, J=8.48 Hz, 2H); 7.65 (d, J=8.82 Hz, 2H); 8.33 (s, 1H); 8.61 (s, 1H); 8.90 (s, 1H).

EXAMPLE 221

N-[4-(4-amino-6-bromothieno[2,3-d]pyrimidin-5-yl)phenyl]-N'-(3-bromophenyl)urea

The desired product was prepared by substituting Example 61B and 3-bromophenyl isocyanate for Example 1E and phenyl isocyanate, respectively, in Example 1F. MS (ESI(+)) m/e 520 (M+H)$^+$; $^1$H NMR (300 MHz, DMSO-d$_6$) δ 7.17 (d, J=7.80 Hz, 1H); 7.26 (t, J=7.97 Hz, 1H); 7.34 (d, J=7.80 Hz, 1H); 7.37 (d, J=8.48 Hz, 2H); 7.66 (d, J=8.48 Hz, 2H); 7.88 (s, 1H); 8.33 (s, 1H); 8.99 (s, 1H); 9.03 (s, 1H).

EXAMPLE 222

N-[4-(4-amino-6-bromothieno[2,3-d]pyrimidin-5-yl)phenyl]-N'-(3,4-dimethylphenyl)urea The desired product was prepared by substituting Example 61B and 3,4-dimethylphenyl isocyanate for Example 1E and phenyl isocyanate, respectively, in Example 1F. MS (ESI(+)) m/e 466, 468 (M+H)$^+$; $^1$H NMR (300 MHz, DMSO-d$_6$) δ 2.16 (s, 3H); 2.20 (s, 3H); 7.04 (d, J=8.48 Hz, 1H); 7.19 (d, J=10.17 Hz, 1H); 7.25 (s, 1H); 7.34 (d, J=8.48 Hz, 2H); 7.64 (d, J=8.48 Hz, 2H); 8.32 (s, 1H); 8.58 (s, 1H); 8.88 (s, 1H).

EXAMPLE 223

N-[4-(4-amino-6-bromothieno[2,3-d]pyrimidin-5-yl)phenyl]-N'-[4-fluoro-3-(trifluoromethyl)phenyl]urea The desired product was prepared by substituting Example 61B and 3-fluoro-4-trifluoromethylphenyl isocyanate for Example 1E and phenyl isocyanate, respectively, in Example 1F. MS (ESI(+)) m/e 526, 528 (M+H)$^+$; $^1$H NMR (300 MHz, DMSO-d$_6$) δ 7.37 (d, J=8.82 Hz, 2H); 7.46 (t, J=9.83 Hz, 1H); 7.66 (m, 3H); 8.03 (dd, J=6.44, 2.71 Hz, 1H); 8.33 (s, 1H); 9.08 (s, 1H); 9.15 (s, 1H).

EXAMPLE 224

N-[4-(4-amino-6-bromothieno[2,3-d]pyrimidin-5-yl)phenyl]-N'-(4-bromo-3-methylphenyl)urea The desired product was prepared by substituting Example 61B and 4-bromo-3-methylphenyl isocyanate for Example 1E and phenyl isocyanate, respectively, in Example 1F. MS (ESI(+)) m/e 534 (M+H)$^+$; $^1$H NMR (300 MHz, DMSO-d$_6$) δ 2.32 (d, J=5.09 Hz, 3H); 7.28 (dd, J=8.48, 2.71 Hz, 1H); 7.36 (d, J=8.48 Hz, 2H); 7.47 (m, 2H); 7.65 (d, J=8.48 Hz, 2H); 8.33 (s, 1H); 8.85 (s, 1H); 8.98 (s, 1H).

EXAMPLE 225

N-{4-[4-amino-6-(4-pyridinylmethyl)thieno[2,3-d]pyrimidin-5-yl]phenyl}-N'-(3-cyanophenyl)urea The desired product was prepared by substituting Example 14B and 3-cyanophenyl isocyanate for Example 1A and phenyl isocyanate, respectively, in Examples 1B-1F. MS (ESI(+)) m/e 478 (M+H)$^+$; $^1$H NMR (300 MHz, DMSO-d$_6$) δ 4.04 (s, 2H); 7.28-7.33 (m, 1H); 7.37-7.40 (d, 2H, J=8.4 Hz); 7.42-7.46 (td, 1H, J=1.2, 9 Hz); 7.49-7.56 (m, 2H); 7.65-7.67 (d, 2H, J=8.7 Hz); 7.68-7.72 (m, 1H); 7.99-7.80 (t, 1H, J=1.8 Hz); 8.27 (s, 1H); 8.33-8.34 (d, 1H, J=1.5 Hz); 8.41-8.44 (dd, 1H, J=1.5, 4.8 Hz); 9.09 (s, 1H); 9.12 (s, 1H).

EXAMPLE 226

N-{4-[4-amino-6-(3-pyridinylmethyl)thieno[2,3-d]pyrimidin-5-yl]phenyl}-N'-(3-bromophenyl)urea The desired product was prepared by substituting Example 115A and 3-bromophenyl isocyanate for Example 1A and phenyl isocyanate, respectively, in Examples 1B-1F. MS (ESI(+)) m/e 531, 533 (M+H)$^+$; $^1$H NMR (300 MHz, DMSO-d$_6$) δ 4.04 (s, 2H); 7.15-7.35 (m, 4H); 7.36-7.39 (d, 2H, J=8.7 Hz); 7.52-7.56 (td, 1H, J=2.4, 7.5 Hz); 7.64-7.67 (d, 2H, J=9 Hz); 7.87-7.88 (t, 1H, J=2.1 Hz); 8.27 (s, 1H); 8.34-8.35 (d, 1H, J=1.5 Hz); 8.41-8.44 (dd, 11H, J=1.8, 4.8 Hz); 8.97 (s, 1H); 8.99 (s, 1H).

EXAMPLE 227

N-{4-[4-amino-6-(3-pyridinylmethyl)thieno[2,3-d]pyrimidin-5-yl]phenyl}-N'-(3-ethylphenyl)urea The desired product was prepared by substituting Example 115A and 3-ethylphenyl isocyanate for Example 1A and phenyl isocyanate, respectively, in Examples 1B-1F. MS(ESI(+)) m/e 481 (M+H)$^+$; $^1$H NMR (300 MHz, DMSO-d$_6$) δ 1.16-1.21 (t, 3H, J=7.5 Hz); 2.55-2.62 (q, 2H, J=7.5 Hz); 4.04 (s, 2H); 6.83-6.86 (d, 1H, J=7.5 Hz); 7.17-7.22 (t, 1H, J=7.5 Hz); 7.26-7.38 (m, 5H); 7.53-7.56 (td, 1H, J=1.5, 8.1 Hz); 7.63-7.66 (d, 2H, J=9 Hz); 8.27 (s, 1H); 8.34-8.35 (d, 1H, J=1.5 Hz); 8.42-8.44 (dd, 1H, J=1.8, 4.8 Hz); 8.70 (s, 1H); 8.9 (s, 1H).

EXAMPLE 228

N-{4-[4-amino-6-(3-pyridinylmethyl)thieno[2,3-d]pyrimidin-5-yl]phenyl}-N'-(2-fluoro-5-methylphenyl)urea The desired product was prepared by substituting Example 115A and 5-methyl-2-fluorophenyl isocyanate for Example 1A and phenyl isocyanate, respectively, in Examples 1B-1F. MS(ESI(+)) m/e 485 (M+H)$^+$; $^1$H NMR (300 MHz, DMSO-d$_6$) δ 2.28 (s, 3H); 4.04 (s, 2H); 6.79-6.85 (m 1H); 7.08-7.15 (dd, 1H, J=8.4, 11.7 Hz); 7.30-7.34 (dd, 1H, J=4.5, 7.2 Hz); 7.36-7.39 (d, 2H, J=8.4 Hz); 7.53-7.57 (td, 1H, J=1.8, 7.8 Hz); 7.63-7.66 (d, 2H, J=8.7 Hz); 7.97-8.01 (dd, 1H, J=2.1, 7.8 Hz); 8.27 (s, 1H); 8.34-8.35 (d, 1H, J=1.8 Hz); 8.42-8.44 (dd, 1H, J=1.5, 4.8 Hz); 8.56-8.57 (d, 1H, J=2.4 Hz); 9.30 (s, 1H).

EXAMPLE 229

N-{4-[4-amino-6-(2-hydroxyethyl)thieno[2,3-d]pyrimidin-5-yl]phenyl}-N'-[2-fluoro-5-(trifluoromethyl)phenyl]urea

EXAMPLE 229A

N-{4-[4-amino-6-(2-{[tert-butyl(dimethyl)silyl]oxy}ethyl)thieno[2,3-d]pyrimidin-5-yl]phenyl}-N'-[2-fluoro-5-(trifluoromethyl)phenyl]urea The desired product was prepared by substituting Example 104B and 5-trifluoromethyl-2-fluorophenyl isocyanate for Example 1E and phenyl isocyanate, respectively, in Example 1F.

EXAMPLE 229B

N-{4-[4-amino-6-(2-hydroxyethyl)thieno[2,3-d]pyrimidin-5-yl]phenyl}-N'-[2-fluoro-5-(trifluoromethyl)phenyl]urea The desired product was prepared by substituting Example 229A for Example 104C in Example 104D. MS (ESI(+)) m/e 492 (M+H)$^+$; $^1$H NMR (300 MHz, DMSO-d$_6$) δ 2.74-2.79 (t, 2H, J=6.6 Hz); 3.54-3.60 (q, 2H, J=6.6 Hz); 4.87-4.91 (t, 1H, J=5.4 Hz); 7.33-7.36 (d, 2H, J=8.7 Hz); 7.38-7.44 (m, 1H); 7.49-7.55 (m, 1H); 7.63-7.66 (d, 2H, J=8.4 Hz); 8.27 (s, 1H); 8.62-8.65 (dd, 1H, J=1.8, 6.9 Hz); 8.98-8.99 (d, 1H, J=3.7 Hz); 9.39 (s, 1H).

EXAMPLE 230

N-{4-[4-amino-6-(2-hydroxyethyl)thieno[2,3-d]pyrimidin-5-yl]phenyl}-N'-(3-ethylphenyl)urea

EXAMPLE 230A

N-{4-[4-amino-6-(2-{[tert-butyl(dimethyl)silyl]oxy}ethyl)thieno[2,3-d]pyrimidin-5-yl]phenyl}-N'-(3-ethylphenyl)urea The desired product was prepared by substituting Example 104B and 3-ethylphenyl isocyanate for Example 1E and phenyl isocyanate, respectively, in Example 1F.

EXAMPLE 230B

N-{4-[4-amino-6-(2-hydroxyethyl)thieno[2,3-d]pyrimidin-5-yl]phenyl}-N'-(3-ethylphenyl)urea The desired product was prepared by substituting Example 230A for Example 104C in Example 104D. MS (ESI(+)) m/e 434 (M+H)$^+$; $^1$H NMR (300 MHz, DMSO-d$_6$) δ 1.16-1.21 (t, 3H, J=7.8 Hz); 2.55-2.62 (q, 2H, J=7.8 Hz); 2.75-2.79 (t, 2H, J=6.3 Hz); 3.54-3.58 (q, 2H, J=5.4 Hz); 4.85-4.89 (t, 1H, J=5.7 Hz); 6.83-6.85 (d, 1H, J=7.2 Hz); 7.17-7.22 (t, 1H, J=7.5 Hz); 7.26-7.34 (m, 4H,), 7.61-7.64 (d, 2H, J=8.4 Hz); 8.26 (s, 1H); 8.68 (s, 1H); 8.86 (s, 1H).

EXAMPLE 231

N-{4-[4-amino-6-(2-hydroxyethyl)thieno[2,3-d]pyrimidin-5-yl]phenyl}-N'-(3-cyanophenyl)urea

EXAMPLE 231A

N-{4-[4-amino-6-(2-{[tert-butyl(dimethyl)silyl]oxy}ethyl)thieno[2,3-d]pyrimidin-5-yl]phenyl}-N'-(3-cyanophenyl)urea The desired product was prepared by substituting Example 104B and 3-cyanophenyl isocyanate for Example 1E and phenyl isocyanate, respectively, in Example 1F.

EXAMPLE 2311B

N-{4-[4-amino-6-(2-hydroxyethyl)thieno[2,3-d]pyrimidin-5-yl]phenyl}-N'-(3-cyanophenyl)urea The desired product was prepared by substituting Example 231A for Example 104C in Example 104D. MS (ESI(+)) m/e 431 (M+H)$^+$; $^1$H NMR (300 MHz, DMSO-d$_6$) δ 2.75-2.79 (t, 2H, J=6.9 Hz); 3.54-3.60 (q, 2H, J=5.1 Hz); 4.86-4.89 (t, 1H, J=5.1 Hz); 7.32-7.35 (d, 2H, J=8.7 Hz); 7.42-7.46 (td, 1H, J=1.2, 7.5 Hz); 7.49-7.54 (t, 1H, J=7.8 Hz); 7.62-7.65 (d, 2H, J=8.4 Hz); 7.69-7.73 (td, 1H, J=1.2, 8.1 Hz); 7.99-8.00 (t, 1H, J=1.8 Hz); 8.27 (s, 1H); 9.07 (s, 1H); 9.12 (s, 11H).

EXAMPLE 232

N-{4-[4-amino-6-(2-hydroxyethyl)thieno[2,3-d]pyrimidin-5-yl]phenyl}-N'-(3-bromophenyl)urea

EXAMPLE 232A

N-{4-[4-amino-6-(2-{[tert-butyl(dimethyl)silyl]oxy}ethyl)thieno[2,3-d]pyrimidin-5-yl]phenyl}-N'-(3-bromophenyl)urea The desired product was prepared by substituting Example 104B and 3-bromophenyl isocyanate for Example 1E and phenyl isocyanate, respectively, in Example 1F.

EXAMPLE 232B

N-{4-[4-amino-6-(2-hydroxyethyl)thieno[2,3-d]pyrimidin-5-yl]phenyl}-N'-(3-bromophenyl)urea The desired product was prepared by substituting Example 232A for Example 104C in Example 104D. MS (ESI(+)) m/e 484, 486 (M+H)$^+$; $^1$H NMR (300 MHz, DMSO-d$_6$) δ 2.74-2.79 (t, 2H, J=6.3 Hz); 3.54-3.59 (t, 2H, J=6.0 Hz); 4.81-4.90 (br, 1H); 7.15-7.18 (m, 1H); 7.23-7.28 (t, 1H, J=7.8 Hz); 7.31-7.36 (m, 3H); 7.61-7.64 (d, 2H, J=8.7 Hz); 7.87-7.88 (t, 1H, J=1.8 Hz); 8.27 (s, 1H); 8.96 (s, 1H); 8.98 (s, 1H).

EXAMPLE 233

N-{4-[4-amino-6-(2-methoxyethyl)thieno[2,3-d]pyrimidin-5-yl]phenyl}-N'-(3-cyanophenyl)urea The desired product was prepared by substituting Example 108 and 3-cyanophenyl isocyanate for Example 1E and phenyl isocyanate, respectively, in Example 1F. MS (ESI(+)) m/e 445 (M+H)$^+$; $^1$H NMR (300 MHz, DMSO-d$_6$) δ 2.83-2.87 (t, 2H, J=6.3 Hz); 3.22 (s, 3H); 3.47-3.52 (t, 2H, J=6.3 Hz); 7.32-7.35 (d, 2H, J=8.7 Hz); 7.43-7.46 (td, 1H, J=1.2, 7.8 Hz); 7.49-7.54 (t, 1H, J=7.8 Hz); 7.63-7.66 (d, 2H, J=8.7 Hz); 7.68-7.73 (m, 1H); 7.99-8.00 (t, 1H, J=1.8 Hz); 8.27 (s, 1H); 9.08 (s, 1H); 9.12 (s, 1H).

EXAMPLE 234

N-{4-[4-amino-6-(2-methoxyethyl)thieno[2,3-d]pyrimidin-5-yl]phenyl}-N'-(3-ethylphenyl)urea The desired product was prepared by substituting Example 108 and 3-ethylphenyl isocyanate for Example 1E and phenyl isocyanate, respectively, in Example 1F. MS (ESI(+)) m/e 448 (M+H)$^+$; $^1$H NMR (300 MHz, DMSO-d$_6$) δ 1.16-1.21 (t, 3H, J=7.5 Hz); 2.55-2.62 (q, 2H, J=7.5 Hz); 2.83-2.87 (t, 2H, J=6.0 Hz); 3.22 (s, 3H); 3.48-3.52 (t, 2H, J=6.6 Hz); 6.83-6.86 (d, 1H, J=7.5 Hz); 7.17-7.22 (t, 1H, J=7.5 Hz); 7.26-7.34 (m, 4H); 7.61-7.64 (d, 2H, J=8.4 Hz); 8.27 (s, 1H); 8.70 (s, 1H); 8.75 (s, 1H).

EXAMPLE 235

N-{4-[4-amino-6-(2-methoxyethyl)thieno[2,3-d]pyrimidin-5-yl]phenyl}-N'-(3-bromophenyl)urea The desired product was prepared by substituting Example 108 and 3-bromophenyl isocyanate for Example 1E and phenyl isocyanate, respectively, in Example 1F. MS (ESI(+)) m/e 498, 500 (M+H)$^+$; $^1$H NMR (300 MHz, DMSO-d$_6$) δ 2.83-

2.87 (t, 2H, J=6 Hz); 3.22 (s, 3H); 3.47-3.52 (t, 2H, J=6.3 Hz); 7.15-7.19 (td, 1H, J=1.5, 8.1 Hz); 7.23-7.28 (t, 1H, J=7.8 Hz); 7.31-7.36 (m, 3H); 7.62-7.65 (d, 2H, J=9 Hz); 7.87-7.88 (t, 1H, J=1.8 Hz); 8.27 (s, 1H); 8.97 (s, 1H); 8.98 (s, 1H).

EXAMPLE 236

N-{4-[4-amino-6-(2-methoxyethyl)thieno[2,3-d]pyrimidin-5-yl]phenyl}-N'-(3-chlorophenyl)urea The desired product was prepared by substituting Example 108 and 3-chlorophenyl isocyanate for Example 1E and phenyl isocyanate, respectively, in Example 1F. MS (ESI(+)) m/e 454, 456 (M+H)$^+$; $^1$H NMR (300 MHz, DMSO-$d_6$) δ 2.83-2.87 (t, 2H, J=6.3 Hz); 3.22 (s, 3H); 3.48-3.52 (t, 2H, J=6.6 Hz); 7.02-7.06 (td, 1H, J=2.1, 6.6 Hz); 7.30-7.34 (m, 4H); 7.62-7.65 (d, 2H, J=8.7 Hz); 7.72-7.75 (br, 1H); 8.27(s, 1H); 8.99 (s, 2H).

EXAMPLE 237

N-{4-[4-amino-6-(3-pyridinylmethyl)thieno[2,3-d]pyrimidin-5-yl]phenyl}-N'-(3,5-dimethylphenyl)urea The desired product was prepared by substituting Example 115A and 3,5-dimethylphenyl isocyanate for Example 1A and phenyl isocyanate, respectively, in Examples 1B-1F. MS(ESI(+)) m/e 481 (M+H)$^+$; $^1$H NMR (300 MHz, DMSO-$d_6$) δ 3.24 (s, 6H); 4.04 (s, 2H); 6.63 (s, 1H); 7.09 (s, 2H); 7.29-7.37 (m, 3H); 7.52-7.56 (td, 1H, J=1.8, 7.8 Hz); 7.62-7.65 (d, 2H, J=8.7 Hz); 8.27 (s, 1H); 8.34-8.35 (d, 1H, J=1.5 Hz); 8.41-8.44 (dd, 1H, J=1.8, 4.8 Hz); 8.59 (s, 1H); 8.88 (s, 1H).

EXAMPLE 238

3-(4-amino-5-{4-[({[2-fluoro-5-(trifluoromethyl)phenyl]amino}carbonyl)amino]phenyl}thieno[2,3-d]pyrimidin-6-yl)propanamide

EXAMPLE 238A

3-[4-amino-5-(4-aminophenyl)thieno[2,3-d]pyrimidin-6-yl]propanamide

The desired product was prepared by substituting 5-oxo-5-phenyl-pentanoic acid for 1-(3-chlorophenyl)propan-1-one in Examples 143A-C. MS (ESI(+)) m/e 314 (M+H)$^+$.

EXAMPLE 238B 3-(4-amino-5-{4-[({[2-fluoro-5-(trifluoromethyl)phenyl]amino}carbonyl)amino]phenyl}thieno[2,3-d]pyrimidin-6-yl)propanamide The desired product was prepared by substituting Example 238A and 2-fluoro-5-trifluoromethylphenyl isocyanate for Example 1E and phenyl isocyanate, respectively, in Example 1F. MS (ESI(+)) m/e 519 (M+H)$^+$; $^1$H NMR (300 MHz, DMSO-$d_6$) δ 2.36 (t, J=7.63 Hz, 2H); 2.84 (t, J=7.46 Hz, 2H); 6.84 (s, 1H); 7.34 (s, 1H); 7.35 (d, J=8.48 Hz, 2H); 7.42 (m, J=4.41, 2.71 Hz, 1H); 7.52 (m, 1H); 7.65 (d, J=8.81 Hz, 2H); 8.27 (s, 1H); 8.64 (dd, J=6.95, 2.20 Hz, 1H); 8.99 (d, J=2.71 Hz, 1H); 9.41 (s, 1H).

EXAMPLE 239

3-{4-amino-5-[4-({[(3-methylphenyl)amino]carbonyl}amino)phenyl]thieno[2,3-d]pyrimidin-6-yl}propanamide The desired product was prepared by substituting Example 238A and 3-methylphenyl isocyanate for Example 1E and phenyl isocyanate, respectively, in Example 1F. The product was purified by HPLC using the conditions described in Example 179 to provide the trifluoroacetate salt. MS (ESI(+)) m/e 447 (M+H)$^+$; $^1$H NMR (300 MHz, DMSO-$d_6$) δ 2.29 (s, 3H); 2.36 (t, J=7.63 Hz, 2H); 2.85 (t, J=7.46 Hz, 2H); 6.81 (d, J=7.46 Hz, 1H); 6.85 (m, 1H); 7.17 (t, J=7.80 Hz, 1H); 7.26 (d, J=9.00 Hz, 1H); 7.32 (m, 4H); 7.64 (d, J=8.81 Hz, 2H); 8.33 (s, 1H); 8.71 (s, 1H); 8.93 (s, 1H).

EXAMPLE 240

3-(4-amino-5-{4-[({[3-(trifluoromethyl)phenyl]amino}carbonyl)amino]phenyl}thieno[2,3-d]pyrimidin-6-yl)propanamide The desired product was prepared by substituting Example 238A and 3-trifluoromethylphenyl isocyanate for Example 1E and phenyl isocyanate, respectively, in Example 1F. The product was purified by HPLC using the conditions described in Example 179 to provide the trifluoroacetate salt. MS (ESI(+)) m/e 501 (M+H)$^+$; $^1$H NMR (300 MHz, DMSO-$d_6$) δ 2.36 (t, J=7.46 Hz, 2H); 2.84 (t, J=7.63 Hz, 2H); 6.85 (s, 1H); 7.34 (m, 4H); 7.53 (t, J=7.80 Hz, 1H); 7.61 (d, J=10.17 Hz, 1H); 7.65 (d, J=8.48 Hz, 2H); 8.04 (s, 1H); 8.29 (s, 1H); 9.05 (s, 1H); 9.17 (s, 1H).

EXAMPLE 241

3-{4-amino-5-[4-({[(2-fluoro-5-methylphenyl)amino]carbonyl}amino)phenyl]thieno[2,3-d]pyrimidin-6-yl}propanamide The desired product was prepared by substituting Example 238A and 2-fluoro-5-methylphenyl isocyanate for Example 1E and phenyl isocyanate, respectively, in Example 1F. The product was purified by HPLC using the conditions described in Example 179 to provide the trifluroacetate salt. MS (ESI(+)) m/e 465 (M+H)$^+$; $^1$H NMR (300 MHz, DMSO-$d_6$) δ 2.28 (s, 3H); 2.36 (t, J=7.46 Hz, 2H); 2.85 (t, J=7.29 Hz, 2H); 6.82 (m, 2H); 7.12 (dd, J=11.36, 8.31 Hz, 1H); 7.33 (m, 3H); 7.64 (d, J=8.48 Hz, 2H); 7.99 (dd, J=7.80, 2.03 Hz, 1H); 8.33 (s, 1H); 8.57 (d, J=2.37 Hz, 1H); 9.31 (s, 1H).

EXAMPLE 242

3-{4-amino-5-[4-({[(3,5-dimethylphenyl)amino]carbonyl}amino)phenyl]thieno[2,3-d]pyrimidin-6-yl}propanamide The desired product was prepared by substituting Example 238A and 3,5-dimethylphenyl isocyanate for Example 1E and phenyl isocyanate, respectively, in Example 1F. The product was purified by HPLC using the conditions described in Example 179 to provide the trifluoroacetate salt. MS (ESI (+)) m/e 461 (M+H)$^+$; $^1$H NMR (300 MHz, DMSO-$d_6$) δ 2.24 (s, 6H); 2.36 (t, J=7.46 Hz, 2H); 2.85 (t, J=7.46 Hz, 2H); 6.63 (s, 1H); 6.85 (s, 1H); 7.09 (s, 2H); 7.29-7.35 (m, 3H); 7.63 (d, J=8.48 Hz, 2H); 8.33 (s, 1H); 8.63 (s, 1H); 8.91 (s, 1H).

EXAMPLE 243

3-{4-amino-5-[4-({[(3-chlorophenyl)amino]carbonyl}amino)phenyl]thieno[2,3-d]pyrimidin-6-yl}propanamide The desired product was prepared by substituting Example 238A and 3-chlorophenyl isocyanate for Example 1E and phenyl isocyanate, respectively, in Example 1F. The product was purified by HPLC using the conditions described in Example 179 to provide the trifluoroacetate salt. MS (ESI(+)) m/e 467 (M+H)$^+$; $^1$H NMR (300 MHz, DMSO-d$_6$) δ 2.36 (t, J=7.63 Hz, 2H); 2.85 (t, J=7.63 Hz, 2H); 6.85 (s, 1H); 7.04 (m, 1H); 7.29-7.37 (m, 5H); 7.64 (d, J=8.81 Hz, 2H); 7.74 (m, 1H); 8.33 (s, 1H); 9.03 (s, 1H); 9.04 (s, 1H).

EXAMPLE 244

3-{4-amino-5-[4-({[(3-bromophenyl)amino]carbonyl}amino)phenyl]thieno[2,3-d]pyrimidin-6-yl}propanamide The desired product was prepared by substituting Example 238A and 3-bromophenyl isocyanate for Example 1E and phenyl isocyanate, respectively, in Example 1F. The product was purified by HPLC using the conditions described in Example 179 to provide the trifluoroacetate salt. MS (ESI(+)) m/e 511, 513 (M+H)$^+$; $^1$H NMR (300 MHz, DMSO-d$_6$) δ 2.36 (t, J=7.63 Hz, 2H); 2.85 (t, J=7.63 Hz, 2H); 6.85 (s, 1H); 7.17 (m, 1H); 7.26 (t, J=7.97 Hz, 1H); 7.31-7.37 (m, 4H); 7.64 (d, J=8.81 Hz, 2H); 7.88 (t, J=2.03 Hz, 1H); 8.32 (s, 1H); 9.00 (s, 1H); 9.03 (s, 1H).

EXAMPLE 245

3-{4-amino-5-[4-({[(3-fluorophenyl)amino]carbonyl}amino)phenyl]thieno[2,3-d]pyrimidin-6-yl}propanamide The desired product was prepared by substituting Example 238A and 3-fluorophenyl isocyanate for Example 1E and phenyl isocyanate, respectively, in Example 1F. The product was purified by HPLC using the conditions described in Example 179 to provide the trifluoroacetate salt. MS (ESI(+)) m/e 451 (M+H)$^+$; $^1$H NMR (300 MHz, DMSO-d$_6$) δ 6.81 (m, 1H); 6.85 (s, 1H); 7.15 (m, 1H); 7.28-7.37 (m, 4H); 7.52 (m, 1H); 7.52 (dt, J=11.70, 2.30 Hz, 1H); 7.64 (d, J=8.48 Hz, 2H); 8.33 (s, 1H); 9.03 (s, 1H); 9.04 (s, 1H).

EXAMPLE 246

3-{4-amino-5-[4-({[(3-ethylphenyl)amino]carbonyl}amino)phenyl]thieno[2,3-d]pyrimidin-6-yl}propanamide The desired product was prepared by substituting Example 238A and 3-ethylphenyl isocyanate for Example 1E and phenyl isocyanate, respectively, in Example 1F. The product was purified by HPLC using the conditions described in Example 179 to provide the trifluoroacetate salt. MS (ESI(+)) m/e 461 (M+H)$^+$; $^1$H NMR (300 MHz, DMSO-d$_6$) δ 1.19 (t, J=7.63 Hz, 3H); 2.36 (t, J=7.46 Hz, 2H); 2.59 (q, J=7.46 Hz, 2H); 2.85 (t, J=7.46 Hz, 2H); 6.84-6.87(m, 2H); 7.19 (t, J=7.80 Hz, 1H); 7.28 (d, J=9.49 Hz, 1H); 7.30-7.37 (m, J=8.81 Hz, 4H); 7.62 (s, 1H); 7.65 (s, 1H); 8.33 (s, 1H); 8.72 (s, 1H); 8.92 (s, 1H).

EXAMPLE 247

3-(4-amino-5-{4-[({[3-(trifluoromethyl)phenyl]amino}carbonyl)amino]phenyl}thieno[2,3-d]pyrimidin-6-yl)-N,N-dimethylpropanamide

EXAMPLE 247A 6,6-dicyano-N,N-dimethyl-5-phenyl-5-hexenamide

The desired product was prepared by substituting 6,6-dicyano-5-phenyl-5-hexenoic acid (prepared by substituting 5-oxo-5-phenylpentanoic acid for Example 1A in Example 1B) and dimethylamine hydrochloride for Example 66B and aniline, respectively, in Example 66C. MS (ESI(−)) m/e 266 (M−H)$^−$.

EXAMPLE 247B 3-(4-amino-5-phenylthieno[2,3-d]pyrimidin-6-yl)-N,N-dimethylpropanamide The desired product was prepared by substituting Example 247A for Example 1B in Examples 1C-D

EXAMPLE 247C

3-[4-amino-5-(4-aminophenyl)thieno[2,3-d]pyrimidin-6-yl]-N,N-dimethylpropanamide The desired product was prepared by substituting Example 247B for Example 143A in Examples 143B-C. MS (ESI(+)) m/e 342 (M+H)$^+$.

EXAMPLE 247D 3-(4-amino-5-{4-[({[3-(trifluoromethyl)phenyl]amino}carbonyl)amino]phenyl}thieno[2,3-d]pyrimidin-6-yl)-N,N-dimethylpropanamide The desired product was prepared by substituting Example 247C and 3-trifluoromethylphenyl isocyanate for Example 1E and phenyl isocyanate, respectively, in Example 1F. The product was purified by HPLC using the conditions described in Example 179 to provide the trifluoroacetate salt. MS (ESI(+)) m/e 529 (M+H)$^+$; $^1$H NMR (300 MHz, DMSO-d$_6$) δ 2.60 (t, J=7.29 Hz, 2H); 2.80 (s, 3H); 2.86 (t, J=7.12 Hz, 2H); 2.89 (s, 3H); 7.33 (d, J=8.14 Hz, 1H); 7.36 (d, J=8.81 Hz, 2H); 7.53 (t, J=6.95 Hz, 1H); 7.61 (d, J=9.83 Hz, 1H); 7.66 (d, J=8.81 Hz, 2H); 8.04 (s, 1H); 8.33 (s, 1H); 9.09 (s, 1H); 9.20 (s, 1H).

EXAMPLE 248

3-(4-amino-5-{4-[({[2-fluoro-5-(trifluoromethyl)phenyl]amino}carbonyl)amino]phenyl}thieno[2,3-d]pyrimidin-6-yl)-N,N-dimethylpropanamide The desired product was prepared by substituting Example 247C and 2-fluoro-5-trifluoromethylphenyl isocyanate for Example 1E and phenyl isocyanate, respectively, in Example 1F. The product was purified by HPLC using the conditions described in Example 179 to provide the trifluoroacetate salt. MS (ESI(+)) m/e 493 (M+H)$^+$; $^1$H NMR (300 MHz, DMSO-d$_6$) δ 2.28 (s, 3H); 2.60 (t, J=7.29 Hz, 2H); 2.80 (s, 3H); 2.85 (t, J=7.12 Hz, 2H); 2.89 (s, 3H); 6.83 (m, 1H); 7.12 (dd, J=11.36, 8.31 Hz, 1H); 7.35 (d, J=8.82 Hz, 2H); 7.64 (d, J=8.82 Hz, 2H); 7.99 (dd, J=7.80, 2.03 Hz, 1H); 8.34 (s, 1H); 8.57 (d, J=2.71 Hz, 1H); 9.30 (s, 1H).

EXAMPLE 249

3-{4-amino-5-[4-({[(3-chlorophenyl)amino]carbonyl}amino)phenyl]thieno[2,3-d]pyrimidin-6-yl}-N,N-dimethylpropanamide The desired product was prepared by substituting Example 247C and 3-chlorophenyl isocyanate for Example 1E and phenyl isocyanate, respectively, in Example 1F. The product was purified by HPLC using the conditions described in Example 179 to provide the trifluoroacetate salt. MS (ESI(+)) m/e 495 (M+H)$^+$; $^1$H NMR (300 MHz, DMSO-d$_6$) δ 2.60 (t, J=7.29 Hz, 2H); 2.80 (s, 3H); 2.85 (t, J=7.12 Hz, 2H); 2.89 (s, 3H); 7.04 (m, 1H); 7.29-733 (m, 2H); 7.35 (d, J=8.82 Hz, 2H); 7.65 (d, J=8.81 Hz, 2H); 7.73 (m, 1H); 8.34 (s, 1H); 9.05 (s, 1H); 9.06 (s, 1H).

EXAMPLE 250

3-(4-amino-5-{4-[({[4-chloro-3-(trifluoromethyl)phenyl]amino}carbonyl)amino]phenyl}thieno[2,3-d]pyrimidin-6-yl)-N,N-dimethylpropanamide The desired product was prepared by substituting Example 247C and 3-trifluoromethyl-4-chlorophenyl isocyanate for Example 1E and phenyl isocyanate, respectively, in Example 1F. The product was purified by HPLC using the conditions described in Example 179 to provide the trifluoroacetate salt. $^1$H NMR (300 MHz, DMSO-d$_6$) δ 2.59 (t, J=7.29 Hz, 2H); 2.80 (s, 3H); 2.84 (d, J=7.46 Hz, 2H); 2.89 s, 3H); 7.36 (d, J=8.48 Hz, 2H); 7.60-7.68 (m, 4H); 8.14 (d, J=2.37 Hz, 1H); 8.33 (s, 1H); 9.13 (s, 1H); 9.31 (s, 1H).

EXAMPLE 251

3-{4-amino-5-[4-({[(4-fluorophenyl)amino]carbonyl}amino)phenyl]thieno[2,3-d]pyrimidin-6-yl}-N,N-dimethylpropanamide The desired product was prepared by substituting Example 247C and 4-fluorophenyl isocyanate for Example 1E and phenyl isocyanate, respectively, in Example 1F. The product was purified by HPLC using the conditions described in Example 179 to provide the trifluoroacetate salt. MS (ESI(+)) m/e 479 (M+H)$^+$; $^1$H NMR (300 MHz, DMSO-d$_6$) δ 2.60 (t, J=7.29 Hz, 2H); 2.80 (s, 3H); 2.86 (t, J=7.46 Hz, 2H); 2.89 (s, 3H); 7.13 (m, 2H); 7.34 (d, J=8.48 Hz, 2H); 7.49 (m, 2H); 7.64 (d, J=8.48 Hz, 2H); 8.35 (s, 1H); 8.85 (s, 1H); 8.96 (s, 1H).

EXAMPLE 252

3-{4-amino-5-[4-({[(3-chlorophenyl)amino]carbonyl}amino)phenyl]thieno[2,3-d]pyrimidin-6-yl}-N,N-dimethylpropanamide The desired product was prepared by substituting Example 247C and 3-chlorophenyl isocyanate for Example 1E and phenyl isocyanate, respectively, in Example 1F. The product was purified by HPLC using the conditions described in Example 179 to provide the trifluoroacetate salt. MS (ESI(+)) m/e 475 (M+H)$^+$; $^1$H NMR (300 MHz, DMSO-d$_6$) δ 2.29 (s, 3H); 2.60 (t, J=7.12 Hz, 2H); 2.80 (s, 3H); 2.87 (t, J=7.12 Hz, 2H); 2.89 (s, 3H); 6.81 (d, J=7.12 Hz, 1H); 7.17 (m, 1H); 7.26 (d, J=6.0 Hz, 1H); 7.32 (s, 1H); 7.34 (d, J=8.48 Hz, 2H); 7.64 (d, J=8.48 Hz, 2H); 8.36 (s, 1H); 8.73 (s, 1H); 8.94 (s, 1H).

EXAMPLE 253

3-{4-amino-5-[4-({[(3-bromophenyl)amino]carbonyl}amino)phenyl]thieno[2,3-d]pyrimidin-6-yl}-N,N-dimethylpropanamide The desired product was prepared by substituting Example 247C and 3-bromophenyl isocyanate for Example 1E and phenyl isocyanate, respectively, in Example 1F. The product was purified by HPLC using the conditions described in Example 179 as the trifluoroacetate salt. MS (ESI(+)) m/e 561 (M+Na)$^+$; $^1$H NMR (300 MHz, DMSO-d$_6$) δ 2.60 (t, J=7.29 Hz, 2H); 2.80 (s, 3H); 2.86 (t, J=7.46 Hz, 2H); 2.89 (s, 3H); 7.14-7.19 (m, 1H); 7.26 (t, J=7.97 Hz, 1H); 7.32-7.38 (m, 3H); 7.65 (d, J=8.81 Hz, 2H); 7.88 (t, J=2.03 Hz, 1H); 8.36 (s, 1H); 9.04 (s, 1H); 9.06 (s, 1H).

EXAMPLE 254

3-{4-amino-5-[4-({[(3-fluorophenyl)amino]carbonyl}amino)phenyl]thieno[2,3-d]pyrimidin-6-yl}-N,N-dimethylpropanamide The desired product was prepared by substituting Example 247C and 3-fluorophenyl isocyanate for Example 1E and phenyl isocyanate, respectively, in Example 1F. The product was purified by HPLC using the conditions described in Example 179 as the trifluoroacetate salt. MS (ESI(+)) m/e 479 (M+H)$^+$; $^1$H NMR (300 MHz, DMSO-d$_6$) δ 2.60 (t, J=7.46 Hz, 2H); 2.80 (s, 3H); 2.86 (t, J=7.46 Hz, 2H); 2.89 (s, 3H); 6.80 (m, 1H); 7.15 (m, 1H); 7.26-7.38 (m, 3H); 7.47-7.55 (m, 1H); 7.64 (d, J=8.81 Hz, 2H); 8.34 (s, 1H); 9.03 (s, 1H); 9.05 (s, 1H).

EXAMPLE 255

3-{4-amino-5-[4-({[(3-fluoro-4-methylphenyl)amino]carbonyl}amino)phenyl]thieno[2,3-d]pyrimidin-6-yl}-N,N-dimethylpropanamide The desired product was prepared by substituting Example 247C and 3-fluoro-4-methylphenyl isocyanate for Example 1E and phenyl isocyanate, respectively, in Example 1F. The product was purified by HPLC using the conditions described in Example 179 to provide the trifluoroacetate salt. MS (ESI(+)) m/e 493 (M+H)$^+$; $^1$H NMR (300 MHz, DMSO-d$_6$) δ 2.60 (t, J=7.46 Hz, 2H); 2.80 (s, 3H); 2.86 (t, J=7.46 Hz, 2H); 2.89 (s, 3H); 6.80 (m, 1H); 7.15 (m, 11H); 7.33 (m, 3H); 7.51 (m, 1H); 7.64 (d, J=8.81 Hz, 2H); 8.34 (s, 1H); 9.03 (s, 1H); 9.05 (s, 1H).

EXAMPLE 256

3-{4-amino-5-[4-({[(3-chloro-4-fluorophenyl)amino]carbonyl}amino)phenyl]thieno[2,3-d]pyrimidin-6-yl}-N,N-dimethylpropanamide The desired product was prepared by substituting Example 247C and 3-chloro-4-fluorophenyl isocyanate for Example 1E and phenyl isocyanate, respectively, in Example 1F. The product was purified by HPLC using the conditions described in Example 179 to provide the trifluoroacetate salt. MS (ESI(+)) m/e 513 (M+H)$^+$; $^1$H NMR (300 MHz, DMSO-d$_6$) δ 2.60 (t, J=7.12 Hz, 2H); 2.80 (s, 3H); 2.86 (t, J=7.46 Hz, 2H); 2.89

(s, 3H); 7.32-7.38 (m, 4H); 7.65 (d, J=8.48 Hz, 2H); 7.83 (m, 1H); 8.36 (s, 1H); 9.06 (s, 1H); 9.08 (s, 1H).

EXAMPLE 257

3-(4-amino-5-{4-[(anilinocarbonyl)amino]phenyl}thieno[2,3-d]pyrimidin-6-yl)-N,N-dimethylpropanamide The desired product was prepared by substituting Example 247C for Example 1E in Example 1F. The product was purified by HPLC using the conditions described in Example 179 to provide the trifluoroacetate salt. MS (ESI(+)) m/e 461 (M+H)$^+$; $^1$H NMR (300 MHz, DMSO-d$_6$) δ 2.60 (t, J=7.29 Hz, 2H); 2.80 (s, 3H); 2.86 (t, J=7.46 Hz, 2H); 2.89 (s, 3H); 6.99 (t, J=7.29 Hz, 1H); 7.30 (m, 2H); 7.34 (d, J=8.48 Hz, 2H); 7.48 (d, J=7.46 Hz, 2H); 7.64 (d, J=8.48 Hz, 2H); 8.34 (s, 1H); 8.79 (s, 1H); 8.94 (s, 1H).

EXAMPLE 258

3-[4-amino-5-(4-{[(2,3-dihydro-1H-inden-5-ylamino)carbonyl]amino}phenyl)thieno[2,3-d]pyrimidin-6-yl]-N,N-dimethylpropanamide The desired product was prepared by substituting Example 247C and 5-isocyanatoindane for Example 1E and phenyl isocyanate, respectively, in Example 1F. The product was purified by HPLC using the conditions described in Example 179 to provide the trifluoracetate salt. MS (ESI(+)) m/e 501 (M+H)$^+$; $^1$H NMR (300 MHz, DMSO-d$_6$) δ 2.01 (m, 2H); 2.59 (t, J=7.29 Hz, 2H); 2.80 (s, 3H); 2.75-2.90 (m, 6H); 2.89 (s, 3H); 7.14 (m, 2H); 7.33 (d, J=8.48 Hz, 2H); 7.39 (s, 1H); 7.63 (d, J=8.81 Hz, 2H); 8.33 (s, 1H); 8.65 (s, 1H); 8.89 (s, 1H).

EXAMPLE 259

3-{4-amino-5-[4-({[(3-cyanophenyl)amino]carbonyl}amino)phenyl]thieno[2,3-d]pyrimidin-6-yl}-N,N-dimethylpropanamide The desired product was prepared by substituting Example 247C and 3-cyanophenyl isocyanate for Example 1E and phenyl isocyanate, respectively, in Example 1F. The product was purified by HPLC using the conditions described in Example 179 to provide the trifluoroacetate salt. MS (ESI(+)) m/e 486 (M+H)$^+$; $^1$H NMR (300 MHz, DMSO-d$_6$) δ 2.60 (t, J=7.29 Hz, 2H); 2.80 (s, 3H); 2.86 (t, J=7.12 Hz, 2H); 2.89 (s, 3H); 7.36 (d, J=8.81 Hz, 2H); 7.44 (m, 1H); 7.52 (t, J=7.80 Hz, 1H); 7.66 (d, J=8.48 Hz, 2H); 7.70 (m, 1H); 8.00 (t, J=1.70 Hz, 1H); 8.34 (s, 1H); 9.15 (s, 1H); 9.19 (s, 1H).

EXAMPLE 260

3-(4-amino-5-{4-[({[4-fluoro-3-(trifluoromethyl)phenyl]amino}carbonyl)amino]phenyl}thieno[2,3-d]pyrimidin-6-yl)-N,N-dimethylpropanamide The desired product was prepared by substituting Example 247C and 4-fluoro-3-trifluoromethylphenyl isocyanate for Example 1E and phenyl isocyanate, respectively, in Example 1F. The product was purified by HPLC using the conditions described in Example 179 to provide the trifluoroacetate salt. MS (ESI(+)) m/e 547 (M+H)$^+$; $^1$H NMR (300 MHz, DMSO-d$_6$) δ 2.59 (t, J=7.29 Hz, 2H); 2.80 (s, 3H); 2.86 (t, J=7.46 Hz, 2H); 2.89 (s, 3H); 7.36 (d, J=8.48 Hz, 2H); 7.46 (m, 1H); 7.60-7.71 (m, 3H); 8.03 (dd, J=6.44, 2.71 Hz, 1H); 8.33 (s, 1H); 9.09 (s, 1H); 9.18 (s, 1H).

EXAMPLE 261

3-{4-amino-5-[4-({[(3-methylphenyl)amino]carbonyl}amino)phenyl]thieno[2,3-d]pyrimidin-6-yl}-N-methylpropanamide

EXAMPLE 261A

3-[4-amino-5-(4-aminophenyl)thieno[2,3-d]pyrimidin-6-yl]-N-methylpropanamide

The desired product was prepared by substituting methylamine hydrochloride for dimethylamine hydrochloride in Examples 247A-C. MS (ESI(+)) m/e 328 (M+H)$^+$.

EXAMPLE 261B

3-{4-amino-5-[4-({[(3-methylphenyl)amino]carbonyl}amino)phenyl]thieno[2,3-d]pyrimidin-6-yl}-N-methylpropanamide The desired product was prepared by substituting Example 261A and 3-methylphenyl isocyanate for Example 1E and phenyl isocyanate, respectively, in Example 1F. The product was purified by HPLC using the conditions described in Example 179 to provide the trifluoroacetate salt. MS (ESI(+)) m/e 461 (M+H)$^+$; $^1$H NMR (300 MHz, DMSO-d$_6$) δ 2.29 (s, 3H); 2.36 (t, J=7.46 Hz, 2H); 2.54 (d, J=4.75 Hz, 3H); 2.86 (t, J=7.29 Hz, 2H); 6.81 (d, J=7.46 Hz, 1H); 7.17 (t, J=7.80 Hz, 1H); 7.26 (m, 1H); 7.29-7.34 (m, 3H); 7.64 (d, J=8.81 Hz, 2H); 7.80 (m, 1H); 8.33 (s, 1H); 8.71 (s, 1H); 8.93 (s, 1H).

EXAMPLE 262

3-(4-amino-5-{4-[({[3-(trifluoromethyl)phenyl]amino}carbonyl)amino]phenyl}thieno[2,3-d]pyrimidin-6-yl)-N-methylpropanamide The desired product was prepared by substituting Example 261A and 3-trifluoromethylphenyl isocyanate for Example 1E and phenyl isocyanate, respectively, in Example 1F. The product was purified by HPLC using the conditions described in Example 179 to provide the trifluoroacetate salt. MS (ESI(+)) m/e 515 (M+H)$^+$; $^1$H NMR (300 MHz, DMSO-d$_6$) δ 2.37 (t, J=7.46 Hz, 2H); 2.55 (d, J=4.75 Hz, 3H); 2.86 (t, J=7.46 Hz, 2H); 7.33 (m, 3H); 7.59 (m, 4H); 7.80 (q, J=4.18 Hz, 1H); 8.04 (s, 1H); 8.33 (m, 1H); 9.08 (s, 1H); 9.19 (s, 1H).

EXAMPLE 263

3-(4-amino-5-{4-[({[2-fluoro-5-(trifluoromethyl)phenyl]amino}carbonyl)amino]phenyl}thieno[2,3-d]pyrimidin-6-yl)-N-methylpropanamide The desired product was prepared by substituting Example 261A and 2-fluoro-5-trifluoromethylphenyl isocyanate for Example 1E and phenyl isocyanate, respectively, in Example 1F. The product was purified by HPLC using the conditions described in Example 179 to provide the trifluoroacetate salt. MS (ESI(+)) m/e 533 (M+H)$^+$; $^1$H NMR (300 MHz, DMSO-d$_6$) δ 2.36 (t, J=7.63 Hz, 2H); 2.54 (d, J=4.41 Hz, 3H); 2.86 (t, J=7.46 Hz, 2H); 7.35 (d, J=8.48 Hz, 2H); 7.48-7.45 (m, J=4.24, 2.54 Hz, 1H); 7.46-7.57 (m, 1H); 7.65 (d, J=8.48 Hz, 2H); 7.80 (m, J=4.75 Hz, 1H); 8.32 (s, 1H); 8.63 (dd, J=7.29, 2.20 Hz, 1H); 9.00 (d, J=3.05 Hz, 1H); 9.41 (s, 1H).

EXAMPLE 264

3-{4-amino-5-[4-({[(3,5-dimethylphenyl)amino]carbonyl}amino)phenyl]thieno[2,3-d]pyrimidin-6-yl}-N-methylpropanamide The desired product was prepared by substituting Example 261A and 3,5-dimethylphenyl isocyanate for Example 1E and phenyl isocyanate, respectively, in Example 1F. The product was purified by HPLC using the conditions described in Example 179 to provide the trifluoroacetate salt. MS (ESI (+)) m/e 475 (M+H)$^+$; $^1$H NMR (300 MHz, DMSO-d$_6$) δ 2.24 (s, 6H); 2.36 (t, J=7.63 Hz, 2H); 2.54 (d, J=4.75 Hz, 3H); 2.86 (t, J=7.29 Hz, 1H); 2.86 (t, J=7.29 Hz, 2H); 7.09 (s, 2H); 7.31 (d, J=8.48 Hz, 2H); 7.63 (d, J=8.81 Hz, 2H); 7.80 (q, J=4.07 Hz, 1H); 8.33 (s, 1H); 8.63 (s, 1H); 8.91 (s, 1H).

EXAMPLE 265

3-{4-amino-5-[4-({[(3-chlorophenyl)amino]carbonyl}amino)phenyl]thieno[2,3-d]pyrimidin-6-yl}-N-methylpropanamide The desired product was prepared by substituting Example 261A and 3-chlorophenyl isocyanate for Example 1E and phenyl isocyanate, respectively, in Example 1F. The product was purified by HPLC using the conditions described in Example 179 to provide the trifluoroacetate salt. MS (ESI(+)) m/e 481 (M+H)$^+$; $^1$H NMR (300 MHz, DMSO-d$_6$) δ 2.37 (t, J=7.46 Hz, 2H); 2.54 (d, J=4.75 Hz, 3H); 2.86 (t, J=7.46 Hz, 2H); 7.04 (m, 1H); 7.27-7.35 (m, 4H); 7.65 (d, J=8.81 Hz, 2H); 7.74 (d, J=2.71 Hz, 1H); 7.80 (q, J=4.18 Hz, 1H); 8.34 (s, 1H); 9.04 (s, 1H); 9.05 (s, 1H).

EXAMPLE 266

3-{4-amino-5-[4-({[(3-bromophenyl)amino]carbonyl}amino)phenyl]thieno[2,3-d]pyrimidin-6-yl}-N-methylpropanamide The desired product was prepared by substituting Example 261A and 3-bromophenyl isocyanate for Example 1E and phenyl isocyanate, respectively, in Example 1F. The product was purified by HPLC using the conditions described in Example 179 to provide the trifluoroacetate salt. $^1$H NMR (300 MHz, DMSO-d$_6$) δ 2.37 (t, J=7.46 Hz, 2H); 2.55 (d, J=4.75 Hz, 3H); 2.86 (t, J=7.46 Hz, 2H); 7.17 (m, 1H); 7.26 (t, J=7.97 Hz, 1H); 7.30-7.37 (m, 3H); 7.65 (d, J=8.48 Hz, 2H); 7.80 (m, 1H); 7.88 (t, J=1.86 Hz, 1H); 8.34 (s, 1H); 9.03 (s, 1H); 9.06 (s, 1H).

EXAMPLE 267

N-{4-[4-amino-6-(3-methoxypropyl)thieno[2,3-d]pyrimidin-5-yl]phenyl}-N'-[2-fluoro-5-(trifluoromethyl)phenyl]urea

EXAMPLE 267A 5-(4-aminophenyl)-6-(3-methoxypropyl)thieno[2,3-d]pyrimidin-4-amine The desired product was prepared by substituting 1-iodo-4-methoxybutane for tert-butyl(3-iodopropoxy)dimethylsilane in Examples 104A and 104B.

EXAMPLE 267B

N-{4-[4-amino-6-(3-methoxypropyl)thieno[2,3-d]pyrimidin-5-yl]phenyl}-N'-[2-fluoro-5-(trifluoromethyl)phenyl]urea The desired product was prepared by substituting Example 267A and 2-fluoro-5-trifluoromethylphenyl isocyanate for Example 1E and phenyl isocyanate, respectively, in Example 1F. MS (ESI(+)) m/e 520 (M+H)$^+$; $^1$H NMR (300 MHz, DMSO-d$_6$) δ 1.72-1.82 (m, 2H); 2.66-2.71 (t, 2H, J=7.5 Hz); 3.16 (s, 3H); 3.25-3.29 (t, 2H, J=4.2 Hz); 7.32-7.35 (d, 2H, J=8.7 Hz); 7.38-7.45 (m, 1H); 7.49-7.55 (t, 1H, J=8.7 Hz); 7.63-7.66 (d, 2H, J=8.4 Hz); 8.27 (s, 1H); 8.62-8.65 (dd, 1H, J=2.1, 7.2 Hz); 8.98-8.99 (d, 1H, J=2.7 Hz); 9.39 (s, 1H); MS (ESI(−)) m/e 518 (M−H)$^−$.

EXAMPLE 268

N-{4-[4-amino-6-(3-methoxypropyl)thieno[2,3-d]pyrimidin-5-yl]phenyl}-N'-(3-methylphenyl)urea The desired product was prepared by substituting Example 267A and 3-methylphenyl isocyanate for Example 1E and phenyl isocyanate, respectively, in Example 1F. MS (ESI(+)) m/e 448 (M+H)$^+$; $^1$H NMR (300 MHz, DMSO-d$_6$) δ 1.72-1.82 (m 2H); 2.29 (s, 3H); 2.66-2.71 (t, 2H, J=7.2 Hz); 3.16 (s, 3H); 3.24-3.29 (t, 2H, J=6.3 Hz); 6.79-6.82 (d, 1H, J=7.2 Hz); 7.14-7.19 (t, 1H, J=7.8 Hz); 7.24-7.31 (m 4H); 7.61-7.64 (d, 2H, J=9 Hz); 8.27 (s, 1H); 8.67 (s, 1H); 8.87 (s, 1H).

EXAMPLE 269

N-(4-{4-amino-6-[4-(dimethylamino)benzyl]thieno[2,3-d]pyrimidin-5-yl}phenyl)-N'-(3-methylphenyl)urea

EXAMPLE 269A 5-(4-aminophenyl)-6-[4-(dimethylamino)benzyl]thieno[2,3-d]pyrimidin-4-amine The desired product was prepared by substituting N-[4-(2-iodoethyl)phenyl]-N,N-dimethylamine for tert-butyl(3-iodopropoxy)dimethylsilane in Examples 104A and 104B. MS (ESI(+)) m/e 376 (M+H)$^+$.

EXAMPLE 269B

N-(4-{4-amino-6-[4-(dimethylamino)benzyl]thieno[2,3-d]pyrimidin-5-yl}phenyl)-N'-(3-methylphenyl)urea The desired product was prepared by substituting Example 269A and 3-methylphenyl isocyanate for Example 1E and phenyl isocyanate, respectively, in Example 1F. MS (ESI(+)) m/e 509 (M+H)$^+$; $^1$H NMR (300 MHz, DMSO-d$_6$) δ 2.29 (s, 3H); 2.85 (s, 6H); 3.85(s, 2H); 6.63-6.66 (d, 2H, J=9 Hz); 6.79-6.82 (d, 1H, J=7.8 Hz); 6.95-6.98 (d, 2H, J=8.7 Hz); 7.14-7.19 (t, 1H, J=7.5 Hz); 7.24-7.31 (m, 2H); 7.35-7.38 (d, 2H, J=9 Hz); 7.63-7.66 (d, 2H, J=8.7 Hz); 8.25 (s, 1H); 8.68 (s, 1H); 8.89 (s, 1H).

EXAMPLE 270

N-(4-{4-amino-6-[4-(dimethylamino)benzyl]thieno[2,3-d]pyrimidin-5-yl}phenyl)-N'-[3-(trifluoromethyl)phenyl]urea The desired product was prepared by substituting Example 269A and 3-trifluomethylphenyl isocyanate for Example 1E and phenyl isocyanate, respectively, in Example 1F. MS (ESI (+)) m/e 563 (M+H)$^+$; $^1$H NMR (300 MHz, DMSO-d$_6$) δ 2.85 (s, 6H); 3.85 (s, 2H); 6.63-6.66 (d, 2H, J=9 Hz); 6.95-6.98 (d, 2H, J=8.7 Hz); 7.32-7.37 (m, 1H); 7.37-7.39 (d, 2H, J=8.7 Hz); 7.50-7.56 (t, 1H, J=7.5 Hz); 7.59-7.63 (m, 1H); 7.66-7.68 (d, 2H, J=8.4 Hz); 8.04 (s, 1H); 8.25 (s, 1H); 9.03 (s, 1H); 9.14 (s, 1H).

EXAMPLE 271

N-(4-{4-amino-6-[4-(dimethylamino)benzyl]thieno[2,3-d]pyrimidin-5-yl}phenyl)-N'-(3-chlorophenyl)urea The desired product was prepared by substituting Example 269A and 3-chlorophenyl isocyanate for Example 1E and phenyl isocyanate, respectively, in Example 1F. MS (ESI(+)) m/e 529 (M+H)$^+$; $^1$H NMR (300 MHz, DMSO-d$_6$) δ 2.85 (s, 6H); 3.85 (s, 2H); 6.63-6.66 (d, 2H, J=9 Hz); 6.95-6.98 (d, 2H, J=8.7 Hz); 7.02-7.06 (td, 1H, J=2.1, 6.9 Hz); 7.30-7.32 (m, 2H); 7.36-7.39 (d, 2H, J=8.4 Hz); 7.64-7.67 (d, 2H, J=8.4 Hz); 7.73-7.74 (m, 1H); 8.25 (s, 1H); 8.98 (s, 1H); 8.99 (s, 1H).

EXAMPLE 272

N-(4-{4-amino-6-[4-(dimethylamino)benzyl]thieno[2,3-d]pyrimidin-5-yl}phenyl)-N'-(3-ethylphenyl)urea The desired product was prepared by substituting Example 269A and 3-ethylphenyl isocyanate for Example 1E and phenyl isocyanate, respectively, in Example 1F. MS (ESI(+)) m/e 523 (M+H)$^+$; $^1$H NMR (300 MHz, DMSO-d$_6$) δ 1.16-1.21 (t, 3H, J=7.5 Hz); 2.51-2.62 (q, 2H, J=7.2 Hz); 2.85 (s, 6H); 3.85 (s, 2H); 6.63-6.66 (d, 2H, J=9 Hz); 6.83-6.85 (m, 1H); 6.95-6.98 (d, 2H, J=8.7 Hz); 7.17-7.22 (t, 1H, J=7.2 Hz); 7.26-7.29 (m, 1H); 7.34-7.38 (m, 3H); 7.64-7.66 (d, 2H, J=8.7 Hz); 8.25 (s, 1H); 8.69 (s, 1H); 8.88 (s, 1H).

EXAMPLE 273

N-(4-{4-amino-6-[4-(dimethylamino)benzyl]thieno[2,3-d]pyrimidin-5-yl}phenyl)-N'-(3-bromophenyl)urea The desired product was prepared by substituting Example 269A and 3-bromophenyl isocyanate for Example 1E and phenyl isocyanate, respectively, in Example 1F. MS (ESI(+)) m/e 573, 575 (M+H)$^+$; $^1$H NMR (300 MHz, DMSO-d$_6$) δ 2.85 (s, 6H); 3.85 (s, 2H); 6.63-6.66 (d, 2H, J=99 Hz); 6.95-6.98 (d, 2H, J=8.7 Hz); 7.15-7.18 (td, 1H, J=1.5, 7.8 Hz); 7.23-7.28 (t, 1H, J=7.8 Hz); 7.32-7.39 (m, 3H); 7.64-7.67 (d, 2H, J=8.4 Hz); 7.87-7.88 (t, 1H, J=1.8 Hz); 8.25 (s, 1H); 8.96 (s, 1H); 8.99 (s, 1H).

EXAMPLE 274

N-(4-{4-amino-6-[4-(dimethylamino)benzyl]thieno[2,3-d]pyrimidin-5-yl}phenyl)-N'-[2-fluoro-5-(trifluoromethyl)phenyl]urea The desired product was prepared by substituting Example 269A and 2-fluoro-5-trifluomethylphenyl isocyanate for Example 1E and phenyl isocyanate, respectively, in Example 1F. MS (ESI(+)) m/e 581 (M+H)$^+$; $^1$H NMR (300 MHz, DMSO-d$_6$) δ 2.85 (s, 6H); 3.85 (s, 2H); 6.63-6.66 (d, 2H, J=9 Hz); 6.95-6.98 (d, 2H, J=8.7 Hz); 7.38-7.44 (m, 3H); 7.48-7.55 (m, 1H); 7.66-7.68 (d, 2H, J=8.4 Hz); 8.25 (s, 1H); 8.62-8.65 (dd, 1H, J=2.4, 7.5 Hz); 8.98-8.99 (d, 1H, J=2.7 Hz); 9.41 (s, 1H).

EXAMPLE 275

N-(4-{4-amino-6-[4-(dimethylamino)benzyl]thieno[2,3-d]pyrimidin-5-yl}phenyl)-N'-(3-cyanophenyl)urea The desired product was prepared by substituting Example 269A and 3-cyanophenyl isocyanate for Example 1E and phenyl isocyanate, respectively, in Example 1F. MS (ESI(+)) m/e 520 (M+H)$^+$; $^1$H NMR (300 MHz, DMSO-d$_6$) δ 2.85 (s, 6H); 3.85 (s, 2H); 6.63-6.66 (d, 2H, J=9 Hz); 6.95-6.98 (d, 2H, J=8.7 Hz); 7.37-7.40 (d, 2H, J=8.7 Hz); 7.42-7.46 (td, 1H, J=2.1, 6.6 Hz); 7.48-7.54 (t, 1H, J=7.8 Hz); 7.65-7.73 (m, 3H); 7.99-8.00 (t, 1H, J=1.8 Hz); 8.25 (s, 1H); 9.08 (s, 1H); 9.12 (s, 1H).

EXAMPLE 276

N-(4-{4-amino-6-[4-(dimethylamino)benzyl]thieno[2,3-d]pyrimidin-5-yl}phenyl)-N'-(3,5-dimethylphenyl)urea The desired product was prepared by substituting Example 269A and 3,5-dimethylphenyl isocyanate for Example 1E and phenyl isocyanate, respectively, in Example 1F. MS (ESI (+)) m/e 523 (M+H)$^+$; $^1$H NMR (300 MHz, DMSO-d$_6$) δ 2.24 (s, 6H); 2.85 (s, 6H); 3.85 (s, 2H); 6.63-6.66 (d, 3H, J=9 Hz); 6.95-6.98 (d, 2H, J=8.7 Hz); 7.09 (s, 2H); 7.34-7.37 (d, 2H, J=9 Hz); 7.63-7.66 (d, 2H, J=8.7 Hz); 8.25 (s, 1H); 8.59 (s, 1H); 8.87 (s, 1H).

EXAMPLE 277

N-[4-(4-amino-6-{2-[4-(dimethylamino)phenyl]ethyl}thieno[2,3-d]pyrimidin-5-yl)phenyl]-N'-(3-methylphenyl)urea

EXAMPLE 277A 5-(4-aminophenyl)-6-{2-[4-(dimethylamino)phenyl]ethyl}thieno[2,3-d]pyrimidin-4-amine The desired product was prepared by substituting N-[4-(3-iodopropyl)phenyl]-N,N-dimethylamine for tert-butyl(3-iodopropoxy)dimethylsilane in Examples 104A and 104B. MS (ESI(+)) m/e 390 (M+H)$^+$.

EXAMPLE 277B

N-[4-(4-amino-6-{2-[4-(dimethylamino)phenyl]
ethyl}thieno[2,3-d]pyrimidin-5-yl)phenyl]-N'-(3-
methylphenyl)urea The desired product was prepared by substituting Example 277A and 3-methylphenyl isocyanate for Example 1E and phenyl isocyanate, respectively, in Example 1F. MS (ESI(+)) m/e 523 (M+H)$^+$; $^1$H NMR (300 MHz, DMSO-d$_6$) δ 2.28 (s, 3H); 2.73-2.88 (s and m, 10H); 6.60-6.63 (d, 2H, J=9 Hz); 6.79-6.82 (d, 1H, J=7.5 Hz); 6.87-6.90 (d, 2H, J=8.7 Hz); 7.09-7.12 (d, 2H, J=6.3 Hz); 7.14-7.19 (t, 1H, J=7.5 Hz); 7.24-7.31 (m, 2H); 7.55-7.58 (d, 2H, J=8.4), 8.25 (s, 1H); 8.66 (s, 1H); 8.86 (s, 1H).

EXAMPLE 278

N-[4-(4-amino-6-{2-[4-(dimethylamino)phenyl]
ethyl}thieno[2,3-d]pyrimidin-5-yl)phenyl]-N'-[3-
(trifluoromethyl)phenyl]urea The desired product was prepared by substituting Example 277A and 3-trifluoromethylphenyl isocyanate for Example 1E and phenyl isocyanate, respectively, in Example 1F. MS (ESI(+)) m/e 577 (M+H)$^+$; $^1$H NMR (300 MHz, DMSO-d$_6$) δ 2.73-2.88 (s and m, 10H); 6.60-6.63 (d, 2H, J=9 Hz); 6.87-6.90 (d, 2H, J=8.4 Hz); 7.11-7.14 (d, 2H, J=8.7 Hz); 7.32-7.34 (d, 1H, J=6.9 Hz); 7.50-7.60 (m, 4H); 8.03 (s, 1H); 8.26 (s, 1H); 9.01 (s, 1H); 9.13 (s, 1H).

EXAMPLE 279

N-[4-(4-amino-6-{2-[4-(dimethylamino)phenyl]
ethyl}thieno[2,3-d]pyrimidin-5-yl)phenyl]-N'-[2-
fluoro-5-(trifluoromethyl)phenyl]urea The desired product was prepared by substituting Example 277A and 2-fluoro-5-trifluoromethylphenyl isocyanate for Example 1E and phenyl isocyanate, respectively, in Example 1F. MS (ESI(+)) m/e 595 (M+H)$^+$; $^1$H NMR (300 MHz, DMSO-d$_6$) δ 2.73-2.88 (s and m, 10H); 6.60-6.63 (d, 2H, J=9 Hz); 6.87-6.90 (d, 2H, J=8.4 Hz); 7.13-7.16 (d, 2H, J=8.7 Hz); 7.38-7.44 (m, 1H); 7.48-7.55 (m, 1H); 7.58-7.61 (d, 2H, J=8.7 Hz); 8.26 (s, 1H); 8.61-8.65 (dd, 1H, J=2.4, 7.8 Hz); 8.97-8.98 (d, 1H, J=2.7 Hz); 9.38 (s, 1H).

EXAMPLE 280

N-[4-(4-amino-6-{2-[4-(dimethylamino)phenyl]
ethyl}thieno[2,3-d]pyrimidin-5-yl)phenyl]-N'-(3,5-
dimethylphenyl)urea The desired product was prepared by substituting Example 277A and 3,5-dimethylphenyl isocyanate for Example 1E and phenyl isocyanate, respectively, in Example 1F. MS (ESI (+)) m/e 537 (M+H)$^+$; $^1$H NMR (300 MHz, DMSO-d$_6$) δ 2.24 (s, 6H); 2.73-2.89 (s and m, 10H); 6.60-6.63 (d, 3H, J=9 Hz); 6.87-6.90 (d, 2H, J=7.8 Hz); 7.09-7.12 (d, 4H, J=8.4 Hz); 7.55-7.58 (d, 2H, J=8.7 Hz); 8.26 (s, 1H); 8.58 (s, 1H); 8.84 (s, 1H).

EXAMPLE 281

N-(4-{4-amino-6-[2-(dimethylamino)ethyl]thieno[2,
3-d]pyrimidin-5-yl}phenyl)-N'-(3-methylphenyl)urea

EXAMPLE 281A

N-(4-{4-amino-6-[2-(dimethylamino)ethyl]thieno[2,
3-d]pyrimidin-5-yl}phenyl)-N'-(3-methylphenyl)urea A 0° C. solution of 4-hydroxy-1-(4-nitrophenyl)-1-butanone (5.68 g, 29.4 mmol, prepared by substituting Example 104A for Example 104C in Example 104D] in dichloromethane (60 mL) was treated with triethylamine (4.9 mL, 35 mmol), CH$_3$SO$_2$Cl (2.7 mL, 35 mmol), stirred at 0° C. for 3 hours, poured into water, and extracted three times with dichloromethane. The combined extracts were washed with brine, dried (Na$_2$SO$_4$), filtered and concentrated. The concentrate was purified by silica gel chromatography with 50% ethyl acetate/hexanes to provide 6.42 g (76% yield) of the desired product. R$_f$ (50% ethyl acetate/hexanes)=0.2.

EXAMPLE 281B 4-(dimethylamino)-1-(4-nitrophenyl)-1-butanone

A mixture of Example 281A (3 g, 10.5 mmol), dimethylamine (21 mL, 2M in THF), and triethylamine (2.9 mL, 21 mmol) in DMF (25 mL) was heated to 85-90° C. for 1.5 hours, cooled to room temperature, diluted with water, and extracted twice with ethyl acetate. The combined extracts were washed with brine, dried (Na$_2$SO$_4$), filtered, and concentrated. The concentrate was purified by silica gel chromatography eluting with 10% methanol/dichloromethane to provide 1.27 g (51% yield) of the desired product. MS (ESI(+)) m/e 237 (M+H)$^+$.

EXAMPLE 281C 2-amino-5-[2-(dimethylamino)ethyl]-4-(4-nitrophenyl)-3-thiophenecarbonitrile The desired product was prepared by substituting Example 281B for Example 1A in Examples 1B-C. MS ((ESI(+)) m/e 317 (M+H)$^+$.

EXAMPLE 281D AND 281E

6-[2-(dimethylamino)ethyl]-5-(4-nitrophenyl)thieno
[2,3-d]pyrimidin-4-amine and 5-(4-nitrophenyl)-6-
vinylthieno[2,3-d]pyrimidin-4-amine A solution of Example 281C (100 mg) in formamide (3 mL) in a 5 mL capped vial was heated to 200° C. for 15 minutes in a Smith Synthesizer microwave oven at 300W. The reaction was repeated 10 times. The combined solutions were diluted with water and extracted twice with ethyl acetate. The combined extracts were washed with brine, dried (Na$_2$SO$_4$), filtered, and concentrated. The residue was purified by silica gel chromatography with 7% methanol/dichloromethane to provide 0.73 g (59% yield) of Example 281D, and 0.28 g (26% yield) of Example 281E. Example 281D: MS ((ESI(+)) m/e 344 (M+H)$^+$; Example 281E: MS ((ESI(+)) m/e 299 (M+H)$^+$.

EXAMPLE 281F 5-(4-aminophenyl)-6-[2-(dimethylamino)ethyl]thieno[2,3-d]pyrimidin-4-amine The desired product was prepared by substituting Example 281D for Example 1D in Example 1E. MS ((ESI(+)) m/e 314 (M+H)$^+$.

EXAMPLE 281G

N-(4-{4-amino-6-[2-(dimethylamino)ethyl]thieno[2,3-d]pyrimidin-5-yl}phenyl)-N'-(3-methylphenyl)urea The desired product was prepared by substituting Example 281F and 3-methylphenyl isocyanate for Example 1E and phenyl isocyanate, respectively, in Example 1F. MS (ESI(+)) m/e 447 (M+H)$^+$; $^1$H NMR (300 MHz, DMSO-d$_6$) δ 2.11 (s, 6H); 2.29 (s, 3H); 2.42-2.46 (t, 2H, J=7.2 Hz); 2.72-2.77 (t, 2H, J=6 Hz); 6.79-6.82 (d, 1H, J=7.5 Hz); 7.14-7.19 (t, 1H, J=7.5 Hz); 7.24-7.32 (m, 4H); 7.61-7.64 (d, 2H, J=6.6 Hz); 8.26 (s, 1H); 8.67 (s, 1H); 8.87 (s, 1H).

EXAMPLE 282

N-(4-{4-amino-6-[2-(dimethylamino)ethyl]thieno[2,3-d]pyrimidin-5-yl}phenyl)-N'-[3-(trifluoromethyl)phenyl]urea The desired product was prepared by substituting Example 281F and 3-trifluoromethylphenyl isocyanate for Example 1E and phenyl isocyanate, respectively, in Example 1F. MS (ESI(+)) m/e 501 (M+H)$^+$; $^1$H NMR (300 MHz, DMSO-d$_6$) δ 2.10 (s, 6H); 2.41-2.46 (t, 2H, J=7.2 Hz); 2.72-2.77 (t, 2H, J=6 Hz); 7.31-7.34 (m, 3H); 7.50-7.56 (t, 1H, J=7.2 Hz); 7.59-7.67 (m, 3H); 8.03 (br s, 11H); 8.26 (s, 1H); 9.02 (s, 1H); 9.14 (s, 1H).

EXAMPLE 283

N-(4-{4-amino-6-[2-(dimethylamino)ethyl]thieno[2,3-d]pyrimidin-5-yl}phenyl)-N'-(3-ethylphenyl)urea The desired product was prepared by substituting Example 281F and 3-ethylphenyl isocyanate for Example 1E and phenyl isocyanate, respectively, in Example 1F. MS (ESI(+)) m/e 461 (M+H)$^+$; $^1$H NMR (300 MHz, DMSO-d$_6$) δ 1.16-1.21 (t, 3H, J=7.5 Hz); 2.11 (s, 6H); 2.41-2.46 (t, 2H, J=7.2 Hz); 2.55-2.62 (q, 2H, J=7.5 Hz); 2.72-2.77 (t, 2H, J=6 Hz); 6.83-6.85 (d, 1H, J=7.5 Hz); 7.17-7.22 (t, 1H, J=7.5 Hz); 7.26-7.34 (m, 4H); 7.61-7.64 (d, 2H, J=8.4 Hz); 8.26 (s, 1H); 8.69 (s, 1H); 8.88 (s, 1H).

EXAMPLE 284

N-(4-{4-amino-6-[2-(dimethylamino)ethyl]thieno[2,3-d]pyrimidin-5-yl}phenyl)-N'-[2-fluoro-5-(trifluoromethyl)phenyl]urea The desired product was prepared by substituting Example 281F and 2-fluoro-5-trifluoromethylphenyl isocyanate for Example 1E and phenyl isocyanate, respectively, in Example 1F. MS (ESI(+)) m/e 519 (M+H)$^+$; $^1$H NMR (300 MHz, DMSO-d$_6$) δ 2.10 (s, 6H); 2.41-2.46 (t, 2H, J=7.2 Hz); 2.72-2.77 (t, 2H, J=6 Hz); 7.33-7.36 (d, 2H, J=8.7 Hz); 7.41-7.55 (m, 2H); 7.63-7.66 (d, 2H, J=8.4 Hz); 8.26 (s, 1H); 8.62-8.65 (dd, 1H, J=1.8, 6.9 Hz); 8.98-8.99 (d, 1H, J=2.7 Hz); 9.39 (s, 1H).

EXAMPLE 285

N-(4-{4-amino-6-[2-(dimethylamino)ethyl]thieno[2,3-d]pyrimidin-5-yl}phenyl)-N'-(3-cyanophenyl)urea The desired product was prepared by substituting Example 281F and 3-cyanophenyl isocyanate for Example 1E and phenyl isocyanate, respectively, in Example 1F. MS (ESI(+)) m/e 458 (M+H)$^+$; $^1$H NMR (300 MHz, DMSO-d$_6$) δ 2.11 (s, 6H); 2.42-2.47 (t, 2H, J=7.2 Hz); 2.73-2.77 (t, 2H, J=7.2 Hz); 7.32-7.34 (d, 2H, J=8.1 Hz); 7.42-7.46 (td, 1H, J=1.5, 7.2 Hz); 7.49-7.54 (t, 1H, J=7.8 Hz); 7.63-7.66 (d, 2H, J=8.4 Hz); 7.68-7.72 (td, 1H, J=1.2, 9.3 Hz); 7.99-8.00 (t, 1H, J=2.4 Hz); 8.26 (s, 1H); 9.11 (s, 1H); 9.16 (s, 1H).

EXAMPLE 286

N-(4-{4-amino-6-[2-(dimethylamino)ethyl]thieno[2,3-d]pyrimidin-5-yl}phenyl)-N'-(2-fluoro-5-methylphenyl)urea The desired product was prepared by substituting Example 281F and 2-fluoro-5-methylphenyl isocyanate for Example 1E and phenyl isocyanate, respectively, in Example 1F. MS (ESI(+)) m/e 485 (M+H)$^+$; $^1$H NMR (300 MHz, DMSO-d$_6$) δ 2.12 (s, 6H); 2.28 (s, 3H); 2.73-2.76 (t, 2H, J=3.5 Hz); 6.78-6.86 (m 1H); 7.09-7.15 (dd, 1H, J=8.47, 11.4 Hz); 7.30-7.33 (d, 2H, J=8.4 Hz); 7.61-7.64 (d, 2H, J=8.7 Hz); 7.98-9.01 (d, 1H, J=2.1, 8.1 Hz); 8.26 (s, 1H); 8.56-8.57 (d, 1H, J=2.4 Hz); 9.29 (s, 1H).

EXAMPLE 287

N-[4-(4-amino-6-vinylthieno[2,3-d]pyrimidin-5-yl)phenyl]-N'-(3-methylphenyl)urea

EXAMPLE 287A 5-(4-aminophenyl)-6-vinylthieno[2,3-d]pyrimidin-4-amine

The desired product was prepared by substituting Example 281E for Example 1D in Example 1E. MS ((ESI(+)) m/e 269 (M+H)$^+$.

EXAMPLE 287B

N-[4-(4-amino-6-vinylthieno[2,3-d]pyrimidin-5-yl)phenyl]-N'-(3-methylphenyl)urea The desired product was prepared by substituting Example 287A and 3-methylphenyl isocyanate for Example 1E and phenyl isocyanate, respectively, in Example 1F. MS (ESI(+)) m/e 402 (M+H)$^+$; $^1$H NMR (300 MHz, DMSO-d$_6$) δ 2.29 (s, 3H); 5.28-5.32 (d, 1H, J=11.4 Hz); 5.59-5.64 (d, 1H, J=17.1 Hz); 6.50-6.60 (dd, 1H, J=10.8, 17.1 Hz); 6.80-6.82 (d, 1H, J=7.5 Hz); 7.14-7.20 (t, 1H, J=7.8 Hz); 7.24-7.27 (d, 1H, J=8.4 Hz); 7.30-7.33 (m, 3H); 7.63-7.66 (d, 2H, J=8.4 Hz); 8.31 (s, 1H); 8.68 (s, 1H); 8.91 (s, 1H).

EXAMPLE 288

N-[4-(4-amino-6-vinylthieno[2,3-d]pyrimidin-5-yl)phenyl]-N'-[2-fluoro-5-(trifluoromethyl)phenyl]urea The desired product was prepared by substituting Example 287A and 2-fluoro-5-trifluoromethylphenyl isocyanate for Example 1E and phenyl isocyanate, respectively, in Example 1F. MS (ESI(+)) m/e 474 (M+H)+; 1H NMR (300 MHz, DMSO-d6) δ 5.29-5.32 (d, 1H, J=11.1 Hz); 5.59-5.65 (d, 1H, J=17.1 Hz); 6.50-6.59 (dd, 1H, J=10.8, 17.1 Hz); 7.34-7.37 (d, 2H, J=8.4 Hz); 7.38-7.45 (m, 1H); 7.49-7.55 (t, 1H, J=8.7 Hz); 7.65-7.68 (d, 2H, J=8.4 Hz); 8.31 (s, 1H); 8.62-8.65 (dd, 1H, J=2.1, 7.2 Hz); 8.98-8.99 (d, 1H, J=2.7 Hz); 9.43 (s, 1H).

EXAMPLE 289

N-[4-(4-amino-6-vinylthieno[2,3-d]pyrimidin-5-yl)phenyl]-N!-[3-(trifluoromethyl)phenyl]urea The desired product was prepared by substituting Example 287A and 3-trifluoromethylphenyl isocyanate for Example 1E and phenyl isocyanate, respectively, in Example 1F. MS (ESI(+)) m/e 456 (M+H)+; 1H NMR (300 MHz, DMSO-d6) δ 5.29-5.33 (d, 1H, J=11.1 Hz); 5.59-5.65 (d, 1H, J=17.4 Hz); 6.50-6.60 (dd, 1H, J=10.8, 17.4 Hz); 7.32-7.35 (m, 3H); 7.51-7.56 (t, 1H, J=7.5 Hz); 7.59-6.25 (m, 1H); 7.65-7.68 (d, 2H, J=8.4 Hz); 8.04 (s, 1H); 8.31 (s, 1H); 9.07 (s, 1H); 9.15 (s, 1H).

EXAMPLE 290

N-[4-(4-amino-6-propylthieno[2,3-d]pyrimidin-5-yl)phenyl]-N'-(3-chlorophenyl)urea

EXAMPLE 290A 5-(4-aminophenyl)-6-propylthieno[2,3-d]pyrimidin-4-amine

The desired product was prepared by substituting n-butyl iodide for tert-butyl(3-iodopropoxy)dimethylsilane in Examples 104A and B. 1H NMR (300 MHz, DMSO-d6) δ 0.84 (t, J=7.46 Hz, 3H); 1.50-1.60 (m, 2H); 2.60 (t, J=7.46 Hz, 2H); 5.39 (s, 2H); 6.69 (d, J=8.48 Hz, 2H); 6.99 (d, J=8.48 Hz, 2H); 8.23 (s, 1H).

EXAMPLE 290B

N-[4-(4-amino-6-propylthieno[2,3-d]pyrimidin-5-yl)phenyl]-N'-(3-chlorophenyl)urea The desired product was prepared by substituting Example 290A and 3-chlorophenyl isocyanate for Example 1E and phenyl isocyanate, respectively, in Example 1F. MS (ESI(+)) m/e 438 (M+H)+; 1H NMR (300 MHz, DMSO-d6) δ 0.84 (t, J=7.29 Hz, 3H); 1.50-1.68 (m, 2H); 2.61 (t, J=7.46 Hz, 2H); 7.04 (dt, J=6.53, 2.33 Hz, 1H); 7.31 (m, 4H); 7.63 (d, J=8.81 Hz, 2H); 7.73 (m, 1H); 8.27 (s, 1H); 8.96 (s, 2H).

EXAMPLE 291

N-[4-(4-amino-6-propylthieno[2,3-d]pyrimidin-5-yl)phenyl]-N'-(3-methylphenyl)urea The desired product was prepared by substituting Example 290A and 3-methylphenyl isocyanate for Example 1E and phenyl isocyanate, respectively, in Example 1F. MS (ESI(+)) m/e 418 (M+H)+; 1H NMR (300 MHz, DMSO-d6) δ 0.85 (t, J=7.29 Hz, 3H); 1.50-1.68 (m, 2H); 2.29 (s, 3H); 2.61 (t, J=7.63 Hz, 2H); 6.81 (d, J=7.80 Hz, 1H); 7.24 (m, 5H); 7.62 (d, J=8.48 Hz, 2H); 8.26 (s, 1H); 8.67 (s, 1H); 8.87 (s, 1H).

EXAMPLE 292

N-[4-(4-amino-6-propylthieno[2,3-d]pyrimidin-5-yl)phenyl]-N'-(3-ethylphenyl)urea The desired product was prepared by substituting Example 290A and 3-ethylphenyl isocyanate for Example 1E and phenyl isocyanate, respectively, in Example 1F. MS (ESI(+)) m/e 432 (M+H)+; 1H NMR (300 MHz, DMSO-d6) δ 0.85 (t, J=7.29 Hz, 3H); 1.19 (t, J=7.46 Hz, 3H); 1.58 (q, J=7.50, 2H); 2.45-2.70 (m, 4H); 6.84 (d, J=7.46 Hz, 1H); 7.15-7.40 (m, 5H); 7.62 (d, J=8.48 Hz, 2H); 8.27 (s, 1H); 8.69 (s, 1H); 8.87 (s, 1H).

EXAMPLE 293

N-[4-(4-amino-6-propylthieno[2,3-d]pyrimidin-5-yl)phenyl]-N'-[4-(trifluoromethyl)phenyl]urea The desired product was prepared by substituting Example 290A and 4-trifluoromethylphenyl isocyanate for Example 1E and phenyl isocyanate, respectively, in Example 1F. MS (ESI(+)) m/e 472 (M+H)+; 1H NMR (300 MHz, DMSO-d6) δ 0.85 (t, J=7.29, 3H); 1.50-1.68 (m, J=6.78 Hz, 2H); 2.61 (t, J=7.80 Hz, 2H); 7.32 (d, J=8.48 Hz, 2H); 7.60-7.7.78 (m, 6H); 8.27 (s, 1H); 9.03 (s, 1H); 9.19 (s, 1H).

EXAMPLE 294

N-[4-(4-amino-6-propylthieno[2,3-d]pyrimidin-5-yl)phenyl]-N'-[3-(trifluoromethyl)phenyl]urea The desired product was prepared by substituting Example 290A and 3-trifluoromethylphenyl isocyanate for Example 1E and phenyl isocyanate, respectively, in Example 1F. MS (ESI(+)) m/e 472 (M+H)+; 1H NMR (300 MHz, DMSO-d6) δ 0.85 (t, J=7.29 Hz, 3H); 1.50-1.68 (m, 2H); 2.62 (t, J=7.46 Hz, 2H); 7.30-7.40 (m, 3H); 7.50-7.80 (m, 4H); 8.04 (s, 1H); 8.27 (s, 1H); 9.01 (s, 1H); 9.13 (s, 1H).

EXAMPLE 295

N-[4-(4-amino-6-propylthieno[2,3-d]pyrimidin-5-yl)phenyl]-N'-phenylurea

The desired product was prepared by substituting Example 290A for Example 1E in Example 1F. MS (ESI(+)) m/e 404 (M+H)+; 1H NMR (300 MHz, DMSO-d6) δ 0.85 (t, J=7.29 Hz, 3H); 1.50-1.68 (m, 2H); 2.62 (t, J=7.46 Hz, 2H); 6.99 (t, J=7.29 Hz, 1H); 7.30 (m, 4H); 7.47 (d, J=7.46 Hz, 2H); 7.63 (d, J=8.48 Hz, 2H); 8.27 (s, 1H); 8.75 (s, 1H); 8.89 (s, 1H).

EXAMPLE 296

N-[4-(4-amino-6-propylthieno[2,3-d]pyrimidin-5-yl)phenyl]-N'-cyclohexylurea

The desired product was prepared by substituting Example 290A and isocyanatocyclohexane for Example 1E and phenyl isocyanate, respectively, in Example 1F. MS (ESI(+)) m/e 410 (M+H)+; 1H NMR (300 MHz, DMSO-d6) δ 0.83 (t, J=7.29 Hz, 3H); 1.00-1.90 (m, 13H); 2.59 (t, J=7.80 Hz, 2H); 6.17 (d, J=7.80 Hz, 1H); 7.22 (d, J=8.48 Hz, 2H); 7.54 (d, J=8.48 Hz, 2H); 8.25 (s, 1H); 8.53 (s, 1H).

EXAMPLE 297

N-[4-(4-amino-6-propylthieno[2,3-d]pyrimidin-5-yl)phenyl]-N'-(3-phenoxyphenyl)urea The desired product was prepared by substituting Example 290A and 3-phenoxyphenyl isocyanate for Example 1E and phenyl isocyanate, respectively, in Example 1F. MS (ESI(+)) m/e 496 (M+H)$^+$; $^1$H NMR (300 MHz, DMSO-d$_6$) δ 0.84 (t, J=7.46 Hz, 3H); 1.45-1.55 (m, 2H); 2.60 (t, J=7.46 Hz, 2H); 6.63 (dd, J=8.14, 1.70 Hz, 1H); 7.00-7.50 (m, 10H); 7.59 (d, J=8.48 Hz, 2H); 8.26 (s, 1H); 8.86 (s, 1H); 8.88 (s, 1H).

EXAMPLE 298

N-[4-(4-amino-6-ethylthieno[2,3-d]pyrimidin-5-yl)phenyl]-N'-phenylurea

The desired product was prepared by substituting Example 78A for Example 1E in Example 1F. MS (ESI(+)) m/e 390 (M+H)$^+$; $^1$H NMR (300 MHz, DMSO-d$_6$) δ 1.17 (t, J=7.63 Hz, 3H); 2.66 (q, J=7.46 Hz, 2H); 6.99 (t, J=7.46 Hz, 1H); 7.30 (t, J=8.48 Hz, 4H); 7.48 (d, J=7.46 Hz, 2H); 7.63 (d, J=8.48 Hz, 2H); 8.29 (s, 1H); 8.78 (s, 1H); 8.93 (s, 1H).

EXAMPLE 299

N-[4-(4-amino-6-ethylthieno[23-d]pyrimidin-5-yl)phenyl]-N'-cyclohexylurea

The desired product was prepared by substituting Example 78A and isocyanatocyclohexane for Example 1E and phenyl isocyanate, respectively, in Example 1F. MS (ESI(+)) m/e 396 (M+H)$^+$; $^1$H NMR (300 MHz, DMSO-d$_6$) δ 1.00-1.90 (m, 14H); 2.63 (q, J=7.69 Hz, 2H); 6.17 (d, J=7.80 Hz, 1H); 7.23 (d, J=8.48 Hz, 2H); 7.54 (d, J=8.48 Hz, 2H); 8.27 (s, 1H); 8.54 (s, 1H).

EXAMPLE 300

N-[4-(4-amino-6-ethylthieno[2,3-d]pyrimidin-5-yl)phenyl]-N'-[4-(dimethylamino)phenyl]urea The desired product was prepared by substituting Example 78A and 4-dimethylaminoaniline for Example 58D and 3-methylbutylamine, respectively, in Example 179. MS (ESI(+)) m/e 433 (M+H)$^+$; $^1$H NMR (300 MHz, DMSO-d$_6$) δ 1.16 (t, J=7.46 Hz, 3H); 2.65 (q, J=7.35 Hz, 2H); 2.84 (s, 6H); 6.71 (d, J=8.82 Hz, 2H); 7.27 (d, J=2.37 Hz, 2H); 7.30 (d, J=2.03 Hz, 2H); 7.61 (d, J=8.48 Hz, 2H); 8.26 (s, 1H); 8.38 (s, 1H); 8.76 (s, 1H).

EXAMPLE 301

N-[4-(4-amino-6-ethylthieno[2,3-d]pyrimidin-5-yl)phenyl]-N'-{4-[2-(dimethylamino)ethyl]phenyl}urea The desired product was prepared by substituting Example 78A and 4-[2-(dimethylamino)ethyl]aniline for Example 58D and 3-methylbutylamine, respectively, in Example 179. MS (ESI(+)) m/e 461 (M+H)$^+$; $^1$H NMR (300 MHz, DMSO-d$_6$) δ 1.16 (t, J=7.63 Hz, 3H); 2.47 (s, 6H); 2.65 (m, 2H); 2.70-2.90 (m, 4H); 7.17 (d, J=8.81 Hz, 2H); 7.30 (d, J=8.48 Hz, 2H); 7.41 (d, J=8.48 Hz, 2H); 7.62 (d, J=8.48 Hz, 2H); 8.26 (s, 1H); 8.87 (s, 1H); 9.06 (s, 1H).

EXAMPLE 302

N-[4-(4-aminoisothiazolo[5,4-d]pyrimidin-3-yl)phenyl]-N'-(2-fluoro-5-methylphenyl)urea The desired product was prepared by substituting Example 97 and 2-fluoro-5-methylphenyl isocyanate for Example 1E and phenyl isocyanate, respectively, in Example 1F. MS(ESI(+)) m/e 395 (M+H)$^+$; $^1$H NMR (300 MHz, DMSO-d$_6$) δ 2.28 (s, 3H); 6.75-6.90 (m, 1H); 7.05-7.20 (m, 1H); 7.55-7.70 (m, 4H); 7.95-8.05 (m, 1H); 8.47 (s, 1H); 8.58 (s, 1H); 9.35 (s, 11H).

EXAMPLE 303

3-{4-amino-5-[4-({[(3-methylphenyl)amino]carbonyl}amino)phenyl]thieno[2,3-d]pyrimidin-6-yl}-N-[2-(diethylamino)ethyl]propanamide

EXAMPLE 303A

3-[4-amino-5-(4-aminophenyl)thieno[2,3-d]pyrimidin-6-yl]-N-[2-(diethylamino)ethyl]propanamide The desired product was prepared by substituting N,N-diethylethylenediamine for dimethylamine hydrochloride in Examples 247A-B. MS (ESI(+)) m/e 413 (M+H)$^+$.

EXAMPLE 303B

3-{4-amino-5-[4-({[(3-methylphenyl)amino]carbonyl}amino)phenyl]thieno[2,3-d]pyrimidin-6-yl}-N-[2-(diethylamino)ethyl]propanamide The desired product was prepared by substituting Example 303A and 3-methylphenyl isocyanate for Example 1E and phenyl isocyanate, respectively, in Example 1F. The product was purified by HPLC using the conditions described in Example 179 to provide the trifluoroacetate salt. MS (ESI(+)) m/e 546 (M+H)$^+$; $^1$H NMR (300 MHz, DMSO-d$_6$) δ 1.15 (t, J=7.29 Hz, 6H); 2.29 (s, 3H); 2.43 (t, J=7.46 Hz, 2H); 2.89 (t, J=7.46 Hz, 2H); 3.00-3.20 (m, 6H); 3.32-3.42 (m, 2H); 6.81 (d, J=6.78 Hz, 1H); 7.17 (t, J=7.63 Hz, 1H); 7.25-7.35 (m, 4H); 7.60-7.68 (m, 2H); 8.19 (t, J=5.76 Hz, 1H); 8.29 (s, 1H); 8.84 (s, 1H); 9.06 (s, 1H).

EXAMPLE 304

3-{4-amino-5-[4-({[(3-chlorophenyl)amino]carbonyl}amino)phenyl]thieno[2,3-d]pyrimidin-6-yl}-N-[2-(diethylamino)ethyl]propanamide The desired product was prepared by substituting Example 303A and 3-chlorophenyl isocyanate for Example 1E and phenyl isocyanate, respectively, in Example 1F. The product was purified by HPLC using the conditions described in Example 179 to provide the trifluoroacetate salt. MS (ESI(+)) m/e 566 (M+H)$^+$; $^1$H NMR (300 MHz, DMSO-d$_6$) δ 1.15 (t, J=7.29 Hz, 6H); 2.43 (t, J=7.63 Hz, 2H); 2.89 (t, J=7.29 Hz, 2H); 3.00-3.20 (m, 6H); 3.37 (q, J=5.99 Hz, 2H); 6.95-7.08 (m, 1H); 7.25-7.38 (m, 4H); 7.66 (d, J=8.48 Hz, 2H); 7.72-7.78 (m, 1H); 8.19 (t, J=5.76 Hz, 1H); 8.29 (s, 1H); 9.26 (s, 1H); 9.27 (s, 1H).

EXAMPLE 305

3-(4-amino-5-{4-[({[3-(trifluoromethyl)phenyl]amino}carbonyl)amino]phenyl}thieno[2,3-d]pyrimidin-6-yl)-N-[2-(diethylamino)ethyl]propanamide The desired product was prepared by substituting Example 303A and 3-trifluoromethylphenyl isocyanate for Example 1E and phenyl isocyanate, respectively, in Example 1F. MS (ESI(+)) m/e 600 (M+H)$^+$; $^1$H NMR (300 MHz, DMSO-$d_6$) δ 1.15 (t, J=7.29 Hz, 6H); 2.43 (t, J=7.29 Hz, 2H); 2.89 (t, J=7.29 Hz, 2H); 3.00-3.20 (m, 6H); 3.30-3.45 (m, 2H); 7.33 (d, J=8.48 Hz, 3H); 7.45-7.65 (m, 2H); 7.67 (d, J=8.48 Hz, 2H); 8.06 (s, 1H); 8.19 (t, J=5.76 Hz, 1H); 8.29 (s, 1H); 9.31 (s, 1H); 9.42 (s, 1H).

EXAMPLE 306

3-{4-amino-5-[4-({[(3,5-dimethylphenyl)amino]carbonyl}amino)phenyl]thieno[2,3-d]pyrimidin-6-yl}-N-[2-(diethylamino)ethyl]propanamide The desired product was prepared by substituting Example 303A and 3,5-dimethylphenyl isocyanate for Example 1E and phenyl isocyanate, respectively, in Example 1F. The product was purified by HPLC using the conditions described in Example 179 to provide the trifluoroacetate salt. MS (ESI (+)) m/e 560 (M+H)$^+$; $^1$H NMR (300 MHz, DMSO-$d_6$) δ 1.15 (t, J=7.29 Hz, 6H); 2.24 (s, 6H); 2.43 (t, J=7.46 Hz, 2H); 2.89 (t, J=7.46 Hz, 2H); 3.00-3.20 (m, 6H); 3.32-3.42 (m, 2H); 6.63 (s, 1H); 7.11 (s, 2H); 7.31 (d, J=8.48 Hz, 2H); 7.65 (d, J=8.82 Hz, 2H); 8.20 (t, J=5.26 Hz, 1H); 8.30 (s, 1H); 8.83 (s, 1H); 9.12 (s, 1H).

EXAMPLE 307

3-{4-amino-5-[4-({[(2-fluoro-5-methylphenyl)amino]carbonyl}amino)phenyl]thieno[2,3-d]pyrimidin-6-yl}-N-[2-(diethylamino)ethyl]propanamide The desired product was prepared by substituting Example 303A and 2-fluoro-5-methylphenyl isocyanate for Example 1E and phenyl isocyanate, respectively, in Example 1F. The product was purified by HPLC using the conditions described in Example 179 to provide the trifluoroacetate salt. MS (ESI (+)) m/e 564 (M+H)$^+$; $^1$H NMR (300 MHz, DMSO-$d_6$) δ 1.15 (t, J=7.29 Hz, 6H); 2.28 (s, 3H); 2.43 (t, J=7.63 Hz, 2H); 2.89 (t, J=7.63 Hz, 2H); 3.00-3.20 (m, 6H); 3.32-3.42 (m, 2H); 6.78-6.88 (m, 1H); 7.12 (dd, J=11.53, 8.48 Hz, 1H); 7.33 (d, J=8.48 Hz, 2H); 7.64 (d, J=8.81 Hz, 2H); 7.98 (dd, J=7.46, 2.03 Hz, 1H); 8.19 (t, J=5.59 Hz, 1H); 8.29 (s, 1H); 8.60 (d, J=2.37 Hz, 1H); 9.34 (s, 1H).

EXAMPLE 308

3-(4-amino-5-{4-[({[2-fluoro-5-(trifluoromethyl)phenyl]amino}carbonyl)amino]phenyl}thieno[2,3-d]pyrimidin-6-yl)-N-[2-(diethylamino)ethyl]propanamide The desired product was prepared by substituting Example 303A and 2-fluoro-5-trifluoromethylphenyl isocyanate for Example 1E and phenyl isocyanate, respectively, in Example 1F. MS (ESI(+)) m/e 618 (M+H)$^+$; $^1$H NMR (300 MHz, DMSO-$d_6$) δ 1.16 (t, J=7.29 Hz, 6H); 2.43 (t, J=7.63 Hz, 2H); 2.89 (t, J=7.63 Hz, 2H); 3.00-3.20 (m, 6H); 3.32-3.42 (m, 2H); 7.36 (d, J=8.48 Hz, 2H); 7.36-7.60 (m, 2H); 7.67 (d, J=8.48 Hz, 2H); 8.27 (t, J=5.60 Hz, 1H); 8.31 (s, 1H); 8.63 (dd, J=7.29, 2.20 Hz, 1H); 9.14 (d, J=2.03 Hz, 1H); 9.75 (s, 1H).

Examples 309-334 were synthesized in an automated parallel fashion as follows: Example 78A (10 mg, 0.04 mmol) was dissolved in dichloromethane (2 mL) and added to a reaction vessel containing PS-diethylamine (23 mg). The solution was treated with a solution of p-nitrophenylchloroformate (9 mg) in dichloromethane (1 mL), mixed for 2 hours, treated with a solution of the desired amine (0.06 mmol), mixed for 16 hours, treated with the scavenger resins PS-trisamine (12 mg) and PS-isocyanate (12 mg), and concentrated. The product was purified by HPLC using the conditions described in Example 179.

EXAMPLE 309

N-[4-(4-amino-6-ethylthieno[2,3-d]pyrimidin-5-yl)phenyl]-N'-(4-ethylphenyl)urea

Amine: 4-ethylaniline. MS (ESI(+)) m/e 418 (M+H)$^+$; $^1$H NMR (500 MHz, DMSO-$d_6$) δ 1.16 (t, J=7.64 Hz, 6H); 2.55 (q, J=7.49 Hz, 2H); 2.65 (q, J=7.70 Hz, 2H); 7.13 (d, J=8.42 Hz, 2H); 7.30 (d, J=8.73 Hz, 2H); 7.37 (d, J=8.42 Hz, 2H); 7.62 (d, J=8.73 Hz, 2H); 8.28 (s, 1H); 8.65 (s, 1H); 8.86 (s, 1H).

EXAMPLE 310

N-[4-(4-amino-6-ethylthieno[2,3-d]pyrimidin-5-yl)phenyl]-N'-(4-isopropylphenyl)urea Amine: 4-isopropylaniline. MS (ESI(+)) m/e 432 (M+H)$^+$; $^1$H NMR (500 MHz, DMSO-$d_6$) δ 1.10-1.25 (m, 9H); 2.65 (q, J=7.49 Hz, 2H); 2.84 (m, 1H); 7.16 (d, J=8.42 Hz, 2H); 7.30 (d, J=8.42 Hz, 2H); 7.38 (d, J=8.42 Hz, 2H); 7.62 (d, J=8.42 Hz, 2H); 8.28 (s, 1H); 8.65 (s, 1H); 8.85 (s, 1H).

EXAMPLE 311

N-[4-(4-amino-6-ethylthieno[2,3-d]pyrimidin-5-yl)phenyl]-N'-(3-tert-butylphenyl)urea Amine: 3-tert-butylaniline. MS (ESI(+)) m/e 446 (M+H)$^+$; $^1$H NMR (500 MHz, DMSO-$d_6$) δ 1.17 (t, J=7.49 Hz, 3H); 1.28 (s, 9H); 2.66 (q, J=7.49 Hz, 2H); 7.03 (d, J=7.80 Hz, 1H); 7.21 (t, J=7.96 Hz, 1H); 7.31 (d, J=8.73 Hz, 3H); 7.48 (t, J=1.87 Hz, 1H); 7.63 (d, J=8.42 Hz, 2H); 8.29 (s, 1H); 8.73 (s, 1H); 8.86 (s, 1H).

EXAMPLE 312

N-[4-(4-amino-6-ethylthieno[2,3-d]pyrimidin-5-yl)phenyl]-N=-(4-tert-butylphenyl)urea Amine: 4-tert-butylaniline. MS (ESI(+)) m/e 446 (M+H)$^+$; $^1$H NMR (500 MHz, DMSO-$d_6$) δ 1.15 (t, J=7.49 Hz, 3H); 1.26 (s, 9H); 2.64 (q, J=7.49 Hz, 2H); 7.25-7.32 (m, 4H); 7.35-7.40 (m, 2H); 7.56-7.65 (m, 2H); 8.27 (s, 1H); 8.65 (s, 1H); 8.84 (s, 1H).

EXAMPLE 313

N-[4-(4-amino-6-ethylthieno[2,3-d]pyrimidin-5-yl)phenyl]-N'-(3-fluoro-2-methylphenyl)urea Amine: 2-methyl-3-fluoroaniline. MS (ESI(+)) m/e 422 (M+H)$^+$; $^1$H NMR (500 MHz, DMSO-d$_6$) δ 1.17 (t, J=7.49 Hz, 3H); 2.17 (s, 3H); 2.65 (q, J=7.49 Hz, 2H); 6.88 (t, J=8.89 Hz, 1H); 7.15-7.25 (m, 1H); 7.32 (d, J=8.42 Hz, 2H); 7.60-7.72 (m, 3H); 8.19 (s, 1H); 8.28 (s, 1H); 9.27 (s, 1H).

EXAMPLE 314

N-[4-(4-amino-6-ethylthieno[2,3-d]pyrimidin-5-yl)phenyl]-N'-(2-fluoro-4-methylphenyl)urea Amine: 2-fluoro-4-methylaniline. MS (ESI(+)) m/e 422 (M+H)$^+$; $^1$H NMR (500 MHz, DMSO-d$_6$) δ 1.16 (t, J=7.49 Hz, 3H); 2.32 (s, 3H); 2.65 (q, J=7.49 Hz, 2H); 6.96 (d, J=9.36 Hz, 1H); 7.07 (d, J=12.17 Hz, 1H); 7.25-7.35 (m, 2H); 7.55-7.65 (m, 2H); 7.98 (t, J=8.58 Hz, 1H); 8.28 (s, 1H); 8.50 (d, J=2.18 Hz, 1H); 9.22 (s, 1H).

EXAMPLE 315

N-[4-(4-amino-6-ethylthieno[2,3-d]pyrimidin-5-yl)phenyl]-N'-(3-fluoro-5-methylphenyl)urea Amine: 3-fluoro-5-methylaniline. MS (ESI(+)) m/e 422 (M+H)$^+$; $^1$H NMR (500 MHz, DMSO-d$_6$) δ 1.16 (t, J=7.49 Hz, 3H); 2.30 (s, 3H); 2.65 (q, J=7.49 Hz, 2H); 7.05 (dd, J=8.27, 2.03 Hz, 1H); 7.17 (t, J=8.73 Hz, 1H); 7.31 (d, J=8.73 Hz, 2H); 7.44 (dd, J=12.48, 2.18 Hz, 1H); 7.62 (d, J=8.74 Hz, 2H); 8.27 (s, 1H); 8.89 (s, 1H); 8.95 (s, 1H).

EXAMPLE 316

N-[4-(4-amino-6-ethylthieno[2,3-d]pyrimidin-5-yl)phenyl]-N'-(4-fluoro-2-methylphenyl)urea Amine: 4-fluoro-2-methylaniline. MS (ESI(+)) m/e 422 (M+H)$^+$; $^1$H NMR (500 MHz, DMSO-d$_6$) δ 1.16 (t, J=7.49 Hz, 3H); 2.28 (s, 3H); 2.65 (q, J=7.49 Hz, 2H); 6.99 (td, J=8.73, 3.12 Hz, 1H); 7.08 (dd, J=9.51, 2.96 Hz, 1H); 7.30 (d, J=8.42 Hz, 2H); 7.63 (d, J=8.42 Hz, 2H); 7.72 (dd, J=8.73, 5.62 Hz, 1H); 8.02 (s, 1H); 8.27 (s, 1H); 9.17 (s, 1H).

EXAMPLE 317

N-[4-(4-amino-6-ethylthieno[2,3-d]pyrimidin-5-yl)phenyl]-N'-(4-fluoro-3-methylphenyl)urea Amine: 4-fluoro-3-methylaniline. MS (ESI(+)) m/e 422 (M+H)$^+$; $^1$H NMR (500 MHz, DMSO-d$_6$) δ 1.16 (t, J=7.49 Hz, 3H); 2.30 (s, 3H); 2.65 (q, J=7.49 Hz, 2H); 7.06 (t, J=9.20 Hz, 1H); 7.25-7.35 (m, J=8.42 Hz, 3H); 7.37 (dd, J=6.86, 2.50 Hz, 1H); 7.62 (d, J=8.42 Hz, 2H); 8.28 (s, 1H); 8.71 (s, 1H); 8.90 (s, 1H).

EXAMPLE 318

N-[4-(4-amino-6-ethylthieno[2,3-d]pyrimidin-5-yl)phenyl]-N'-(3-chloro-4-methylphenyl)urea Amine: 3-chloro-4-methylaniline. MS (ESI(+)) m/e 438 (M+H)$^+$; $^1$H NMR (500 MHz, DMSO-d$_6$) δ 1.17 (t, J=7.49 Hz, 3H); 2.27 (s, 3H); 2.65 (q, J=7.49 Hz, 2H); 7.20-7.30 (m, 2H); 7.31 (d, J=8.42 Hz, 2H); 7.63 (d, J=8.42 Hz, 2H); 7.71 (d, J=1.87 Hz, 1H); 8.29 (s, 1H); 8.88 (s, 1H); 8.96 (s, 1H).

EXAMPLE 319

N-[4-(4-amino-6-ethylthieno[2,3-d]pyrimidin-5-yl)phenyl]-N'-(4-chloro-3-methylphenyl)urea Amine: 4-chloro-3-methylaniline. MS (ESI(+)) m/e 438 (M+H)$^+$; $^1$H NMR (500 MHz, DMSO-d$_6$) δ 1.16 (t, J=7.49 Hz, 3H); 2.31 (s, 3H); 2.65 (q, J=7.49 Hz, 2H); 7.20-7.40 (m, 4H); 7.46 (d, J=2.50 Hz, 1H); 7.63 (d, J=8.73 Hz, 2H); 8.28 (s, 1H); 8.83 (s, 1H); 8.94 (s, 1H).

EXAMPLE 320

N-[4-(4-amino-6-ethylthieno[2,3-d]pyrimidin-5-yl)phenyl]-N'-(3-bromo-4-methylphenyl)urea Amine: 3-bromo-4-methylaniline. MS (ESI(+)) m/e 482, 484 (M+H)$^+$; $^1$H NMR (500 MHz, DMSO-d$_6$) δ 1.17 (t, J=7.64 Hz, 3H); 2.29 (s, 3H); 2.65 (q, J=7.59 Hz, 2H); 7.26 (d, J=0.94 Hz, 2H); 7.31 (d, J=8.73 Hz, 2H); 7.63 (d, J=8.73 Hz, 2H); 7.88 (s, 1H); 8.29 (s, 1H); 8.87 (s, 1H); 8.96 (s, 1H).

EXAMPLE 321

N-[4-(4-amino-6-ethylthieno[2,3-d]pyrimidin-5-yl)phenyl]-N'-(4-bromo-3-methylphenyl)urea Amine: 4-bromo-3-methylaniline. MS (ESI(+)) m/e 482, 484 (M+H)$^+$; $^1$H NMR (500 MHz, DMSO-d$_6$) δ 1.16 (t, J=7.49 Hz, 3H); 2.33 (s, 3H); 2.65 (q, J=7.70 Hz, 2H); 7.25-7.35 (m, 3H); 7.40-7.55 (m, 2H); 7.63 (d, J=8.73 Hz, 2H); 8.29 (s, 1H); 8.84 (s, 1H); 8.95 (s, 1H).

EXAMPLE 322

N-[4-(4-amino-6-ethylthieno[2,3-d]pyrimidin-5-yl)phenyl]-N'-(3-fluoro-4-methoxyphenyl)urea Amine: 3-fluoro-4-methoxyaniline. MS (ESI(+)) m/e 438 (M+H)$^+$; $^1$H NMR (500 MHz, DMSO-d$_6$) δ 1.16 (t, J=7.49 Hz, 3H); 2.65 (q, J=7.49 Hz, 2H); 3.80 (s, 3H); 7.05-7.15 (m, J=1.87 Hz, 2H); 7.31 (d, J=8.42 Hz, 2H); 7.45-7.55 (m, 1H); 7.62 (d, J=8.73 Hz, 2H); 8.29 (s, 1H); 8.78 (s, 1H); 8.91 (s, 1H).

EXAMPLE 323

N-[4-(4-amino-6-ethylthieno[2,3-d]pyrimidin-5-yl)phenyl]-N'-[3-methoxy-5-(trifluoromethyl)phenyl]urea Amine: 3-methoxy-5-trifluoromethylaniline. MS (ESI(+)) m/e 488 (M+H)$^+$; $^1$H NMR (500 MHz, DMSO-d$_6$) δ 1.17 (t, J=7.49 Hz, 3H); 2.65 (q, J=7.49 Hz, 2H); 3.83 (s, 3H); 6.86 (s, 1H); 7.25-7.35 (m, 3H); 7.50 (s, 1H); 7.64 (d, J=8.42 Hz, 2H); 8.28 (s, 1H); 9.04 (s, 1H); 9.15 (s, 11H).

EXAMPLE 324

N-[4-(4-amino-6-ethylthieno[2,3-d]pyrimidin-5-yl)phenyl]-N'-[4-(hydroxymethyl)phenyl]urea Amine: 4-hydroxymethylaniline. MS (ESI(+)) m/e 420 (M+H)$^+$; $^1$H NMR (500 MHz, DMSO-d$_6$) δ 1.26 (t, J=6.86

Hz, 3H); 2.65 (q, J=7.49 Hz, 2H); 4.43 (s, 2H); 7.23 (d, J=8.42 Hz, 2H); 7.30 (d, J=8.73 Hz, 2H); 7.42 (d, J=8.42 Hz, 2H); 7.63 (d, J=8.73 Hz, 2H); 8.27 (s, 1H); 8.73 (s, 1H); 8.90 (s, 1H).

EXAMPLE 325

N-[4-(4-amino-6-ethylthieno[2,3-d]pyrimidin-5-yl) phenyl]-N'(2-methoxy-4-methylphenyl)urea Amine: 2-methoxy-4-methylaniline. MS (ESI(+)) m/e 434 (M+H)$^+$; $^1$H NMR (500 MHz, DMSO-d$_6$) δ 1.17 (t, J=7.49 Hz, 3H); 2.24 (s, 3H); 2.66 (q, J=7.49 Hz, 2H); 3.86 (s, 3H); 6.76 (m, J=7.80, 1.87 Hz, 1H); 6.91 (d, J=8.11 Hz, 1H); 7.31 (d, J=8.42 Hz, 2H); 7.63 (d, J=8.74 Hz, 2H); 8.00 (d, J=2.18 Hz, 1H); 8.23 (s, 1H); 8.29 (s, 1H); 9.52 (s, 1H).

EXAMPLE 326

N-[4-(4-amino-6-ethylthieno[2,3-d]pyrimidin-5-yl) phenyl]-N'-(2-ethoxyphenyl)urea Amine: 2-ethoxyaniline. MS (ESI(+)) m/e 434 (M+H)$^+$; $^1$H NMR (500 MHz, DMSO-d$_6$) δ 1.17 (t, J=7.49 Hz, 3H); 1.43 (t, J=7.02 Hz, 3H); 2.66 (q, J=7.49 Hz, 2H); 4.16 (q, J=7.07 Hz, 2H); 6.85-6.98 (m, 2H); 7.00-7.05 (m, 1H); 7.31 (d, J=8.42 Hz, 2H); 7.64 (d, J=8.42 Hz, 2H); 8.12-8.17 (m, 2H); 8.28 (s, 1H); 9.61 (s, 1H).

EXAMPLE 327

N-[4-(4-amino-6-ethylthieno[2,3-d]pyrimidin-5-yl) phenyl]-N'-[4-(methylsulfanyl)phenyl]urea Amine: 4-(methylsulfanyl)aniline. MS (ESI(+)) m/e 436 (M+H)$^+$; $^1$H NMR (500 MHz, DMSO-d$_6$) δ 1.16 (t, J=7.33 Hz, 3H); 2.44 (s, 3H); 2.60-2.70 (m, J=7.49 Hz, 2H); 7.24 (d, J=8.73 Hz, 2H); 7.31 (d, J=8.73 Hz, 2H); 7.44 (d, J=8.73 Hz, 2H); 7.62 (d, J=8.73 Hz, 2H); 8.28 (s, 1H); 8.79 (s, 1H); 8.90 (s, 1H).

EXAMPLE 328

N-[4-(4-amino-6-ethylthieno[2,3-d]pyrimidin-5-yl) phenyl]-N'-[3-(methylsulfanyl)phenyl]urea Amine: 3-(methylsulfanyl)aniline. MS (ESI(+)) m/e 436 (M+H)$^+$; $^1$H NMR (500 MHz, DMSO-d$_6$) δ 1.17 (t, J=7.49 Hz, 3H); 2.47 (s, 3H); 2.65 (q, J=7.49 Hz, 2H); 6.88 (d, J=8.74 Hz, 1H); 7.22 (m, J=7.80 Hz, 1H); 7.31 (d, J=8.73 Hz, 2H); 7.40-7.55 (m, 1H); 7.63 (d, J=8.73 Hz, 2H); 8.28 (s, 1H); 8.81 (s, 1H); 8.92 (s, 1H).

EXAMPLE 329

N-[4-(4-amino-6-ethylthieno[2,3-d]pyrimidin-5-yl) phenyl]-N'-2,3-dihydro-1,4-benzodioxin-6-ylurea Amine: 2,3-dihydro-1,4-benzodioxin-6-amine. MS (ESI(+)) m/e 448 (M+H)$^+$; $^1$H NMR (500 MHz, DMSO-d$_6$) δ 1.16 (t, J=7.64 Hz, 3H); 2.65 (q, J=7.49 Hz, 2H); 4.10-4.30 (m, 4H); 6.65-6.85 (m, 2H); 7.11 (d, J=2.50 Hz, 1H); 7.30 (d, J=8.73 Hz, 2H); 7.61 (d, J=8.73 Hz, 2H); 8.29 (s, 1H); 8.58 (s, 1H); 8.83 (s, 1H).

EXAMPLE 330

N-[4-(4-amino-6-ethylthieno[2,3-d]pyrimidin-5-yl) phenyl]-N'-{4-[(4-methoxyphenyl)amino] phenyl}urea Amine: N-(4-aminophenyl)-N-(4-methoxyphenyl)amine; MS (ESI(+)) m/e 511 (M+H)$^+$; $^1$H NMR (500 MHz, DMSO-d$_6$) δ 1.17 (t, J=7.49 Hz, 3H); 2.65 (q, J=7.59 Hz, 2H); 3.70 (s, 3H); 6.84 (d, J=8.74 Hz, 2H); 6.91 (d, J=8.73 Hz, 2H); 6.98 (d, J=8.74 Hz, 2H); 7.25-7.33 (m, 4H); 7.61 (d, J=8.42 Hz, 2H); 8.27 (s, 1H); 8.46 (s, 1H); 8.78 (s, 1H).

EXAMPLE 331

N-[4-(4-amino-6-ethylthieno[2,3-d]pyrimidin-5-yl) phenyl]-N'-(5-chloro-2,4-dimethoxyphenyl)urea Amine: 5-chloro-2,4-dimethoxyaniline. MS (ESI(+)) m/e 484 (M+H)$^+$; $^1$H NMR (500 MHz, DMSO-d$_6$) δ 1.16 (t, J=7.49 Hz, 3H); 2.65 (q, J=7.49 Hz, 2H); 3.86 (s, 3H); 3.95 (s, 3H); 6.88 (s, 1H); 7.31 (d, J=8.74 Hz, 2H); 7.61 (d, J=8.42 Hz, 2H); 8.16 (s, 1H); 8.23 (s, 1H); 8.28 (s, 1H); 9.45 (s, 1H).

EXAMPLE 332

N-[4-(4-amino-6-ethylthieno[2,3-d]pyrimidin-5-yl) phenyl]-N'-6-quinolinylurea

Amine: 6-quinolinamine. MS (ESI(+)) m/e 441 (M+H)$^+$; $^1$H NMR (500 MHz, DMSO-d$_6$) δ 1.16 (t, J=7.49, 3H); 2.67 (q, J=7.49 Hz, 2H); 7.34 (d, J=8.42 Hz, 2H); 7.52 (dd, J=8.42, 4.37 Hz, 1H); 7.68 (d, J=8.42 Hz, 2H); 7.78 (dd, J=9.05, 2.50 Hz, 1H); 7.98 (d, J=9.05 Hz, 1H); 8.23 (d, J=2.18 Hz, 1H); 8.28 (s, 1H); 8.34 (d, J=8.73 Hz, 1H); 8.79 (dd, J=4.06, 1.25 Hz, 1H); 9.10 (s, 1H); 9.22 (s, 1H).

EXAMPLE 333

N-[4-(4-amino-6-ethylthieno[2,3-d]pyrimidin-5-yl) phenyl]-N'-[4-(4-morpholinyl)phenyl]urea Amine: 4-(4-morpholinyl)aniline. MS (ESI(+)) m/e 475 (M+H)$^+$; $^1$H NMR (500 MHz, DMSO-d$_6$) δ 1.17 (t, J=7.02 Hz, 3H); 2.66 (q, J=7.59 Hz, 2H); 3.07 (m, 4H); 3.75 (m, 4H); 7.30 (d, J=8.73 Hz, 2H); 7.36 (d, J=9.05 Hz, 2H); 7.63 (d, J=8.73 Hz, 2H); 8.10-8.14 (m, 2H); 8.32 (s, 1H); 8.60 (s, 1H); 8.89 (s, 1H).

EXAMPLE 334

N-[4-(4-amino-6-ethylthieno[2,3-d]pyrimidin-5-yl) phenyl]-N'-(3-hydroxy-4-methylphenyl)urea Amine: 5-amino-2-methylphenol. MS (ESI(+)) m/e 420 (M+H)$^+$; $^1$H NMR (500 MHz, DMSO-d$_6$) δ 1.16 (t, J=7.49 Hz, 3H); 2.05 (s, 3H); 2.65 (q, J=7.49 Hz, 2H); 6.73 (dd, J=7.96, 2.03 Hz, 1H); 6.88-6.95 (m, 1H); 7.08 (d, J=1.87 Hz, 1H); 7.29 (d, J=8.42 Hz, 2H); 7.61 (d, J=8.73 Hz, 2H); 8.28 (s, 1H); 8.56 (s, 1H); 8.80 (s, 1H).

EXAMPLE 335

1-[4-(4-amino-6-methylthieno[2,3-d]pyrimidin-5-yl) phenyl]-3-phenylacetone

A mixture of Example 66A (100 mg, 0.31 mmol), 2-propynylbenzene (0.042 mL, 0.34 mmol), Pd(PPh$_3$)$_2$Cl$_2$ (11 mg, 0.016 mmol), CuI (3 mg, 0.016 mmol), diethylamine (0.48 mL, 4.68 mmol), and triphenylphosphine (16 mg, 0.062 mmol) in DMF (0.5 mL) in capped 5 mL vial was stirred while heating to 120° C. for 25 minutes in a Smith Synthesizer microwave at 300 W. The mixture cooled using 40 psi pressurized air, diluted with water, and extracted three times with ethyl acetate. The combined extracts were washed with water and brine, dried (MgSO$_4$), filtered, and concentrated. The concentrate was purified by silica gel chromatography with ethyl acetate to provide 38 mg of the desired product. MS (ESI(+)) m/e 374 (M+H)$^+$; $^1$H NMR (300 MHz, DMSO-d$_6$) δ 2.28 (s, 3H); 3.91 (s, 2H); 3.97 (s, 2H); 7.16-7.36 (m, 9H); 8.27 (s, 1H).

EXAMPLE 336

6-methyl-5-[4-(3-phenoxy-1-propynyl)phenyl]thieno[2,3-d]pyrimidin-4-amine

The desired product was prepared by substituting (2-propynyloxy)benzene for 2-propynylbenzene in Example 335. MS (ESI(+)) m/e 372 (M+H)$^+$; $^1$H NMR (300 MHz, DMSO-d$_6$) δ 2.28 (s, 3H); 5.09 (s, 2H); 6.99 (t, J=7.29 Hz, 1H); 7.07 (d, J=7.80 Hz, 2H); 7.35 (m, 2H); 7.41 (d, J=8.14 Hz, 2H); 7.60 (d, J=8.48 Hz, 2H); 8.27 (s, 1H).

EXAMPLE 337

N-[4-(2,4-diaminothieno[2,3-d]pyrimidin-5-yl)phenyl]-N'-(3-methylphenyl)urea

EXAMPLE 337A 5-(4-nitrophenyl)thieno[2,3-d]pyrimidine-2,4-diamine

A suspension of Example 58B (1 g, 4.08 mmol) and chloroformamidine hydrochloride (1.17 g, 10.2 mmol) in diglyme (40 mL) was heated to 130° C. for 15 hours. The mixture was cooled to room temperature, diluted with water, and extracted twice with ethyl acetate. The combined extracts were washed with brine, dried (MgSO$_4$), filtered, and concentrated. The residue was further concentrated under a stream of nitrogen, and purified by silica gel chromatography with 5 to 7% methanol/dichloromethane to provide 0.26 g of the desired product. MS (ESI(+)) m/e 288 (M+H)$^+$.

EXAMPLE 337B 5-(4-aminophenyl)thieno[2,3-d]pyrimidine-2,4-diamine

A suspension of Example 337A (0.26 g) in methanol (5 mL) was stirred under a hydrogen atmosphere (balloon) in the presence of 10% Pd/C (100 mg) for 24 hours, and filtered through diatomaceous earth (Celite®). The pad was washed with methanol and the combined filtrates were concentrated and purified by silica gel chromatography with 7% methanol/dichloromethane to provide 0.127 g of the desired product. MS (ESI(+)) m/e 258 (M+H)$^+$.

EXAMPLE 337C

N-[4-(2,4-diaminothieno[2,3-d]pyrimidin-5-yl)phenyl]-N'-(3-methylphenyl)urea

The desired product was prepared by substituting Example 337B and 3-methylphenyl isocyanate for Example 1E and phenyl isocyanate, respectively, in Example 1F. MS (ESI(+)) m/e 391 (M+H)$^+$; $^1$H NMR (300 MHz, DMSO-d6) δ 2.28 (s, 3H); 6.14 (s, 2H); 6.80 (m, 2H); 7.16 (t, J=7.8 Hz, 1H); 7.25 (d, J=8.5 Hz, 1H); 7.31 (br s, 1H); 7.34 (d, J=8.5 Hz, 2H); 7.57 (d, J=8.8 Hz, 2H); 8.64 (s, 1H); 8.82 (s, 1H).

EXAMPLE 338

N-{4-[(4-aminoisothiazolo[5,4-d]pyrimidin-3-yl)methyl]phenyl}-N'-(3-methylphenyl)urea

EXAMPLE 338A 5-amino-3-(4-nitrobenzyl)-4-isothiazolecarbonitrile

The desired product was prepared by substituting (4-nitrophenyl)acetyl chloride for 4-nitrobenzoyl chloride in Examples 96A-E. MS (ESI(−)) m/e 259 (M−H)$^−$.

EXAMPLE 338B

N'-[4-cyano3-(4-nitrobenzyl)-5-isothiazolyl]imidoformamide

A suspension of Example 338A (1 g, 3.8 mmol) and ammonium sulfate (50 mg, 0.38 mmol) in triethylorthoformate (25 mL) was stirred at reflux for 18 hours, cooled to 0° C., treated with ammonia (40 mL, 2M in propanol), stirred at room temperature for 4 hours, and concentrated. The residue was purified by silica gel chromatography with 35% ethyl acetate/hexanes to provide 0.38 g of the desired product. MS (ESI(−)) m/e 286 (M−H)$^−$.

EXAMPLE 338C 3-(4-nitrobenzyl)isothiazolo[5,4-d]pyrimidin-4-amine

A solution of Example 338B (0.37 g, 1.29 mmol) in methanol (3 mL) was treated with LiOCH$_3$ (1.4 mL, 1M in methanol), and heated to 70° C. for 4 hours. The reaction was cooled to room temperature resulting in a brown precipitate which was collected by filtration. The filter cake was washed with cold methanol and dried to provide 0.175 g of the desired product. MS (ESI(+)) m/e 288 (M+H)$^+$.

EXAMPLE 338D 3-(4-aminobenzyl)isothiazolo[5,4-d]pyrimidin-4-amine

The desired product was prepared by substituting Example 338C for Example 96F in Example 97. MS (ESI(+)) m/e 258 (M+H)$^+$.

EXAMPLE 338E

N-{4-[(4-aminoisothiazolo[5,4-d]pyrimidin-3-yl)methyl]phenyl}-N'-(3-methylphenyl)urea The desired product was prepared by substituting Example 338D and 3-methylphenyl isocyanate for Example 1E and phenyl isocyanate, respectively, in Example 1F. MS (ESI(+)) m/e 391 (M+H)$^+$; $^1$H NMR (300 MHz, DMSO-d$_6$) δ 2.27 (s, 3H); 4.50 (s, 2H); 6.77 (d, J=7.46 Hz, 1H); 6.96 (s, 1H); 7.05-7.45 (m, 6H); 8.37 (s, 1H); 8.66 (s, 1H); 8.72 (s, 1H).

EXAMPLE 339

N-{4-[(4-aminoisothiazolo[5,4-d]pyrimidin-3-yl)methyl]phenyl}-N'-[2-fluoro-5-(trifluoromethyl)phenyl]urea The desired product was prepared by substituting Example 338D and 2-fluoro-5-trifluomethylphenyl isocyanate for Example 1E and phenyl isocyanate, respectively, in Example 1F. MS (ESI(+)) m/e 463 (M+H)$^+$; $^1$H NMR (300 MHz, DMSO-d$_6$) δ 4.51 (s, 2H); 7.10-7.60 (m, 6H); 8.00 (s, 1H); 8.37 (s, 1H); 8.76 (s, 1H); 9.03 (s, 1H).

EXAMPLE 340

N-{4-[(4-aminoisothiazolo[5,4-d]pyrimidin-3-yl)methyl]phenyl}-N'-[3-(trifluoromethyl)phenyl]urea The desired product was prepared by substituting Example 338D and 3-trifluoromethylphenyl isocyanate for Example 1E and phenyl isocyanate, respectively, in Example 1F. MS (ESI(+)) m/e 445 (M+H)$^+$; $^1$H NMR (300 MHz, DMSO-d$_6$) δ 4.52 (s, 2H); 7.16 (d, J=8.48 Hz, 2H); 7.35-7.55 (m, 5H); 8.37 (s, 1H); 8.61 (dd, J=7.46, 2.71 Hz, 1H); 8.87 (d, J=2.71 Hz, 1H); 9.15 (s, 1H).

EXAMPLE 341

(2E)-N-[4-(4-amino-6-ethylthieno[2,3-d]pyrimidin-5-yl)phenyl]-3-(3-methylphenyl)acrylamide The desired product was prepared by substituting Example 78A and (2E)-3-(3-methylphenyl)acrylic acid for aniline and Example 66B, respectively, in Example 66C. MS (ESI(+)) m/e 415 (M+H)$^+$; $^1$H NMR (300 MHz, DMSO-d$_6$) δ 1.17 (t, J=7.46 Hz, 3H); 2.36 (s, 3H); 2.65 (q, J=7.69 Hz, 2H); 6.86 (d, J=15.60 Hz, 1H); 7.35-7.80 (m, 6H); 7.59 (d, J=15.60 Hz, 1H); 7.88 (d, J=8.48 Hz, 2H); 8.27 (s, 1H); 10.28 (s, 1H).

EXAMPLE 342

(2E)-N-[4-(4-amino-6-ethylthieno[2,3-d]pyrimidin-5-yl)phenyl]-3-[3-(trifluoromethyl)phenyl]acrylamide The desired product was prepared by substituting Example 78A and (2E)-3-[3-(trifluoromethyl)phenyl]acryloyl chloride for Example 1E and benzoyl chloride, respectively, in Example 4. MS (ESI(+)) m/e 469 (M+H)$^+$; $^1$H NMR (300 MHz, DMSO-d$_6$) δ 1.17 (t, J=7.46 Hz, 3H); 2.65 (q, J=7.46 Hz, 2H); 7.00 (d, J=15.93 Hz, 1H); 7.39 (d, J=8.48 Hz, 2H); 7.60-8.05 (m, 7H); 8.27 (s, 1H); 10.48 (s, 1H).

EXAMPLE 343

N-[4-(4-amino-6-ethylthieno[2,3-d]pyrimidin-5-yl)phenyl]urea

A mixture of Example 78A (0.27 g, 1 mmol) and NaOCN (0.13 g, 2 mmol) in water (1.5 mL) and acetic acid (1.5 mL) was stirred overnight at room temperature and partitioned between water and ethyl acetate. The organic extract was washed with saturated aqueous NaHCO$_3$ and brine, dried (MgSO$_4$), filtered, and concentrated to provide 0.3 g of the desired product. MS (ESI(+)) m/e 314 (M+H)$^+$; $^1$H NMR (300 MHz, DMSO-d$_6$) δ 1.15 (t, J=7.46 Hz, 3H); 2.63 (q, J=7.57 Hz, 2H); 5.94 (m, 2H); 7.24 (d, J=8.48 Hz, 2H); 7.56 (d, J=8.48 Hz, 2H); 8.25 (s, 1H); 8.75 (s, 1H).

EXAMPLE 344

3-{[4-(4-amino-6-ethylthieno[2,3-d]pyrimidin-5-yl)phenyl]amino}-4-[(3-methylphenyl)amino]-3-cyclobutene-1,2-dione

EXAMPLE 344A

3-{[4-(4-amino-6-ethylthieno[2,3-d]pyrimidin-5-yl)phenyl]amino}-4-ethoxy-3-cyclobutene-1,2-dione A mixture of Example 78A (0.135 g, 0.5 mmol) and 3,4-diethoxy-3-cyclobutene-1,2-dione (0.22 mL, 1.5 mmol) in ethanol (5 mL) was heated at 70-80° C. for 48 hours, then filtered while still hot. The filtrate was concentrated and the resulting residue was washed with hexanes and diethyl ether, and dried to provide 0.11 g of the desired product. MS (ESI(+)) m/e 395 (M+H)$^+$.

EXAMPLE 344B

3-{[4-(4-amino-6-ethylthieno[2,3-d]pyrimidin-5-yl)phenyl]amino}-4-[(3-methylphenyl)amino]-3-cyclobutene-1,2-dione A mixture of Example 344A (0.027 g, 0.068 mol) and 3-methylaniline (0.073 mL, 0.68 mmol) in ethanol (2 mL) was stirred at reflux for 48 hours and concentrated. The residue was purified by silica gel chromatography with 5% methanol/dichloromethane to provide 8 mg of the desired product. MS (ESI(+)) m/e 346 (M+H)$^+$; $^1$H NMR (300 MHz, DMSO-d$_6$) δ 1.17 (t, J=7.46 Hz, 3H); 2.32 (s, 3H); 2.66 (q, J=7.12 Hz, 2H); 6.80-7.00 (m, 2H); 7.20-7.50 (m, 4H); 7.67 (d, J=8.48 Hz, 2H); 8.28 (s, 1H); 10.11 (s, 1H); 10.30 (s, 1H).

EXAMPLE 345

3-{[4-(4-amino-6-ethylthieno[2,3-d]pyrimidin-5-yl)phenyl]amino}-4-[(3-chlorophenyl)amino]-3-cyclobutene-1,2-dione The desired product was prepared by substituting 3-chloroaniline for 3-methylaniline in Example 344B. MS (ESI(+)) m/e 476 (M+H)$^+$; $^1$H NMR (300 MHz, DMSO-d$_6$) δ 1.17 (t, J=7.46 Hz, 3H); 2.65 (q, J=7.57 Hz, 2H); 7.14 (d, J=7.46 Hz, 1H); 7.30-7.50 (m, 4H); 7.50-7.80 (m, 3H); 8.28 (s, 1H); 10.14 (s, 1H); 10.24 (s, 1H).

EXAMPLE 346 ethyl{[4-(4-amino-6-ethylthieno[2,3-d]pyrimidin-5-yl)phenyl]amino}(oxo)acetate

A solution of Example 78A (0.065 g, 0.25 mmol), ethyl chloro(oxo)acetate (0.028 mL, 0.25 mmol), and pyridine (0.02 mL, 0.25 mmol) in dichloromethane (5 mL) was stirred at room temperature overnight and partitioned between water and dichloromethane. The organic extract was washed with brine, dried (MgSO$_4$), filtered, and concentrated. The concentrate was purified by silica gel column chromatography with 5% methanol/dichloromethane to provide 60 mg of the desired product. MS (ESI(+)) m/e 371(M+H)$^+$; $^1$H NMR (300 MHz, DMSO-d$_6$) δ 1.15 (t, J=7.46 Hz, 3H); 1.34 (t, J=7.12 Hz, 3H); 2.64 (q, J=7.46 Hz, 2H); 4.34 (q, J=7.12 Hz, 2H); 7.41 (d, J=8.48 Hz, 2H); 7.93 (d, J=8.82 Hz, 2H); 8.27 (s, 1H); 11.00 (s, 1H).

EXAMPLE 347

3-{4-[(5,7-dimethyl-1,3-benzoxazol-2-yl)amino]phenyl}isothiazolo[5,4-d]pyrimidin-4-amine The desired product was prepared by substituting Example 97 and 2-amino-4,6-dimethylphenol for Example 1E and 2-aminophenol, respectively in Example 3. MS (ESI(+)) m/e 389 (M+H)$^+$; $^1$H NMR (300 MHz, DMSO-d$_6$) δ ppm 2.35 (s, 3H); 2.41 (s, 3H); 6.81 (s, 1H); 7.13 (s, 1H); 7.67 (d, J=8.48 Hz, 2H); 7.96 (d, J=8.48 Hz, 2H); 8.47 (s, 1H); 10.96 (s, 1H).

EXAMPLE 348

3-[({[4-(4-aminothieno[2,3-d]pyrimidin-5-yl)phenyl]amino}carbonyl)amino]benzoic acid

EXAMPLE 348A methyl 3-[({[4-(4-aminothieno[2,3-d]pyrimidin-5-yl)phenyl]amino}carbonyl)amino]benzoate The desired product was prepared by substituting methyl 3-isocyanatobenzoate and Example 58D for phenyl isocyanate and Example 1E, respectively, in Example 1F. MS(ESI(+)) m/e 420 (M+H)$^+$.

EXAMPLE 348B

3-[({[4-(4-aminothieno[2,3-d]pyrimidin-5-yl)phenyl]amino}carbonyl)amino]benzoic acid A suspension of Example 348A (0.5 g, 1.19 mmol) in methanol (50 mL) and THF (20 mL) was treated with 2N NaOH (3.6 mL, 7.2 mmol), stirred at room temperature for 4 hours, and heated to reflux for 1 hour. The mixture was cooled to room temperature, diluted with water, acidified to pH 3 with 4N HCl, and diluted with brine resulting in the formation of a precipitate. The solid was collected by filtration and dried to give 0.417 g of the desired product. MS (ESI(+)) m/e 406 (M+H)$^+$; $^1$H NMR (300 MHz, DMSO-d$_6$) δ 7.41 (m, 3H); 7.55 (s, 1H); 7.56 (d, J=6.0 Hz, 1H); 7.66-7.71 (m, 3H); 8.14 (s, 1H); 8.47 (s, 1H); 9.30 (s, 1H); 9.32 (s, 1H).

EXAMPLE 349

N-(4-{4-amino-6-[2-(dimethylamino)ethyl]thieno[2,3-d]pyrimidin-5-yl}phenyl)-N'-(3,5-dimethylphenyl)urea The desired product was prepared by substituting Example 281F and 3,5-dimethylphenylisocyanate for Example 1E and phenylisocyanate, respectively, in Example 1F. MS (ESI(+)) m/e 461 (M+H)$^+$; $^1$H NMR (300 MHz, DMSO-d$_6$) δ 2.10 (s, 6H); 2.24 (s, 6H); 2.43 (t, J=7.12 Hz, 2H); 2.74 (t, J=7.12 Hz, 2H); 6.63 (s, 1H); 7.09 (s, 2H); 7.30 (d, J=8.81 Hz, 2H); 7.62 (d, J=8.48 Hz, 2H); 8.26 (s, 1H); 8.59 (s, 1H); 8.86 (s, 1H).

EXAMPLE 350

N-{4-[4-amino-6-(2-hydroxyethyl)thieno[2,3-d]pyrimidin-5-yl]phenyl}-2-(3-methylphenyl)acetamide The desired product was prepared by substituting Example 104B and 3-methylphenylacetic acid for aniline and Example 66B, respectively, in Example 66C. The crude product was purified by silica gel chromatography with 7% methanol/dichloromethane to provide the desired product. m.p. 142-144° C.; MS (ESI(+)) m/e 419 (M+H)$^+$; $^1$H NMR (300 MHz, DMSO-d$_6$) δ 2.31 (s, 3H); 2.74 (t, J=6.61 Hz, 2H); 3.55 (m, 2H); 3.64 (s, 2H); 4.87 (t, J=5.26 Hz, 1H); 7.07 (d, J=6.78 Hz, 1H); 7.12-7.27 (m, 3H); 7.33 (d, J=8.14 Hz, 2H); 7.77 (d, J=8.48 Hz, 2H); 8.26 (s, 1H); 10.38 (s, 1H).

EXAMPLE 351

N-[4-(4-aminothieno[2,3-d]pyrimidin-5-yl)-3-hydroxyphenyl]-N'-[2-fluoro-5-(trifluoromethyl)phenyl]urea

EXAMPLE 351A

5-[4-amino-2-(benzyloxy)phenyl]thieno[2,3-d]pyrimidin-4-amine

The desired product was prepared by substituting 2-benzyloxy-4-nitro-benzoyl chloride for 3-methoxy-4-nitrobenzoyl chloride in Examples 165A-D. MS (ESI(+)) m/e 348.9 (M+H)$^+$.

EXAMPLE 351B

N-[4-(4-aminothieno[2,3-d]pyrimidin-5-yl)-3-(benzyloxy)phenyl]-N'-[2-fluoro-5-(trifluoromethyl)phenyl]urea The desired product was prepared by substituting Example 351A and 2-fluoro-5-trifluoromethylphenyl isocyanate for Example 1E and phenyl isocyanate, respectively in Example 1F. MS (ESI(+)) m/e 554 (M+H)$^+$.

EXAMPLE 351C

N-[4-(4-aminothieno[2,3-d]pyrimidin-5-yl)-3-hydroxyphenyl]-N'-[2-fluoro-5-(trifluoromethyl)phenyl]urea A solution of Example 351B (99 mg, 0.18 mmol) in 30% HBr/acetic acid (1 mL) and acetic acid (2 mL) was stirred at 70° C. for 3 hours, cooled to room temperature, poured into water, basified with 2N NaOH, adjusted to pH to 7-8 with 1N HCl, and extracted with methanol/dichloromethane. The extract was concentrated and the residue was purified by silica gel chromatography with 5% methanol/dichloromethane to provide 16 mg (19% yield) of the desired product. MS(ESI(+)) m/e 464.0 (M+H)$^+$; $^1$H NMR (300 MHz, DMSO-$d_6$) δ 6.94 (dd, J=8.5, 2.0 Hz, 1H); 7.15 (d, J=8.1 Hz, 1H); 7.31 (s, 1H); 7.38-7.43 (m, 2H); 7.48-7.55 (m, 1H); 8.30 (s, 1H); 8.64 (dd, J=7.5, 2.4 Hz, 1H); 8.91 (d, J=2.7 Hz, 1H); 9.29 (s, 1H); 9.87 (s, 1H)

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

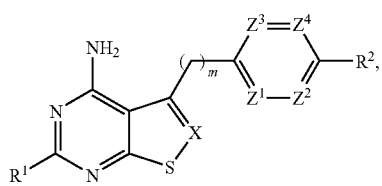

(I)

or a therapeutically acceptable salt thereof, wherein
X is N;
$Z^1$ is $CR^4$;
$Z^2$ is $CR^5$;
$Z^3$ is $CR^6$;
$Z^4$ is $CR^7$;
$R^1$ is hydrogen;
m is 0;
$R^2$ is nitro, —$NR^aR^b$ or —$LR^8$;
$R^4$, $R^5$, $R^6$, and $R^7$ are independently selected from the group consisting of hydrogen, alkoxy, alkyl, $NR^aR^b$, halo, and hydroxy;
$R^a$ and $R^b$ are hydrogen;
$R^8$ is phenyl, which is unsubstituted or substituted with one or two of independently selected alkyl, halo or haloalkyl;
L is —O— or —$(CH_2)_nNR^9C(O)NR^{10}(CH_2)_p$— wherein each group is drawn with its right side attached to $R^8$, and wherein $R^9$ and $R^{10}$ are independently selected from the group consisting of hydrogen, and alkyl; and
n and p are 0.

2. A compound of claim 1 selected from the group consisting of
3-(4-nitrophenyl)isothiazolo[5,4-d]pyrimidin-4-amine;
3-(4-aminophenyl)isothiazolo[5,4-d]pyrimidin-4-amine;
N-[4-(4-aminoisothiazolo[5,4-d]pyrimidin-3-yl)phenyl]-N'-[3-(trifluoromethyl)phenyl]urea;
N-[4-(4-aminoisothiazolo[5,4-d]pyrimidin-3-yl)phenyl]-N'-(3-methylphenyl)urea;
N-[4-(4-aminoisothiazolo[5,4-d]pyrimidin-3-yl)phenyl]-N'-(3-chlorophenyl)urea;
N-[4-(4-aminoisothiazolo[5,4-d]pyrimidin-3-yl)phenyl]-N'-(3-ethylphenyl)urea;
3-(4-phenoxyphenyl)isothiazolo[5,4-d]pyrimidin-4-amine; and
N-[4-(4-aminoisothiazolo[5,4-d]pyrimidin-3-yl)phenyl]-N'-[2-fluoro-5-(trifluoromethyl)phenyl]urea.

* * * * *